United States Patent
Aponte et al.

(10) Patent No.: US 10,087,460 B2
(45) Date of Patent: Oct. 2, 2018

(54) TRANSGENIC OR NON-TRANSGENIC PLANTS WITH MUTATED PROTOPORPHYRINOGEN OXIDASE HAVING INCREASED TOLERANCE TO HERBICIDES

(71) Applicant: BASF AGRO B.V., EA Arnheim (NL)

(72) Inventors: Raphael Aponte, Mannheim (DE); Stefan Tresch, Kirchheim (DE); Matthias Witschel, Bad Duerkheim (DE); Jens Lerchl, Golm (DE); Dario Massa, Mannheim (DE); Tobias Seiser, Mannheim (DE); Thomas Mietzner, Annweiler (DE); Jill Marie Paulik, Cary, NC (US); Chad Brommer, Raleigh, NC (US)

(73) Assignee: BASF AGRO B.V., Arnhem (NL)

( * ) Notice: Subject to any disclaimer, the term of this patent is extended or adjusted under 35 U.S.C. 154(b) by 0 days.

(21) Appl. No.: 14/911,824

(22) PCT Filed: Aug. 12, 2014

(86) PCT No.: PCT/IB2014/063873
§ 371 (c)(1),
(2) Date: Feb. 12, 2016

(87) PCT Pub. No.: WO2015/022636
PCT Pub. Date: Feb. 19, 2015

(65) Prior Publication Data
US 2016/0194655 A1    Jul. 7, 2016

Related U.S. Application Data

(60) Provisional application No. 61/864,671, filed on Aug. 12, 2013, provisional application No. 61/864,672, filed on Aug. 12, 2013.

(51) Int. Cl.
*C12N 15/82* (2006.01)
*C12N 9/02* (2006.01)
*A01H 5/00* (2018.01)

(52) U.S. Cl.
CPC .......... *C12N 15/8274* (2013.01); *A01H 5/00* (2013.01); *C12N 9/001* (2013.01); *C12Y 103/03004* (2013.01)

(58) Field of Classification Search
None
See application file for complete search history.

(56) References Cited

U.S. PATENT DOCUMENTS

| | | |
|---|---|---|
| 5,169,770 A | 12/1992 | Chee et al. |
| 5,198,013 A | 3/1993 | Hirai et al. |
| 5,322,783 A | 6/1994 | Tomes et al. |
| 5,366,892 A | 11/1994 | Foncerrada et al. |
| 5,376,543 A | 12/1994 | Chee et al. |
| 5,380,831 A | 1/1995 | Adang et al. |
| 5,436,391 A | 7/1995 | Fujimoto et al. |
| 5,485,192 A | 1/1996 | Nagahata et al. |
| 5,593,881 A | 1/1997 | Thompson et al. |
| 5,723,756 A | 3/1998 | Peferoen et al. |
| 5,737,514 A | 4/1998 | Stiffler |
| 5,747,450 A | 5/1998 | Ohba et al. |
| 5,767,373 A | 6/1998 | Ward et al. |
| 5,773,702 A | 6/1998 | Penner et al. |
| 5,859,348 A | 1/1999 | Penner et al. |
| 5,939,360 A | 8/1999 | Adachi et al. |
| 5,939,602 A * | 8/1999 | Volrath ............. C12N 5/04 435/320.1 |
| 5,948,917 A | 9/1999 | Adachi et al. |
| 5,990,387 A | 11/1999 | Tomes et al. |
| 6,018,105 A | 1/2000 | Johnson et al. |
| 6,027,945 A | 2/2000 | Smith et al. |
| 6,084,155 A | 7/2000 | Volrath et al. |
| 6,160,206 A | 12/2000 | Sato et al. |
| 6,308,458 B1 | 10/2001 | Volrath et al. |
| 6,368,800 B1 | 4/2002 | Smith et al. |
| 6,653,529 B2 | 11/2003 | Peng et al. |
| 6,905,852 B1 | 6/2005 | Horikoshi et al. |

(Continued)

FOREIGN PATENT DOCUMENTS

| | | |
|---|---|---|
| CA | 2382090 A1 | 2/2001 |
| CA | 2807035 A1 | 2/2012 |

(Continued)

OTHER PUBLICATIONS

Che et al., Localization of target-site of the protoporphyrinogen oxidase-inhibiting herbicide, S-23142, in Spinacia oleracea L., Z. Naturforsch, 48e:350-5 (1992).
Cole-Strauss et al., Targeted gene repair directed by the chimeric RNA/DNA oligonucleotide in a mammalian cell-free extract, Nucleic Acids Res., 27(5)1 323-30 (1999).
Dailey et al., Expression of a cloned protoporphyrinogen oxidase, J. Biol. Chem., 289(2):813-15 (1994).
Dayan et al., Biochemical and structural consequences of a glycine deletion in the alpha-8 helix of protoporphyrinogen oxidase, Biochim. Biophys. Acta, 1804(7)1 548-56 (2010).
Duke et al., Protoporphyrinogen oxidase-inhibiting herbicides, Weed Sci., 39:465-73 (1991).

(Continued)

*Primary Examiner* — Eileen B O Hara
(74) *Attorney, Agent, or Firm* — Marshall, Gerstein & Borun LLP

(57) ABSTRACT

The present invention refers to a method for controlling undesired vegetation at a plant cultivation site, the method comprising the steps of providing, at said site, a plant that comprises at least one nucleic acid comprising a nucleotide sequence encoding a wild-type or a mutated protoporphyrinogen oxidase (PPO) which is resistant or tolerant to a PPO-inhibiting herbicide by applying to said site an effective amount of said herbicide. The invention further refers to plants comprising wild-type or mutated PPO enzymes, and methods of obtaining such plants.

28 Claims, 8 Drawing Sheets
Specification includes a Sequence Listing.

(56) References Cited

U.S. PATENT DOCUMENTS

| | | | |
|---|---|---|---|
| 7,671,254 B2 | 3/2010 | Tranel et al. | |
| 7,705,200 B2 | 4/2010 | Dam et al. | |
| 7,745,699 B2 | 6/2010 | Nakajima et al. | |
| 7,842,856 B2 | 11/2010 | Tranel et al. | |
| 8,097,774 B2 | 1/2012 | Hawkes et al. | |
| 8,129,589 B2 | 3/2012 | Tanaka et al. | |
| 8,338,337 B2 | 12/2012 | Song et al. | |
| 2003/0236208 A1 | 12/2003 | Kmiec et al. | |
| 2004/0082770 A1 | 4/2004 | Castle et al. | |
| 2005/0084859 A1 | 4/2005 | Nakajima et al. | |
| 2007/0021515 A1 | 1/2007 | Glenn et al. | |
| 2007/0039067 A1 | 2/2007 | Feldmann et al. | |
| 2007/0050863 A1 | 3/2007 | Tranel et al. | |
| 2007/0214515 A1 | 9/2007 | Dam et al. | |
| 2009/0049567 A1 | 2/2009 | Olhoft et al. | |
| 2010/0100988 A1 | 4/2010 | Tranel et al. | |
| 2011/0201501 A1 | 8/2011 | Song et al. | |
| 2012/0122223 A1 | 5/2012 | Gocal et al. | |
| 2013/0184155 A1 | 7/2013 | Newton et al. | |
| 2014/0123340 A1* | 5/2014 | Aponte | A01N 43/84 800/278 |
| 2014/0189906 A1 | 7/2014 | Gocal et al. | |
| 2015/0299725 A1* | 10/2015 | Lerchl | C12N 9/001 504/225 |
| 2016/0194654 A1* | 7/2016 | Aponte | C12N 9/0071 800/300 |
| 2016/0201078 A1* | 7/2016 | Aponte | C12N 9/0071 504/128 |

FOREIGN PATENT DOCUMENTS

| | | |
|---|---|---|
| CN | 1150820 A | 5/1997 |
| CN | 1036571 C | 12/1997 |
| CN | 1212724 A | 3/1999 |
| CN | 1175107 C | 11/2004 |
| CN | 1894408 A | 10/2007 |
| CN | 101215289 A | 7/2008 |
| CN | 101437844 A | 5/2009 |
| CN | 101998988 A | 3/2011 |
| DE | 19505995 A1 | 8/1996 |
| EP | 0397687 A1 | 11/1990 |
| EP | 0424047 A1 | 4/1991 |
| EP | 0900795 A1 | 3/1999 |
| WO | WO-93/07256 A1 | 4/1993 |
| WO | WO-95/34659 | 12/1995 |
| WO | WO-96/26202 A1 | 8/1996 |
| WO | WO-1997/004088 A1 | 2/1997 |
| WO | WO-1997/032011 A1 | 9/1997 |
| WO | WO-97/41116 A1 | 11/1997 |
| WO | WO-97/41117 A1 | 11/1997 |
| WO | WO-97/41118 A1 | 11/1997 |
| WO | WO-1998/029554 A1 | 7/1998 |
| WO | WO-1998/033927 A1 | 8/1998 |
| WO | WO-2001/012815 A1 | 2/2001 |
| WO | WO-2001/068826 A2 | 9/2001 |
| WO | WO-01/83459 A2 | 11/2001 |
| WO | WO-02/068607 A2 | 9/2002 |
| WO | WO-2005/107437 A2 | 11/2005 |
| WO | WO-2006/024820 A1 | 3/2006 |
| WO | WO-2006/037945 A1 | 4/2006 |
| WO | WO-2007/024739 A2 | 3/2007 |
| WO | WO-2007/071900 A1 | 6/2007 |
| WO | WO-2007/096576 A1 | 8/2007 |
| WO | WO-2008/124495 A2 | 10/2008 |
| WO | WO-2008/141154 A2 | 11/2008 |
| WO | WO-2010/049269 A1 | 5/2010 |
| WO | WO-2010/049409 A1 | 5/2010 |
| WO | WO-2010/145992 A1 | 12/2010 |
| WO | WO-2011/018486 A2 | 2/2011 |
| WO | WO-2012/018862 A2 | 2/2012 |
| WO | WO-2012/041789 A1 | 4/2012 |
| WO | WO-2012/080975 A1 | 6/2012 |
| WO | WO-2013/189984 A2 | 12/2013 |
| WO | WO-2015/022636 A2 | 2/2015 |
| WO | WO-2015/022639 A2 | 2/2015 |
| WO | WO-2015/092706 A1 | 6/2015 |

OTHER PUBLICATIONS

Geiser et al., The hypervariable region in the genes coding for entomopathogenic crystal proteins of Bacillus thuringiensis: nucleotide sequence of the kurhd1 gene of subsp. kurstaki HD1, Gene, 48(1):109-18 (1986).

GenBank Accession No. ACF78832, unknown [*Zea mays*], Jul. 30, 2008.

International Preliminary Report on Patentability, International Application No. PCT/IB2014/063873, dated Feb. 16, 2016.

International Search Report and Written Opinion, International Application No. PCT/IB2014/063873, dated Feb. 9, 2015.

Jacobs et al., Assay for enzymatic protoporphyrinogen oxidation, a late step in heme synthesis, Enzyme, 28)2-3):206-19 (1982).

Kataoka et al., Isolation and partial characterization of mutant Chlamydomonas reinhardtii resistant to herbicide S-23142, J. Pesticide Sci., 15:449-51 (1990).

Lee et al., Cellular localization of protoporphyrinogen-oxidizing activities of etiolated barley (*Hordeum vulgare* L.) leaves, Plant Physiol., 102:881-9 (1993).

Loppes, A new class of arginine-requiring mutants in Chlamydomonas reinhardi, Mol. Gen. Genet., 104(2):172-7 (1969).

Matringe et al., Protoporphyrinogen oxidase as a molecular target for diphenyl ether herbicides, Biochem. J., 260(1):231-5 (1989).

Matringe et al., Protoporphyrinogen oxidase inhibition by three peroxidizing herbicides: oxadiazon, LS 82-556 and M&B 39279, FEBS Lett., 245(1-20:35-8 (1989).

Murray et al., Codon usage in plant genes, Nucleic Acids Res., 17(2):477-98 (1989).

Nandihalli et al., Quantative structure-activity relationships of protoporphyrinogen oxidase-inhibiting diphenyl ether herbicides, Pesticide Biochem Physbiol., 43:193-211 (1992).

Oshio et al., Isolation and characterization of a Chlamydomonas reinhardtii mutant resistant to photobleaching herbicides, Z. Naturforsch, 48c:339-44 (1993).

Patzoldt et al., A codon deletion confers resistance to herbicides inhibiting protoporphyrinogen oxidase, Proc. Natl. Acad. Sci. USA, 103(33):12329-34 (2006).

Randolph-Anderson et al., Isolation and characterization of a mutant protoporphyrinogen oxidase gene from Chlamydomonas reinhardtii conferring resistance to porphyric herbicides, Plant Mol. Biol., 38(5):839-59 (1998).

Sasarman et al., Mapping of a new hem gene in *Escherichia coli* K12, J. Gen. Microbiol., 113(2):297-303 (1979).

Sasarman et al., Nucleotide sequence of the hemG gene involved in the protoporphyrinogen oxidase activity of *Escherichia coli* K12, Can. J. Microbiol., 39(12):1155-61 (1993).

Shibata et al., Isolation and characterization of a Chlamydomonas reinhardtii mutant resistant to an experimental herbicide S-23142, which inhibits chlorophyll synthesis, in: Murata (ed.), Research in Photosynthesis, vol. III, pp. 567-70 (1992).

Su et al., The development of protoporphyrinogen oxidase inhibiting herbicides, Agrochemicals Research & Application, 15(1):1-5 (2011).

Yanase et al., Porphyrin synthesis involvement in diphenyl ether-like mode of action of TNPP-ethyl, a novel phenylpyrazole herbicide, Pesticide Biochemistry and Physiology, 35:70-80 (1989).

Arnould et al., The domain structure of protoporphyrinogen oxidase, the molecular target of diphenyl ether-type herbicides.*Proc. Natl. Acad. Sci. USA*, 95: 10553-8 (1998).

Che et al., Molecular characterization and subcellular localization of protoporphyrinogen oxidase in spinach chloroplasts. *Plant Physiol.* 124: 59-70 (2000).

Choi et al., Generation of resistance to the diphenyl ether herbicide, oxyfluorfen, via expression of the *Bacillus subtilis* protoporphyrinogen oxidase gene in transgenic tobacco plants. *Biosci. Biotechnol. Biochem*. 62(3): 558-60 (1998).

(56) References Cited

OTHER PUBLICATIONS

Corradi et al., Crystal structure of protoporphyrinogen oxidase from *Myxococcus Xanthus* and it complex with the inhibitor acifluorfen. *J Biol Chem.* 281(50): 38625-33 (2006).
Dayan et al., Phytotoxicity of Protoporphyrinogen Oxidase Inhibitors: Phenomenology, Mode of Action and Mechanisms of Resistance, *Herbicide Activity: Toxicology, Biochemistry and Molecular Biology*, eds. Roe et al., pp. 11-35 (1997).
Extended European Search Report, issued in co-assigned application No. 11848519.2, dated Apr. 23, 2014.
GenBank Accession No. AX084732, submitted on Mar. 9, 2001.
GenBank Accession No. DQ386114, Amaranthus tuberculatus biotype herbicide-susceptible WC mitochrondrial protoporphyrinogen oxidase (PPX2L) mRNA, complete cds; nuclear gene for mitochrondrial product, Aug. 18, 2006.
GenBank Accession No. XP_004976030.1, Predicted: protoporhyrinogen oxidase, mitochondrial [Setaria italica] (Nov. 30, 2015).
GenBank Accession No. XM_004975973, Predicted: Setaria italica protoporphyrinogen oxidase, mitochondrial (LOC101781148), mRNA (Nov. 30, 2015).
Ha et al., The plastidic *Arabidopsis* protoporhyrinogen IX oxidase gene, with or without the transit sequence, confers resistance to the diphenyl ether herbicide in rice. *Plant Cell Environ.* 27: 79-88 (2003).
Hanin et al., Gene targeting in *Arabidopsis*. *Plant J.* 28: 671-7 (2001).
Hao et al., Protoporphyrinogen oxidase inhibitor: An ideal target for herbicide discovery. *Chimia*, 65(12): 961-9 (2011).
Heinemann et al., Functional definition of the tobacco protoporphyrinogen IX oxidase substrate-binding site. *Biochem. J.* 402: 575-80 (2007).
Holmberg, A fine line: New herbicide-tolerant crops blur the fine line between weed control and crop injury. *Successful Farm.* 98(5): 25-7 (2000).
Huang et al., Synthesis and herbicidal activity of isoindoline-1,3-dione substituted benzoxazinone derivatives containing a carboxylic ester group. *J. Agric. Food Chem.* 57: 9585-92 (2009).
International Search Report, issued in PCT/IB2011/055701, dated May 3, 2012.
International Preliminary Report on Patentability, issued in PCT/IB2011/055701, dated Jun. 27, 2013.
International Search Report, corresponding International Application No. PCT/EP2013/062744, dated Dec. 10, 2014.
International Search Report and Written Opinion, International Application No. PCT/IB2014/063876, dated Jan. 28, 2015.
International Preliminary Report on Patentability, International Application No. PCT/IB2014/063876, dated Feb. 16, 2016.
International Search Report and Written Opinion, International Application No. PCT/IB2014/063877, dated Feb. 10, 2015.
International Preliminary Report on Patentability, International Application No. PCT/IB2014/063877, dated Feb. 16, 2016.
Jung et al., Dual targeting of *Myxococcus xanthus* protoporphyrinogen oxidase into chloroplasts and mitochondria and high level oxyfluorfen resistance. *Plant Cell Environ.* 27: 1436-46 (2004).
Jung et al., Resistance mechanisms in protoporphyrinogen oxidase (PROTOX) inhibitor-resistant transgenic rice. *J. Plant Biol.* 50(3): 586-94 (2007).
Koch et al., Crystal structure of protoporphyrinogen IX oxidase: A key enzyme in Haem and chlorophyll biosynthesis. *EMBO J.* 23: 1720-8 (2004).
Layer et al., Structure and function of enzymes in Heme biosynthesis. *Protein Sci.* 19: 1137-61 (2010).
Lee et al., Expression of human protoporphyrinogen oxidase in transgenic rice induces both a photodynamic response and oxyfluorfen resistance. *Pesticide Biochem. Physiol.* 80: 65-74 (2004).
Lee et al., Transgenic rice plants expressing a *Bacillus subtilis* protoporphyrinogen oxidase gene are resistant to diphenyl ether herbicide oxyfluorfen. *Plant Cell Physiol.* 41(6): 743-9 (2000).
Lermontova et al., Cloning and characterization of a plastidal and a mitochondria' isoform of tobacco protoporphyrinogen IX oxidase. *Proc. Natl. Acad. Sci. USA*, 94: 8895-900 (1997).
Lermontova et al., Overexpression of plastidic protoporphyrinogen IX oxidase leads to resistance to the diphenyl-ether herbicide acifluorfen. *Plant Physiol.* 122: 75-83 (2000).
Lewis et al., Interactions between redox partners in various cytochrome P450 systems: functional and structural aspects, Biochim. Biophys. Acta, 1460(2-3):353-74 (2000).
Li et al., Development of PPO inhibitor-resistant cultures and crops, Pest Management Science, 61(3):277-85 (2005).
Li et al., Development of protoporphyrinogen oxidase as an efficient selection marker for *Agrobacterium* tumefaciens-mediated transformation of maize. *Plant Physiol.* 133: 736-47 (2003).
Lyga et al., Structural replacements for the benzoxazinone protox inhibitors. *Pesticide Sci.* 55: 281-7 (1999).
Macias et al., Optimization of benzoxazinones as natural herbicide models by lipophilicity enhancement. *J. Acric. Food Chem.* 54: 9357-65 (2006).
Mulwa et al., Biotechnology approaches to developing herbicide tolerance/selectivity in crops. *Afr. J. Biotechnol.* 5(5): 396-404 (2006).
Rousonelos, S., Master's Thesis, University of Illinois, published Aug. 2010.
Watanabe et al., Molecular characterization of photomixotrophic tobacco cells resistant to protoporphyrinogen oxidase-inhibiting herbicides. *Plant Physiol.* 118: 751-8 (1998).
U.S. Appl. No. 14/408,439, filed Dec. 16, 2014, Jens Lerchl et al.
U.S. Appl. No. 13/918,212, filed Jun. 14, 2013, Raphael Aponte et al.
U.S. Appl. No. 13/994,374, filed Oct. 9, 2013, Johannes Hutzler et al.
Extended European Search Report, issued in application No. EP 14836729.5, dated Jun. 6, 2017.
EBI Accession No. GSP:BBB23069, Amaranthus tuberculatus PPO variant R128A/T208S/F420V #1 (Feb. 13, 2014).
Extended European Search Report, European Patent Application No. 14836899.6, dated Jun. 30, 2017 (4 pp.).
Partial Supplementary European Search Report, European patent application No. 14836729.5, dated Mar. 28, 2017.
NCBI Reference Sequence XM_004975973.1, Predicted: Setaria italica protoporphyrinogen oxidase, chloroplastic/mitochrondrial-like (LOC101781148), mRNA, Jun. 26, 2013.
Supplemental Partial European Search Report, European patent application No. EP 14836899, dated Mar. 20, 2017.

* cited by examiner

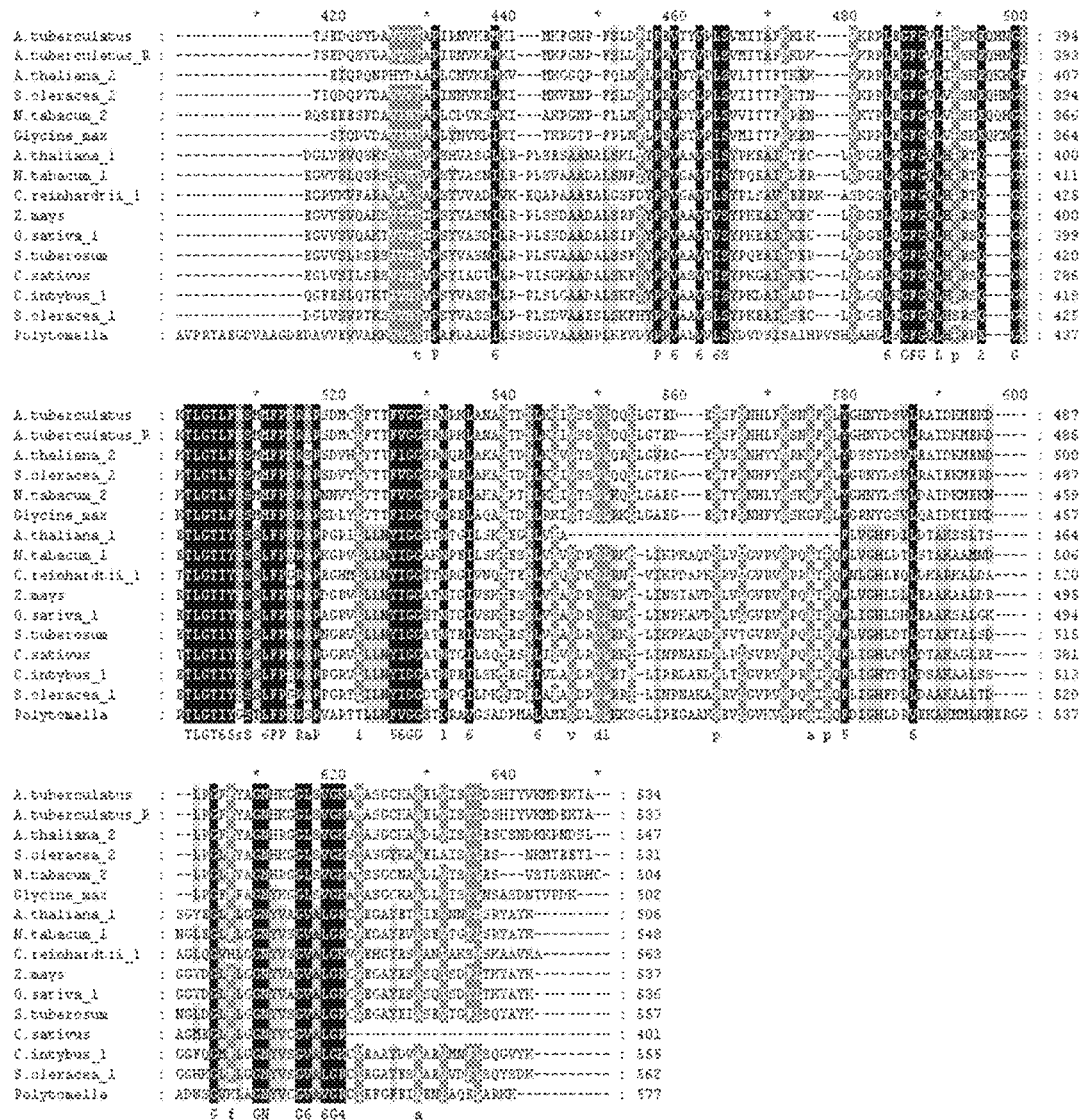
Figure 1 - continued

TRANSGENIC OR NON-TRANSGENIC PLANTS WITH MUTATED PROTOPORPHYRINOGEN OXIDASE HAVING INCREASED TOLERANCE TO HERBICIDES

This application is a National Stage application of International Application No. PCT/IB2014/063873, filed Aug. 12, 2014, which claims the benefit of U.S. Provisional Application No. 61/864,671, filed Aug. 12, 2013 and U.S. Provisional Application No. 61/864,672, filed Aug. 12, 2013, the entire contents of which are hereby incorporated herein by reference in their entirety.

REFERENCE TO SEQUENCE LISTING SUBMITTED VIA EFS-WEB

This amendment was filed electronically via EFS-Web and includes an electronically submitted sequence listing in .txt format. The .txt file contains a sequence listing entitled "74831_SubSeqlisting.txt" created on Sep. 2, 2016, and is 171,417 bytes in size. The sequence listing contained in this .txt file is part of the specification and is hereby incorporated by reference herein in its entirety.

FIELD OF THE INVENTION

The present invention relates in general to methods for conferring on plants agricultural level tolerance to a herbicide. Particularly, the invention refers to plants having an increased tolerance to PPO-inhibiting herbicides. More specifically, the present invention relates to methods and plants obtained by mutagenesis and cross-breeding and transformation that have an increased tolerance to PPO-inhibiting herbicides.

BACKGROUND OF THE INVENTION

Herbicides that inhibit protoporphyrinogen oxidase (hereinafter referred to as Protox or PPO; EC:1.3.3.4), a key enzyme in the biosynthesis of protoporphyrin IX, have been used for selective weed control since the 1960s. PPO catalyzes the last common step in chlorophyll and heme biosynthesis which is the oxidation of protoporphyrinogen IX to protoporphyrin IX. (Matringe et al. 1989. Biochem. 1. 260: 231). PPO-inhibiting herbicides include many different structural classes of molecules (Duke et al. $_{1991}$. Weed Sci. 39: 465; Nandihalli et al. 1992. Pesticide Biochem. Physiol. 43: 193; Matringe et al. 1989. FEBS Lett. 245: 35; Yanase and Andoh. 1989. Pesticide Biochem. Physiol. 35: 70). These herbicidal compounds include the diphenylethers {e.g. lactofen, (+−)-2-ethoxy-1-methyl-2-oxoethyl 5-{2-chloro-4-(trifluoromethyl)phenoxy}-2-nitrobenzoate; acifluorfen, 5-{2-chloro-4-(trifluoromethyl)phenoxy}-2-nitrobenzoic acid; its methyl ester; or oxyfluorfen, 2-chloro-1-(3-ethoxy-4-nitrophenoxy)-4-(trifluorobenzene)}, oxidiazoles, (e.g. oxidiazon, 3-{2,4-dichloro-5-(1-methylethoxy)phenyl}-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-{1-(2,3,4-trichlorophenyl)-4-nitropyrazolyl-5-oxy}propionate; M&B 39279), pyridine derivatives (e.g. LS 82-556), and phenopylate and its 0-phenylpyrrolidino- and piperidinocarbamate analogs. Many of these compounds competitively inhibit the normal reaction catalyzed by the enzyme, apparently acting as substrate analogs.

Application of PPO-inhibiting herbicides results in the accumulation of protoporphyrinogen IX in the chloroplast and mitochondria, which is believed to leak into the cytosol where it is oxidized by a peroxidase. When exposed to light, protoporphyrin IX causes formation of singlet oxygen in the cytosol and the formation of other reactive oxygen species, which can cause lipid peroxidation and membrane disruption leading to rapid cell death (Lee et al. 1993. Plant Physiol. 102: 881).

Not all PPO enzymes are sensitive to herbicides which inhibit plant PPO enzymes. Both the *Escherichia coli* and *Bacillus subtilis* PPO enzymes (Sasarmen et al. 1993. Can. J. Microbiol. 39: 1155; Dailey et al. 1994. J. Biol. Chem. 269: 813) are resistant to these herbicidal inhibitors. Mutants of the unicellular alga *Chlamydomonas reinhardtii* resistant to the phenylimide herbicide S-23142 have been reported (Kataoka et al. 1990. J. Pesticide Sci. 15: 449; Shibata et al. 1992. In Research in Photosynthesis, Vol. III, N. Murata, ed. Kluwer:Netherlands. pp. 567-70). At least one of these mutants appears to have an altered PPO activity that is resistant not only to the herbicidal inhibitor on which the mutant was selected, but also to other classes of protox inhibitors (Oshio et al. 1993. Z. Naturforsch. 48c: 339; Sato et al. 1994. In ACS Symposium on Porphyric Pesticides, S. Duke, ed. ACS Press: Washington, D.C.). A mutant tobacco cell line has also been reported that is resistant to the inhibitor S-21432 (Che et al. 1993. Z. Naturforsch. 48c: 350). Auxotrophic *E. coli* mutants have been used to confirm the herbicide resistance of cloned plant PPO-inhibiting herbicides.

Three main strategies are available for making plants tolerant to herbicides, i.e. (1) detoxifying the herbicide with an enzyme which transforms the herbicide, or its active metabolite, into nontoxic products, such as, for example, the enzymes for tolerance to bromoxynil or to basta (EP242236, EP337899); (2) mutating the target enzyme into a functional enzyme which is less sensitive to the herbicide, or to its active metabolite, such as, for example, the enzymes for tolerance to glyphosate (EP293356, Padgette S. R. et al., J. Biol. Chem., 266, 33, 1991); or (3) overexpressing the sensitive enzyme so as to produce quantities of the target enzyme in the plant which are sufficient in relation to the herbicide, in view of the kinetic constants of this enzyme, so as to have enough of the functional enzyme available despite the presence of its inhibitor. The third strategy was described for successfully obtaining plants which were tolerant to PPO inhibitors (see e.g. U.S. Pat. No. 5,767,373 or U.S. Pat. No. 5,939,602, and patent family members thereof.). In addition, US 2010/0100988 and WO 2007/024739 discloses nucleotide sequences encoding amino acid sequences having enzymatic activity such that the amino acid sequences are resistant to PPO inhibitor herbicidal chemicals, in particular 3-phenyluracil inhibitor specific PPO mutants.

WO 2012/080975 discloses plants the tolerance of which to a PPO-inhibiting herbicide named "benzoxazinone-derivative" herbicide (1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione) had been increased by transforming said plants with nucleic acids encoding mutated PPO enzymes. In particular, WO 2012/080975 discloses that the introduction of nucleic acids which code for a mutated PPO of an *Amaranthus* type II PPO in which the Arginine at position 128 had been replaced by a leucine, alanine, or valine, and the phenylalanine at position 420 had been replaced by a methionine, cysteine, isoleucine, leucine, or threonine, confers increased tolerance/resistance to a benzoxazinone-derivative herbicide.

The inventors of the present invention have now surprisingly found that those types of double-mutants and, furthermore, novel substitutions for R128 and F420 which are not disclosed in WO 2012/080975 confer increased tolerance/resistance to a wide variety of PPO inhibitors including, but not limited to a "benzoxazinone-derivative" (1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione) herbicide described in WO 2012/080975. Thus, to date, the prior art has not described PPO-inhibiting herbicide tolerant plants containing a mutated PPO nucleic acid according to the present invention, which are tolerant/resistant to a broad spectrum of PPO inhibitors. Therefore, what is needed in the art are crop plants and crop plants having increased tolerance to herbicides such as PPO-inhibiting herbicide and containing at least one wildtype and/or mutated PPO nucleic acid according to the present invention. Also needed are methods for controlling weed growth in the vicinity of such crop plants or crop plants. These compositions and methods would allow for the use of spray over techniques when applying herbicides to areas containing crop plants or crop plants.

SUMMARY OF THE INVENTION

The problem is solved by the present invention which refers to a method for controlling undesired vegetation at a plant cultivation site, the method comprising the steps of:
a) providing, at said site, a plant that comprises at least one nucleic acid comprising a nucleotide sequence encoding a wild type protoporphyrinogen oxidase (PPO) or a mutated protoporphyrinogen oxidase (PPO) which is resistant or tolerant to a PPO-inhibiting herbicide,
b) applying to said site an effective amount of said herbicide.

In addition, the present invention refers to a method for identifying a PPO-inhibiting herbicide by using a wild-type or mutated PPO of the present invention encoded by a nucleic acid which comprises the nucleotide sequence of SEQ ID NO: 1, 3, 5, 7, 9, 11, 13, 15, 17, 19, 21, 23, 25, 27, 29, 31, 33, 35, 37, 39, 41, 43, 45, or 47, or a variant thereof.

Said method comprises the steps of:
a) generating a transgenic cell or plant comprising a nucleic acid encoding a mutated PPO of the present invention, wherein the mutated PPO of the present invention is expressed;
b) applying a PPO-inhibiting herbicide to the transgenic cell or plant of a) and to a control cell or plant of the same variety;
c) determining the growth or the viability of the transgenic cell or plant and the control cell or plant after application of said test compound, and
d) selecting test compounds which confer reduced growth to the control cell or plant as compared to the growth of the transgenic cell or plant.

Another object refers to a method of identifying a nucleotide sequence encoding a mutated PPO which is resistant or tolerant to a PPO-inhibiting herbicide, the method comprising:
a) generating a library of mutated PPO-encoding nucleic acids,
b) screening a population of the resulting mutated PPO-encoding nucleic acids by expressing each of said nucleic acids in a cell or plant and treating said cell or plant with a PPO-inhibiting herbicide,
c) comparing the PPO-inhibiting herbicide-tolerance levels provided by said population of mutated PPO encoding nucleic acids with the PPO-inhibiting herbicide-tolerance level provided by a control PPO-encoding nucleic acid,
d) selecting at least one mutated PPO-encoding nucleic acid that provides a significantly increased level of tolerance to a PPO-inhibiting herbicide as compared to that provided by the control PPO-encoding nucleic acid.

In a preferred embodiment, the mutated PPO-encoding nucleic acid selected in step d) provides at least 2-fold as much tolerance to a PPO-inhibiting herbicide as compared to that provided by the control PPO-encoding nucleic acid.

The resistance or tolerance can be determined by generating a transgenic plant comprising a nucleic acid sequence of the library of step a) and comparing said transgenic plant with a control plant.

Another object refers to a method of identifying a plant or algae containing a nucleic acid encoding a mutated PPO which is resistant or tolerant to a PPO-inhibiting herbicide, the method comprising:
a) identifying an effective amount of a PPO-inhibiting herbicide in a culture of plant cells or green algae.
b) treating said plant cells or green algae with a mutagenizing agent,
c) contacting said mutagenized cells population with an effective amount of PPO-inhibiting herbicide, identified in a),
d) selecting at least one cell surviving these test conditions,
e) PCR-amplification and sequencing of PPO genes from cells selected in d) and comparing such sequences to wild-type PPO gene sequences, respectively.

In a preferred embodiment, the mutagenizing agent is ethylmethanesulfonate.

Another object refers to an isolated and/or recombinantly produced and/or chemically synthesized (synthetic) nucleic acid encoding a mutated PPO, the nucleic acid comprising the sequence of SEQ ID NO: 1, 3, 5, 7, 9, 11, 13, 15, 17, 19, 21, 23, 25, 27, 29, 31, 33, 35, 37, 39, 41, 43, 45, or 47, or a variant thereof, as defined hereinafter.

Another object refers to an isolated mutated PPO polypeptide, the polypeptide comprising the sequence set forth in SEQ ID NO: 2, 4, 6, 8, 10, 12, 14, 16, 18, 20, 22, 24, 26, 28, 30, 32, 34, 36, 38, 40, 42, 44, 46, or 48, a variant, derivative, orthologue, paralogue or homologue thereof, as defined hereinafter.

In a preferred embodiment, the nucleic acid being identifiable by a method as defined above.

In another embodiment, the invention refers to a plant cell transformed by and expressing a wild-type or a mutated PPO nucleic acid according to the present invention or a plant which has been mutated to obtain a plant expressing, preferably over-expressing a wild-type or a mutated PPO nucleic acid according to the present invention, wherein expression of said nucleic acid in the plant cell results in increased resistance or tolerance to a PPO-inhibiting herbicide as compared to a wild type variety of the plant cell.

In another embodiment, the invention refers to a plant comprising a plant cell according to the present invention, wherein expression of the nucleic acid in the plant results in the plant's increased resistance to PPO-inhibiting herbicide as compared to a wild type variety of the plant.

In another embodiment, the invention refers to a plant that expresses a mutagenized or recombinant mutated PPO polypeptide, and wherein said mutated PPO confers upon the plant increased herbicide tolerance as compared to the corresponding wild-type variety of the plant when expressed therein The plants of the present invention can be transgenic or non-transgenic.

Preferably, the expression of the nucleic acid of the invention in the plant results in the plant's increased resistance to PPO-inhibiting herbicides as compared to a wild type variety of the plant.

In another embodiment, the invention refers to a method for growing the plant according to the present invention while controlling weeds in the vicinity of said plant, said method comprising the steps of:

a) growing said plant; and
b) applying a herbicide composition comprising a PPO-inhibiting herbicide to the plant and weeds, wherein the herbicide normally inhibits protoporphyrinogen oxidase, at a level of the herbicide that would inhibit the growth of a corresponding wild-type plant.

In another embodiment, the invention refers to a seed produced by a transgenic plant comprising a plant cell of the present invention, or to a seed produced by the non-transgenic plant that expresses a mutagenized PPO polypeptide, wherein the seed is true breeding for an increased resistance to a PPO-inhibiting herbicide as compared to a wild type variety of the seed.

In another embodiment, the invention refers to a method of producing a transgenic plant cell with an increased resistance to a PPO-inhibiting herbicide as compared to a wild type variety of the plant cell comprising, transforming the plant cell with an expression cassette comprising a wild-type or a mutated PPO nucleic acid.

In another embodiment, the invention refers to a method of producing a transgenic plant comprising, (a) transforming a plant cell with an expression cassette comprising a wild-type or a mutated PPO nucleic acid, and (b) generating a plant with an increased resistance to PPO-inhibiting herbicide from the plant cell.

Preferably, the expression cassette further comprises a transcription initiation regulatory region and a translation initiation regulatory region that are functional in the plant.

In another embodiment, the invention relates to using the mutated PPO of the invention as selectable marker. The invention provides a method of identifying or selecting a transformed plant cell, plant tissue, plant or part thereof comprising a) providing a transformed plant cell, plant tissue, plant or part thereof, wherein said transformed plant cell, plant tissue, plant or part thereof comprises an isolated nucleic acid encoding a mutated PPO polypeptide of the invention as described hereinafter, wherein the polypeptide is used as a selection marker, and wherein said transformed plant cell, plant tissue, plant or part thereof may optionally comprise a further isolated nucleic acid of interest; b) contacting the transformed plant cell, plant tissue, plant or part thereof with at least one PPO-inhibiting inhibiting compound; c) determining whether the plant cell, plant tissue, plant or part thereof is affected by the inhibitor or inhibiting compound; and d) identifying or selecting the transformed plant cell, plant tissue, plant or part thereof.

The invention is also embodied in purified mutated PPO proteins that contain the mutations described herein, which are useful in molecular modeling studies to design further improvements to herbicide tolerance. Methods of protein purification are well known, and can be readily accomplished using commercially available products or specially designed methods, as set forth for example, in Protein Biotechnology, Walsh and Headon (Wiley, 1994).

In another embodiment, the invention relates to a combination useful for weed control, comprising (a) a polynucleotide encoding a mutated PPO polypeptide according to the present invention, which polynucleotide is capable of being expressed in a plant to thereby provide to that plant tolerance to a PPO inhibiting herbicide; and (b) a PPO inhibiting herbicide.

In another embodiment, the invention relates to a process for preparing a combination useful for weed control comprising (a) providing a polynucleotide encoding a mutated PPO polypeptide according to the present invention, which polynucleotide is capable of being expressed in a plant to thereby provide to that plant tolerance to a PPO inhibiting herbicide; and (b) providing a PPO inhibiting herbicide.

In a preferred embodiment, said step of providing a polynucleotide comprises providing a plant containing the polynucleotide.

In another preferred embodiment, said step of providing a polynucleotide comprises providing a seed containing the polynucleotide.

In another preferred embodiment, said process further comprises a step of applying the PPO inhibiting herbicide to the seed.

In another embodiment, the invention relates to the use of a combination useful for weed control, comprising (a) a polynucleotide encoding a mutated PPO polypeptide according to the present invention, which polynucleotide is capable of being expressed in a plant to thereby provide to that plant tolerance to a PPO inhibiting herbicide; and (b) a PPO inhibiting herbicide, to control weeds at a plant cultivation site.

BRIEF DESCRIPTION OF THE DRAWINGS

MSO at the V2-V3 stage. 1=wildtype, 2=AmatuPPX2L_R128L_F420M; 3=AmatuPPX2L_R128A_F420I; 4=AmatuPPX2L_R128A_F420V; 5=AmatuPPX2L_R128A_F420L; 6=AmatuPPX2LR128M_F420I; 7=AmatuPPX2L_R128M_F420L; 8=AmatuPPX2L_R128M_F420V

KEY TO SEQUENCE LISTING

TABLE 1

Figure 1:
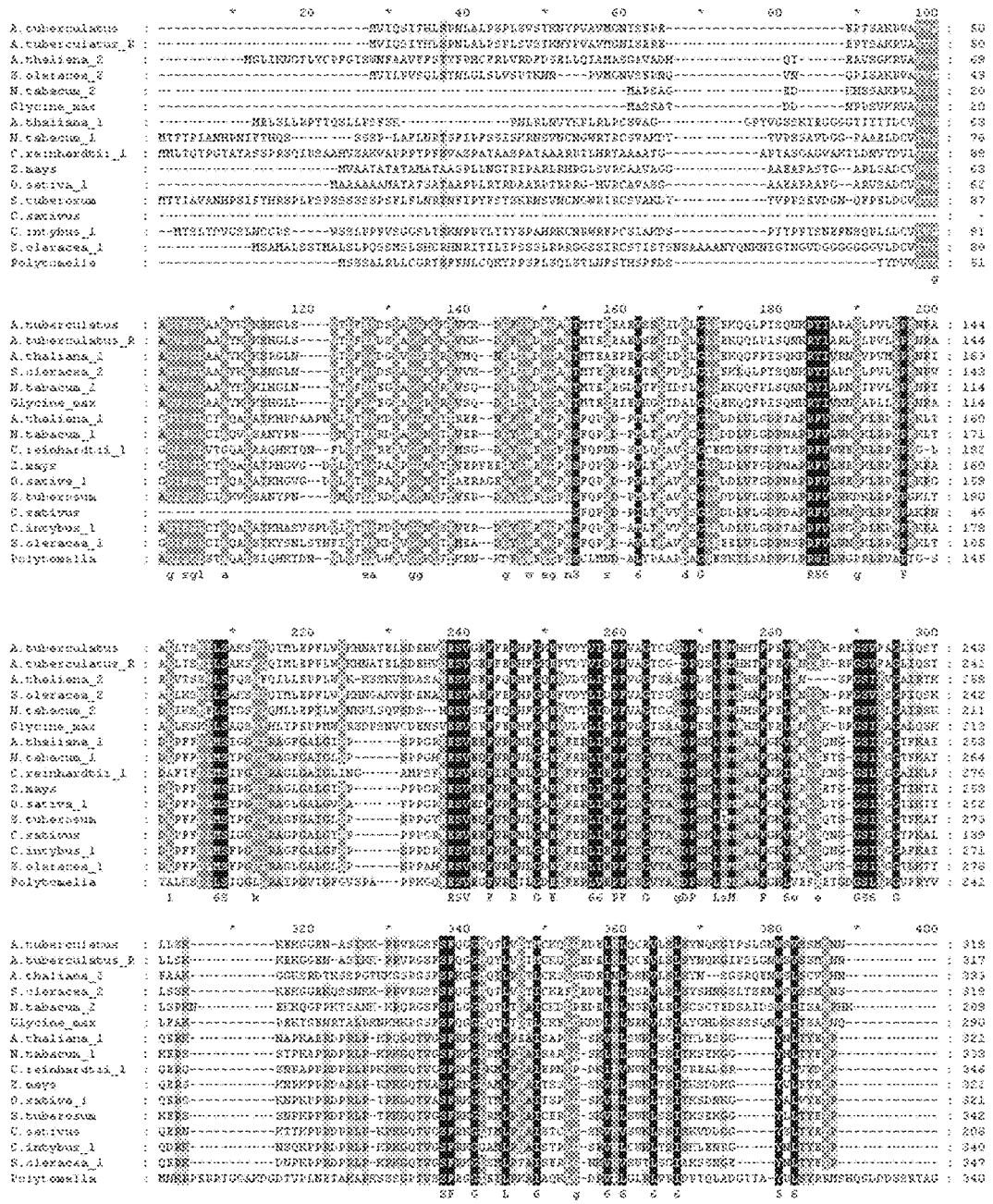
FIG. 1 shows an amino acid sequence alignment of *Amaranthus tuberculatus* (*A. tuberculatus*) (SEQ ID NO: 4), *Amaranthus tuberculatus* resistant (*A. tuberculatus*_R) (SEQ ID NO: 6), *Arabidopsis thaliana* long (*A. thaliana*_2) (SEQ ID NO: 10), *Spinacia oleracea* short (*S. oleracea*_2) (SEQ ID NO: 18), *Nicotiana tabacum* short (*N. tabacum*_2) (SEQ ID NO: 38), *Glycine max* (*Glycine_max*) (SEQ ID NO: 40), *Arabidopsis thaliana* short (*A. thaliana*_1) (SEQ ID NO: 36), *Nicotiana tabacum* long (*N. tabacum*_1) (SEQ ID NO: 12), *Chlamydomonas reinhardtii* long (*C. reinhardtii*_1) (SEQ ID NO: 26), *Zea mays* (*Z. mays*) (SEQ ID NO: 56), *Oryza sativa* (*O. sativa*_1) (SEQ ID NO: 32), *Solanum tuberosum* (*S. tuberosum*) (SEQ ID NO: 20), *Cucumis sativus* (*C. sativus*) (SEQ ID NO: 42), *Cichorium intybus* (*C. intybus*_1) (SEQ ID NO: 14), *Spinacia oleracea* long (*S. oleracea*_1) (SEQ ID NO: 16), *Polytomella* sp. Pringsheim 198.80 (*Polytomella*) (SEQ ID NO: 28) PPO sequences. Conserved regions are indicated in light grey, grey and black.

| SEQ. ID NO: | Description | Organism | Gene | Accession No: |
|---|---|---|---|---|
| 1 | PPO nucleic acid | *Amaranthus tuberculatus* | PPX2L_WC | DQ386114 |
| 2 | PPO amino acid | *Amaranthus tuberculatus* | ABD52326 | |
| 3 | PPO nucleic acid | *Amaranthus tuberculatus* | PPX2L_AC | DQ386117 |
| 4 | PPO amino acid | *Amaranthus tuberculatus* | ABD52329 | |
| 5 | PPO nucleic acid | *Amaranthus tuberculatus* | PPX2L_CC_R | DQ386118 |
| 6 | PPO amino acid | *Amaranthus tuberculatus* | ABD52330 | |
| 7 | PPO nucleic acid | *Amaranthus tuberculatus* | PPX2L_AC_R | DQ386116 |
| 8 | PPO amino acid | *Amaranthus tuberculatus* | ABD52328 | |
| 9 | PPO nucleic acid | *Arabidopsis thaliana* | PPX | AB007650 |
| 10 | PPO amino acid | *Arabidopsis thaliana* | BAB08301 | |
| 11 | PPO nucleic acid | *Nicotiana tabacum* | ppx1 | AF044128 |
| 12 | PPO amino acid | *Nicotiana tabacum* | AAD02290 | |
| 13 | PPO nucleic acid | *Cichorium intybus* | PPX1 | AF160961 |
| 14 | PPO amino acid | *Cichorium intybus* | AF160961_1 | |
| 15 | PPO nucleic acid | *Spinacia oleracea* | SO-POX1 | AB029492 |
| 16 | PPO amino acid | *Spinacia oleracea* | BAA96808 | |
| 17 | PPO nucleic acid | *Spinacia oleracea* | SO-POX2 | AB046993 |
| 18 | PPO amino acid | *Spinacia oleracea* | BAB60710 | |
| 19 | PPO nucleic acid | *Solanum tuberosum* | PPOX | AJ225107 |
| 20 | PPO amino acid | *Solanum tuberosum* | CAA12400 | |
| 21 | PPO nucleic acid | *Zea mays* | ZM_BFc0091B03 | BT063659 |
| 22 | PPO amino acid | *Zea mays* | ACN28356 | |
| 23 | PPO nucleic acid | *Zea mays* | prpo2 | NM_001111534 |
| 24 | PPO amino acid | *Zea mays* | NP_001105004 | |
| 25 | PPO nucleic acid | *Chlamydomonas* | Ppx1 | AF068635 |
| 26 | PPO amino acid | *Chlamydomonas* | AAC79685 | |
| 27 | PPO nucleic acid | *Polytomella* | PPO | AF332964 |

TABLE 1-continued

| SEQ. ID NO: | Description | Organism | Gene | Accession No: |
|---|---|---|---|---|
| 28 | PPO amino acid | *Polytomella* | AF332964_1 | |
| 29 | PPO nucleic acid | *Sorghum bicolor* | Hyp. Protein | XM_002446665 |
| 30 | PPO amino acid | *Sorghum bicolor* | XP_002446710 | |
| 31 | PPO nucleic acid | *Oryza sativa* | PPOX1 | AB057771 |
| 32 | PPO amino acid | *Oryza sativa* | BAB39760 | |
| 33 | PPO nucleic acid | *Amaranthus tuberculatus* | PPX2 | DQ386113 |
| 34 | PPO amino acid | *Amaranthus tuberculatus* | ABD52325 | |
| 35 | PPO nucleic acid | *Arabidopsis thaliana* | PPOX | NM_178952 |
| 36 | PPO amino acid | *Arabidopsis thaliana* | NP_849283 | |
| 37 | PPO nucleic acid | *Nicotiana tabacum* | ppxII | AF044129 |
| 38 | PPO amino acid | *Nicotiana tabacum* | AAD02291 | |
| 39 | PPO nucleic acid | *Glycine max* | hemG | AB025102 |
| 40 | PPO amino acid | *Glycine max* | BAA76348 | |
| 41 | PPO nucleic acid | *Cucumis sativus* | CsPPO | AB512426 |
| 42 | PPO amino acid | *Cucumis sativus* | BAH84864.1 | |
| 43 | PPO nucleic acid | *Oryza sativa* | Hyp. Protein | AL606613 |
| 44 | PPO amino acid | *Oryza sativa* | CAE01661 | |
| 45 | PPO nucleic acid | *Oryza sativa* | amine oxidase | |
| 46 | PPO amino acid | *Oryza sativa* | Os04g41260.1 | |
| 47 | PPO nucleic acid | *Amaranthus tuberculatus* | PPX1 | |
| 48 | PPO amino acid | *Amaranthus tuberculatus* | PPO1 | |

DETAILED DESCRIPTION

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The inventors of the present invention have found, that the tolerance or resistance of a plant to a PPO-inhibiting herbicide could be remarkably increased by overexpressing a nucleic acid encoding a mutated PPO polypeptide comprising the sequence set forth in SEQ ID NO: 2, 4, 6, 8, 10, 12, 14, 16, 18, 20, 22, 24, 26, 28, 30, 32, 34, 36, 38, 40, 42, 44, 46, or 48, a variant, derivative, orthologue, paralogue or homologue thereof.

The present invention refers to a method for controlling undesired vegetation at a plant cultivation site, the method comprising the steps of:

a) providing, at said site, a plant that comprises at least one nucleic acid comprising a nucleotide sequence encoding a wild-type protoporphyrinogen oxidase or a mutated protoporphyrinogen oxidase (mutated PPO) which is resistant or tolerant to a PPO-inhibiting herbicide, b) applying to said site an effective amount of said herbicide.

The term "control of undesired vegetation" is to be understood as meaning the killing of weeds and/or otherwise retarding or inhibiting the normal growth of the weeds. Weeds, in the broadest sense, are understood as meaning all those plants which grow in locations where they are undesired, e.g. (crop) plant cultivation sites. The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus,* and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus,* and *Apera*. In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

The term "plant" is used in its broadest sense as it pertains to organic material and is intended to encompass eukaryotic organisms that are members of the Kingdom Plantae, examples of which include but are not limited to vascular plants, vegetables, grains, flowers, trees, herbs, bushes, grasses, vines, ferns, mosses, fungi and algae, etc, as well as clones, offsets, and parts of plants used for asexual propagation (e.g. cuttings, pipings, shoots, rhizomes, underground stems, clumps, crowns, bulbs, corms, tubers, rhizomes, plants/tissues produced in tissue culture, etc.). The term "plant" further encompasses whole plants, ancestors and progeny of the plants and plant parts, including seeds, shoots, stems, leaves, roots (including tubers), flowers, florets, fruits, pedicles, peduncles, stamen, anther, stigma, style, ovary, petal, sepal, carpel, root tip, root cap, root hair, leaf hair, seed hair, pollen grain, microspore, cotyledon, hypocotyl, epicotyl, xylem, phloem, parenchyma, endosperm, a companion cell, a guard cell, and any other known organs, tissues, and cells of a plant, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana*, *Agropyron* spp., *Agrostis stolonifera*, *Allium* spp., *Amaranthus* spp., *Ammophila arenaria*, *Ananas comosus*, *Annona* spp., *Apium graveolens*, *Arachis* spp., *Artocarpus* spp., *Asparagus officinalis*, *Avena* spp. (e.g. *Avena sativa*, *Avena fatua*, *Avena byzantina*, *Avena fatua* var. *sativa*, *Avena hybrida*), *Averrhoa carambola*, *Bambusa* sp., *Benincasa hispida*, *Bertholletia excelsea*, *Beta vulgaris*, *Brassica* spp. (e.g. *Brassica napus*, *Brassica rapa* ssp. [canola, oilseed rape, turnip rape]), *Cadaba farinosa*, *Camellia sinensis*, *Canna indica*, *Cannabis sativa*, *Capsicum* spp., *Carex elata*, *Carica papaya*, *Carissa macrocarpa*, *Carya* spp., *Carthamus tinctorius*, *Castanea* spp., *Ceiba pentandra*, *Cichorium endivia*, *Cinnamomum* spp., *Citrullus lanatus*, *Citrus* spp., *Cocos* spp., *Coffea* spp., *Colocasia esculenta*, *Cola* sp., *Corchorus* sp., *Coriandrum sativum*, *Corylus* spp., *Crataegus* spp., *Crocus sativus*, *Cucurbita* spp., *Cucumis* spp., *Cynara* spp., *Daucus carota*, *Desmodium* spp., *Dimocarpus longan*, *Dioscorea* spp., *Diospyros* spp., *Echinochloa* spp., *Elaeis* (e.g. *Elaeis guineensis*, *Elaeis oleifera*), *Eleusine coracana*, *Eragrostis tef*, *Erianthus* sp., *Eriobotrya japonica*, *Eucalyptus* sp., *Eugenia uniflora*, *Fagopyrum* spp., *Fagus* spp., *Festuca arundinacea*, *Ficus carica*, *Fortunella* spp., *Fragaria* spp., *Ginkgo biloba*, *Glycine* spp. (e.g. *Glycine max*, *Soja hispida* or *Soja max*), *Gossypium hirsutum*, *Helianthus* spp. (e.g. *Helianthus annuus*), *Hemerocallis fulva*, *Hibiscus* spp., *Hordeum* spp. (e.g. *Hordeum vulgare*), *Ipomoea batatas*, *Juglans* spp., *Lactuca sativa*, *Lathyrus* spp., *Lens culinaris*, *Linum usitatissimum*, *Litchi chinensis*, *Lotus* spp., *Luffa acutangula*, *Lupinus* spp., *Luzula sylvatica*, *Lycopersicon* spp. (e.g. *Lycopersicon esculentum*, *Lycopersicon lycopersicum*, *Lycopersicon pyriforme*), *Macrotyloma* spp., *Malus* spp., *Malpighia emarginata*, *Mammea americana*, *Mangifera indica*, *Manihot* spp., *Manilkara zapota*, *Medicago sativa*, *Melilotus* spp., *Mentha* spp., *Miscanthus sinensis*, *Momordica* spp., *Morus nigra*, *Musa* spp., *Nicotiana* spp., *Olea* spp., *Opuntia* spp., *Ornithopus* spp., *Oryza* spp. (e.g. *Oryza sativa*, *Oryza latifolia*), *Panicum miliaceum*, *Panicum virgatum*, *Passiflora edulis*, *Pastinaca sativa*, *Pennisetum* sp., *Persea* spp., *Petroselinum crispum*, *Phalaris arundinacea*, *Phaseolus* spp., *Phleum pratense*, *Phoenix* spp., *Phragmites australis*, *Physalis* spp., *Pinus* spp., *Pistacia vera*, *Pisum* spp., *Poa* spp., *Populus* spp., *Prosopis* spp., *Prunus* spp., *Psidium* spp., *Punica granatum*, *Pyrus communis*, *Quercus* spp., *Raphanus sativus*, *Rheum rhabarbarum*, *Ribes* spp., *Ricinus communis*, *Rubus* spp., *Saccharum* spp., *Salix* sp., *Sambucus* spp., *Secale cereale*, *Sesamum* spp., *Sinapis* sp., *Solanum* spp. (e.g. *Solanum tuberosum*, *Solanum integrifolium* or *Solanum lycopersicum*), *Sorghum bicolor*, *Spinacia* spp., *Syzygium* spp., *Tagetes* spp., *Tamarindus indica*, *Theobroma cacao*, *Trifolium* spp., *Tripsacum dactyloides*, *Triticosecale rimpaui*, *Triticum* spp. (e.g. *Triticum aestivum*, *Triticum durum*, *Triticum turgidum*, *Triticum hybernum*, *Triticum macha*, *Triticum sativum*, *Triticum monococcum* or *Triticum vulgare*), *Tropaeolum minus*, *Tropaeolum majus*, *Vaccinium* spp., *Vicia* spp., *Vigna* spp., *Viola odorata*, *Vitis* spp., *Zea mays*, *Zizania palustris*, *Ziziphus* spp., amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant. Examples of crop plants include inter alia soybean, sunflower, canola, alfalfa, rapeseed, cotton, tomato, potato or tobacco. Further preferably, the plant is a monocotyledonous plant, such as sugarcane. Further preferably, the plant is a cereal, such as rice, maize, wheat, barley, millet, rye, *sorghum* or oats.

In a preferred embodiment, the plant has been previously produced by a process comprising recombinantly preparing a plant by introducing and over-expressing a wild-type or mutated PPO transgene according to the present invention, as described in greater detail hereinafter.

In another preferred embodiment, the plant has been previously produced by a process comprising in situ mutagenizing plant cells, to obtain plant cells which express a mutated PPO.

As disclosed herein, the nucleic acids of the invention find use in enhancing the herbicide tolerance of plants that comprise in their genomes a gene encoding a herbicide-tolerant wild-type or mutated PPO protein. Such a gene may be an endogenous gene or a transgene, as described hereinafter.

Therefore, in another embodiment the present invention refers to a method of increasing or enhancing the PPO-inhibitor herbicide tolerance or resistance of a plant, the method comprising overexpressing a nucleic acid encoding a mutated PPO polypeptide comprising the sequence set forth in SEQ ID NO: 2, 4, 6, 8, 10, 12, 14, 16, 18, 20, 22, 24, 26, 28, 30, 32, 34, 36, 38, 40, 42, 44, 46, or 48, a variant, derivative, orthologue, paralogue or homologue thereof.

Additionally, in certain embodiments, the nucleic acids of the present invention can be stacked with any combination of polynucleotide sequences of interest in order to create plants with a desired phenotype. For example, the nucleic acids of the present invention may be stacked with any other polynucleotides encoding polypeptides having pesticidal and/or insecticidal activity, such as, for example, the *Bacil*-

*lus thuringiensis* toxin proteins (described in U.S. Pat. Nos. 5,366,892; 5,747,450; 5,737,514; 5,723,756; 5,593,881; and Geiser et al (1986) Gene 48: 109).

By way of example, polynucleotides that may be stacked with the nucleic acids of the present invention include nucleic acids encoding polypeptides conferring resistance to pests/pathogens such as viruses, nematodes, insects or fungi, and the like. Exemplary polynucleotides that may be stacked with nucleic acids of the invention include polynucleotides encoding: polypeptides having pesticidal and/or insecticidal activity, such as other *Bacillus thuringiensis* toxic proteins (described in U.S. Pat. Nos. 5,366,892; 5,747,450; 5,737, 514; 5,723,756; 5,593,881; and Geiser et al., (1986) Gene 48:109), lectins (Van Damme et al. (1994) Plant Mol. Biol. 24:825, pentin (described in U.S. Pat. No. 5,981,722), and the like; traits desirable for disease or herbicide resistance (e.g., fumonisin detoxification genes (U.S. Pat. No. 5,792, 931); avirulence and disease resistance genes (Jones et al. (1994) Science 266:789; Martin et al., (1993) Science 262: 1432; Mindrinos et al. (1994) Cell 78:1089); acetolactate synthase (ALS) mutants that lead to herbicide resistance such as the S4 and/or Hra mutations; glyphosate resistance (e.g., 5-enol-pyrovyl-shikimate-3-phosphate-synthase (EPSPS) gene, described in U.S. Pat. Nos. 4,940,935 and 5,188,642; or the glyphosate N-acetyltransferase (GAT) gene, described in Castle et al. (2004) Science, 304:1151-1154; and in U.S. Patent App. Pub. Nos. 20070004912, 20050246798, and 20050060767)); glufosinate resistance (e.g, phosphinothricin acetyl transferase genes PAT and BAR, described in U.S. Pat. Nos. 5,561,236 and 5,276,268); resistance to herbicides including sulfonyl urea, DHT (2,4D), and PPO herbicides (e.g., glyphosate acetyl transferase, aryloxy alkanoate dioxygenase, acetolactate synthase, and protoporphyrinogen oxidase); a cytochrome P450 or variant thereof that confers herbicide resistance or tolerance to, inter alia, HPPD herbicides (U.S. patent application Ser. No. 12/156,247; U.S. Pat. Nos. 6,380,465; 6,121,512; 5,349,127; 6,649,814; and 6,300,544; and PCT Patent App. Pub. No. WO2007000077); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)); the disclosures of which are herein incorporated by reference.

In a particularly preferred embodiment, the plant comprises at least one additional heterologous nucleic acid comprising a nucleotide sequence encoding a herbicide tolerance enzyme selected, for example, from the group consisting of 5-enolpyruvylshikimate-3-phosphate synthase (EPSPS), Glyphosate acetyl transferase (GAT), Cytochrome P450, phosphinothricin acetyltransferase (PAT), Acetohydroxyacid synthase (AHAS; EC 4.1.3.18, also known as acetolactate synthase or ALS), Protoporphyrinogen oxidase (PPGO), Phytoene desaturase (PD) and dicamba degrading enzymes as disclosed in WO 02/068607. The combinations generated can also include multiple copies of any one of the polynucleotides of interest.

Generally, the term "herbicide" is used herein to mean an active ingredient that kills, controls or otherwise adversely modifies the growth of plants. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art. Herbicidal activity is exhibited by herbicides useful for the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the herbicide postemergence to relatively immature undesirable vegetation to achieve the maximum control of weeds.

By a "herbicide-tolerant" or "herbicide-resistant" plant, it is intended that a plant that is tolerant or resistant to at least one herbicide at a level that would normally kill, or inhibit the growth of, a normal or wild-type plant. By "herbicide-tolerant wildtype or mutated PPO protein" or "herbicide-resistant wildtype or mutated PPO protein", it is intended that such a PPO protein displays higher PPO activity, relative to the PPO activity of a wild-type PPO protein, when in the presence of at least one herbicide that is known to interfere with PPO activity and at a concentration or level of the herbicide that is known to inhibit the PPO activity of the wild-type mutated PPO protein. Furthermore, the PPO activity of such a herbicide-tolerant or herbicide-resistant mutated PPO protein may be referred to herein as "herbicide-tolerant" or "herbicide-resistant" PPO activity.

Generally, if the PPO-inhibiting herbicides (also referred to as compounds A) and/or the herbicidal compounds B as described herein, which can be employed in the context of the present invention, are capable of forming geometrical isomers, for example E/Z isomers, it is possible to use both, the pure isomers and mixtures thereof, in the compositions useful for the present the invention. If the PPO-inhibiting herbicides A and/or the herbicidal compounds B as described herein have one or more centers of chirality and, as a consequence, are present as enantiomers or diastereomers, it is possible to use both, the pure enantiomers and diastereomers and their mixtures, in the compositions according to the invention. If the PPO-inhibiting herbicides A and/or the herbicidal compounds B as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds. Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl) ammonium (diolamine salt), tris(2-hydroxyethyl) ammonium (trolamine salt), tris(2-hydroxypropyl) ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri ($C_1$-$C_4$-alkyl)sulfoxonium, and finally the salts of polybasic amines such as N,N-bis-(3-aminopropyl)methylamine and diethylenetriamine. Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

The PPO-inhibiting herbicides A and/or the herbicidal compounds B as described herein having a carboxyl group can be employed in the form of the acid, in the form of an agriculturally suitable salt as mentioned above or else in the form of an agriculturally acceptable derivative, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters, tefuryl ((tetrahydrofuran-2-yl)methyl) esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

Examples of PPO inhibiting herbicides which can be used according to the present invention are acifluorfen, acifluorfen-sodium, aclonifen, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, chlornitrofen, flumipropyn, fluoronitrofen, flupropacil, furyloxyfen, nitrofluorfen, ethyl [3-[2-chloro-4-fluoro-5-(1-methyl-6-trifluoromethyl-2,4-dioxo-1, 2,3,4-tetrahydropyrimidin-3-yl)phenoxy]-2-pyridyloxy] acetate (CAS 353292-31-6; S3100), N-ethyl-3-2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 1,5-dimethyl-6-thioxo-3-(2,2,7-trifluoro-3-oxo-4-(prop-2-ynyl)-3, 4-dihydro-2H-benzo[b][1,4]oxazin-6-yl)-1,3,5-triazinane-2, 4-dione (CAS 1258836-72-4), 2-(2,2,7-Trifluoro-3-oxo-4-prop-2-ynyl-3,4-dihydro-2H-benzo[1,4]oxazin-6-yl)-4,5,6, 7-tetrahydro-isoindole-1,3-dione (CAS 1300118-96-0), 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, methyl (E)-4-[2-chloro-5-[4-chloro-5-(difluoromethoxy)-1H-methyl-pyrazol-3-yl]-4-fluorophenoxy]-3-methoxy-but-2-enoate [CAS 948893-00-3], 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4), and uracils of formula III

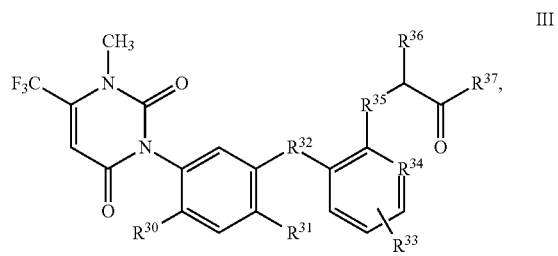

wherein
$R^{30}$ and $R^{31}$ independently of one another are F, Cl or CN;
$R^{32}$ is O or S;
$R^{33}$ is H, F, Cl, $CH_3$ or $OCH_3$;
$R^{34}$ is CH or N;
$R^{35}$ is O or S;
$R^{36}$ is H, CN, $CH_3$, $CF_3$, $OCH_3$, $OC_2H_5$, $SCH_3$, $SC_2H_5$, (CO)$OC_2H_5$ or $CH_2R^{38}$,
  wherein $R^{38}$ is F, Cl, $OCH_3$, $SCH_3$, $SC_2H_5$, $CH_2F$, $CH_2Br$ or $CH_2OH$;
and
$R^{37}$ is ($C_1$-$C_6$-alkyl)amino, ($C_1$-$C_6$-dialkyl)amino, (NH) $OR^{39}$, OH, $OR^{40}$ or $SR^{40}$
  wherein $R^{39}$ is $CH_3$, $C_2H_5$ or phenyl; and
  $R^{40}$ is independently of one another $C_1$-$C_6$-alkyl, $C_2$-$C_6$-alkenyl, $C_3$-$C_6$-alkynyl, $C_1$-$C_6$-haloalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_2$-$C_6$-cyanoalkyl, $C_1$-$C_4$-alkoxy-carbonyl-$C_1$-$C_4$-alkyl, $C_1$-$C_4$-alkyl-carbonyl-amino, $C_1$-$C_6$-alkylsulfinyl-$C_1$-$C_6$-alkyl, $C_1$-$C_6$-alkyl-sulfonyl-$C_1$-$C_6$-alkyl, $C_1$-$C_6$-dialkoxy-$C_1$-$C_6$-alkyl, $C_1$-$C_6$-alkyl-carbonyloxy-$C_1$-$C_6$-alkyl, phenyl-carbonyl-$C_1$-$C_6$-alkyl, tri($C_1$-$C_3$-alkyl)-silyl-$C_1$-$C_6$-alkyl, tri($C_1$-$C_3$-alkyl)-silyl-$C_1$-$C_6$-alkenyl, tri($C_1$-$C_3$-alkyl)-silyl-$C_1$-$C_6$-alkynyl, tri($C_1$-$C_3$-alkyl)-silyl-$C_1$-$C_6$-alkoxy-$C_1$-$C_6$-alkyl, dimethylamino, tetrahydropyranyl, tetrahydrofuranyl-$C_1$-$C_3$-alkyl, phenyl-$C_1$-$C_6$-alkoxy-$C_1$-$C_6$-alkyl, phenyl-$C_1$-$C_3$-alkyl, pyridyl-$C_1$-$C_3$-alkyl, pyridyl, phenyl,
    which pyridyls and phenyls independently of one another are substituted by one to five substituents selected from the group consisting of halogen, $C_1$-$C_3$-alkyl or $C_1$-$C_2$-haloalkyl;
  $C_3$-$C_6$-cycloalkyl or $C_3$-$C_6$-cycloalkyl-$C_1$-$C_4$-alkyl, which cycloalkyls independently of one another are unsubstituted or substituted by one to five substituents selected from the group consisting of halogen, $C_1$-$C_3$-alkyl and $C_1$-$C_2$-haloalkyl;

including their agriculturally acceptable alkali metal salts or ammonium salts.

Preferred PPO-inhibiting herbicides that can be used according to the present invention are: Acifluorfen, acifluorfen-sodium, azafenidin, bencarbazone, benzfendizone, butafenacil, carfentrazone-ethyl, cinidon-ethyl, flufenpyr-ethyl, flumiclorac-pentyl, flumioxazin, fluoroglycofen-ethyl, fluthiacet-methyl, fomesafen, lactofen, oxadiargyl, oxadiazon, oxyfluorfen, pentoxazone, pyraflufen-ethyl, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]-acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0); 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4)

uracils of formula III.1 (corresponding to uracils of formula III, wherein $R^{30}$ is F, $R^{31}$ is Cl, $R^{32}$ is O; $R^{33}$ is H; $R^{34}$ is CH; $R^{35}$ is O and $R^{37}$ is $OR^{40}$)

and uracils of formula III.2 (corresponding to uracils of formula III, wherein $R^{30}$ is F; $R^{31}$ is Cl; $R^{32}$ is O; $R^{33}$ is H; $R^{34}$ is N; $R^{35}$ is O and $R^{37}$ is $OR^{40}$ with $R^{40}$ is $C_1$-$C_6$-alkyl)

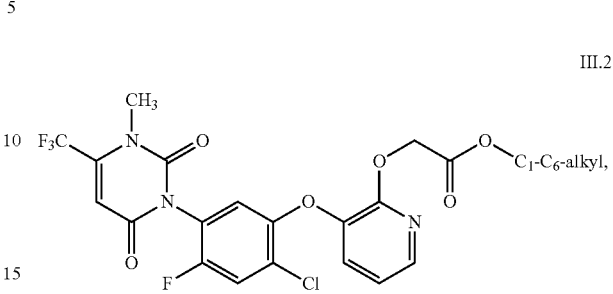

III.2

Particularly preferred PPO-inhibiting herbicides that can be used according to the present invention are:

acifluorfen, acifluorfen-sodium, butafenacil, carfentrazone-ethyl, cinidon-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)-phenoxy]-2-pyridyloxy]acetate (CAS 353292-31-6; S-3100), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), and 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-M ethyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), uracils of formula III.1.1 (corresponding to uracils of formula III, wherein $R^{30}$ is F, $R^{31}$ is Cl, $R^{32}$ is O; $R^{33}$ is H; $R^{34}$ is CH; $R^{35}$ is O, $R^{36}$ is $OCH_3$ and $R^{37}$ is $OR^{40}$)

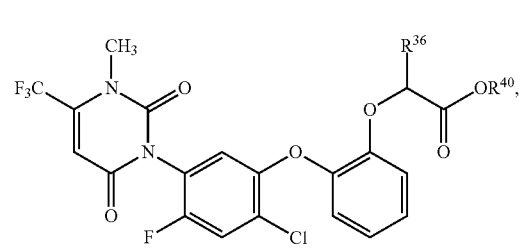

III.1

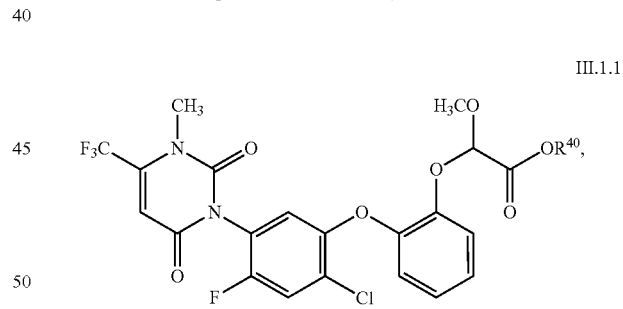

III.1.1 wherein $R^{36}$ is $OCH_3$, $OC_2H_5$, $SCH_3$ or $SC_2H_5$;

and $R^{40}$ is $C_1$-$C_6$-alkyl, $C_2$-$C_6$-alkenyl, $C_3$-$C_6$-alkynyl, $C_1$-$C_6$-haloalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_3$-cyanoalkyl, phenyl-$C_1$-$C_3$-alkyl, pyridyl-$C_1$-$C_3$-alkyl, $C_3$-$C_6$-cycloalkyl or $C_3$-$C_6$-cycloalkyl-$C_1$-$C_4$-alkyl, which cycloalkyls are unsubstituted or substituted by one to five substituents selected from the group consisting of halogen, $C_1$-$C_3$-alkyl and $C_1$-$C_2$-haloalkyl;

wherein $R^{40}$ is $C_1$-$C_6$-alkyl, $C_2$-$C_6$-alkenyl, $C_3$-$C_6$-alkynyl, $C_1$-$C_6$-haloalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_3$-cyanoalkyl, phenyl-$C_1$-$C_3$-alkyl, pyridyl-$C_1$-$C_3$-alkyl, $C_3$-$C_6$-cycloalkyl or $C_3$-$C_6$-cycloalkyl-$C_1$-$C_4$-alkyl, which cycloalkyls are unsubstituted or substituted by one to five substituents selected from the group consisting of halogen, $C_1$-$C_3$-alkyl and $C_1$-$C_2$-haloalkyl; is preferably $CH_3$, $CH_2CH_2OC_2H_5$, $CH_2CHF_2$, cyclohexyl, (1-methylcyclopropyl)methyl or $CH_2$(pyridine-4-yl);

uracils of formula III.2.1 (corresponding to uracils of formula Ill, wherein $R^{30}$ is F; $R^{31}$ is Cl; $R^{32}$ is O; $R^{33}$ is H; $R^{34}$ is N; $R^{35}$ is O and $R^{37}$ is $OR^{40}$ with $R^{40}$ is $CH_3$)

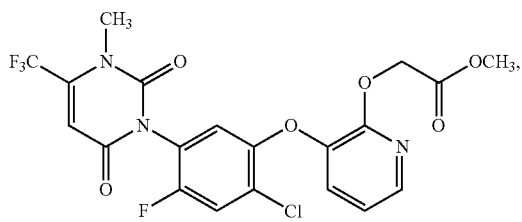

III.2.1 and
uracils of formula III.2.2 (corresponding to uracils of formula III, wherein $R^{30}$ is F; $R^{31}$ is Cl; $R^{32}$ is O; $R^{33}$ is H; $R^{34}$ is N; $R^{35}$ is O and $R^{37}$ is $OR^{40}$ with $R^{40}$ is $C_2H_5$)

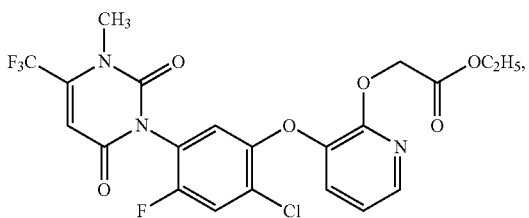

III.2.2

Especially preferred PPO-inhibiting herbicides are the PPO-inhibiting herbicides.1 to A.14 listed below in table A:

TABLE A

| A.1 | acifluorfen |
|---|---|
| A.2 | butafenacil |
| A.3 | carfentrazone-ethyl |
| A.4 | cinidon-ethyl |
| A.5 | flumioxazin |
| A.6 | fluthiacet-methyl |
| A.7 | fomesafen |
| A.8 | lactofen |
| A.9 | oxadiargyl |
| A.10 | oxyfluorfen |
| A.11 | saflufenacil |
| A.12 | sulfentrazone |
| A.13 | ethyl [3-[2-chloro-4-fluoro-5-(1-methyl-6-trifluoromethyl-2,4-dioxo-1,2,3,4-tetra-hydropyrimidin-3-yl)phenoxy]-2-pyridyloxy]-acetate (CAS 353292-31-6) |
| A.14 | 1,5-dimethyl-6-thioxo-3-(2,2,7-trifluoro-3-oxo-4-(prop-2-ynyl)-3,4-dihydro-2H-benzo[b]-[1,4]oxazin-6-yl)-1,3,5-triazinane-2,4-dione (CAS 1258836-72-4) |

The PPO-inhibiting herbicides described above that are useful to carry out the present invention are often best applied in conjunction with one or more other herbicides to obtain control of a wider variety of undesirable vegetation. For example, PPO-inhibiting herbicides may further be used in conjunction with additional herbicides to which the crop plant is naturally tolerant, or to which it is resistant via expression of one or more additional transgenes as mentioned supra, or to which it is resistant via mutagenesis and breeding methods as described hereinafter.

When used in conjunction with other targeting herbicides, the PPO-inhibiting herbicides, to which the plant of the present invention had been made resistant or tolerant, can be formulated with the other herbicide or herbicides, tank mixed with the other herbicide or herbicides, or applied sequentially with the other herbicide or herbicides.

Suitable components for mixtures are, for example, selected from the herbicides of class b1) to b15)

B) herbicides of class b1) to b15):
 b1) lipid biosynthesis inhibitors;
 b2) acetolactate synthase inhibitors (ALS inhibitors);
 b3) photosynthesis inhibitors;
 b4) protoporphyrinogen-IX oxidase inhibitors,
 b5) bleacher herbicides;
 b6) enolpyruvyl shikimate 3-phosphate synthase inhibitors (EPSP inhibitors);
 b7) glutamine synthetase inhibitors;
 b8) 7,8-dihydropteroate synthase inhibitors (DHP inhibitors);
 b9) mitosis inhibitors;
 b10) inhibitors of the synthesis of very long chain fatty acids (VLCFA inhibitors);
 b11) cellulose biosynthesis inhibitors;
 b12) decoupler herbicides;
 b13) auxinic herbicides;
 b14) auxin transport inhibitors; and
 b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;
including their agriculturally acceptable salts or derivatives.

Examples of herbicides B which can be used in combination with the PPO-inhibiting herbicides according to the present invention are:

b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[, 1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[, 1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1, 1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5 (4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2', 4'-dichloro-4-ethyl[1,1'-biphenyl]-3-yl)-3,6-dihydro-2,2,6, 6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:

sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy] benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;

among these, a preferred embodiment of the invention relates to those compositions comprising at least one imidazolinone herbicide;

b3) from the group of the photosynthesis inhibitors:

amicarbazone, inhibitors of the photosystem II, e.g. triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4] oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1, 3,5-triazinane-2,4-dione (CAS 1258836-72-4), 2-(2,2,7-Trifluoro-3-oxo-4-prop-2-ynyl-3,4-dihydro-2H-benzo[1,4] oxazin-6-yl)-4,5,6,7-tetrahydro-isoindole-1,3-dione, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl) pyrimidine (CAS 180608-33-7), HPPD inhibitors: benzobicyclon, benzofenap, clomazone, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole and flumeturon;

b6) from the group of the EPSP synthase inhibitors:

glyphosate, glyphosate-isopropylammonium, glyposate-potassium and glyphosate-trimesium (sulfosate);

b7) from the group of the glutamine synthase inhibitors:

bilanaphos (bialaphos), bilanaphos-sodium, glufosinate, glufosinate-P and glufosinate-ammonium;

b8) from the group of the DHP synthase inhibitors:

asulam;

b9) from the group of the mitosis inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the group of the VLCFA inhibitors:

chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide and napropamide, tetrazolinones such as fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9 the isoxazoline compounds of the formula (I)I are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors:

chlorthiamid, dichlobenil, flupoxam, indaziflam, triaziflam, isoxaben and 1-Cyclohexyl-5-pentafluorphenyloxy-1$^4$-[1,2,4,6]thiatriazin-3-ylamine;

b12) from the group of the decoupler herbicides:

dinoseb, dinoterb and DNOC and its salts;

b13) from the group of the auxinic herbicides:

2,4-D and its salts and esters such as clacyfos, 2,4-DB and its salts and esters, aminocyclopyrachlor and its salts and esters, aminopyralid and its salts such as aminopyralid-tris (2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters and triclopyr and its salts and esters;

b14) from the group of the auxin transport inhibitors:

diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam and tridiphane.

Preferred herbicides B that can be used in combination with the PPO-inhibiting herbicides according to the present invention are:

b1) from the group of the lipid biosynthesis inhibitors:
clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, 4-(4'-Chloro-4-cyclopropyl-2'-fluoro[,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); benfuresate, dimepiperate, EPTC, esprocarb, ethofumesate, molinate, orbencarb, prosulfocarb, thiobencarb and triallate;

b2) from the group of the ALS inhibitors:
amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl, tritosulfuron and triafamone;

b3) from the group of the photosynthesis inhibitors:
ametryn, amicarbazone, atrazine, bentazon, bentazone-sodium, bromoxynil and its salts and esters, chloridazone, chlorotoluron, cyanazine, desmedipham, diquat-dibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine and thidiazuron;

b4) from the group of the protoporphyrinogen-IX oxidase inhibitors:
acifluorfen, acifluorfen-sodium, azafenidin, bencarbazone, benzfendizone, butafenacil, carfentrazone-ethyl, cinidon-ethyl, flufenpyr-ethyl, flumiclorac-pentyl, flumioxazin, fluoroglycofen-ethyl, fluthiacet-methyl, fomesafen, lactofen, oxadiargyl, oxadiazon, oxyfluorfen, pentoxazone, pyraflufen-ethyl, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]-acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione; 1-M ethyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:
aclonifen, beflubutamid, benzobicyclon, clomazone, diflufenican, flurochloridone, flurtamone, isoxaflutole, mesotrione, norflurazon, picolinafen, pyrasulfotole, pyrazolynate, sulcotrione, tefuryltrione, tembotrione, topramezone, bicyclopyrone, 4-(3-trifluoromethylphenoxy)-2-(4-trifluoromethylphenyl)pyrimidine (CAS 180608-33-7), amitrole and flumeturon;

b6) from the group of the EPSP synthase inhibitors:
glyphosate, glyphosate-isopropylammonium, glyphosate-potassium and glyphosate-trimesium (sulfosate);

b7) from the group of the glutamine synthase inhibitors:
glufosinate, glufosinate-P, glufosinate-ammonium;

b8) from the group of the DHP synthase inhibitors:
asulam;

b9) from the group of the mitosis inhibitors:
benfluralin, dithiopyr, ethalfluralin, oryzalin, pendimethalin, thiazopyr and trifluralin;

b10) from the group of the VLCFA inhibitors:
acetochlor, alachlor, anilofos, butachlor, cafenstrole, dimethenamid, dimethenamid-P, fentrazamide, flufenacet, mefenacet, metazachlor, metolachlor, S-metolachlor, naproanilide, napropamide, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

b11) from the group of the cellulose biosynthesis inhibitors: dichlobenil, flupoxam, isoxaben and 1-Cyclohexyl-5-pentafluorphenyloxy-1$^4$-[1,2,4,6]thiatriazin-3-ylamine;

b13) from the group of the auxinic herbicides:

2,4-D and its salts and esters, aminocyclopyrachlor and its salts and esters, aminopyralid and its salts such as aminopyralid-tris(2-hydroxypropyl)ammonium and its esters, clopyralid and its salts and esters, dicamba and its salts and esters, dichlorprop-P and its salts and esters, fluroxypyr-meptyl, halauxifen and its salts and esters (CAS 943832-60-8), MCPA and its salts and esters, MCPB and its salts and esters, mecoprop-P and its salts and esters, picloram and its salts and esters, quinclorac, quinmerac and triclopyr and its salts and esters;

b14) from the group of the auxin transport inhibitors: diflufenzopyr and diflufenzopyr-sodium;

b15) from the group of the other herbicides: bromobutide, cinmethylin, cumyluron, cyclopyrimorate (CAS 499223-49-3) and its salts and esters, dalapon, difenzoquat, difenzoquat-metilsulfate, DSMA, dymron (=daimuron), flamprop, flamprop-isopropyl, flamprop-methyl, flamprop-M-isopropyl, flamprop-M-methyl, indanofan, indaziflam, metam, methylbromide, MSMA, oxaziclomefone, pyributicarb, triaziflam and tridiphane.

Particularly preferred herbicides B that can be used in combination with the PPO-inhibiting herbicides according to the present invention are:

b1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, 4-(4'-Chloro-4-cyclopropyl-2'-fluoro[, 1'-biphenyl]-3-yl)-5-hydroxy-2,2,6,6-tetramethyl-2H-pyran-3 (6H)-one (CAS 1312337-72-6); 4-(2',4'-Dichloro-4-cyclopropyl[, 1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); esprocarb, prosulfocarb, thiobencarb and triallate;

b2) from the group of the ALS inhibitors: bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, nicosulfuron, penoxsulam, propoxycarbazon-sodium, propyrisulfuron, pyrazosulfuron-ethyl, pyroxsulam, rimsulfuron, sulfosulfuron, thiencarbazon-methyl, tritosulfuron and triafamone;

b3) from the group of the photosynthesis inhibitors: ametryn, atrazine, diuron, fluometuron, hexazinone, isoproturon, linuron, metribuzin, paraquat, paraquat-dichloride, propanil, terbutryn and terbuthylazine;

b4) from the group of the protoporphyrinogen-IX oxidase inhibitors: acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), and 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, and 1-M ethyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione;

b5) from the group of the bleacher herbicides: clomazone, diflufenican, flurochloridone, isoxaflutole, mesotrione, picolinafen, sulcotrione, tefuryltrione, tembotrione, topramezone, bicyclopyrone, amitrole and flumeturon;

b6) from the group of the EPSP synthase inhibitors: glyphosate, glyphosate-isopropylammonium and glyphosate-trimesium (sulfosate);

b7) from the group of the glutamine synthase inhibitors: glufosinate, glufosinate-P and glufosinate-ammonium;

b9) from the group of the mitosis inhibitors: pendimethalin and trifluralin;

b10) from the group of the VLCFA inhibitors: acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;

b11) from the group of the cellulose biosynthesis inhibitors: isoxaben;

b13) from the group of the auxinic herbicides: 2,4-D and its salts and esters such as clacyfos, and aminocyclopyrachlor and its salts and esters, aminopyralid and its salts and its esters, clopyralid and its salts and esters, dicamba and its salts and esters, fluroxypyr-meptyl, quinclorac and quinmerac;

b14) from the group of the auxin transport inhibitors: diflufenzopyr and diflufenzopyr-sodium, b15) from the group of the other herbicides: dymron (=daimuron), indanofan, indaziflam, oxaziclomefone and triaziflam.

Moreover, it may be useful to apply the PPO-inhibiting herbicides, when used in combination with a compound B described SUPRA, in combination with safeners. Safeners are chemical compounds which prevent or reduce damage on useful plants without having a major impact on the herbicidal action of herbicides towards unwanted plants. They can be applied either before sowings (e.g. on seed treatments, shoots or seedlings) or in the pre-emergence application or post-emergence application of the useful plant.

Furthermore, the safeners C, the PPO-inhibiting herbicides and/or the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, diethotate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro [4.5]decane (MON4660, CAS 71526-07-3) and 2,2,5-trimethyl-3-(dichloroacetyl)-1,3-oxazolidine (R-29148, CAS 52836-31-4).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Particularly preferred safeners C are benoxacor, cloquintocet, cyprosulfamide, dichlormid, fenchlorazole, fenclorim, furilazole, isoxadifen, mefenpyr, naphthalic anhydride, 4-(dichloroacetyl)-1-oxa-4-azaspiro[4.5]decane (MON4660, CAS 71526-07-3), and 2,2,5-trimethyl-3-(dichloroacetyl)-1,3-oxazolidine (R-29148, CAS 52836-31-4).

Also preferred safeners C are benoxacor, cloquintocet, cyprosulfamide, dichlormid, fenchlorazole, fenclorim, furilazole, isoxadifen, mefenpyr, 4-(dichloroacetyl)-1-oxa-4-azaspiro-[4.5]decane (MON4660, CAS 71526-07-3) and 2,2,5-trimethyl-3-(dichloroacetyl)-1,3-oxazolidine (R-29148, CAS 52836-31-4).

Particularly preferred safeners C, which, as component C, are constituent of the composition according to the invention are the safeners C as defined above; in particular the safeners C.1-C.12 listed below in table C:

TABLE C

| Safener C |
| --- |
| C.1 benoxacor |
| C.2 cloquintocet |
| C.3 cyprosulfamide |
| C.4 dichlormid |
| C.5 fenchlorazole |
| C.6 fenclorim |
| C.7 furilazole |
| C.8 isoxadifen |
| C.9 mefenpyr |
| C.10 naphtalic acid anhydride |
| C.11 4-(dichloroacetyl)-1-oxa-4-azaspiro[4.5]decane (MON4660, CAS 71526-07-3) |
| C.12 2,2,5-trimethyl-3-(dichloroacetyl)-1,3-oxazolidine (R-29148, CAS 52836-31-4) |

The PPO-inhibiting herbicides (compounds A) and the active compounds B of groups b1) to b15) and the active compounds C are known herbicides and safeners, see, for example, The Compendium of Pesticide Common Names (www.alanwood.net/pesticides); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine.

Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanolammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium.

Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl) ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium and aminopyralid-tris(2-hydroxypropyl) ammonium.

Suitable salts of glyphosate are for example glyphosate-ammonium, glyphosate-diammonium, glyphosate-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinclorac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

The preferred embodiments of the invention mentioned herein below have to be understood as being preferred either independently from each other or in combination with one another.

According to a preferred embodiment of the invention, the composition comprises as component B at least one, preferably exactly one herbicide B.

According to another preferred embodiment of the invention, the composition comprises at least two, preferably exactly two, herbicides B different from each other.

According to another preferred embodiment of the invention, the composition comprises at least three, preferably exactly three, herbicides B different from each other.

According to another preferred embodiment of the invention, the composition comprises as component A at least one, preferably exactly one PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)-phenoxy]-2-pyridyloxy]acetate (CAS 353292-31-6; S-3100; 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), and as component B at least one, preferably exactly one, herbicide B.

According to another preferred embodiment of the invention, the composition comprises as component A at least one, preferably exactly preferably exactly one PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), and at least two, preferably exactly two, herbicides B different from each other.

According to another preferred embodiment of the invention, the composition comprises as component A at least one, preferably exactly preferably exactly one PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro- 5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) and at least three, preferably exactly three, herbicides B different from each other.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b1), in particular selected from the group consisting of clethodim, clodinafop-propargyl, cycloxydim, cyhalofop-butyl, fenoxaprop-P-ethyl, fluazifop, pinoxaden, profoxydim, quizalofop, sethoxydim, tepraloxydim, tralkoxydim, esprocarb, prosulfocarb, thiobencarb and triallate.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b2), in particular selected from the group consisting of bensulfuron-methyl, bispyribac-sodium, cloransulam-methyl, cyclosulfamuron, diclosulam, flumetsulam, flupyrsulfuron-methyl-sodium, foramsulfuron, halosulfuron-methyl, imazamox, imazapic, imazapyr, imazaquin, imazethapyr, imazosulfuron, iodosulfuron, iodosulfuron-methyl-sodium, mesosulfuron-methyl, metazosulfuron, nicosulfuron, penoxsulam, propoxycarbazon-sodium, pyrazosulfuron-ethyl, pyrithiobac-sodium, pyroxsulam, rimsulfuron, sulfosulfuron, thiencarbazon-methyl, thifensulfuron-methyl, trifloxysulfuron and tritosulfuron.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b3), in particular selected from the group consisting of ametryn, atrazine, bentazon, bromoxynil, diuron, fluometuron, hexazinone, isoproturon, linuron, metribuzin, paraquat, paraquat-dichloride, prometryne, propanil, terbutryn and terbuthylazine.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b4), in particular selected from the group consisting of acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4).

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b5), in particular selected from the group consisting of clomazone, diflufenican, flurochloridone, isoxaflutole, mesotrione, picolinafen, sulcotrione, tefuryltrione, tembotrione, topramezone, bicyclopyrone, amitrole and flumeturon.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b6), in particular selected from the group consisting of glyphosate, glyphosate-isopropylammonium and glyphosate-trimesium (sulfosate).

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b7), in particular selected from the group consisting of glufosinate, glufosinate-P and glufosinate-ammonium.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b9), in particular selected from the group consisting of pendimethalin and trifluralin.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4)), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b10), in particular selected from the group consisting of acetochlor, cafenstrole, dimethenamid-P, fentrazamide, flufenacet, mefenacet, metazachlor, metolachlor, S-metolachlor, fenoxasulfone and pyroxasulfone. Likewise, preference is given to compositions comprising in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b10), in particular selected from the group consisting of isoxazoline compounds of the formulae II.1, II.2, II.3, II.4, II.5, II.6, II.7, II.8 and II.9, as defined above.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b13), in particular selected from the group consisting of 2,4-D and its salts and esters, aminocyclopyrachlor and its salts and esters, aminopyralid and its salts such as aminopyralid-tris (2-hydroxypropyl)ammonium and its esters, clopyralid and its salts and esters, dicamba and its salts and esters, fluroxypyr-meptyl, quinclorac and quinmerac.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b14), in particular selected from the group consisting of diflufenzopyr and diflufenzopyr-sodium.

According to another preferred embodiment of the invention, the composition comprises, in addition to a PPO-inhibiting herbicide, preferably acifluorfen, acifluorfen-sodium, butafenacil, cinidon-ethyl, carfentrazone-ethyl, flumioxazin, fluthiacet-methyl, fomesafen, lactofen, oxadiargyl, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), especially preferred saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), at least one and especially exactly one herbicidally active compound from group b15), in particular selected from the group consisting of dymron (=daimuron), indanofan, indaziflam, oxaziclomefone and triaziflam.

Here and below, the term "binary compositions" includes compositions comprising one or more, for example 1, 2 or 3, active compounds of the PPO-inhibiting herbicide and either one or more, for example 1, 2 or 3, herbicides B.

In binary compositions comprising at least one PPO-inhibiting herbicide as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

Particularly preferred herbicides B are the herbicides B as defined above; in particular the herbicides B.1-B.229 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | fluazifop |
| B.8 | metamifop |
| B.9 | pinoxaden |
| B.10 | profoxydim |
| B.11 | quizalofop |
| B.12 | sethoxydim |
| B.13 | tepraloxydim |
| B.14 | tralkoxydim |
| B.15 | esprocarb |

TABLE B-continued

| | Herbicide B |
|---|---|
| B.16 | ethofumesate |
| B.17 | molinate |
| B.18 | prosulfocarb |
| B.19 | thiobencarb |
| B.20 | triallate |
| B.21 | bensulfuron-methyl |
| B.22 | bispyribac-sodium |
| B.23 | cloransulam-methyl |
| B.24 | chlorsulfuron |
| B.25 | clorimuron |
| B.26 | cyclosulfamuron |
| B.27 | diclosulam |
| B.28 | florasulam |
| B.29 | flumetsulam |
| B.30 | flupyrsulfuron-methyl-sodium |
| B.31 | foramsulfuron |
| B.32 | halosulfuron-methyl |
| B.33 | imazamox |
| B.34 | imazamox-ammonium |
| B.35 | imazapic |
| B.36 | imazapic-ammonium |
| B.37 | imazapic-isopropylammonium |
| B.38 | imazapyr |
| B.39 | imazapyr-ammonium |
| B.40 | imazapyr-isopropylammonium |
| B.41 | imazaquin |
| B.42 | imazaquin-ammonium |
| B.43 | imazethapyr |
| B.44 | imazethapyr-ammonium |
| B.45 | imazethapyr-isopropylammonium |
| B.46 | imazosulfuron |
| B.47 | iodosulfuron-methyl-sodium |
| B.48 | iofensulfuron |
| B.49 | iofensulfuron-sodium |
| B.50 | mesosulfuron-methyl |
| B.51 | metazosulfuron |
| B.52 | metsulfuron-methyl |
| B.53 | metosulam |
| B.54 | nicosulfuron |
| B.55 | penoxsulam |
| B.56 | propoxycarbazon-sodium |
| B.57 | pyrazosulfuron-ethyl |
| B.58 | pyribenzoxim |
| B.59 | pyriftalid |
| B.60 | pyrithiobac-sodium |
| B.61 | pyroxsulam |
| B.62 | propyrisulfuron |
| B.63 | rimsulfuron |
| B.64 | sulfosulfuron |
| B.65 | thiencarbazone-methyl |
| B.66 | thifensulfuron-methyl |
| B.67 | tribenuron-methyl |
| B.68 | trifloxysulfuron |
| B.69 | tritosulfuron |
| B.70 | triafamone |
| B.71 | ametryne |
| B.72 | atrazine |
| B.73 | bentazon |
| B.74 | bromoxynil |
| B.75 | bromoxynil-octanoate |
| B.76 | bromoxynil-heptanoate |
| B.77 | bromoxynil-potassium |
| B.78 | diuron |
| B.79 | fluometuron |
| B.80 | hexazinone |
| B.81 | isoproturon |
| B.82 | linuron |
| B.83 | metamitron |
| B.84 | metribuzin |
| B.85 | prometryne |
| B.86 | propanil |
| B.87 | simazin |
| B.88 | terbuthylazine |
| B.89 | terbutryn |
| B.90 | paraquat-dichloride |
| B.91 | acifluorfen |
| B.92 | acifluorfen-sodium |

TABLE B-continued

| | Herbicide B |
|---|---|
| B.93 | azafenidin |
| B.94 | bencarbazone |
| B.95 | benzfendizone |
| B.96 | bifenox |
| B.97 | butafenacil |
| B.98 | carfentrazone |
| B.99 | carfentrazone-ethyl |
| B.100 | chlomethoxyfen |
| B.101 | cinidon-ethyl |
| B.102 | fluazolate |
| B.103 | flufenpyr |
| B.104 | flufenpyr-ethyl |
| B.105 | flumiclorac |
| B.106 | flumiclorac-pentyl |
| B.107 | flumioxazin |
| B.108 | fluoroglycofen |
| B.109 | fluoroglycofen-ethyl |
| B.110 | fluthiacet |
| B.111 | fluthiacet-methyl |
| B.112 | fomesafen |
| B.113 | halosafen |
| B.114 | lactofen |
| B.115 | oxadiargyl |
| B.116 | oxadiazon |
| B.117 | oxyfluorfen |
| B.118 | pentoxazone |
| B.119 | profluazol |
| B.120 | pyraclonil |
| B.121 | pyraflufen |
| B.122 | pyraflufen-ethyl |
| B.123 | saflufenacil |
| B.124 | sulfentrazone |
| B.125 | thidiazimin |
| B.126 | tiafenacil |
| B.127 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6) |
| B.128 | 1,5-dimethyl-6-thioxo-3-(2,2,7-trifluoro-3-oxo-4-(prop-2-ynyl)-3,4-dihydro-2H-benzo[b][1,4]-oxazin-6-yl)-1,3,5-triazinane-2,4-dione (CAS 1258836-72-4) |
| B.129 | N-ethyl-3-(2,6-dichloro-4-trifluoromethylphenoxy)-5-methyl-1H-pyrazole-1-carboxamide (CAS 452098-92-9) |
| B.130 | N-tetrahydrofurfuryl-3-(2,6-dichloro-4-trifluoromethylphenoxy)-5-methyl-1H-pyrazole-1-carboxamide (CAS 915396-43-9) |
| B.131 | N-ethyl-3-(2-chloro-6-fluoro-4-trifluoromethylphenoxy)-5-methyl-1H-pyrazole-1-carboxamide (CAS 452099-05-7) |
| B.132 | N-tetrahydrofurfuryl-3-(2-chloro-6-fluoro-4-trifluoromethylphenoxy)-5-methyl-1H-pyrazole-1-carboxamide (CAS 452100-03-7) |
| B.133 | 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione |
| B.134 | 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione |
| B.135 | 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione |
| B.136 | methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3] |
| B.137 | 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4) |
| B.138 | benzobicyclon |
| B.139 | clomazone |
| B.140 | diflufenican |
| B.141 | flurochloridone |
| B.142 | isoxaflutole |
| B.143 | mesotrione |
| B.144 | norflurazon |
| B.145 | picolinafen |
| B.146 | sulcotrione |
| B.147 | tefuryltrione |
| B.148 | tembotrione |
| B.149 | topramezone |
| B.150 | topramezone-sodium |
| B.151 | bicyclopyrone |
| B.152 | amitrole |
| B.153 | fluometuron |
| B.154 | glyphosate |
| B.155 | glyphosate-ammonium |
| B.156 | glyphosate-dimethylammonium |
| B.157 | glyphosate-isopropylammonium |
| B.158 | glyphosate-trimesium (sulfosate) |
| B.159 | glyphosate-potassium |
| B.160 | glufosinate |
| B.161 | glufosinate-ammonium |
| B.162 | glufosinate-P |
| B.163 | glufosinate-P-ammonium |
| B.164 | pendimethalin |
| B.165 | trifluralin |
| B.166 | acetochlor |
| B.167 | butachlor |
| B.168 | cafenstrole |
| B.169 | dimethenamid-P |
| 8.170 | fentrazamide |
| B.171 | flufenacet |
| B.172 | mefenacet |
| B.173 | metazachlor |
| B.174 | metolachlor |
| B.175 | S-metolachlor |
| B.176 | pretilachlor |
| B.177 | fenoxasulfone |
| B.178 | isoxaben |
| B.179 | ipfencarbazone |
| B.180 | pyroxasulfone |
| B.181 | 2,4-D |
| B.182 | 2,4-D-isobutyl |
| B.183 | 2,4-D-dimethylammonium |
| B.184 | 2,4-D-N,N,N-trimethylethanolammonium |
| B.185 | aminopyralid |
| B.186 | aminopyralid-methyl |
| B.187 | aminopyralid-tris(2-hydroxypropyl)ammonium |
| B.188 | clopyralid |
| B.189 | clopyralid-methyl |
| B.190 | clopyralid-olamine |
| B.191 | dicamba |
| B.192 | dicamba-butotyl |
| B.193 | dicamba-diglycolamine |
| B.194 | dicamba-dimethylammonium |
| B.195 | dicamba-diolamine |
| B.196 | dicamba-isopropylammonium |
| B.197 | dicamba-potassium |

TABLE B-continued

Herbicide B

| | |
|---|---|
| B.198 | dicamba-sodium |
| B.199 | dicamba-trolamine |
| B.200 | dicamba-N,N-bis-(3-aminopropyl)methylamine |
| B.201 | dicamba-diethylenetriamine |
| B.202 | fluroxypyr |
| B.203 | fluroxypyr-meptyl |
| B.204 | MCPA |
| B.205 | MCPA-2-ethylhexyl |
| B.206 | MCPA-dimethylammonium |
| B.207 | quinclorac |
| B.208 | quinclorac-dimethylammonium |
| B.209 | quinmerac |
| B.210 | quinmerac-dimethylammonium |
| B.211 | aminocyclopyrachlor |
| B.212 | aminocyclopyrachlor-potassium |
| B.213 | aminocyclopyrachlor-methyl |
| B.214 | diflufenzopyr |
| B.215 | diflufenzopyr-sodium |
| B.216 | dymron |
| B.217 | indanofan |
| B.218 | indaziflam |
| B.219 | oxaziclomefone |
| B.220 | triaziflam |
| B.221 | II.1 |
| B.222 | II.2 |
| B.223 | II.3 |
| B.224 | II.4 |
| B.225 | II.5 |
| B.226 | II.6 |
| B.227 | II.7 |
| B.228 | II.8 |
| B.229 | II.9 |

Particularly preferred are compositions 1.1 to 1.229, comprising acifluorfen and the substance(s) as defined in the respective row of table B-1:

TABLE B-1

(compositions 1.1 to 1.229):

| comp. no. | herbicide B |
|---|---|
| 1.1 | B.1 |
| 1.2 | B.2 |
| 1.3 | B.3 |
| 1.4 | B.4 |
| 1.5 | B.5 |
| 1.6 | B.6 |
| 1.7 | B.7 |
| 1.8 | B.8 |
| 1.9 | B.9 |
| 1.10 | B.10 |
| 1.11 | B.11 |
| 1.12 | B.12 |
| 1.13 | B.13 |
| 1.14 | B.14 |
| 1.15 | B.15 |
| 1.16 | B.16 |
| 1.17 | B.17 |
| 1.18 | B.18 |
| 1.19 | B.19 |
| 1.20 | B.20 |
| 1.21 | B.21 |
| 1.22 | B.22 |
| 1.23 | B.23 |
| 1.24 | B.24 |
| 1.25 | B.25 |
| 1.26 | B.26 |
| 1.27 | B.27 |
| 1.28 | B.28 |
| 1.29 | B.29 |
| 1.30 | B.30 |
| 1.31 | B.31 |
| 1.32 | B.32 |
| 1.33 | B.33 |
| 1.34 | B.34 |
| 1.35 | B.35 |
| 1.36 | B.36 |
| 1.37 | B.37 |
| 1.38 | B.38 |
| 1.39 | B.39 |
| 1.40 | B.40 |
| 1.41 | B.41 |
| 1.42 | B.42 |
| 1.43 | B.43 |
| 1.44 | B.44 |
| 1.45 | B.45 |
| 1.46 | B.46 |
| 1.47 | B.47 |
| 1.48 | B.48 |
| 1.49 | B.49 |
| 1.50 | B.50 |
| 1.51 | B.51 |
| 1.52 | B.52 |
| 1.53 | B.53 |
| 1.54 | B.54 |
| 1.55 | B.55 |
| 1.56 | B.56 |
| 1.57 | B.57 |
| 1.58 | B.58. |
| 1.59 | B.59 |
| 1.60 | B.60 |
| 1.61 | B.61 |
| 1.62 | B.62 |
| 1.63 | B.63 |
| 1.64 | B.64 |
| 1.65 | B.65 |
| 1.66 | B.66 |
| 1.67 | B.67 |
| 1.68 | B.68 |
| 1.69 | B.69 |
| 1.70 | B.70 |
| 1.71 | B.71 |
| 1.72 | B.72 |
| 1.73 | B.73 |
| 1.74 | B.74 |
| 1.75 | B.75 |
| 1.76 | B.76 |
| 1.77 | B.77 |
| 1.78 | B.78 |
| 1.79 | B.79 |
| 1.80 | B.80 |
| 1.81 | B.81 |
| 1.82 | B.82 |
| 1.83 | B.83 |
| 1.84 | B.84 |
| 1.85 | B.85 |
| 1.86 | B.86 |
| 1.87 | B.87 |
| 1.88 | B.88 |
| 1.89 | B.89 |
| 1.90 | B.90 |
| 1.91 | B.91 |
| 1.92 | B.92 |
| 1.93 | B.93 |
| 1.94 | B.94 |
| 1.95 | B.95 |
| 1.96 | B.96 |
| 1.97 | B.97 |
| 1.98 | B.98 |
| 1.99 | B.99 |
| 1.100 | B.100 |
| 1.101 | B.101 |
| 1.102 | B.102 |
| 1.103 | B.103 |
| 1.104 | B.104 |
| 1.105 | B.105 |
| 1.106 | B.106 |

TABLE B-1-continued (compositions 1.1 to 1.229):

| comp. no. | herbicide B |
|---|---|
| 1.107 | B.107 |
| 1.108 | B.108 |
| 1.109 | B.109 |
| 1.110 | B.110 |
| 1.111 | B.111 |
| 1.112 | B.112 |
| 1.113 | B.113 |
| 1.114 | B.114 |
| 1.115 | B.115 |
| 1.116 | B.116 |
| 1.117 | B.117 |
| 1.118 | B.118 |
| 1.119 | B.119 |
| 1.120 | B.120 |
| 1.121 | B.121 |
| 1.122 | B.122 |
| 1.123 | B.123 |
| 1.124 | B.124 |
| 1.125 | B.125 |
| 1.126 | B.126 |
| 1.127 | B.127 |
| 1.128 | B.128 |
| 1.129 | B.129 |
| 1.130 | B.130 |
| 1.131 | B.131 |
| 1.132 | B.132 |
| 1.133 | B.133 |
| 1.134 | B.134 |
| 1.135 | B.135 |
| 1.136 | B.136 |
| 1.137 | B.137 |
| 1.138 | B.138 |
| 1.139 | B.139 |
| 1.140 | B.140 |
| 1.141 | B.141 |
| 1.142 | B.142 |
| 1.143 | B.143 |
| 1.144 | B.144 |
| 1.145 | B.145 |
| 1.146 | B.146 |
| 1.147 | B.147 |
| 1.148 | B.148 |
| 1.149 | B.149 |
| 1.150 | B.150 |
| 1.151 | B.151 |
| 1.152 | B.152 |
| 1.153 | B.153 |
| 1.154 | B.154 |
| 1.155 | B.155 |
| 1.156 | B.156 |
| 1.157 | B.157 |
| 1.158 | B.158 |
| 1.159 | B.159 |
| 1.160 | B.160 |
| 1.161 | B.161 |
| 1.162 | B.162 |
| 1.163 | B.163 |
| 1.164 | B.164 |
| 1.165 | B.165 |
| 1.166 | B.166 |
| 1.167 | B.167 |
| 1.168 | B.168 |
| 1.169 | B.169 |
| 1.170 | B.170 |
| 1.171 | B.171 |
| 1.172 | B.172 |
| 1.173 | B.173 |
| 1.174 | B.174 |
| 1.175 | B.175 |
| 1.176 | B.176 |
| 1.177 | B.177 |
| 1.178 | B.178 |
| 1.179 | B.179 |
| 1.180 | B.180 |
| 1.181 | B.181 |
| 1.182 | B.182 |
| 1.183 | B.183 |
| 1.184 | B.184 |
| 1.185 | B.185 |
| 1.186 | B.186 |
| 1.187 | B.187 |
| 1.188 | B.188 |
| 1.189 | B.189 |
| 1.190 | B.190 |
| 1.191 | B.191 |
| 1.192 | B.192 |
| 1.193 | B.193 |
| 1.194 | B.194 |
| 1.195 | B.195 |
| 1.196 | B.196 |
| 1.197 | B.197 |
| 1.198 | B.198 |
| 1.199 | B.199 |
| 1.200 | B.200 |
| 1.201 | B.201 |
| 1.202 | B.202 |
| 1.203 | B.203 |
| 1.204 | B.204 |
| 1.205 | B.205 |
| 1.206 | B.206 |
| 1.207 | B.207 |
| 1.208 | B.208 |
| 1.209 | B.209 |
| 1.210 | B.210 |
| 1.211 | B.211 |
| 1.212 | B.212 |
| 1.213 | B.213 |
| 1.214 | B.214 |
| 1.215 | B.215 |
| 1.216 | B.216 |
| 1.217 | B.217 |
| 1.218 | B.218 |
| 1.219 | B.219 |
| 1.220 | B.220 |
| 1.221 | B.221 |
| 1.222 | B.222 |
| 1.223 | B.223 |
| 1.224 | B.224 |
| 1.225 | B.225 |
| 1.226 | B.226 |
| 1.227 | B.227 |
| 1.228 | B.228 |
| 1.229 | B.229 |

Also especially preferred are compositions 2.1. to 2.229 which differ from the corresponding compositions 1.1 to 1.229 only in that they comprise as component A acifluorfen-sodium.

Also especially preferred are compositions 3.1. to 3.229 which differ from the corresponding compositions 1.1 to 1.229 only in that they comprise as component A azafenidin.

Also especially preferred are compositions 4.1. to 4.229 which differ from the corresponding compositions 1.1 to 1.229 only in that they comprise as component A bencarbazone.

Also especially preferred are compositions 5.1. to 5.229 which differ from the corresponding compositions 1.1 to 1.229 only in that they comprise as component A benzfendizone.

Also especially preferred are compositions 6.1. to 6.229 which differ from the corresponding compositions 1.1 to 1.229 only in that they comprise as component A bifenox.

Also especially preferred are compositions 7.1. to 7.229 which differ from the corresponding compositions 1.1 to 1.227 only in that they comprise as component A butafenacil.

Also especially preferred are compositions 8.1. to 8.229 which differ from the corresponding compositions 1.1 to 1.229 only in that they comprise as component A carfentrazone.

Also especially preferred are compositions 9.1. to 9.229 which differ from the corresponding compositions 1.1 to 1.229 only in that they comprise as component A carfentrazone-ethyl.

Also especially preferred are compositions 10.1. to 10.229 which differ from the corresponding compositions 1.1 to 1.229 only in that they comprise as component A chlomethoxyfen.

Also especially preferred are compositions 11.1. to 11.229 which differ from the corresponding compositions 1.1 to 1.229 only in that they comprise as component A cinidon-ethyl.

Also especially preferred are compositions 12.1. to 12.229 which differ from the corresponding compositions 1.1 to 1.229 only in that they comprise as component A fluazolate.

Also especially preferred are compositions 13.1. to 13.229 which differ from the corresponding compositions 1.1 to 1.229 only in that they comprise as component A flufenpyr.

Also especially preferred are compositions 14.1. to 14.229 which differ from the corresponding compositions 1.1 to 1.229 only in that they comprise as component A flufenpyr-ethyl.

Also especially preferred are compositions 15.1. to 15.229 which differ from the corresponding compositions 1.1 to 1.229 only in that they comprise as component A flumiclorac.

Also especially preferred are compositions 16.1. to 16.229 which differ from the corresponding compositions 1.1 to 1.229 only in that they comprise as component A flumiclorac-pentyl.

Also especially preferred are compositions 17.1. to 17.229 which differ from the corresponding compositions 1.1 to 1.229 only in that they comprise as component A flumioxazin.

Also especially preferred are compositions 18.1. to 18.229 which differ from the corresponding compositions 1.1 to 1.229 only in that they comprise as component A fluoroglycofen.

Also especially preferred are compositions 19.1. to 19.229 which differ from the corresponding compositions 1.1 to 1.229 only in that they comprise as component A fluoroglycofen-ethyl.

Also especially preferred are compositions 20.1. to 20.229 which differ from the corresponding compositions 1.1 to 1.229 only in that they comprise as component A fluthiacet.

Also especially preferred are compositions 21.1. to 21.229 which differ from the corresponding compositions 1.1 to 1.229 only in that they comprise as component A fluthiacet-methyl.

Also especially preferred are compositions 22.1. to 22.229 which differ from the corresponding compositions 1.1 to 1.229 only in that they comprise as component A fomesafen.

Also especially preferred are compositions 23.1. to 23.229 which differ from the corresponding compositions 1.1 to 1.229 only in that they comprise as component A halosafen.

Also especially preferred are compositions 24.1. to 24.229 which differ from the corresponding compositions 1.1 to 1.229 only in that they comprise as component A lactofen.

Also especially preferred are compositions 25.1. to 25.229 which differ from the corresponding compositions 1.1 to 1.229 only in that they comprise as component A oxadiargyl.

Also especially preferred are compositions 26.1. to 26.229 which differ from the corresponding compositions 1.1 to 1.229 only in that they comprise as component A oxadiazon.

Also especially preferred are compositions 27.1. to 27.229 which differ from the corresponding compositions 1.1 to 1.229 only in that they comprise as component A oxyfluorfen.

Also especially preferred are compositions 28.1. to 28.229 which differ from the corresponding compositions 1.1 to 1.229 only in that they comprise as component A pentoxazone.

Also especially preferred are compositions 29.1. to 29.229 which differ from the corresponding compositions 1.1 to 1.229 only in that they comprise as component A profluazol.

Also especially preferred are compositions 30.1. to 30.229 which differ from the corresponding compositions 1.1 to 1.229 only in that they comprise as component A pyraclonil.

Also especially preferred are compositions 31.1. to 31.229 which differ from the corresponding compositions 1.1 to 1.229 only in that they comprise as component A pyraflufen.

Also especially preferred are compositions 32.1. to 32.229 which differ from the corresponding compositions 1.1 to 1.229 only in that they comprise as component A pyraflufen-ethyl.

Also especially preferred are compositions 33.1. to 33.229 which differ from the corresponding compositions 1.1 to 1.229 only in that they comprise as component A saflufenacil.

Also especially preferred are compositions 34.1. to 34.229 which differ from the corresponding compositions 1.1 to 1.229 only in that they comprise as component A sulfentrazone.

Also especially preferred are compositions 35.1. to 35.229 which differ from the corresponding compositions 1.1 to 1.229 only in that they comprise as component A thidiazimin.

Also especially preferred are compositions 36.1. to 36.229 which differ from the corresponding compositions 1.1 to 1.229 only in that they comprise as component A tiafenacil.

Also especially preferred are compositions 37.1. to 37.229 which differ from the corresponding compositions 1.1 to 1.229 only in that they comprise as component A ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100).

Also especially preferred are compositions 38.1. to 38.229 which differ from the corresponding compositions 1.1 to 1.229 only in that they comprise as component A 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4)

Also especially preferred are compositions 39.1. to 39.229 which differ from the corresponding compositions 1.1 to 1.229 only in that they comprise as component A N-ethyl-3-(2,6-dichloro-4-trifluoromethylphenoxy)-5-methyl-1H-pyrazole-1-carboxamide (CAS 452098-92-9).

Also especially preferred are compositions 40.1. to 40.229 which differ from the corresponding compositions 1.1 to 1.229 only in that they comprise as component A N-tetrahydrofurfuryl-3-(2,6-dichloro-4-trifluoromethylphenoxy)-5-methyl-1H-pyrazole-1-carboxamide (CAS 915396-43-9).

Also especially preferred are compositions 41.1. to 41.229 which differ from the corresponding compositions 1.1 to 1.229 only in that they comprise as component A N-ethyl-3-(2-chloro-6-fluoro-4-trifluoromethylphenoxy)-5-methyl-1H-pyrazole-1-carboxamide (CAS 452099-05-7).

Also especially preferred are compositions 42.1. to 42.229 which differ from the corresponding compositions 1.1 to 1.229 only in that they comprise as component A N-tetrahydrofurfuryl-3-(2-chloro-6-fluoro-4-trifluoromethylphenoxy)-5-methyl-1H-pyrazole-1-carboxamide (CAS 452100-03-7).

Also especially preferred are compositions 43.1. to 43.229 which differ from the corresponding compositions 1.1 to 1.229 only in that they comprise as component A 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione.

Also especially preferred are compositions 44.1. to 44.229 which differ from the corresponding compositions 1.1 to 1.229 only in that they comprise as component A methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3).

Also especially preferred are compositions 45.1. to 45.229 which differ from the corresponding compositions 1.1 to 1.229 only in that they comprise as component A 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4).

Also especially preferred are compositions 46.1. to 46.229 which differ from the corresponding compositions 1.1 to 1.229 only in that they comprise as component A 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione.

Also especially preferred are compositions 47.1. to 47.229 which differ from the corresponding compositions 1.1 to 1.229 only in that they comprise as component A 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione Also especially preferred are compositions 48.1. to 48.229 which differ from the corresponding compositions 1.1 to 1.229 only in that they additionally comprise benoxacor as safener C.

Also especially preferred are compositions 49.1. to 49.229 which differ from the corresponding compositions 1.1 to 1.229 only in that they additionally comprise cloquintocet as safener C.

Also especially preferred are compositions 50.1. to 50.229 which differ from the corresponding compositions 1.1 to 1.229 only in that they additionally comprise cyprosulfamide as safener C.

Also especially preferred are compositions 51.1. to 51.229 which differ from the corresponding compositions 1.1 to 1.229 only in that they additionally comprise dichlormid as safener C.

Also especially preferred are compositions 52.1. to 52.229 which differ from the corresponding compositions 1.1 to 1.229 only in that they additionally comprise fenchlorazole as safener C.

Also especially preferred are compositions 53.1. to 53.229 which differ from the corresponding compositions 1.1 to 1.229 only in that they additionally comprise fenclorim as safener C.

Also especially preferred are compositions 54.1. to 54.229 which differ from the corresponding compositions 1.1 to 1.229 only in that they additionally comprise furilazole as safener C.

Also especially preferred are compositions 55.1. to 55.229 which differ from the corresponding compositions 1.1 to 1.229 only in that they additionally comprise isoxadifen as safener C.

Also especially preferred are compositions 56.1. to 56.229 which differ from the corresponding compositions 1.1 to 1.229 only in that they additionally comprise mefenpyr as safener C.

Also especially preferred are compositions 57.1. to 57.229 which differ from the corresponding compositions 1.1 to 1.229 only in that they additionally comprise 4-(dichloroacetyl)-1-oxa-4-azaspiro[4.5]decane (MON4660, CAS 71526-07-3) as safener C.

Also especially preferred are compositions 58.1. to 58.229 which differ from the corresponding compositions 1.1 to 1.229 only in that they additionally comprise 2,2,5-trimethyl-3-(dichloroacetyl)-1,3-oxazolidine (R-29148, CAS 52836-31-4) as safener C.

It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

It is recognized that the polynucleotide molecules and polypeptides of the invention encompass polynucleotide molecules and polypeptides comprising a nucleotide or an amino acid sequence that is sufficiently identical to nucleotide sequences set forth in SEQ ID Nos: 1, 3, 5, 7, 9, 11, 13, 15, 17, 19, 21, 23, 25, 27, 29, 31, 33, 35, 37, 39, 41, 43, 45, or 47, or to the amino acid sequences set forth in SEQ ID Nos: 2, 4, 6, 8, 10, 12, 14, 16, 18, 20, 22, 24, 26, 28, 30, 32, 34, 36, 38, 40, 42, 44, 46, or 48. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity.

Generally, "sequence identity" refers to the extent to which two optimally aligned DNA or amino acid sequences are invariant throughout a window of alignment of components, e.g., nucleotides or amino acids. An "identity fraction" for aligned segments of a test sequence and a reference sequence is the number of identical components that are shared by the two aligned sequences divided by the total number of components in reference sequence segment, i.e., the entire reference sequence or a smaller defined part of the reference sequence. "Percent identity" is the identity fraction times 100. Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG. Wisconsin Package. (Accelrys Inc. Burlington, Mass.)

Polynucleotides and Oligonucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. That means other nucleic acid molecules are present in an amount less than 5% based on weight of the amount of the desired nucleic acid, preferably less than 2% by weight, more preferably less than 1% by weight, most preferably less than 0.5% by weight. Preferably, an "isolated" nucleic acid is free of some of the sequences that naturally flank the nucleic acid (i.e., sequences located at the 5' and 3' ends of the nucleic acid) in the genomic DNA of the organism from which the nucleic acid is derived. For example, in various embodiments, the isolated herbicide resistance and/or tolerance related protein encoding nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized. Preferably, the isolated polynucleotide is at least 60% free, preferably at least 75% free, and most preferably at least 90% free from other components with which they are naturally associated. As the skilled addressee would be aware, an isolated polynucleotide can be an exogenous polynucleotide present in, for example, a transgenic organism which does not naturally comprise the polynucleotide.

Furthermore, the terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

The term "mutated PPO nucleic acid" refers to a PPO nucleic acid having a sequence that is mutated from a wild-type PPO nucleic acid and that confers increased PPO-inhibiting herbicide tolerance to a plant in which it is expressed. Furthermore, the term "mutated protoporphyrinogen oxidase (mutated PPO)" refers to the replacement of an amino acid of the wild-type primary sequences SEQ ID NO: 2, 4, 6, 8, 10, 12, 14, 16, 18, 20, 22, 24, 26, 28, 30, 32, 34, 36, 38, 40, 42, 44, 46, or 48, or a variant, a derivative, a homologue, an orthologue, or paralogue thereof, with another amino acid. The expression "mutated amino acid" will be used below to designate the amino acid which is replaced by another amino acid, thereby designating the site of the mutation in the primary sequence of the protein.

In a preferred embodiment, the PPO nucleotide sequence encoding a mutated PPO comprises the sequence of SEQ ID NO: 1, 3, 23, 29, 37, 45, or 47, or a variant or derivative thereof.

Furthermore, it will be understood by the person skilled in the art that the PPO nucleotide sequences encompasse homologues, paralogues and orthologues of SEQ ID NO: 1, 3, 23, 29, 37, 45, or 47, as defined hereinafter.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein, e.g. the mutated PPO according to the present invention as disclosed herein. Generally, nucleotide sequence variants of the invention will have at least 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide "sequence identity" to the nucleotide sequence of SEQ ID NO: SEQ ID NO: 1, 3, 5, 7, 9, 11, 13, 15, 17, 19, 21, 23, 25, 27, 29, 31, 33, 35, 37, 39, 41, 43, 45, or 47. The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

Polypeptides

By "substantially purified polypeptide" or "purified" a polypeptide is meant that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated. As the skilled addressee will appreciate, the purified polypeptide can be a recombinantly produced polypeptide. The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, modifications, analogous and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

With regard to a defined polypeptide, it will be appreciated that % identity figures higher than those provided above will encompass preferred embodiments. Thus, where applicable, in light of the minimum % identity figures, it is preferred that the PPO polypeptide of the invention comprises an amino acid sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to SEQ ID NO: 2, 4, 6, 8, 10, 12, 14, 16, 18, 20, 22, 24, 26, 28, 30, 32, 34, 36, 38, 40, 42, 44, 46, or 48.

By "variant" polypeptide is intended a polypeptide derived from the protein of SEQ ID NO: 2, 4, 6, 8, 10, 12, 14, 16, 18, 20, 22, 24, 26, 28, 30, 32, 34, 36, 38, 40, 42, 44, 46, or 48 by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

"Derivatives" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds).

TABLE 2

Examples of conserved amino acid substitutions

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

"Derivatives" further include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

"Orthologues" and "paralogues" encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene. A non-limiting list of examples of such orthologues are shown in Table 1.

It is well-known in the art that paralogues and orthologues may share distinct domains harboring suitable amino acid residues at given sites, such as binding pockets for particular substrates, compounds such as e.g. herbicides, or binding motifs for interaction with other proteins.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif" or "consensus sequence" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISM B-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The inventors of the present invention have found that by substituting one or more of the key amino acid residues, employing e.g. one of the above described methods to mutate the encoding nucleic acids, the herbicide tolerance or resistance could be remarkably increased as compared to the activity of the wild type PPO enzymes with SEQ ID NO: 2, 4, 6, 8, 10, 12, 14, 16, 18, 20, 22, 24, 26, 28, 30, 32, 34, 36, 38, 40, 42, 44, 46, or 48. Preferred substitutions of mutated PPO are those that increase the herbicide tolerance of the plant, but leave the biological activity of the oxidase activity substantially unaffected.

Accordingly, in another object of the present invention the key amino acid residues of a PPO enzyme comprising SEQ ID NO: 2, 4, 6, 8, 10, 12, 14, 16, 18, 20, 22, 24, 26, 28, 30, 32, 34, 36, 38, 40, 42, 44, 46, or 48, a variant, derivative, orthologue, paralogue or homologue thereof, is substituted by any other amino acid.

In one embodiment, the key amino acid residues of a PPO enzyme, a variant, derivative, orthologue, paralogue or homologue thereof, is substituted by a conserved amino acid as depicted in Table 2.

It will be understood by the person skilled in the art that amino acids located in a close proximity to the positions of amino acids mentioned below may also be substituted. Thus, in another embodiment the variant of SEQ ID NO: 2, 4, 6, 8, 10, 12, 14, 16, 18, 20, 22, 24, 26, 28, 30, 32, 34, 36, 38, 40, 42, 44, 46, or 48, a variant, derivative, orthologue, paralogue or homologue thereof comprises a mutated PPO, wherein an amino acid ±3, ±2 or ±1 amino acid positions from a key amino acid is substituted by any other amino acid.

Based on techniques well-known in the art, a highly characteristic sequence pattern can be developed, by means of which further of mutated PPO candidates with the desired activity may be searched.

Searching for further mutated PPO candidates by applying a suitable sequence pattern would also be encompassed by the present invention. It will be understood by a skilled reader that the present sequence pattern is not limited by the exact distances between two adjacent amino acid residues of said pattern. Each of the distances between two neighbours in the above patterns may, for example, vary independently of each other by up to ±10, ±5, ±3, ±2 or ±1 amino acid positions without substantially affecting the desired activity.

Furthermore, by applying the method of site directed mutagenesis, in particular saturation mutagenes (see e.g. Schenk et al., Biospektrum March 2006, pages 277-279), the inventors of the present invention have identified and generated specific amino acid substitutions and combinations thereof, which—when introduced into a plant by transforming and expressing the respective mutated PPO encoding nucleic acid—confer increased herbicide resistance or tolerance to a PPO inhibiting herbicide to said plant.

Thus, in a particularly preferred embodiment, the variant or derivative of the mutated PPO refers to a polypeptide comprising SEQ ID NO: 2, SEQ ID NO: 4, SEQ ID NO: 24, SEQ ID NO: 30, SEQ ID NO: 38, SEQ ID NO: 46, or SEQ ID NO: 48, comprising a single amino acid substitution of the following Table 3a.

TABLE 3a

Single amino acid substitutions within SEQ ID NO: 2, SEQ ID NO: 4, SEQ ID NO: 24, SEQ ID NO: 30, SEQ ID NO: 38, SEQ ID NO: 46, SEQ ID NO: 48,

| Mutation Number | SEQ ID NO: | Key amino acid position combination | Preferred Substitution |
|---|---|---|---|
| 1 | 2 | Arg128 | Ala |
| 2 | 2 | Arg128 | Leu |
| 3 | 2 | Arg128 | Val |
| 4 | 2 | Arg128 | Ile |
| 5 | 2 | Arg128 | Met |
| 6 | 2 | Arg128 | His |
| 7 | 2 | Arg128 | Lys |
| 8 | 2 | Arg128 | Asp |
| 9 | 2 | Arg128 | Glu |
| 10 | 2 | Arg128 | Ser |
| 11 | 2 | Arg128 | Thr |
| 12 | 2 | Arg128 | Asn |
| 13 | 2 | Arg128 | Gln |
| 14 | 2 | Arg128 | Cys |
| 15 | 2 | Arg128 | Gly |
| 16 | 2 | Arg128 | Pro |
| 17 | 2 | Arg128 | Phe |
| 18 | 2 | Arg128 | Tyr |
| 19 | 2 | Arg128 | Trp |
| 20 | 2 | Phe420 | Ala |
| 21 | 2 | Phe420 | Leu |
| 22 | 2 | Phe420 | Val |
| 23 | 2 | Phe420 | Ile |
| 24 | 2 | Phe420 | Met |
| 25 | 2 | Phe420 | His |
| 26 | 2 | Phe420 | Lys |
| 27 | 2 | Phe420 | Asp |
| 28 | 2 | Phe420 | Glu |
| 29 | 2 | Phe420 | Ser |
| 30 | 2 | Phe420 | Thr |
| 31 | 2 | Phe420 | Asn |
| 32 | 2 | Phe420 | Gln |
| 33 | 2 | Phe420 | Cys |
| 34 | 2 | Phe420 | Gly |
| 35 | 2 | Phe420 | Pro |
| 36 | 2 | Phe420 | Phe |
| 37 | 2 | Phe420 | Tyr |
| 38 | 2 | Phe420 | Trp |
| 39 | 4 | Arg128 | Ala |
| 40 | 4 | Arg128 | Leu |
| 41 | 4 | Arg128 | Val |
| 42 | 4 | Arg128 | Ile |
| 43 | 4 | Arg128 | Met |
| 44 | 4 | Arg128 | His |
| 45 | 4 | Arg128 | Lys |
| 46 | 4 | Arg128 | Asp |
| 47 | 4 | Arg128 | Glu |
| 48 | 4 | Arg128 | Ser |
| 49 | 4 | Arg128 | Thr |
| 50 | 4 | Arg128 | Asn |
| 51 | 4 | Arg128 | Gln |
| 52 | 4 | Arg128 | Cys |
| 53 | 4 | Arg128 | Gly |
| 54 | 4 | Arg128 | Pro |
| 55 | 4 | Arg128 | Phe |
| 56 | 4 | Arg128 | Tyr |
| 57 | 4 | Arg128 | Trp |
| 58 | 4 | Phe420 | Ala |
| 59 | 4 | Phe420 | Leu |
| 60 | 4 | Phe420 | Val |
| 61 | 4 | Phe420 | Ile |
| 62 | 4 | Phe420 | Met |
| 63 | 4 | Phe420 | His |
| 64 | 4 | Phe420 | Lys |
| 65 | 4 | Phe420 | Asp |
| 66 | 4 | Phe420 | Glu |
| 67 | 4 | Phe420 | Ser |
| 68 | 4 | Phe420 | Thr |
| 69 | 4 | Phe420 | Asn |
| 70 | 4 | Phe420 | Gln |
| 71 | 4 | Phe420 | Cys |
| 72 | 4 | Phe420 | Gly |
| 73 | 4 | Phe420 | Pro |
| 74 | 4 | Phe420 | Phe |
| 75 | 4 | Phe420 | Tyr |
| 76 | 4 | Phe420 | Trp |
| 77 | 24 | Arg130 | Ala |
| 78 | 24 | Arg130 | Leu |
| 79 | 24 | Arg130 | Val |
| 80 | 24 | Arg130 | Ile |
| 81 | 24 | Arg130 | Met |
| 82 | 24 | Arg130 | His |
| 83 | 24 | Arg130 | Lys |
| 84 | 24 | Arg130 | Asp |
| 85 | 24 | Arg130 | Glu |
| 86 | 24 | Arg130 | Ser |
| 87 | 24 | Arg130 | Thr |
| 88 | 24 | Arg130 | Asn |
| 89 | 24 | Arg130 | Gln |
| 90 | 24 | Arg130 | Cys |
| 91 | 24 | Arg130 | Gly |
| 92 | 24 | Arg130 | Pro |
| 93 | 24 | Arg130 | Phe |
| 94 | 24 | Arg130 | Tyr |
| 95 | 24 | Arg130 | Trp |
| 96 | 24 | Phe433 | Ala |
| 97 | 24 | Phe433 | Leu |
| 98 | 24 | Phe433 | Val |
| 99 | 24 | Phe433 | Ile |
| 100 | 24 | Phe433 | Met |
| 101 | 24 | Phe433 | His |
| 102 | 24 | Phe433 | Lys |
| 103 | 24 | Phe433 | Asp |
| 104 | 24 | Phe433 | Glu |
| 105 | 24 | Phe433 | Ser |
| 106 | 24 | Phe433 | Thr |
| 107 | 24 | Phe433 | Asn |
| 108 | 24 | Phe433 | Gln |
| 109 | 24 | Phe433 | Cys |
| 110 | 24 | Phe433 | Gly |
| 111 | 24 | Phe433 | Pro |
| 112 | 24 | Phe433 | Phe |
| 113 | 24 | Phe433 | Tyr |
| 114 | 24 | Phe433 | Trp |
| 115 | 30 | Arg130 | Ala |
| 116 | 30 | Arg130 | Leu |
| 117 | 30 | Arg130 | Val |
| 118 | 30 | Arg130 | Ile |
| 119 | 30 | Arg130 | Met |
| 120 | 30 | Arg130 | His |
| 121 | 30 | Arg130 | Lys |

TABLE 3a-continued

Single amino acid substitutions within SEQ ID NO: 2, SEQ ID NO: 4, SEQ ID NO: 24, SEQ ID NO: 30, SEQ ID NO: 38, SEQ ID NO: 46, SEQ ID NO: 48,

| Mutation Number | SEQ ID NO: | Key amino acid position combination | Preferred Substitution |
|---|---|---|---|
| 122 | 30 | Arg130 | Asp |
| 123 | 30 | Arg130 | Glu |
| 124 | 30 | Arg130 | Ser |
| 125 | 30 | Arg130 | Thr |
| 126 | 30 | Arg130 | Asn |
| 127 | 30 | Arg130 | Gln |
| 128 | 30 | Arg130 | Cys |
| 129 | 30 | Arg130 | Gly |
| 130 | 30 | Arg130 | Pro |
| 131 | 30 | Arg130 | Phe |
| 132 | 30 | Arg130 | Tyr |
| 133 | 30 | Arg130 | Trp |
| 134 | 30 | Phe433 | Ala |
| 135 | 30 | Phe433 | Leu |
| 136 | 30 | Phe433 | Val |
| 137 | 30 | Phe433 | Ile |
| 138 | 30 | Phe433 | Met |
| 139 | 30 | Phe433 | His |
| 140 | 30 | Phe433 | Lys |
| 141 | 30 | Phe433 | Asp |
| 142 | 30 | Phe433 | Glu |
| 143 | 30 | Phe433 | Ser |
| 144 | 30 | Phe433 | Thr |
| 145 | 30 | Phe433 | Asn |
| 146 | 30 | Phe433 | Gln |
| 147 | 30 | Phe433 | Cys |
| 148 | 30 | Phe433 | Gly |
| 149 | 30 | Phe433 | Pro |
| 150 | 30 | Phe433 | Phe |
| 151 | 30 | Phe433 | Tyr |
| 152 | 30 | Phe433 | Trp |
| 153 | 38 | Arg98 | Ala |
| 154 | 38 | Arg98 | Leu |
| 155 | 38 | Arg98 | Val |
| 156 | 38 | Arg98 | Ile |
| 157 | 38 | Arg98 | Met |
| 158 | 38 | Arg98 | His |
| 159 | 38 | Arg98 | Lys |
| 160 | 38 | Arg98 | Asp |
| 161 | 38 | Arg98 | Glu |
| 162 | 38 | Arg98 | Ser |
| 163 | 38 | Arg98 | Thr |
| 164 | 38 | Arg98 | Asn |
| 165 | 38 | Arg98 | Gln |
| 166 | 38 | Arg98 | Cys |
| 167 | 38 | Arg98 | Gly |
| 168 | 38 | Arg98 | Pro |
| 169 | 38 | Arg98 | Phe |
| 170 | 38 | Arg98 | Tyr |
| 171 | 38 | Arg98 | Trp |
| 172 | 38 | Phe392 | Ala |
| 173 | 38 | Phe392 | Leu |
| 174 | 38 | Phe392 | Val |
| 175 | 38 | Phe392 | Ile |
| 176 | 38 | Phe392 | Met |
| 177 | 38 | Phe392 | His |
| 178 | 38 | Phe392 | Lys |
| 179 | 38 | Phe392 | Asp |
| 180 | 38 | Phe392 | Glu |
| 181 | 38 | Phe392 | Ser |
| 182 | 38 | Phe392 | Thr |
| 183 | 38 | Phe392 | Asn |
| 184 | 38 | Phe392 | Gln |
| 185 | 38 | Phe392 | Cys |
| 186 | 38 | Phe392 | Gly |
| 187 | 38 | Phe392 | Pro |
| 188 | 38 | Phe392 | Phe |
| 189 | 38 | Phe392 | Tyr |
| 190 | 38 | Phe392 | Trp |
| 191 | 46 | Arg139 | Ala |
| 192 | 46 | Arg139 | Leu |
| 193 | 46 | Arg139 | Val |
| 194 | 46 | Arg139 | Ile |
| 195 | 46 | Arg139 | Met |
| 196 | 46 | Arg139 | His |
| 197 | 46 | Arg139 | Lys |
| 198 | 46 | Arg139 | Asp |
| 199 | 46 | Arg139 | Glu |
| 200 | 46 | Arg139 | Ser |
| 201 | 46 | Arg139 | Thr |
| 202 | 46 | Arg139 | Asn |
| 203 | 46 | Arg139 | Gln |
| 204 | 46 | Arg139 | Cys |
| 205 | 46 | Arg139 | Gly |
| 206 | 46 | Arg139 | Pro |
| 207 | 46 | Arg139 | Phe |
| 208 | 46 | Arg139 | Tyr |
| 209 | 46 | Arg139 | Trp |
| 210 | 46 | Phe465 | Ala |
| 211 | 46 | Phe465 | Leu |
| 212 | 46 | Phe465 | Val |
| 213 | 46 | Phe465 | Ile |
| 214 | 46 | Phe465 | Met |
| 215 | 46 | Phe465 | His |
| 216 | 46 | Phe465 | Lys |
| 217 | 46 | Phe465 | Asp |
| 218 | 46 | Phe465 | Glu |
| 219 | 46 | Phe465 | Ser |
| 220 | 46 | Phe465 | Thr |
| 221 | 46 | Phe465 | Asn |
| 222 | 46 | Phe465 | Gln |
| 223 | 46 | Phe465 | Cys |
| 224 | 46 | Phe465 | Gly |
| 225 | 46 | Phe465 | Pro |
| 226 | 46 | Phe465 | Phe |
| 227 | 46 | Phe465 | Tyr |
| 228 | 46 | Phe465 | Trp |
| 229 | 48 | Arg157 | Ala |
| 230 | 48 | Arg157 | Leu |
| 231 | 48 | Arg157 | Val |
| 232 | 48 | Arg157 | Ile |
| 233 | 48 | Arg157 | Met |
| 234 | 48 | Arg157 | His |
| 235 | 48 | Arg157 | Lys |
| 236 | 48 | Arg157 | Asp |
| 237 | 48 | Arg157 | Glu |
| 238 | 48 | Arg157 | Ser |
| 239 | 48 | Arg157 | Thr |
| 240 | 48 | Arg157 | Asn |
| 241 | 48 | Arg157 | Gln |
| 242 | 48 | Arg157 | Cys |
| 243 | 48 | Arg157 | Gly |
| 244 | 48 | Arg157 | Pro |
| 245 | 48 | Arg157 | Phe |
| 246 | 48 | Arg157 | Tyr |
| 247 | 48 | Arg157 | Trp |
| 248 | 48 | Tyr439 | Ala |
| 249 | 48 | Tyr439 | Leu |
| 250 | 48 | Tyr439 | Val |
| 251 | 48 | Tyr439 | Ile |
| 252 | 48 | Tyr439 | Met |
| 253 | 48 | Tyr439 | His |
| 254 | 48 | Tyr439 | Lys |
| 255 | 48 | Tyr439 | Asp |
| 256 | 48 | Tyr439 | Glu |
| 257 | 48 | Tyr439 | Ser |
| 258 | 48 | Tyr439 | Thr |
| 259 | 48 | Tyr439 | Asn |
| 260 | 48 | Tyr439 | Gln |
| 261 | 48 | Tyr439 | Cys |
| 262 | 48 | Tyr439 | Gly |
| 263 | 48 | Tyr439 | Pro |

TABLE 3a-continued

Single amino acid substitutions within SEQ ID NO: 2, SEQ ID NO: 4, SEQ ID NO: 24, SEQ ID NO: 30, SEQ ID NO: 38, SEQ ID NO: 46, SEQ ID NO: 48,

| Mutation Number | SEQ ID NO: | Key amino acid position combination | Preferred Substitution |
|---|---|---|---|
| 264 | 48 | Tyr439 | Phe |
| 265 | 48 | Tyr439 | Tyr |
| 266 | 48 | Tyr439 | Trp |

In a further particularly preferred embodiment, the variant or derivative of the mutated PPO refers to a polypeptide comprising SEQ ID NO: 2, SEQ ID NO:4, SEQ ID NO: 24, SEQ ID NO: 30, SEQ ID NO: 38, SEQ ID NO: 46, SEQ ID NO: 48, comprising a combination of amino acid substitutions selected from the following Table 3b.

TABLE 3b

SEQ ID NO: 2, SEQ ID NO: 4, SEQ ID NO: 24, SEQ ID NO: 30, SEQ ID NO: 38, SEQ ID NO: 46, SEQ ID NO: 48, (combined amino acid substitutions)

| Combination Number | SEQ ID NO: | Key amino acid position combination | Preferred Substitution |
|---|---|---|---|
| 267 | 2 & 4 | Arg128 Phe420 | Leu Ala |
| 268 | 2 & 4 | Arg128 Phe420 | Leu Leu |
| 269 | 2 & 4 | Arg128 Phe420 | Leu Val |
| 270 | 2 & 4 | Arg128 Phe420 | Leu Ile |
| 271 | 2 & 4 | Arg128 Phe420 | Leu Met |
| 272 | 2 & 4 | Arg128 Phe420 | Ala Ala |
| 273 | 2 & 4 | Arg128 Phe420 | Ala Leu |
| 274 | 2 & 4 | Arg128 Phe420 | Ala Val |
| 275 | 2 & 4 | Arg128 Phe420 | Ala Ile |
| 276 | 2 & 4 | Arg128 Phe420 | Ala Met |
| 277 | 2 & 4 | Arg128 Phe420 | Val Ala |
| 278 | 2 & 4 | Arg128 Phe420 | Val Leu |
| 279 | 2 & 4 | Arg128 Phe420 | Val Val |
| 280 | 2 & 4 | Arg128 Phe420 | Val Ile |
| 281 | 2 & 4 | Arg128 Phe420 | Val Met |
| 282 | 2 & 4 | Arg128 Phe420 | Ile Ala |
| 283 | 2 & 4 | Arg128 Phe420 | Ile Leu |
| 284 | 2 & 4 | Arg128 Phe420 | Ile Val |
| 285 | 2 & 4 | Arg128 Phe420 | Ile Ile |
| 286 | 2 & 4 | Arg128 Phe420 | Ile Met |
| 287 | 2 & 4 | Arg128 Phe420 | Met Ala |
| 288 | 2 & 4 | Arg128 Phe420 | Met Leu |
| 289 | 2 & 4 | Arg128 Phe420 | Met Val |
| 290 | 2 & 4 | Arg128 Phe420 | Met Ile |
| 291 | 2 & 4 | Arg128 Phe420 | Met Met |
| 292 | 2 & 4 | Arg128 Phe420 | Tyr Ala |
| 293 | 2 & 4 | Arg128 Phe420 | Tyr Leu |
| 294 | 2 & 4 | Arg128 Phe420 | Tyr Val |
| 295 | 2 & 4 | Arg128 Phe420 | Tyr Ile |
| 296 | 2 & 4 | Arg128 Phe420 | Tyr Met |
| 297 | 2 & 4 | Arg128 Phe420 | Gly Ala |
| 298 | 2 & 4 | Arg128 Phe420 | Gly Leu |
| 299 | 2 & 4 | Arg128 Phe420 | Gly Val |
| 300 | 2 & 4 | Arg128 Phe420 | Gly Ile |
| 301 | 2 & 4 | Arg128 Phe420 | Gly Met |
| 302 | 2 & 4 | Arg128 Phe420 | Asn Ala |
| 303 | 2 & 4 | Arg128 Phe420 | Asn Leu |
| 304 | 2 & 4 | Arg128 Phe420 | Asn Val |
| 305 | 2 & 4 | Arg128 Phe420 | Asn Ile |
| 306 | 2 & 4 | Arg128 Phe420 | Asn Met |
| 307 | 2 & 4 | Arg128 Phe420 | Cys Ala |
| 308 | 2 & 4 | Arg128 Phe420 | Cys Leu |
| 309 | 2 & 4 | Arg128 Phe420 | Cys Val |
| 310 | 2 & 4 | Arg128 Phe420 | Cys Ile |
| 311 | 2 & 4 | Arg128 Phe420 | Cys Met |
| 312 | 2 & 4 | Arg128 Phe420 | Phe Ala |
| 313 | 2 & 4 | Arg128 Phe420 | Phe Leu |
| 314 | 2 & 4 | Arg128 Phe420 | Phe Val |
| 315 | 2 & 4 | Arg128 Phe420 | Phe Ile |
| 316 | 2 & 4 | Arg128 Phe420 | Phe Met |
| 317 | 2 & 4 | Arg128 Phe420 | Ser Ala |
| 318 | 2 & 4 | Arg128 Phe420 | Ser Leu |
| 319 | 2 & 4 | Arg128 Phe420 | Ser Val |
| 320 | 2 & 4 | Arg128 Phe420 | Ser Ile |
| 321 | 2 & 4 | Arg128 Phe420 | Ser Met |
| 322 | 2 & 4 | Arg128 Phe420 | Thr Ala |
| 323 | 2 & 4 | Arg128 Phe420 | Thr Leu |
| 324 | 2 & 4 | Arg128 Phe420 | Thr Val |
| 325 | 2 & 4 | Arg128 Phe420 | Thr Ile |
| 326 | 2 & 4 | Arg128 Phe420 | Thr Met |

TABLE 3b-continued

SEQ ID NO: 2, SEQ ID NO: 4, SEQ ID NO: 24, SEQ ID NO: 30, SEQ ID NO: 38, SEQ ID NO: 46, SEQ ID NO: 48, (combined amino acid substitutions)

| Combination Number | SEQ ID NO: | Key amino acid position combination | Preferred Substitution |
|---|---|---|---|
| 327 | 2 & 4 | Arg128 | Gln |
|  |  | Phe420 | Ala |
| 328 | 2 & 4 | Arg128 | Gln |
|  |  | Phe420 | Leu |
| 329 | 2 & 4 | Arg128 | Gln |
|  |  | Phe420 | Val |
| 330 | 2 & 4 | Arg128 | Gln |
|  |  | Phe420 | Ile |
| 331 | 2 & 4 | Arg128 | Gln |
|  |  | Phe420 | Met |
| 332 | 2 & 4 | Arg128 | His |
|  |  | Phe420 | Ala |
| 333 | 2 & 4 | Arg128 | His |
|  |  | Phe420 | Leu |
| 334 | 2 & 4 | Arg128 | His |
|  |  | Phe420 | Val |
| 335 | 2 & 4 | Arg128 | His |
|  |  | Phe420 | Ile |
| 336 | 2 & 4 | Arg128 | His |
|  |  | Phe420 | Met |
| 337 | 24 | Arg130 | Leu |
|  |  | Phe433 | Ala |
| 338 | 24 | Arg130 | Leu |
|  |  | Phe433 | Leu |
| 339 | 24 | Arg130 | Leu |
|  |  | Phe433 | Val |
| 340 | 24 | Arg130 | Leu |
|  |  | Phe433 | Ile |
| 341 | 24 | Arg130 | Leu |
|  |  | Phe433 | Met |
| 342 | 24 | Arg130 | Ala |
|  |  | Phe433 | Ala |
| 343 | 24 | Arg130 | Ala |
|  |  | Phe433 | Leu |
| 344 | 24 | Arg130 | Ala |
|  |  | Phe433 | Val |
| 345 | 24 | Arg130 | Ala |
|  |  | Phe433 | Ile |
| 346 | 24 | Arg130 | Ala |
|  |  | Phe433 | Met |
| 347 | 24 | Arg130 | Val |
|  |  | Phe433 | Ala |
| 348 | 24 | Arg130 | Val |
|  |  | Phe433 | Leu |
| 349 | 24 | Arg130 | Val |
|  |  | Phe433 | Val |
| 350 | 24 | Arg130 | Val |
|  |  | Phe433 | Ile |
| 351 | 24 | Arg130 | Val |
|  |  | Phe433 | Met |
| 352 | 24 | Arg130 | Ile |
|  |  | Phe433 | Ala |
| 353 | 24 | Arg130 | Ile |
|  |  | Phe433 | Leu |
| 354 | 24 | Arg130 | Ile |
|  |  | Phe433 | Val |
| 355 | 24 | Arg130 | Ile |
|  |  | Phe433 | Ile |
| 356 | 24 | Arg130 | Ile |
|  |  | Phe433 | Met |
| 357 | 24 | Arg130 | Met |
|  |  | Phe433 | Ala |
| 358 | 24 | Arg130 | Met |
|  |  | Phe433 | Leu |
| 359 | 24 | Arg130 | Met |
|  |  | Phe433 | Val |
| 360 | 24 | Arg130 | Met |
|  |  | Phe433 | Ile |
| 361 | 24 | Arg130 | Met |
|  |  | Phe433 | Met |
| 362 | 24 | Arg130 | Tyr |
|  |  | Phe433 | Ala |
| 363 | 24 | Arg130 | Tyr |
|  |  | Phe433 | Leu |
| 364 | 24 | Arg130 | Tyr |
|  |  | Phe433 | Val |
| 365 | 24 | Arg130 | Tyr |
|  |  | Phe433 | Ile |
| 366 | 24 | Arg130 | Tyr |
|  |  | Phe433 | Met |
| 367 | 24 | Arg130 | Gly |
|  |  | Phe433 | Ala |
| 368 | 24 | Arg130 | Gly |
|  |  | Phe433 | Leu |
| 369 | 24 | Arg130 | Gly |
|  |  | Phe433 | Val |
| 370 | 24 | Arg130 | Gly |
|  |  | Phe433 | Ile |
| 371 | 24 | Arg130 | Gly |
|  |  | Phe433 | Met |
| 372 | 24 | Arg130 | Asn |
|  |  | Phe433 | Ala |
| 373 | 24 | Arg130 | Asn |
|  |  | Phe433 | Leu |
| 374 | 24 | Arg130 | Asn |
|  |  | Phe433 | Val |
| 375 | 24 | Arg130 | Asn |
|  |  | Phe433 | Ile |
| 376 | 24 | Arg130 | Asn |
|  |  | Phe433 | Met |
| 377 | 24 | Arg130 | Cys |
|  |  | Phe433 | Ala |
| 378 | 24 | Arg130 | Cys |
|  |  | Phe433 | Leu |
| 379 | 24 | Arg130 | Cys |
|  |  | Phe433 | Val |
| 380 | 24 | Arg130 | Cys |
|  |  | Phe433 | Ile |
| 381 | 24 | Arg130 | Cys |
|  |  | Phe433 | Met |
| 382 | 24 | Arg130 | Phe |
|  |  | Phe433 | Ala |
| 383 | 24 | Arg130 | Phe |
|  |  | Phe433 | Leu |
| 384 | 24 | Arg130 | Phe |
|  |  | Phe433 | Val |
| 385 | 24 | Arg130 | Phe |
|  |  | Phe433 | Ile |
| 386 | 24 | Arg130 | Phe |
|  |  | Phe433 | Met |
| 387 | 24 | Arg130 | Ser |
|  |  | Phe433 | Ala |
| 388 | 24 | Arg130 | Ser |
|  |  | Phe433 | Leu |
| 389 | 24 | Arg130 | Ser |
|  |  | Phe433 | Val |
| 390 | 24 | Arg130 | Ser |
|  |  | Phe433 | Ile |
| 391 | 24 | Arg130 | Ser |
|  |  | Phe433 | Met |
| 392 | 24 | Arg130 | Thr |
|  |  | Phe433 | Ala |
| 393 | 24 | Arg130 | Thr |
|  |  | Phe433 | Leu |
| 394 | 24 | Arg130 | Thr |
|  |  | Phe433 | Val |
| 395 | 24 | Arg130 | Thr |
|  |  | Phe433 | Ile |
| 396 | 24 | Arg130 | Thr |
|  |  | Phe433 | Met |
| 397 | 24 | Arg130 | Gln |
|  |  | Phe433 | Ala |
| 398 | 24 | Arg130 | Gln |
|  |  | Phe433 | Leu |

TABLE 3b-continued

SEQ ID NO: 2, SEQ ID NO: 4, SEQ ID NO: 24, SEQ ID NO: 30, SEQ ID NO: 38, SEQ ID NO: 46, SEQ ID NO: 48, (combined amino acid substitutions)

| Combination Number | SEQ ID NO: | Key amino acid position combination | Preferred Substitution |
|---|---|---|---|
| 399 | 24 | Arg130 | Gln |
|  |  | Phe433 | Val |
| 400 | 24 | Arg130 | Gln |
|  |  | Phe433 | Ile |
| 401 | 24 | Arg130 | Gln |
|  |  | Phe433 | Met |
| 402 | 24 | Arg130 | His |
|  |  | Phe433 | Ala |
| 403 | 24 | Arg130 | His |
|  |  | Phe433 | Leu |
| 404 | 24 | Arg130 | His |
|  |  | Phe433 | Val |
| 405 | 24 | Arg130 | His |
|  |  | Phe433 | Ile |
| 406 | 24 | Arg130 | His |
|  |  | Phe433 | Met |
| 407 | 30 | Arg130 | Leu |
|  |  | Phe433 | Ala |
| 408 | 30 | Arg130 | Leu |
|  |  | Phe433 | Leu |
| 409 | 30 | Arg130 | Leu |
|  |  | Phe433 | Val |
| 410 | 30 | Arg130 | Leu |
|  |  | Phe433 | Ile |
| 411 | 30 | Arg130 | Leu |
|  |  | Phe433 | Met |
| 412 | 30 | Arg130 | Ala |
|  |  | Phe433 | Ala |
| 413 | 30 | Arg130 | Ala |
|  |  | Phe433 | Leu |
| 414 | 30 | Arg130 | Ala |
|  |  | Phe433 | Val |
| 415 | 30 | Arg130 | Ala |
|  |  | Phe433 | Ile |
| 416 | 30 | Arg130 | Ala |
|  |  | Phe433 | Met |
| 417 | 30 | Arg130 | Val |
|  |  | Phe433 | Ala |
| 418 | 30 | Arg130 | Val |
|  |  | Phe433 | Leu |
| 419 | 30 | Arg130 | Val |
|  |  | Phe433 | Val |
| 420 | 30 | Arg130 | Val |
|  |  | Phe433 | Ile |
| 421 | 30 | Arg130 | Val |
|  |  | Phe433 | Met |
| 422 | 30 | Arg130 | Ile |
|  |  | Phe433 | Ala |
| 423 | 30 | Arg130 | Ile |
|  |  | Phe433 | Leu |
| 424 | 30 | Arg130 | Ile |
|  |  | Phe433 | Val |
| 425 | 30 | Arg130 | Ile |
|  |  | Phe433 | Ile |
| 426 | 30 | Arg130 | Ile |
|  |  | Phe433 | Met |
| 427 | 30 | Arg130 | Met |
|  |  | Phe433 | Ala |
| 428 | 30 | Arg130 | Met |
|  |  | Phe433 | Leu |
| 429 | 30 | Arg130 | Met |
|  |  | Phe433 | Val |
| 430 | 30 | Arg130 | Met |
|  |  | Phe433 | Ile |
| 431 | 30 | Arg130 | Met |
|  |  | Phe433 | Met |
| 432 | 30 | Arg130 | Tyr |
|  |  | Phe433 | Ala |
| 433 | 30 | Arg130 | Tyr |
|  |  | Phe433 | Leu |
| 434 | 30 | Arg130 | Tyr |
|  |  | Phe433 | Val |
| 435 | 30 | Arg130 | Tyr |
|  |  | Phe433 | Ile |
| 436 | 30 | Arg130 | Tyr |
|  |  | Phe433 | Met |
| 437 | 30 | Arg130 | Gly |
|  |  | Phe433 | Ala |
| 438 | 30 | Arg130 | Gly |
|  |  | Phe433 | Leu |
| 439 | 30 | Arg130 | Gly |
|  |  | Phe433 | Val |
| 440 | 30 | Arg130 | Gly |
|  |  | Phe433 | Ile |
| 441 | 30 | Arg130 | Gly |
|  |  | Phe433 | Met |
| 442 | 30 | Arg130 | Asn |
|  |  | Phe433 | Ala |
| 443 | 30 | Arg130 | Asn |
|  |  | Phe433 | Leu |
| 444 | 30 | Arg130 | Asn |
|  |  | Phe433 | Val |
| 445 | 30 | Arg130 | Asn |
|  |  | Phe433 | Ile |
| 446 | 30 | Arg130 | Asn |
|  |  | Phe433 | Met |
| 447 | 30 | Arg130 | Cys |
|  |  | Phe433 | Ala |
| 448 | 30 | Arg130 | Cys |
|  |  | Phe433 | Leu |
| 449 | 30 | Arg130 | Cys |
|  |  | Phe433 | Val |
| 450 | 30 | Arg130 | Cys |
|  |  | Phe433 | Ile |
| 451 | 30 | Arg130 | Cys |
|  |  | Phe433 | Met |
| 452 | 30 | Arg130 | Phe |
|  |  | Phe433 | Ala |
| 453 | 30 | Arg130 | Phe |
|  |  | Phe433 | Leu |
| 454 | 30 | Arg130 | Phe |
|  |  | Phe433 | Val |
| 455 | 30 | Arg130 | Phe |
|  |  | Phe433 | Ile |
| 456 | 30 | Arg130 | Phe |
|  |  | Phe433 | Met |
| 457 | 30 | Arg130 | Ser |
|  |  | Phe433 | Ala |
| 458 | 30 | Arg130 | Ser |
|  |  | Phe433 | Leu |
| 459 | 30 | Arg130 | Ser |
|  |  | Phe433 | Val |
| 460 | 30 | Arg130 | Ser |
|  |  | Phe433 | Ile |
| 461 | 30 | Arg130 | Ser |
|  |  | Phe433 | Met |
| 462 | 30 | Arg130 | Thr |
|  |  | Phe433 | Ala |
| 463 | 30 | Arg130 | Thr |
|  |  | Phe433 | Leu |
| 464 | 30 | Arg130 | Thr |
|  |  | Phe433 | Val |
| 465 | 30 | Arg130 | Thr |
|  |  | Phe433 | Ile |
| 466 | 30 | Arg130 | Thr |
|  |  | Phe433 | Met |
| 467 | 30 | Arg130 | Gln |
|  |  | Phe433 | Ala |
| 468 | 30 | Arg130 | Gln |
|  |  | Phe433 | Leu |
| 469 | 30 | Arg130 | Gln |
|  |  | Phe433 | Val |
| 470 | 30 | Arg130 | Gln |
|  |  | Phe433 | Ile |

TABLE 3b-continued

SEQ ID NO: 2, SEQ ID NO: 4, SEQ ID NO: 24, SEQ ID NO: 30, SEQ ID NO: 38, SEQ ID NO: 46, SEQ ID NO: 48, (combined amino acid substitutions)

| Combination Number | SEQ ID NO: | Key amino acid position combination | Preferred Substitution |
|---|---|---|---|
| 471 | 30 | Arg130 | Gln |
|  |  | Phe433 | Met |
| 472 | 30 | Arg130 | His |
|  |  | Phe433 | Ala |
| 473 | 30 | Arg130 | His |
|  |  | Phe433 | Leu |
| 474 | 30 | Arg130 | His |
|  |  | Phe433 | Val |
| 475 | 30 | Arg130 | His |
|  |  | Phe433 | Ile |
| 476 | 30 | Arg130 | His |
|  |  | Phe433 | Met |
| 477 | 38 | Arg98 | Leu |
|  |  | Phe392 | Ala |
| 478 | 38 | Arg98 | Leu |
|  |  | Phe392 | Leu |
| 479 | 38 | Arg98 | Leu |
|  |  | Phe392 | Val |
| 480 | 38 | Arg98 | Leu |
|  |  | Phe392 | Ile |
| 481 | 38 | Arg98 | Leu |
|  |  | Phe392 | Met |
| 482 | 38 | Arg98 | Ala |
|  |  | Phe392 | Ala |
| 483 | 38 | Arg98 | Ala |
|  |  | Phe392 | Leu |
| 484 | 38 | Arg98 | Ala |
|  |  | Phe392 | Val |
| 485 | 38 | Arg98 | Ala |
|  |  | Phe392 | Ile |
| 486 | 38 | Arg98 | Ala |
|  |  | Phe392 | Met |
| 487 | 38 | Arg98 | Val |
|  |  | Phe392 | Ala |
| 488 | 38 | Arg98 | Val |
|  |  | Phe392 | Leu |
| 489 | 38 | Arg98 | Val |
|  |  | Phe392 | Val |
| 490 | 38 | Arg98 | Val |
|  |  | Phe392 | Ile |
| 491 | 38 | Arg98 | Val |
|  |  | Phe392 | Met |
| 492 | 38 | Arg98 | Ile |
|  |  | Phe392 | Ala |
| 493 | 38 | Arg98 | Ile |
|  |  | Phe392 | Leu |
| 494 | 38 | Arg98 | Ile |
|  |  | Phe392 | Val |
| 495 | 38 | Arg98 | Ile |
|  |  | Phe392 | Ile |
| 496 | 38 | Arg98 | Ile |
|  |  | Phe392 | Met |
| 497 | 38 | Arg98 | Met |
|  |  | Phe392 | Ala |
| 498 | 38 | Arg98 | Met |
|  |  | Phe392 | Leu |
| 499 | 38 | Arg98 | Met |
|  |  | Phe392 | Val |
| 500 | 38 | Arg98 | Met |
|  |  | Phe392 | Ile |
| 501 | 38 | Arg98 | Met |
|  |  | Phe392 | Met |
| 502 | 38 | Arg98 | Tyr |
|  |  | Phe392 | Ala |
| 503 | 38 | Arg98 | Tyr |
|  |  | Phe392 | Leu |
| 504 | 38 | Arg98 | Tyr |
|  |  | Phe392 | Val |
| 505 | 38 | Arg98 | Tyr |
|  |  | Phe392 | Ile |
| 506 | 38 | Arg98 | Tyr |
|  |  | Phe392 | Met |
| 507 | 38 | Arg98 | Gly |
|  |  | Phe392 | Ala |
| 508 | 38 | Arg98 | Gly |
|  |  | Phe392 | Leu |
| 509 | 38 | Arg98 | Gly |
|  |  | Phe392 | Val |
| 510 | 38 | Arg98 | Gly |
|  |  | Phe392 | Ile |
| 511 | 38 | Arg98 | Gly |
|  |  | Phe392 | Met |
| 512 | 38 | Arg98 | Asn |
|  |  | Phe392 | Ala |
| 513 | 38 | Arg98 | Asn |
|  |  | Phe392 | Leu |
| 514 | 38 | Arg98 | Asn |
|  |  | Phe392 | Val |
| 515 | 38 | Arg98 | Asn |
|  |  | Phe392 | Ile |
| 516 | 38 | Arg98 | Asn |
|  |  | Phe392 | Met |
| 517 | 38 | Arg98 | Cys |
|  |  | Phe392 | Ala |
| 518 | 38 | Arg98 | Cys |
|  |  | Phe392 | Leu |
| 519 | 38 | Arg98 | Cys |
|  |  | Phe392 | Val |
| 520 | 38 | Arg98 | Cys |
|  |  | Phe392 | Ile |
| 521 | 38 | Arg98 | Cys |
|  |  | Phe392 | Met |
| 522 | 38 | Arg98 | Phe |
|  |  | Phe392 | Ala |
| 523 | 38 | Arg98 | Phe |
|  |  | Phe392 | Leu |
| 524 | 38 | Arg98 | Phe |
|  |  | Phe392 | Val |
| 525 | 38 | Arg98 | Phe |
|  |  | Phe392 | Ile |
| 526 | 38 | Arg98 | Phe |
|  |  | Phe392 | Met |
| 527 | 38 | Arg98 | Ser |
|  |  | Phe392 | Ala |
| 528 | 38 | Arg98 | Ser |
|  |  | Phe392 | Leu |
| 529 | 38 | Arg98 | Ser |
|  |  | Phe392 | Val |
| 530 | 38 | Arg98 | Ser |
|  |  | Phe392 | Ile |
| 531 | 38 | Arg98 | Ser |
|  |  | Phe392 | Met |
| 532 | 38 | Arg98 | Thr |
|  |  | Phe392 | Ala |
| 533 | 38 | Arg98 | Thr |
|  |  | Phe392 | Leu |
| 534 | 38 | Arg98 | Thr |
|  |  | Phe392 | Val |
| 535 | 38 | Arg98 | Thr |
|  |  | Phe392 | Ile |
| 536 | 38 | Arg98 | Thr |
|  |  | Phe392 | Met |
| 537 | 38 | Arg98 | Gln |
|  |  | Phe392 | Ala |
| 538 | 38 | Arg98 | Gln |
|  |  | Phe392 | Leu |
| 539 | 38 | Arg98 | Gln |
|  |  | Phe392 | Val |
| 540 | 38 | Arg98 | Gln |
|  |  | Phe392 | Ile |
| 541 | 38 | Arg98 | Gln |
|  |  | Phe392 | Met |
| 542 | 38 | Arg98 | His |
|  |  | Phe392 | Ala |

TABLE 3b-continued

SEQ ID NO: 2, SEQ ID NO: 4, SEQ ID NO: 24, SEQ ID NO: 30, SEQ ID NO: 38, SEQ ID NO: 46, SEQ ID NO: 48, (combined amino acid substitutions)

| Combination Number | SEQ ID NO: | Key amino acid position combination | Preferred Substitution |
|---|---|---|---|
| 543 | 38 | Arg98 | His |
|  |  | Phe392 | Leu |
| 544 | 38 | Arg98 | His |
|  |  | Phe392 | Val |
| 545 | 38 | Arg98 | His |
|  |  | Phe392 | Ile |
| 546 | 38 | Arg98 | His |
|  |  | Phe392 | Met |
| 547 | 46 | Arg139 | Leu |
|  |  | Phe465 | Ala |
| 548 | 46 | Arg139 | Leu |
|  |  | Phe465 | Leu |
| 549 | 46 | Arg139 | Leu |
|  |  | Phe465 | Val |
| 550 | 46 | Arg139 | Leu |
|  |  | Phe465 | Ile |
| 551 | 46 | Arg139 | Leu |
|  |  | Phe465 | Met |
| 552 | 46 | Arg139 | Ala |
|  |  | Phe465 | Ala |
| 553 | 46 | Arg139 | Ala |
|  |  | Phe465 | Leu |
| 554 | 46 | Arg139 | Ala |
|  |  | Phe465 | Val |
| 555 | 46 | Arg139 | Ala |
|  |  | Phe465 | Ile |
| 556 | 46 | Arg139 | Ala |
|  |  | Phe465 | Met |
| 557 | 46 | Arg139 | Val |
|  |  | Phe465 | Ala |
| 558 | 46 | Arg139 | Val |
|  |  | Phe465 | Leu |
| 559 | 46 | Arg139 | Val |
|  |  | Phe465 | Val |
| 560 | 46 | Arg139 | Val |
|  |  | Phe465 | Ile |
| 561 | 46 | Arg139 | Val |
|  |  | Phe465 | Met |
| 562 | 46 | Arg139 | Ile |
|  |  | Phe465 | Ala |
| 563 | 46 | Arg139 | Ile |
|  |  | Phe465 | Leu |
| 564 | 46 | Arg139 | Ile |
|  |  | Phe465 | Val |
| 565 | 46 | Arg139 | Ile |
|  |  | Phe465 | Ile |
| 566 | 46 | Arg139 | Ile |
|  |  | Phe465 | Met |
| 567 | 46 | Arg139 | Met |
|  |  | Phe465 | Ala |
| 568 | 46 | Arg139 | Met |
|  |  | Phe465 | Leu |
| 569 | 46 | Arg139 | Met |
|  |  | Phe465 | Val |
| 570 | 46 | Arg139 | Met |
|  |  | Phe465 | Ile |
| 571 | 46 | Arg139 | Met |
|  |  | Phe465 | Met |
| 572 | 46 | Arg139 | Tyr |
|  |  | Phe465 | Ala |
| 573 | 46 | Arg139 | Tyr |
|  |  | Phe465 | Leu |
| 574 | 46 | Arg139 | Tyr |
|  |  | Phe465 | Val |
| 575 | 46 | Arg139 | Tyr |
|  |  | Phe465 | Ile |
| 576 | 46 | Arg139 | Tyr |
|  |  | Phe465 | Met |
| 577 | 46 | Arg139 | Gly |
|  |  | Phe465 | Ala |
| 578 | 46 | Arg139 | Gly |
|  |  | Phe465 | Leu |
| 579 | 46 | Arg139 | Gly |
|  |  | Phe465 | Val |
| 580 | 46 | Arg139 | Gly |
|  |  | Phe465 | Ile |
| 581 | 46 | Arg139 | Gly |
|  |  | Phe465 | Met |
| 582 | 46 | Arg139 | Asn |
|  |  | Phe465 | Ala |
| 583 | 46 | Arg139 | Asn |
|  |  | Phe465 | Leu |
| 584 | 46 | Arg139 | Asn |
|  |  | Phe465 | Val |
| 585 | 46 | Arg139 | Asn |
|  |  | Phe465 | Ile |
| 586 | 46 | Arg139 | Asn |
|  |  | Phe465 | Met |
| 587 | 46 | Arg139 | Cys |
|  |  | Phe465 | Ala |
| 588 | 46 | Arg139 | Cys |
|  |  | Phe465 | Leu |
| 589 | 46 | Arg139 | Cys |
|  |  | Phe465 | Val |
| 590 | 46 | Arg139 | Cys |
|  |  | Phe465 | Ile |
| 591 | 46 | Arg139 | Cys |
|  |  | Phe465 | Met |
| 592 | 46 | Arg139 | Phe |
|  |  | Phe465 | Ala |
| 593 | 46 | Arg139 | Phe |
|  |  | Phe465 | Leu |
| 594 | 46 | Arg139 | Phe |
|  |  | Phe465 | Val |
| 595 | 46 | Arg139 | Phe |
|  |  | Phe465 | Ile |
| 596 | 46 | Arg139 | Phe |
|  |  | Phe465 | Met |
| 597 | 46 | Arg139 | Ser |
|  |  | Phe465 | Ala |
| 598 | 46 | Arg139 | Ser |
|  |  | Phe465 | Leu |
| 599 | 46 | Arg139 | Ser |
|  |  | Phe465 | Val |
| 600 | 46 | Arg139 | Ser |
|  |  | Phe465 | Ile |
| 601 | 46 | Arg139 | Ser |
|  |  | Phe465 | Met |
| 602 | 46 | Arg139 | Thr |
|  |  | Phe465 | Ala |
| 603 | 46 | Arg139 | Thr |
|  |  | Phe465 | Leu |
| 604 | 46 | Arg139 | Thr |
|  |  | Phe465 | Val |
| 605 | 46 | Arg139 | Thr |
|  |  | Phe465 | Ile |
| 606 | 46 | Arg139 | Thr |
|  |  | Phe465 | Met |
| 607 | 46 | Arg139 | Gln |
|  |  | Phe465 | Ala |
| 608 | 46 | Arg139 | Gln |
|  |  | Phe465 | Leu |
| 609 | 46 | Arg139 | Gln |
|  |  | Phe465 | Val |
| 610 | 46 | Arg139 | Gln |
|  |  | Phe465 | Ile |
| 611 | 46 | Arg139 | Gln |
|  |  | Phe465 | Met |
| 612 | 46 | Arg139 | His |
|  |  | Phe465 | Ala |
| 613 | 46 | Arg139 | His |
|  |  | Phe465 | Leu |
| 614 | 46 | Arg139 | His |
|  |  | Phe465 | Val |

TABLE 3b-continued

SEQ ID NO: 2, SEQ ID NO: 4, SEQ ID NO: 24, SEQ ID NO: 30, SEQ ID NO: 38, SEQ ID NO: 46, SEQ ID NO: 48, (combined amino acid substitutions)

| Combination Number | SEQ ID NO: | Key amino acid position combination | Preferred Substitution |
|---|---|---|---|
| 615 | 46 | Arg139 | His |
| | | Phe465 | Ile |
| 616 | 46 | Arg139 | His |
| | | Phe465 | Met |
| 617 | 48 | Arg157 | Leu |
| | | Tyr439 | Ala |
| 618 | 48 | Arg157 | Leu |
| | | Tyr439 | Leu |
| 619 | 48 | Arg157 | Leu |
| | | Tyr439 | Val |
| 620 | 48 | Arg157 | Leu |
| | | Tyr439 | Ile |
| 621 | 48 | Arg157 | Leu |
| | | Tyr439 | Met |
| 622 | 48 | Arg157 | Ala |
| | | Tyr439 | Ala |
| 623 | 48 | Arg157 | Ala |
| | | Tyr439 | Leu |
| 624 | 48 | Arg157 | Ala |
| | | Tyr439 | Val |
| 625 | 48 | Arg157 | Ala |
| | | Tyr439 | Ile |
| 626 | 48 | Arg157 | Ala |
| | | Tyr439 | Met |
| 627 | 48 | Arg157 | Val |
| | | Tyr439 | Ala |
| 628 | 48 | Arg157 | Val |
| | | Tyr439 | Leu |
| 629 | 48 | Arg157 | Val |
| | | Tyr439 | Val |
| 630 | 48 | Arg157 | Val |
| | | Tyr439 | Ile |
| 631 | 48 | Arg157 | Val |
| | | Tyr439 | Met |
| 632 | 48 | Arg157 | Ile |
| | | Tyr439 | Ala |
| 633 | 48 | Arg157 | Ile |
| | | Tyr439 | Leu |
| 634 | 48 | Arg157 | Ile |
| | | Tyr439 | Val |
| 635 | 48 | Arg157 | Ile |
| | | Tyr439 | Ile |
| 636 | 48 | Arg157 | Ile |
| | | Tyr439 | Met |
| 637 | 48 | Arg157 | Met |
| | | Tyr439 | Ala |
| 638 | 48 | Arg157 | Met |
| | | Tyr439 | Leu |
| 639 | 48 | Arg157 | Met |
| | | Tyr439 | Val |
| 640 | 48 | Arg157 | Met |
| | | Tyr439 | Ile |
| 641 | 48 | Arg157 | Met |
| | | Tyr439 | Met |
| 642 | 48 | Arg157 | Tyr |
| | | Tyr439 | Ala |
| 643 | 48 | Arg157 | Tyr |
| | | Tyr439 | Leu |
| 644 | 48 | Arg157 | Tyr |
| | | Tyr439 | Val |
| 645 | 48 | Arg157 | Tyr |
| | | Tyr439 | Ile |
| 646 | 48 | Arg157 | Tyr |
| | | Tyr439 | Met |
| 647 | 48 | Arg157 | Gly |
| | | Tyr439 | Ala |
| 648 | 48 | Arg157 | Gly |
| | | Tyr439 | Leu |
| 649 | 48 | Arg157 | Gly |
| | | Tyr439 | Val |
| 650 | 48 | Arg157 | Gly |
| | | Tyr439 | Ile |
| 651 | 48 | Arg157 | Gly |
| | | Tyr439 | Met |
| 652 | 48 | Arg157 | Asn |
| | | Tyr439 | Ala |
| 653 | 48 | Arg157 | Asn |
| | | Tyr439 | Leu |
| 654 | 48 | Arg157 | Asn |
| | | Tyr439 | Val |
| 655 | 48 | Arg157 | Asn |
| | | Tyr439 | Ile |
| 656 | 48 | Arg157 | Asn |
| | | Tyr439 | Met |
| 657 | 48 | Arg157 | Cys |
| | | Tyr439 | Ala |
| 658 | 48 | Arg157 | Cys |
| | | Tyr439 | Leu |
| 659 | 48 | Arg157 | Cys |
| | | Tyr439 | Val |
| 660 | 48 | Arg157 | Cys |
| | | Tyr439 | Ile |
| 661 | 48 | Arg157 | Cys |
| | | Tyr439 | Met |
| 662 | 48 | Arg157 | Phe |
| | | Tyr439 | Ala |
| 663 | 48 | Arg157 | Phe |
| | | Tyr439 | Leu |
| 664 | 48 | Arg157 | Phe |
| | | Tyr439 | Val |
| 665 | 48 | Arg157 | Phe |
| | | Tyr439 | Ile |
| 666 | 48 | Arg157 | Phe |
| | | Tyr439 | Met |
| 667 | 48 | Arg157 | Ser |
| | | Tyr439 | Ala |
| 668 | 48 | Arg157 | Ser |
| | | Tyr439 | Leu |
| 669 | 48 | Arg157 | Ser |
| | | Tyr439 | Val |
| 670 | 48 | Arg157 | Ser |
| | | Tyr439 | Ile |
| 671 | 48 | Arg157 | Ser |
| | | Tyr439 | Met |
| 672 | 48 | Arg157 | Thr |
| | | Tyr439 | Ala |
| 673 | 48 | Arg157 | Thr |
| | | Tyr439 | Leu |
| 674 | 48 | Arg157 | Thr |
| | | Tyr439 | Val |
| 675 | 48 | Arg157 | Thr |
| | | Tyr439 | Ile |
| 676 | 48 | Arg157 | Thr |
| | | Tyr439 | Met |
| 677 | 48 | Arg157 | Gln |
| | | Tyr439 | Ala |
| 678 | 48 | Arg157 | Gln |
| | | Tyr439 | Leu |
| 679 | 48 | Arg157 | Gln |
| | | Tyr439 | Val |
| 680 | 48 | Arg157 | Gln |
| | | Tyr439 | Ile |
| 681 | 48 | Arg157 | Gln |
| | | Tyr439 | Met |
| 682 | 48 | Arg157 | His |
| | | Tyr439 | Ala |
| 683 | 48 | Arg157 | His |
| | | Tyr439 | Leu |
| 684 | 48 | Arg157 | His |
| | | Tyr439 | Val |

TABLE 3b-continued

SEQ ID NO: 2, SEQ ID NO: 4, SEQ ID NO: 24, SEQ ID NO: 30, SEQ ID NO: 38, SEQ ID NO: 46, SEQ ID NO: 48, (combined amino acid substitutions)

| Combination Number | SEQ ID NO: | Key amino acid position combination | Preferred Substitution |
|---|---|---|---|
| 685 | 48 | Arg157 | His |
|  |  | Tyr439 | Ile |
| 686 | 48 | Arg157 | His |
|  |  | Tyr439 | Met |

It is to be understood that any amino acid besides the ones mentioned in the above tables 3 could be used as a substitutent. Assays to test for the functionality of such mutants are readily available in the art, and respectively, described in the Example section of the present invention.

In a preferred embodiment, the mutated PPO refers to a polypeptide of SEQ ID NO: 2 or SEQ ID NO: 4 in which the amino acid sequence differs from an amino acid sequence of SEQ ID NO: 2 or SEQ ID NO: 4 at position 128, and/or position 420.

Examples of differences at these amino acid positions include, but are not limited to, one or more of the following:

the amino acid at or corresponding to position 128 of SEQ ID NO:2 is other than Arginine;

the amino acid at or corresponding to position 420 of SEQ ID NO:2 is other than Phenylalanine, In some embodiments, the mutated PPO enzyme of SEQ ID NO: 2 or SEQ ID NO: 4 comprises one or more of the following:

the amino acid at or corresponding to position 128 of SEQ ID NO:2 is Leu, Ala, Val, or Ile;

the amino acid at or corresponding to position 420 of SEQ ID NO:2 is Val, Met, Ala, Ile, or Leu;

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Leu, Ala, Val, Ile, Met, Tyr, Gly, Asn, Cys, Phe, Ser, Thr, Gln, or His, and/or the amino acid at or corresponding to position 420 of SEQ ID NO:2 is Ala, Leu, Val, Ile, or Met.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Leu, and the amino acid at or corresponding to position 420 of SEQ ID NO:2 is Ala.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Leu, and the amino acid at or corresponding to position 420 of SEQ ID NO:2 is Leu.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Leu, and the amino acid at or corresponding to position 420 of SEQ ID NO:2 is Val.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Leu, and the amino acid at or corresponding to position 420 of SEQ ID NO:2 is Ile.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Leu, and the amino acid at or corresponding to position 420 of SEQ ID NO:2 is Met.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Ala, and the amino acid at or corresponding to position 420 of SEQ ID NO:2 is Ala.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Ala, and the amino acid at or corresponding to position 420 of SEQ ID NO:2 is Leu.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Ala, and the amino acid at or corresponding to position 420 of SEQ ID NO:2 is Val.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Ala, and the amino acid at or corresponding to position 420 of SEQ ID NO:2 is Ile.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Ala, and the amino acid at or corresponding to position 420 of SEQ ID NO:2 is Met.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Val, and the amino acid at or corresponding to position 420 of SEQ ID NO:2 is Ala.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Val, and the amino acid at or corresponding to position 420 of SEQ ID NO:2 is Leu.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Val, and the amino acid at or corresponding to position 420 of SEQ ID NO:2 is Val.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Val, and the amino acid at or corresponding to position 420 of SEQ ID NO:2 is Ile.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Val, and the amino acid at or corresponding to position 420 of SEQ ID NO:2 is Met.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Ile, and the amino acid at or corresponding to position 420 of SEQ ID NO:2 is Ala.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Ile, and the amino acid at or corresponding to position 420 of SEQ ID NO:2 is Leu.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Ile, and the amino acid at or corresponding to position 420 of SEQ ID NO:2 is Val.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Ile, and the amino acid at or corresponding to position 420 of SEQ ID NO:2 is Ile.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Ile, and the amino acid at or corresponding to position 420 of SEQ ID NO:2 is Met.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Met, and the amino acid at or corresponding to position 420 of SEQ ID NO:2 is Ala.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Met, and the amino acid at or corresponding to position 420 of SEQ ID NO:2 is Leu.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Met, and the amino acid at or corresponding to position 420 of SEQ ID NO:2 is Val.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Met, and the amino acid at or corresponding to position 420 of SEQ ID NO:2 is Ile.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Met, and the amino acid at or corresponding to position 420 of SEQ ID NO:2 is Met.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Tyr, and the amino acid at or corresponding to position 420 of SEQ ID NO:2 is Ala.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Tyr, and the amino acid at or corresponding to position 420 of SEQ ID NO:2 is Leu.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Tyr, and the amino acid at or corresponding to position 420 of SEQ ID NO:2 is Val.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Tyr, and the amino acid at or corresponding to position 420 of SEQ ID NO:2 is Ile.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Tyr, and the amino acid at or corresponding to position 420 of SEQ ID NO:2 is Met.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Gly, and the amino acid at or corresponding to position 420 of SEQ ID NO:2 is Ala.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Gly, and the amino acid at or corresponding to position 420 of SEQ ID NO:2 is Leu.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Gly, and the amino acid at or corresponding to position 420 of SEQ ID NO:2 is Val.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Gly, and the amino acid at or corresponding to position 420 of SEQ ID NO:2 is Ile.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Gly, and the amino acid at or corresponding to position 420 of SEQ ID NO:2 is Met.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Asn, and the amino acid at or corresponding to position 420 of SEQ ID NO:2 is Ala.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Asn, and the amino acid at or corresponding to position 420 of SEQ ID NO:2 is Leu.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Asn, and the amino acid at or corresponding to position 420 of SEQ ID NO:2 is Val.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Asn, and the amino acid at or corresponding to position 420 of SEQ ID NO:2 is Ile.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Asn, and the amino acid at or corresponding to position 420 of SEQ ID NO:2 is Met.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Cys, and the amino acid at or corresponding to position 420 of SEQ ID NO:2 is Ala.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Cys, and the amino acid at or corresponding to position 420 of SEQ ID NO:2 is Leu.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Cys, and the amino acid at or corresponding to position 420 of SEQ ID NO:2 is Val.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Cys, and the amino acid at or corresponding to position 420 of SEQ ID NO:2 is Ile.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Cys, and the amino acid at or corresponding to position 420 of SEQ ID NO:2 is Met.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Phe, and the amino acid at or corresponding to position 420 of SEQ ID NO:2 is Ala.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Phe, and the amino acid at or corresponding to position 420 of SEQ ID NO:2 is Leu.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Phe, and the amino acid at or corresponding to position 420 of SEQ ID NO:2 is Val.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Phe, and the amino acid at or corresponding to position 420 of SEQ ID NO:2 is Ile.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Phe, and the amino acid at or corresponding to position 420 of SEQ ID NO:2 is Met.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Ser, and the amino acid at or corresponding to position 420 of SEQ ID NO:2 is Ala.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Ser, and the amino acid at or corresponding to position 420 of SEQ ID NO:2 is Leu.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Ser, and the amino acid at or corresponding to position 420 of SEQ ID NO:2 is Val.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Ser, and the amino acid at or corresponding to position 420 of SEQ ID NO:2 is Ile.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Ser, and the amino acid at or corresponding to position 420 of SEQ ID NO:2 is Met.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Thr, and the amino acid at or corresponding to position 420 of SEQ ID NO:2 is Ala.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Thr, and the amino acid at or corresponding to position 420 of SEQ ID NO:2 is Leu.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Thr, and the amino acid at or corresponding to position 420 of SEQ ID NO:2 is Val.

In another preferred embodiment, the mutated PPO comprises a sequence of SEQ ID NO: 2, a variant, derivative, orthologue, paralogue or homologue thereof, in which:

the amino acid at or corresponding to position 128 of SEQ ID NO:2 is Thr, and the amino acid at or corresponding to position 420 of SEQ ID NO:2 is Ile.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Thr, and the amino acid at or corresponding to position 420 of SEQ ID NO:2 is Met.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Gln, and the amino acid at or corresponding to position 420 of SEQ ID NO:2 is Ala.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Gln, and the amino acid at or corresponding to position 420 of SEQ ID NO:2 is Leu.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Gln, and the amino acid at or corresponding to position 420 of SEQ ID NO:2 is Val.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Gln, and the amino acid at or corresponding to position 420 of SEQ ID NO:2 is Ile.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is Gln, and the amino acid at or corresponding to position 420 of SEQ ID NO:2 is Met.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is His, and the amino acid at or corresponding to position 420 of SEQ ID NO:2 is Ala.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is His, and the amino acid at or corresponding to position 420 of SEQ ID NO:2 is Leu.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is His, and the amino acid at or corresponding to position 420 of SEQ ID NO:2 is Val.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is His, and the amino acid at or corresponding to position 420 of SEQ ID NO:2 is Ile.

In another preferred embodiment, the mutated PPO comprises a sequence of SEQ ID NO: 2, a variant, derivative, orthologue, paralogue or homologue thereof, in which:
the amino acid at or corresponding to position 128 of SEQ ID NO:2 is His, and the amino acid at or corresponding to position 420 of SEQ ID NO:2 is Met.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Leu, Ala, Val, Ile, Met, Tyr, Gly, Asn, Cys, Phe, Ser, Thr, Gln, His, and the amino acid at or corresponding to position 420 of SEQ ID NO:2 is Ala, Leu, Val, Ile, Met.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Leu, and the amino acid at or corresponding to position 420 of SEQ ID NO:2 is Ala.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Leu, and the amino acid at or corresponding to position 420 of SEQ ID NO:2 is Leu.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Leu, and the amino acid at or corresponding to position 420 of SEQ ID NO:2 is Val.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Leu, and the amino acid at or corresponding to position 420 of SEQ ID NO:2 is Ile.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Leu, and the amino acid at or corresponding to position 420 of SEQ ID NO:2 is Met.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Ala, and the amino acid at or corresponding to position 420 of SEQ ID NO:2 is Ala.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Ala, and the amino acid at or corresponding to position 420 of SEQ ID NO:2 is Leu.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Ala, and the amino acid at or corresponding to position 420 of SEQ ID NO:2 is Val.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Ala, and the amino acid at or corresponding to position 420 of SEQ ID NO:2 is Ile.

In another preferred embodiment, the mutated PPO comprises a sequence of SEQ ID NO: 4, a variant, derivative, orthologue, paralogue or homologue thereof, in which:

the amino acid at or corresponding to position 128 of SEQ ID NO:2 is Ala, and the amino acid at or corresponding to position 420 of SEQ ID NO:2 is Met.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Val, and the amino acid at or corresponding to position 420 of SEQ ID NO:2 is Ala.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Val, and the amino acid at or corresponding to position 420 of SEQ ID NO:2 is Leu.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Val, and the amino acid at or corresponding to position 420 of SEQ ID NO:2 is Val.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Val, and the amino acid at or corresponding to position 420 of SEQ ID NO:2 is Ile.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Val, and the amino acid at or corresponding to position 420 of SEQ ID NO:2 is Met.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Ile, and the amino acid at or corresponding to position 420 of SEQ ID NO:2 is Ala.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Ile, and the amino acid at or corresponding to position 420 of SEQ ID NO:2 is Leu.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Ile, and the amino acid at or corresponding to position 420 of SEQ ID NO:2 is Val.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Ile, and the amino acid at or corresponding to position 420 of SEQ ID NO:2 is Ile.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Ile, and the amino acid at or corresponding to position 420 of SEQ ID NO:2 is Met.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Met, and the amino acid at or corresponding to position 420 of SEQ ID NO:2 is Ala.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Met, and the amino acid at or corresponding to position 420 of SEQ ID NO:2 is Leu.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Met, and the amino acid at or corresponding to position 420 of SEQ ID NO:2 is Val.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Met, and the amino acid at or corresponding to position 420 of SEQ ID NO:2 is Ile.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Met, and the amino acid at or corresponding to position 420 of SEQ ID NO:2 is Met.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Tyr, and the amino acid at or corresponding to position 420 of SEQ ID NO:2 is Ala.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Tyr, and the amino acid at or corresponding to position 420 of SEQ ID NO:2 is Leu.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Tyr, and the amino acid at or corresponding to position 420 of SEQ ID NO:2 is Val.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Tyr, and the amino acid at or corresponding to position 420 of SEQ ID NO:2 is Ile.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Tyr, and the amino acid at or corresponding to position 420 of SEQ ID NO:2 is Met.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Gly, and the amino acid at or corresponding to position 420 of SEQ ID NO:2 is Ala.

In another preferred embodiment, the mutated PPO comprises a sequence of SEQ ID NO: 4, a variant, derivative, orthologue, paralogue or homologue thereof, in which:

the amino acid at or corresponding to position 128 of SEQ ID NO:2 is Gly, and the amino acid at or corresponding to position 420 of SEQ ID NO:2 is Leu.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Gly, and the amino acid at or corresponding to position 420 of SEQ ID NO:2 is Val.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Gly, and the amino acid at or corresponding to position 420 of SEQ ID NO:2 is Ile.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Gly, and the amino acid at or corresponding to position 420 of SEQ ID NO:2 is Met.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Asn, and the amino acid at or corresponding to position 420 of SEQ ID NO:2 is Ala.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Asn, and the amino acid at or corresponding to position 420 of SEQ ID NO:2 is Leu.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Asn, and the amino acid at or corresponding to position 420 of SEQ ID NO:2 is Val.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Asn, and the amino acid at or corresponding to position 420 of SEQ ID NO:2 is Ile.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Asn, and the amino acid at or corresponding to position 420 of SEQ ID NO:2 is Met.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Cys, and the amino acid at or corresponding to position 420 of SEQ ID NO:2 is Ala.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Cys, and the amino acid at or corresponding to position 420 of SEQ ID NO:2 is Leu.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Cys, and the amino acid at or corresponding to position 420 of SEQ ID NO:2 is Val.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Cys, and the amino acid at or corresponding to position 420 of SEQ ID NO:2 is Ile.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Cys, and the amino acid at or corresponding to position 420 of SEQ ID NO:2 is Met.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Phe, and the amino acid at or corresponding to position 420 of SEQ ID NO:2 is Ala.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Phe, and the amino acid at or corresponding to position 420 of SEQ ID NO:2 is Leu.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Phe, and the amino acid at or corresponding to position 420 of SEQ ID NO:2 is Val.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Phe, and the amino acid at or corresponding to position 420 of SEQ ID NO:2 is Ile.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Phe, and the amino acid at or corresponding to position 420 of SEQ ID NO:2 is Met.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Ser, and the amino acid at or corresponding to position 420 of SEQ ID NO:2 is Ala.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Ser, and the amino acid at or corresponding to position 420 of SEQ ID NO:2 is Leu.

In another preferred embodiment, the mutated PPO comprises a sequence of SEQ ID NO: 4, a variant, derivative, orthologue, paralogue or homologue thereof, in which:
the amino acid at or corresponding to position 128 of SEQ ID NO:2 is Ser, and the amino acid at or corresponding to position 420 of SEQ ID NO:2 is Val.

In another preferred embodiment, the mutated PPO comprises a sequence of SEQ ID NO: 4, a variant, derivative, orthologue, paralogue or homologue thereof, in which:

the amino acid at or corresponding to position 128 of SEQ ID NO:2 is Ser, and the amino acid at or corresponding to position 420 of SEQ ID NO:2 is Ile.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is Ser, and the amino acid at or corresponding to position 420 of SEQ ID NO:2 is Met.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is Thr, and the amino acid at or corresponding to position 420 of SEQ ID NO:2 is Ala.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is Thr, and the amino acid at or corresponding to position 420 of SEQ ID NO:2 is Leu.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is Thr, and the amino acid at or corresponding to position 420 of SEQ ID NO:2 is Val.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is Thr, and the amino acid at or corresponding to position 420 of SEQ ID NO:2 is Ile.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is Thr, and the amino acid at or corresponding to position 420 of SEQ ID NO:2 is Met.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is Gin, and the amino acid at or corresponding to position 420 of SEQ ID NO:2 is Ala.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is Gin, and the amino acid at or corresponding to position 420 of SEQ ID NO:2 is Leu.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is Gin, and the amino acid at or corresponding to position 420 of SEQ ID NO:2 is Val.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is Gin, and the amino acid at or corresponding to position 420 of SEQ ID NO:2 is Ile.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is Gin, and the amino acid at or corresponding to position 420 of SEQ ID NO:2 is Met.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is His, and the amino acid at or corresponding to position 420 of SEQ ID NO:2 is Ala.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is His, and the amino acid at or corresponding to position 420 of SEQ ID NO:2 is Leu.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is His, and the amino acid at or corresponding to position 420 of SEQ ID NO:2 is Val.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is His, and the amino acid at or corresponding to position 420 of SEQ ID NO:2 is Ile.

In another preferred embodiment, the mutated PPO comprises a sequence of SEQ ID NO: 4, a variant, derivative, orthologue, paralogue or homologue thereof, in which: the amino acid at or corresponding to position 128 of SEQ ID NO:2 is His, and the amino acid at or corresponding to position 420 of SEQ ID NO:2 is Met.

In a particularly preferred embodiment, the mutated PPO comprises a sequence of SEQ ID NO: 2, or SEQ ID NO: 4, a variant, derivative, orthologue, paralogue or homologue thereof, in which: the amino acid at or corresponding to position 128 of SEQ ID NO:2 is Ala, and the amino acid at or corresponding to position 420 of SEQ ID NO:2 is Met.

In another particularly preferred embodiment, the mutated PPO comprises a sequence of SEQ ID NO: 2, or SEQ ID NO: 4, a variant, derivative, orthologue, paralogue or homologue thereof, in which: the amino acid at or corresponding to position 128 of SEQ ID NO:2 is Ala, and the amino acid at or corresponding to position 420 of SEQ ID NO:2 is Ile.

In another particularly preferred embodiment, the mutated PPO comprises a sequence of SEQ ID NO: 2, or SEQ ID NO: 4, a variant, derivative, orthologue, paralogue or homologue thereof, in which: the amino acid at or corresponding to position 128 of SEQ ID NO:2 is Ala, and the amino acid at or corresponding to position 420 of SEQ ID NO:2 is Leu.

In an especially preferred embodiment, the mutated PPO comprises a sequence of SEQ ID NO: 2, or SEQ ID NO: 4, a variant, derivative, orthologue, paralogue or homologue thereof, in which: the amino acid at or corresponding to position 128 of SEQ ID NO:2 is Ala, and the amino acid at or corresponding to position 420 of SEQ ID NO:2 is Val.

In another especially preferred embodiment, the mutated PPO comprises a sequence of SEQ ID NO: 2, or SEQ ID NO: 4, a variant, derivative, orthologue, paralogue or homologue thereof, in which the amino acid at or corresponding to position 420 of SEQ ID NO:2 is Val.

In another preferred embodiment, the mutated PPO comprises a sequence of SEQ ID NO: 24, a variant, derivative, orthologue, paralogue or homologue thereof, in which:

the amino acid at or corresponding to position 130 is Leu, Ala, Val, Ile, Met, Tyr, Gly, Asn, Cys, Phe, Ser, Thr, Gin, or His, and the amino acid at or corresponding to position 433 is Ala, Leu, Val, Ile, or Met.

In another preferred embodiment, the mutated PPO comprises a sequence of SEQ ID NO: 24, a variant, derivative, orthologue, paralogue or homologue thereof, in which:

the amino acid at or corresponding to position 130 is Leu, and the amino acid at or corresponding to position 433 is Ala.

In another preferred embodiment, the mutated PPO comprises a sequence of SEQ ID NO: 24, a variant, derivative, orthologue, paralogue or homologue thereof, in which:

the amino acid at or corresponding to position 130 is Leu, and the amino acid at or corresponding to position 433 is Leu.

In another preferred embodiment, the mutated PPO comprises a sequence of SEQ ID NO: 24, a variant, derivative, orthologue, paralogue or homologue thereof, in which:

the amino acid at or corresponding to position 130 is Leu, and the amino acid at or corresponding to position 433 is Val.

In another preferred embodiment, the mutated PPO comprises a sequence of SEQ ID NO: 24, a variant, derivative, orthologue, paralogue or homologue thereof, in which:

the amino acid at or corresponding to position 130 is Leu, and the amino acid at or corresponding to position 433 is Ile.

In another preferred embodiment, the mutated PPO comprises a sequence of SEQ ID NO: 24, a variant, derivative, orthologue, paralogue or homologue thereof, in which:

the amino acid at or corresponding to position 130 is Leu, and the amino acid at or corresponding to position 433 is Met.

In another preferred embodiment, the mutated PPO comprises a sequence of SEQ ID NO: 24, a variant, derivative, orthologue, paralogue or homologue thereof, in which:

the amino acid at or corresponding to position 130 is Ala, and the amino acid at or corresponding to position 433 is Ala.

In another preferred embodiment, the mutated PPO comprises a sequence of SEQ ID NO: 24, a variant, derivative, orthologue, paralogue or homologue thereof, in which:

the amino acid at or corresponding to position 130 is Ala, and the amino acid at or corresponding to position 433 is Leu.

In another preferred embodiment, the mutated PPO comprises a sequence of SEQ ID NO: 24, a variant, derivative, orthologue, paralogue or homologue thereof, in which:

the amino acid at or corresponding to position 130 is Ala, and the amino acid at or corresponding to position 433 is Val.

In another preferred embodiment, the mutated PPO comprises a sequence of SEQ ID NO: 24, a variant, derivative, orthologue, paralogue or homologue thereof, in which:

the amino acid at or corresponding to position 130 is Ala, and the amino acid at or corresponding to position 433 is Ile.

In another preferred embodiment, the mutated PPO comprises a sequence of SEQ ID NO: 24, a variant, derivative, orthologue, paralogue or homologue thereof, in which:

the amino acid at or corresponding to position 130 is Ala, and the amino acid at or corresponding to position 433 is Met.

In another preferred embodiment, the mutated PPO comprises a sequence of SEQ ID NO: 24, a variant, derivative, orthologue, paralogue or homologue thereof, in which:

the amino acid at or corresponding to position 130 is Val, and the amino acid at or corresponding to position 433 is Ala.

In another preferred embodiment, the mutated PPO comprises a sequence of SEQ ID NO: 24, a variant, derivative, orthologue, paralogue or homologue thereof, in which:

the amino acid at or corresponding to position 130 is Val, and the amino acid at or corresponding to position 433 is Leu.

In another preferred embodiment, the mutated PPO comprises a sequence of SEQ ID NO: 24, a variant, derivative, orthologue, paralogue or homologue thereof, in which:

the amino acid at or corresponding to position 130 is Val, and the amino acid at or corresponding to position 433 is Val.

In another preferred embodiment, the mutated PPO comprises a sequence of SEQ ID NO: 24, a variant, derivative, orthologue, paralogue or homologue thereof, in which:

the amino acid at or corresponding to position 130 is Val, and the amino acid at or corresponding to position 433 is Ile.

In another preferred embodiment, the mutated PPO comprises a sequence of SEQ ID NO: 24, a variant, derivative, orthologue, paralogue or homologue thereof, in which:

the amino acid at or corresponding to position 130 is Val, and the amino acid at or corresponding to position 433 is Met.

In another preferred embodiment, the mutated PPO comprises a sequence of SEQ ID NO: 24, a variant, derivative, orthologue, paralogue or homologue thereof, in which:

the amino acid at or corresponding to position 130 is Ile, and the amino acid at or corresponding to position 433 is Ala.

In another preferred embodiment, the mutated PPO comprises a sequence of SEQ ID NO: 24, a variant, derivative, orthologue, paralogue or homologue thereof, in which:

the amino acid at or corresponding to position 130 is Ile, and the amino acid at or corresponding to position 433 is Leu.

In another preferred embodiment, the mutated PPO comprises a sequence of SEQ ID NO: 24, a variant, derivative, orthologue, paralogue or homologue thereof, in which:

the amino acid at or corresponding to position 130 is Ile, and the amino acid at or corresponding to position 433 is Val.

In another preferred embodiment, the mutated PPO comprises a sequence of SEQ ID NO: 24, a variant, derivative, orthologue, paralogue or homologue thereof, in which:

the amino acid at or corresponding to position 130 is Ile, and the amino acid at or corresponding to position 433 is Ile.

In another preferred embodiment, the mutated PPO comprises a sequence of SEQ ID NO: 24, a variant, derivative, orthologue, paralogue or homologue thereof, in which:

the amino acid at or corresponding to position 130 is Ile, and the amino acid at or corresponding to position 433 is Met.

In another preferred embodiment, the mutated PPO comprises a sequence of SEQ ID NO: 24, a variant, derivative, orthologue, paralogue or homologue thereof, in which:

the amino acid at or corresponding to position 130 is Met, and the amino acid at or corresponding to position 433 is Ala.

In another preferred embodiment, the mutated PPO comprises a sequence of SEQ ID NO: 24, a variant, derivative, orthologue, paralogue or homologue thereof, in which:

the amino acid at or corresponding to position 130 is Met, and the amino acid at or corresponding to position 433 is Leu.

In another preferred embodiment, the mutated PPO comprises a sequence of SEQ ID NO: 24, a variant, derivative, orthologue, paralogue or homologue thereof, in which:
the amino acid at or corresponding to position 130 is Met, and the amino acid at or corresponding to position 433 is Val.

In another preferred embodiment, the mutated PPO comprises a sequence of SEQ ID NO: 24, a variant, derivative, orthologue, paralogue or homologue thereof, in which:
the amino acid at or corresponding to position 130 is Met, and the amino acid at or corresponding to position 433 is Ile.

In another preferred embodiment, the mutated PPO comprises a sequence of SEQ ID NO: 24, a variant, derivative, orthologue, paralogue or homologue thereof, in which:
the amino acid at or corresponding to position 130 is Met, and the amino acid at or corresponding to position 433 is Met.

In another preferred embodiment, the mutated PPO comprises a sequence of SEQ ID NO: 24, a variant, derivative, orthologue, paralogue or homologue thereof, in which:
the amino acid at or corresponding to position 130 is Tyr, and the amino acid at or corresponding to position 433 is Ala.

In another preferred embodiment, the mutated PPO comprises a sequence of SEQ ID NO: 24, a variant, derivative, orthologue, paralogue or homologue thereof, in which:
the amino acid at or corresponding to position 130 is Tyr, and the amino acid at or corresponding to position 433 is Leu.

In another preferred embodiment, the mutated PPO comprises a sequence of SEQ ID NO: 24, a variant, derivative, orthologue, paralogue or homologue thereof, in which:
the amino acid at or corresponding to position 130 is Tyr, and the amino acid at or corresponding to position 433 is Val.

In another preferred embodiment, the mutated PPO comprises a sequence of SEQ ID NO: 24, a variant, derivative, orthologue, paralogue or homologue thereof, in which:
the amino acid at or corresponding to position 130 is Tyr, and the amino acid at or corresponding to position 433 is Ile.

In another preferred embodiment, the mutated PPO comprises a sequence of SEQ ID NO: 24, a variant, derivative, orthologue, paralogue or homologue thereof, in which:
the amino acid at or corresponding to position 130 is Tyr, and the amino acid at or corresponding to position 433 is Met.

In another preferred embodiment, the mutated PPO comprises a sequence of SEQ ID NO: 24, a variant, derivative, orthologue, paralogue or homologue thereof, in which:
the amino acid at or corresponding to position 130 is Gly, and the amino acid at or corresponding to position 433 is Ala.

In another preferred embodiment, the mutated PPO comprises a sequence of SEQ ID NO: 24, a variant, derivative, orthologue, paralogue or homologue thereof, in which:
the amino acid at or corresponding to position 130 is Gly, and the amino acid at or corresponding to position 433 is Leu.

In another preferred embodiment, the mutated PPO comprises a sequence of SEQ ID NO: 24, a variant, derivative, orthologue, paralogue or homologue thereof, in which:
the amino acid at or corresponding to position 130 is Gly, and the amino acid at or corresponding to position 433 is Val.

In another preferred embodiment, the mutated PPO comprises a sequence of SEQ ID NO: 24, a variant, derivative, orthologue, paralogue or homologue thereof, in which:
the amino acid at or corresponding to position 130 is Gly, and the amino acid at or corresponding to position 433 is Ile.

In another preferred embodiment, the mutated PPO comprises a sequence of SEQ ID NO: 24, a variant, derivative, orthologue, paralogue or homologue thereof, in which:
the amino acid at or corresponding to position 130 is Gly, and the amino acid at or corresponding to position 433 is Met.

In another preferred embodiment, the mutated PPO comprises a sequence of SEQ ID NO: 24, a variant, derivative, orthologue, paralogue or homologue thereof, in which:
the amino acid at or corresponding to position 130 is Asn, and the amino acid at or corresponding to position 433 is Ala.

In another preferred embodiment, the mutated PPO comprises a sequence of SEQ ID NO: 24, a variant, derivative, orthologue, paralogue or homologue thereof, in which:
the amino acid at or corresponding to position 130 is Asn, and the amino acid at or corresponding to position 433 is Leu.

In another preferred embodiment, the mutated PPO comprises a sequence of SEQ ID NO: 24, a variant, derivative, orthologue, paralogue or homologue thereof, in which:
the amino acid at or corresponding to position 130 is Asn, and the amino acid at or corresponding to position 433 is Val.

In another preferred embodiment, the mutated PPO comprises a sequence of SEQ ID NO: 24, a variant, derivative, orthologue, paralogue or homologue thereof, in which:
the amino acid at or corresponding to position 130 is Asn, and the amino acid at or corresponding to position 433 is Ile.

In another preferred embodiment, the mutated PPO comprises a sequence of SEQ ID NO: 24, a variant, derivative, orthologue, paralogue or homologue thereof, in which:
the amino acid at or corresponding to position 130 is Asn, and the amino acid at or corresponding to position 433 is Met.

In another preferred embodiment, the mutated PPO comprises a sequence of SEQ ID NO: 24, a variant, derivative, orthologue, paralogue or homologue thereof, in which:
the amino acid at or corresponding to position 130 is Cys, and the amino acid at or corresponding to position 433 is Ala.

In another preferred embodiment, the mutated PPO comprises a sequence of SEQ ID NO: 24, a variant, derivative, orthologue, paralogue or homologue thereof, in which:
the amino acid at or corresponding to position 130 is Cys, and the amino acid at or corresponding to position 433 is Leu.

In another preferred embodiment, the mutated PPO comprises a sequence of SEQ ID NO: 24, a variant, derivative, orthologue, paralogue or homologue thereof, in which:
the amino acid at or corresponding to position 130 is Cys, and the amino acid at or corresponding to position 433 is Val.

In another preferred embodiment, the mutated PPO comprises a sequence of SEQ ID NO: 24, a variant, derivative, orthologue, paralogue or homologue thereof, in which:
the amino acid at or corresponding to position 130 is Cys, and the amino acid at or corresponding to position 433 is Ile.

In another preferred embodiment, the mutated PPO comprises a sequence of SEQ ID NO: 24, a variant, derivative, orthologue, paralogue or homologue thereof, in which:

the amino acid at or corresponding to position 130 is Cys, and the amino acid at or corresponding to position 433 is Met.

In another preferred embodiment, the mutated PPO comprises a sequence of SEQ ID NO: 24, a variant, derivative, orthologue, paralogue or homologue thereof, in which:

the amino acid at or corresponding to position 130 is Phe, and the amino acid at or corresponding to position 433 is Ala.

In another preferred embodiment, the mutated PPO comprises a sequence of SEQ ID NO: 24, a variant, derivative, orthologue, paralogue or homologue thereof, in which:

the amino acid at or corresponding to position 130 is Phe, and the amino acid at or corresponding to position 433 is Leu.

In another preferred embodiment, the mutated PPO comprises a sequence of SEQ ID NO: 24, a variant, derivative, orthologue, paralogue or homologue thereof, in which:

the amino acid at or corresponding to position 130 is Phe, and the amino acid at or corresponding to position 433 is Val.

In another preferred embodiment, the mutated PPO comprises a sequence of SEQ ID NO: 24, a variant, derivative, orthologue, paralogue or homologue thereof, in which:

the amino acid at or corresponding to position 130 is Phe, and the amino acid at or corresponding to position 433 is Ile.

In another preferred embodiment, the mutated PPO comprises a sequence of SEQ ID NO: 24, a variant, derivative, orthologue, paralogue or homologue thereof, in which:

the amino acid at or corresponding to position 130 is Phe, and the amino acid at or corresponding to position 433 is Met.

In another preferred embodiment, the mutated PPO comprises a sequence of SEQ ID NO: 24, a variant, derivative, orthologue, paralogue or homologue thereof, in which:

the amino acid at or corresponding to position 130 is Ser, and the amino acid at or corresponding to position 433 is Ala.

In another preferred embodiment, the mutated PPO comprises a sequence of SEQ ID NO: 24, a variant, derivative, orthologue, paralogue or homologue thereof, in which:

the amino acid at or corresponding to position 130 is Ser, and the amino acid at or corresponding to position 433 is Leu.

In another preferred embodiment, the mutated PPO comprises a sequence of SEQ ID NO: 24, a variant, derivative, orthologue, paralogue or homologue thereof, in which:

the amino acid at or corresponding to position 130 is Ser, and the amino acid at or corresponding to position 433 is Val.

In another preferred embodiment, the mutated PPO comprises a sequence of SEQ ID NO: 24, a variant, derivative, orthologue, paralogue or homologue thereof, in which:

the amino acid at or corresponding to position 130 is Ser, and the amino acid at or corresponding to position 433 is Ile.

In another preferred embodiment, the mutated PPO comprises a sequence of SEQ ID NO: 24, a variant, derivative, orthologue, paralogue or homologue thereof, in which:

the amino acid at or corresponding to position 130 is Ser, and the amino acid at or corresponding to position 433 is Met.

In another preferred embodiment, the mutated PPO comprises a sequence of SEQ ID NO: 24, a variant, derivative, orthologue, paralogue or homologue thereof, in which:

the amino acid at or corresponding to position 130 is Thr, and the amino acid at or corresponding to position 433 is Ala.

In another preferred embodiment, the mutated PPO comprises a sequence of SEQ ID NO: 24, a variant, derivative, orthologue, paralogue or homologue thereof, in which:

the amino acid at or corresponding to position 130 is Thr, and the amino acid at or corresponding to position 433 is Leu.

In another preferred embodiment, the mutated PPO comprises a sequence of SEQ ID NO: 24, a variant, derivative, orthologue, paralogue or homologue thereof, in which:

the amino acid at or corresponding to position 130 is Thr, and the amino acid at or corresponding to position 433 is Val.

In another preferred embodiment, the mutated PPO comprises a sequence of SEQ ID NO: 24, a variant, derivative, orthologue, paralogue or homologue thereof, in which:

the amino acid at or corresponding to position 130 is Thr, and the amino acid at or corresponding to position 433 is Ile.

In another preferred embodiment, the mutated PPO comprises a sequence of SEQ ID NO: 24, a variant, derivative, orthologue, paralogue or homologue thereof, in which:

the amino acid at or corresponding to position 130 is Thr, and the amino acid at or corresponding to position 433 is Met.

In another preferred embodiment, the mutated PPO comprises a sequence of SEQ ID NO: 24, a variant, derivative, orthologue, paralogue or homologue thereof, in which:

the amino acid at or corresponding to position 130 is Gin, and the amino acid at or corresponding to position 433 is Ala.

In another preferred embodiment, the mutated PPO comprises a sequence of SEQ ID NO: 24, a variant, derivative, orthologue, paralogue or homologue thereof, in which:

the amino acid at or corresponding to position 130 is Gin, and the amino acid at or corresponding to position 433 is Leu.

In another preferred embodiment, the mutated PPO comprises a sequence of SEQ ID NO: 24, a variant, derivative, orthologue, paralogue or homologue thereof, in which:

the amino acid at or corresponding to position 130 is Gin, and the amino acid at or corresponding to position 433 is Val.

In another preferred embodiment, the mutated PPO comprises a sequence of SEQ ID NO: 24, a variant, derivative, orthologue, paralogue or homologue thereof, in which:

the amino acid at or corresponding to position 130 is Gin, and the amino acid at or corresponding to position 433 is Ile.

In another preferred embodiment, the mutated PPO comprises a sequence of SEQ ID NO: 24, a variant, derivative, orthologue, paralogue or homologue thereof, in which:

the amino acid at or corresponding to position 130 is Gin, and the amino acid at or corresponding to position 433 is Met.

In another preferred embodiment, the mutated PPO comprises a sequence of SEQ ID NO: 24, a variant, derivative, orthologue, paralogue or homologue thereof, in which:

the amino acid at or corresponding to position 130 is His, and the amino acid at or corresponding to position 433 is Ala.

In another preferred embodiment, the mutated PPO comprises a sequence of SEQ ID NO: 24, a variant, derivative, orthologue, paralogue or homologue thereof, in which:

the amino acid at or corresponding to position 130 is His, and the amino acid at or corresponding to position 433 is Leu.

In another preferred embodiment, the mutated PPO comprises a sequence of SEQ ID NO: 24, a variant, derivative, orthologue, paralogue or homologue thereof, in which:

the amino acid at or corresponding to position 130 is His, and the amino acid at or corresponding to position 433 is Val.

In another preferred embodiment, the mutated PPO comprises a sequence of SEQ ID NO: 24, a variant, derivative, orthologue, paralogue or homologue thereof, in which:
the amino acid at or corresponding to position 130 is His, and the amino acid at or corresponding to position 433 is Ile.

In another preferred embodiment, the mutated PPO comprises a sequence of SEQ ID NO: 24, a variant, derivative, orthologue, paralogue or homologue thereof, in which:
the amino acid at or corresponding to position 130 is His, and the amino acid at or corresponding to position 433 is Met.

In another preferred embodiment, the mutated PPO comprises a sequence of SEQ ID NO: 30, a variant, derivative, orthologue, paralogue or homologue thereof, in which:
the amino acid at or corresponding to position 130 is Leu, Ala, Val, Ile, Met, Tyr, Gly, Asn, Cys, Phe, Ser, Thr, Gln, His, and the amino acid at or corresponding to position 433 is Ala, Leu, Val, Ile, Met.

In another preferred embodiment, the mutated PPO comprises a sequence of SEQ ID NO: 30, a variant, derivative, orthologue, paralogue or homologue thereof, in which:
the amino acid at or corresponding to position 130 is Leu, and the amino acid at or corresponding to position 433 is Ala.

In another preferred embodiment, the mutated PPO comprises a sequence of SEQ ID NO: 30, a variant, derivative, orthologue, paralogue or homologue thereof, in which:
the amino acid at or corresponding to position 130 is Leu, and the amino acid at or corresponding to position 433 is Leu.

In another preferred embodiment, the mutated PPO comprises a sequence of SEQ ID NO: 30, a variant, derivative, orthologue, paralogue or homologue thereof, in which:
the amino acid at or corresponding to position 130 is Leu, and the amino acid at or corresponding to position 433 is Val.

In another preferred embodiment, the mutated PPO comprises a sequence of SEQ ID NO: 30, a variant, derivative, orthologue, paralogue or homologue thereof, in which:
the amino acid at or corresponding to position 130 is Leu, and the amino acid at or corresponding to position 433 is Ile.

In another preferred embodiment, the mutated PPO comprises a sequence of SEQ ID NO: 30, a variant, derivative, orthologue, paralogue or homologue thereof, in which:
the amino acid at or corresponding to position 130 is Leu, and the amino acid at or corresponding to position 433 is Met.

In another preferred embodiment, the mutated PPO comprises a sequence of SEQ ID NO: 30, a variant, derivative, orthologue, paralogue or homologue thereof, in which:
the amino acid at or corresponding to position 130 is Ala, and the amino acid at or corresponding to position 433 is Ala.

In another preferred embodiment, the mutated PPO comprises a sequence of SEQ ID NO: 30, a variant, derivative, orthologue, paralogue or homologue thereof, in which:
the amino acid at or corresponding to position 130 is Ala, and the amino acid at or corresponding to position 433 is Leu.

In another preferred embodiment, the mutated PPO comprises a sequence of SEQ ID NO: 30, a variant, derivative, orthologue, paralogue or homologue thereof, in which:
the amino acid at or corresponding to position 130 is Ala, and the amino acid at or corresponding to position 433 is Val.

In another preferred embodiment, the mutated PPO comprises a sequence of SEQ ID NO: 30, a variant, derivative, orthologue, paralogue or homologue thereof, in which:
the amino acid at or corresponding to position 130 is Ala, and the amino acid at or corresponding to position 433 is Ile.

In another preferred embodiment, the mutated PPO comprises a sequence of SEQ ID NO: 30, a variant, derivative, orthologue, paralogue or homologue thereof, in which:
the amino acid at or corresponding to position 130 is Ala, and the amino acid at or corresponding to position 433 is Met.

In another preferred embodiment, the mutated PPO comprises a sequence of SEQ ID NO: 30, a variant, derivative, orthologue, paralogue or homologue thereof, in which:
the amino acid at or corresponding to position 130 is Val, and the amino acid at or corresponding to position 433 is Ala.

In another preferred embodiment, the mutated PPO comprises a sequence of SEQ ID NO: 30, a variant, derivative, orthologue, paralogue or homologue thereof, in which:
the amino acid at or corresponding to position 130 is Val, and the amino acid at or corresponding to position 433 is Leu.

In another preferred embodiment, the mutated PPO comprises a sequence of SEQ ID NO: 30, a variant, derivative, orthologue, paralogue or homologue thereof, in which:
the amino acid at or corresponding to position 130 is Val, and the amino acid at or corresponding to position 433 is Val.

In another preferred embodiment, the mutated PPO comprises a sequence of SEQ ID NO: 30, a variant, derivative, orthologue, paralogue or homologue thereof, in which:
the amino acid at or corresponding to position 130 is Val, and the amino acid at or corresponding to position 433 is Ile.

In another preferred embodiment, the mutated PPO comprises a sequence of SEQ ID NO: 30, a variant, derivative, orthologue, paralogue or homologue thereof, in which:
the amino acid at or corresponding to position 130 is Val, and the amino acid at or corresponding to position 433 is Met.

In another preferred embodiment, the mutated PPO comprises a sequence of SEQ ID NO: 30, a variant, derivative, orthologue, paralogue or homologue thereof, in which:
the amino acid at or corresponding to position 130 is Ile, and the amino acid at or corresponding to position 433 is Ala.

In another preferred embodiment, the mutated PPO comprises a sequence of SEQ ID NO: 30, a variant, derivative, orthologue, paralogue or homologue thereof, in which:
the amino acid at or corresponding to position 130 is Ile, and the amino acid at or corresponding to position 433 is Leu.

In another preferred embodiment, the mutated PPO comprises a sequence of SEQ ID NO: 30, a variant, derivative, orthologue, paralogue or homologue thereof, in which:
the amino acid at or corresponding to position 130 is Ile, and the amino acid at or corresponding to position 433 is Val.

In another preferred embodiment, the mutated PPO comprises a sequence of SEQ ID NO: 30, a variant, derivative, orthologue, paralogue or homologue thereof, in which:
the amino acid at or corresponding to position 130 is Ile, and the amino acid at or corresponding to position 433 is Ile.

In another preferred embodiment, the mutated PPO comprises a sequence of SEQ ID NO: 30, a variant, derivative, orthologue, paralogue or homologue thereof, in which:
the amino acid at or corresponding to position 130 is Ile, and the amino acid at or corresponding to position 433 is Met.

In another preferred embodiment, the mutated PPO comprises a sequence of SEQ ID NO: 30, a variant, derivative, orthologue, paralogue or homologue thereof, in which:
the amino acid at or corresponding to position 130 is Met, and the amino acid at or corresponding to position 433 is Ala.

In another preferred embodiment, the mutated PPO comprises a sequence of SEQ ID NO: 30, a variant, derivative, orthologue, paralogue or homologue thereof, in which:
the amino acid at or corresponding to position 130 is Met, and the amino acid at or corresponding to position 433 is Leu.

In another preferred embodiment, the mutated PPO comprises a sequence of SEQ ID NO: 30, a variant, derivative, orthologue, paralogue or homologue thereof, in which:
the amino acid at or corresponding to position 130 is Met, and the amino acid at or corresponding to position 433 is Val.

In another preferred embodiment, the mutated PPO comprises a sequence of SEQ ID NO: 30, a variant, derivative, orthologue, paralogue or homologue thereof, in which:
the amino acid at or corresponding to position 130 is Met, and the amino acid at or corresponding to position 433 is Ile.

In another preferred embodiment, the mutated PPO comprises a sequence of SEQ ID NO: 30, a variant, derivative, orthologue, paralogue or homologue thereof, in which:
the amino acid at or corresponding to position 130 is Met, and the amino acid at or corresponding to position 433 is Met.

In another preferred embodiment, the mutated PPO comprises a sequence of SEQ ID NO: 30, a variant, derivative, orthologue, paralogue or homologue thereof, in which:
the amino acid at or corresponding to position 130 is Tyr, and the amino acid at or corresponding to position 433 is Ala.

In another preferred embodiment, the mutated PPO comprises a sequence of SEQ ID NO: 30, a variant, derivative, orthologue, paralogue or homologue thereof, in which:
the amino acid at or corresponding to position 130 is Tyr, and the amino acid at or corresponding to position 433 is Leu.

In another preferred embodiment, the mutated PPO comprises a sequence of SEQ ID NO: 30, a variant, derivative, orthologue, paralogue or homologue thereof, in which:
the amino acid at or corresponding to position 130 is Tyr, and the amino acid at or corresponding to position 433 is Val.

In another preferred embodiment, the mutated PPO comprises a sequence of SEQ ID NO: 30, a variant, derivative, orthologue, paralogue or homologue thereof, in which:
the amino acid at or corresponding to position 130 is Tyr, and the amino acid at or corresponding to position 433 is Ile.

In another preferred embodiment, the mutated PPO comprises a sequence of SEQ ID NO: 30, a variant, derivative, orthologue, paralogue or homologue thereof, in which:
the amino acid at or corresponding to position 130 is Tyr, and the amino acid at or corresponding to position 433 is Met.

In another preferred embodiment, the mutated PPO comprises a sequence of SEQ ID NO: 30, a variant, derivative, orthologue, paralogue or homologue thereof, in which:
the amino acid at or corresponding to position 130 is Gly, and the amino acid at or corresponding to position 433 is Ala.

In another preferred embodiment, the mutated PPO comprises a sequence of SEQ ID NO: 30, a variant, derivative, orthologue, paralogue or homologue thereof, in which:
the amino acid at or corresponding to position 130 is Gly, and the amino acid at or corresponding to position 433 is Leu.

In another preferred embodiment, the mutated PPO comprises a sequence of SEQ ID NO: 30, a variant, derivative, orthologue, paralogue or homologue thereof, in which:
the amino acid at or corresponding to position 130 is Gly, and the amino acid at or corresponding to position 433 is Val.

In another preferred embodiment, the mutated PPO comprises a sequence of SEQ ID NO: 30, a variant, derivative, orthologue, paralogue or homologue thereof, in which:
the amino acid at or corresponding to position 130 is Gly, and the amino acid at or corresponding to position 433 is Ile.

In another preferred embodiment, the mutated PPO comprises a sequence of SEQ ID NO: 30, a variant, derivative, orthologue, paralogue or homologue thereof, in which:
the amino acid at or corresponding to position 130 is Gly, and the amino acid at or corresponding to position 433 is Met.

In another preferred embodiment, the mutated PPO comprises a sequence of SEQ ID NO: 30, a variant, derivative, orthologue, paralogue or homologue thereof, in which:
the amino acid at or corresponding to position 130 is Asn, and the amino acid at or corresponding to position 433 is Ala.

In another preferred embodiment, the mutated PPO comprises a sequence of SEQ ID NO: 30, a variant, derivative, orthologue, paralogue or homologue thereof, in which:
the amino acid at or corresponding to position 130 is Asn, and the amino acid at or corresponding to position 433 is Leu.

In another preferred embodiment, the mutated PPO comprises a sequence of SEQ ID NO: 30, a variant, derivative, orthologue, paralogue or homologue thereof, in which:
the amino acid at or corresponding to position 130 is Asn, and the amino acid at or corresponding to position 433 is Val.

In another preferred embodiment, the mutated PPO comprises a sequence of SEQ ID NO: 30, a variant, derivative, orthologue, paralogue or homologue thereof, in which:
the amino acid at or corresponding to position 130 is Asn, and the amino acid at or corresponding to position 433 is Ile.

In another preferred embodiment, the mutated PPO comprises a sequence of SEQ ID NO: 30, a variant, derivative, orthologue, paralogue or homologue thereof, in which:
the amino acid at or corresponding to position 130 is Asn, and the amino acid at or corresponding to position 433 is Met.

In another preferred embodiment, the mutated PPO comprises a sequence of SEQ ID NO: 30, a variant, derivative, orthologue, paralogue or homologue thereof, in which:
the amino acid at or corresponding to position 130 is Cys, and the amino acid at or corresponding to position 433 is Ala.

In another preferred embodiment, the mutated PPO comprises a sequence of SEQ ID NO: 30, a variant, derivative, orthologue, paralogue or homologue thereof, in which:
the amino acid at or corresponding to position 130 is Cys, and the amino acid at or corresponding to position 433 is Leu.

In another preferred embodiment, the mutated PPO comprises a sequence of SEQ ID NO: 30, a variant, derivative, orthologue, paralogue or homologue thereof, in which:
the amino acid at or corresponding to position 130 is Cys, and the amino acid at or corresponding to position 433 is Val.

In another preferred embodiment, the mutated PPO comprises a sequence of SEQ ID NO: 30, a variant, derivative, orthologue, paralogue or homologue thereof, in which:
the amino acid at or corresponding to position 130 is Cys, and the amino acid at or corresponding to position 433 is Ile.

In another preferred embodiment, the mutated PPO comprises a sequence of SEQ ID NO: 30, a variant, derivative, orthologue, paralogue or homologue thereof, in which:
the amino acid at or corresponding to position 130 is Cys, and the amino acid at or corresponding to position 433 is Met.

In another preferred embodiment, the mutated PPO comprises a sequence of SEQ ID NO: 30, a variant, derivative, orthologue, paralogue or homologue thereof, in which:
the amino acid at or corresponding to position 130 is Phe, and the amino acid at or corresponding to position 433 is Ala.

In another preferred embodiment, the mutated PPO comprises a sequence of SEQ ID NO: 30, a variant, derivative, orthologue, paralogue or homologue thereof, in which:
the amino acid at or corresponding to position 130 is Phe, and the amino acid at or corresponding to position 433 is Leu.

In another preferred embodiment, the mutated PPO comprises a sequence of SEQ ID NO: 30, a variant, derivative, orthologue, paralogue or homologue thereof, in which:
the amino acid at or corresponding to position 130 is Phe, and the amino acid at or corresponding to position 433 is Val.

In another preferred embodiment, the mutated PPO comprises a sequence of SEQ ID NO: 30, a variant, derivative, orthologue, paralogue or homologue thereof, in which:
the amino acid at or corresponding to position 130 is Phe, and the amino acid at or corresponding to position 433 is Ile.

In another preferred embodiment, the mutated PPO comprises a sequence of SEQ ID NO: 30, a variant, derivative, orthologue, paralogue or homologue thereof, in which:
the amino acid at or corresponding to position 130 is Phe, and the amino acid at or corresponding to position 433 is Met.

In another preferred embodiment, the mutated PPO comprises a sequence of SEQ ID NO: 30, a variant, derivative, orthologue, paralogue or homologue thereof, in which:
the amino acid at or corresponding to position 130 is Ser, and the amino acid at or corresponding to position 433 is Ala.

In another preferred embodiment, the mutated PPO comprises a sequence of SEQ ID NO: 30, a variant, derivative, orthologue, paralogue or homologue thereof, in which:
the amino acid at or corresponding to position 130 is Ser, and the amino acid at or corresponding to position 433 is Leu.

In another preferred embodiment, the mutated PPO comprises a sequence of SEQ ID NO: 30, a variant, derivative, orthologue, paralogue or homologue thereof, in which:
the amino acid at or corresponding to position 130 is Ser, and the amino acid at or corresponding to position 433 is Val.

In another preferred embodiment, the mutated PPO comprises a sequence of SEQ ID NO: 30, a variant, derivative, orthologue, paralogue or homologue thereof, in which:
the amino acid at or corresponding to position 130 is Ser, and the amino acid at or corresponding to position 433 is Ile.

In another preferred embodiment, the mutated PPO comprises a sequence of SEQ ID NO: 30, a variant, derivative, orthologue, paralogue or homologue thereof, in which:
the amino acid at or corresponding to position 130 is Ser, and the amino acid at or corresponding to position 433 is Met.

In another preferred embodiment, the mutated PPO comprises a sequence of SEQ ID NO: 30, a variant, derivative, orthologue, paralogue or homologue thereof, in which:
the amino acid at or corresponding to position 130 is Thr, and the amino acid at or corresponding to position 433 is Ala.

In another preferred embodiment, the mutated PPO comprises a sequence of SEQ ID NO: 30, a variant, derivative, orthologue, paralogue or homologue thereof, in which:
the amino acid at or corresponding to position 130 is Thr, and the amino acid at or corresponding to position 433 is Leu.

In another preferred embodiment, the mutated PPO comprises a sequence of SEQ ID NO: 30, a variant, derivative, orthologue, paralogue or homologue thereof, in which:
the amino acid at or corresponding to position 130 is Thr, and the amino acid at or corresponding to position 433 is Val.

In another preferred embodiment, the mutated PPO comprises a sequence of SEQ ID NO: 30, a variant, derivative, orthologue, paralogue or homologue thereof, in which:
the amino acid at or corresponding to position 130 is Thr, and the amino acid at or corresponding to position 433 is Ile.

In another preferred embodiment, the mutated PPO comprises a sequence of SEQ ID NO: 30, a variant, derivative, orthologue, paralogue or homologue thereof, in which:
the amino acid at or corresponding to position 130 is Thr, and the amino acid at or corresponding to position 433 is Met.

In another preferred embodiment, the mutated PPO comprises a sequence of SEQ ID NO: 30, a variant, derivative, orthologue, paralogue or homologue thereof, in which:
the amino acid at or corresponding to position 130 is Gln, and the amino acid at or corresponding to position 433 is Ala.

In another preferred embodiment, the mutated PPO comprises a sequence of SEQ ID NO: 30, a variant, derivative, orthologue, paralogue or homologue thereof, in which:
the amino acid at or corresponding to position 130 is Gln, and the amino acid at or corresponding to position 433 is Leu.

In another preferred embodiment, the mutated PPO comprises a sequence of SEQ ID NO: 30, a variant, derivative, orthologue, paralogue or homologue thereof, in which:
the amino acid at or corresponding to position 130 is Gln, and the amino acid at or corresponding to position 433 is Val.

In another preferred embodiment, the mutated PPO comprises a sequence of SEQ ID NO: 30, a variant, derivative, orthologue, paralogue or homologue thereof, in which:
the amino acid at or corresponding to position 130 is Gln, and the amino acid at or corresponding to position 433 is Ile.

In another preferred embodiment, the mutated PPO comprises a sequence of SEQ ID NO: 30, a variant, derivative, orthologue, paralogue or homologue thereof, in which:
the amino acid at or corresponding to position 130 is Gln, and the amino acid at or corresponding to position 433 is Met.

In another preferred embodiment, the mutated PPO comprises a sequence of SEQ ID NO: 30, a variant, derivative, orthologue, paralogue or homologue thereof, in which:
the amino acid at or corresponding to position 130 is His, and the amino acid at or corresponding to position 433 is Ala.

In another preferred embodiment, the mutated PPO comprises a sequence of SEQ ID NO: 30, a variant, derivative, orthologue, paralogue or homologue thereof, in which:
the amino acid at or corresponding to position 130 is His, and the amino acid at or corresponding to position 433 is Leu.

In another preferred embodiment, the mutated PPO comprises a sequence of SEQ ID NO: 30, a variant, derivative, orthologue, paralogue or homologue thereof, in which:
the amino acid at or corresponding to position 130 is His, and the amino acid at or corresponding to position 433 is Val.

In another preferred embodiment, the mutated PPO comprises a sequence of SEQ ID NO: 30, a variant, derivative, orthologue, paralogue or homologue thereof, in which:
the amino acid at or corresponding to position 130 is His, and the amino acid at or corresponding to position 433 is Ile.

In another preferred embodiment, the mutated PPO comprises a sequence of SEQ ID NO: 30, a variant, derivative, orthologue, paralogue or homologue thereof, in which:
the amino acid at or corresponding to position 130 is His, and the amino acid at or corresponding to position 433 is Met.

In another preferred embodiment, the mutated PPO comprises a sequence of SEQ ID NO: 38, a variant, derivative, orthologue, paralogue or homologue thereof, in which:
the amino acid at or corresponding to position 98 is Leu, Ala, Val, Ile, Met, Tyr, Gly, Asn, Cys, Phe, Ser, Thr, Gin, His, and the amino acid at or corresponding to position 392 is Ala, Leu, Val, Ile, Met.

In another preferred embodiment, the mutated PPO comprises a sequence of SEQ ID NO: 38, a variant, derivative, orthologue, paralogue or homologue thereof, in which:
the amino acid at or corresponding to position 98 is Leu, and the amino acid at or corresponding to position 392 is Ala.

In another preferred embodiment, the mutated PPO comprises a sequence of SEQ ID NO: 38, a variant, derivative, orthologue, paralogue or homologue thereof, in which:
the amino acid at or corresponding to position 98 is Leu, and the amino acid at or corresponding to position 392 is Leu.

In another preferred embodiment, the mutated PPO comprises a sequence of SEQ ID NO: 38, a variant, derivative, orthologue, paralogue or homologue thereof, in which:
the amino acid at or corresponding to position 98 is Leu, and the amino acid at or corresponding to position 392 is Val.

In another preferred embodiment, the mutated PPO comprises a sequence of SEQ ID NO: 38, a variant, derivative, orthologue, paralogue or homologue thereof, in which:
the amino acid at or corresponding to position 98 is Leu, and the amino acid at or corresponding to position 392 is Ile.

In another preferred embodiment, the mutated PPO comprises a sequence of SEQ ID NO: 38, a variant, derivative, orthologue, paralogue or homologue thereof, in which:
the amino acid at or corresponding to position 98 is Leu, and the amino acid at or corresponding to position 392 is Met.

In another preferred embodiment, the mutated PPO comprises a sequence of SEQ ID NO: 38, a variant, derivative, orthologue, paralogue or homologue thereof, in which:
the amino acid at or corresponding to position 98 is Ala, and the amino acid at or corresponding to position 392 is Ala.

In another preferred embodiment, the mutated PPO comprises a sequence of SEQ ID NO: 38, a variant, derivative, orthologue, paralogue or homologue thereof, in which:
the amino acid at or corresponding to position 98 is Ala, and the amino acid at or corresponding to position 392 is Leu.

In another preferred embodiment, the mutated PPO comprises a sequence of SEQ ID NO: 38, a variant, derivative, orthologue, paralogue or homologue thereof, in which:
the amino acid at or corresponding to position 98 is Ala, and the amino acid at or corresponding to position 392 is Val.

In another preferred embodiment, the mutated PPO comprises a sequence of SEQ ID NO: 38, a variant, derivative, orthologue, paralogue or homologue thereof, in which:
the amino acid at or corresponding to position 98 is Ala, and the amino acid at or corresponding to position 392 is Ile.

In another preferred embodiment, the mutated PPO comprises a sequence of SEQ ID NO: 38, a variant, derivative, orthologue, paralogue or homologue thereof, in which:
the amino acid at or corresponding to position 98 is Ala, and the amino acid at or corresponding to position 392 is Met.

In another preferred embodiment, the mutated PPO comprises a sequence of SEQ ID NO: 38, a variant, derivative, orthologue, paralogue or homologue thereof, in which:
the amino acid at or corresponding to position 98 is Val, and the amino acid at or corresponding to position 392 is Ala.

In another preferred embodiment, the mutated PPO comprises a sequence of SEQ ID NO: 38, a variant, derivative, orthologue, paralogue or homologue thereof, in which:
the amino acid at or corresponding to position 98 is Val, and the amino acid at or corresponding to position 392 is Leu.

In another preferred embodiment, the mutated PPO comprises a sequence of SEQ ID NO: 38, a variant, derivative, orthologue, paralogue or homologue thereof, in which:
the amino acid at or corresponding to position 98 is Val, and the amino acid at or corresponding to position 392 is Val.

In another preferred embodiment, the mutated PPO comprises a sequence of SEQ ID NO: 38, a variant, derivative, orthologue, paralogue or homologue thereof, in which:
the amino acid at or corresponding to position 98 is Val, and the amino acid at or corresponding to position 392 is Ile.

In another preferred embodiment, the mutated PPO comprises a sequence of SEQ ID NO: 38, a variant, derivative, orthologue, paralogue or homologue thereof, in which:
the amino acid at or corresponding to position 98 is Val, and the amino acid at or corresponding to position 392 is Met.

In another preferred embodiment, the mutated PPO comprises a sequence of SEQ ID NO: 38, a variant, derivative, orthologue, paralogue or homologue thereof, in which:
the amino acid at or corresponding to position 98 is Ile, and the amino acid at or corresponding to position 392 is Ala.

In another preferred embodiment, the mutated PPO comprises a sequence of SEQ ID NO: 38, a variant, derivative, orthologue, paralogue or homologue thereof, in which:

the amino acid at or corresponding to position 98 is Ile, and the amino acid at or corresponding to position 392 is Leu.

In another preferred embodiment, the mutated PPO comprises a sequence of SEQ ID NO: 38, a variant, derivative, orthologue, paralogue or homologue thereof, in which: the amino acid at or corresponding to position 98 is Ile, and the amino acid at or corresponding to position 392 is Val.

In another preferred embodiment, the mutated PPO comprises a sequence of SEQ ID NO: 38, a variant, derivative, orthologue, paralogue or homologue thereof, in which: the amino acid at or corresponding to position 98 is Ile, and the amino acid at or corresponding to position 392 is Ile.

In another preferred embodiment, the mutated PPO comprises a sequence of SEQ ID NO: 38, a variant, derivative, orthologue, paralogue or homologue thereof, in which: the amino acid at or corresponding to position 98 is Ile, and the amino acid at or corresponding to position 392 is Met.

In another preferred embodiment, the mutated PPO comprises a sequence of SEQ ID NO: 38, a variant, derivative, orthologue, paralogue or homologue thereof, in which: the amino acid at or corresponding to position 98 is Met, and the amino acid at or corresponding to position 392 is Ala.

In another preferred embodiment, the mutated PPO comprises a sequence of SEQ ID NO: 38, a variant, derivative, orthologue, paralogue or homologue thereof, in which: the amino acid at or corresponding to position 98 is Met, and the amino acid at or corresponding to position 392 is Leu.

In another preferred embodiment, the mutated PPO comprises a sequence of SEQ ID NO: 38, a variant, derivative, orthologue, paralogue or homologue thereof, in which: the amino acid at or corresponding to position 98 is Met, and the amino acid at or corresponding to position 392 is Val.

In another preferred embodiment, the mutated PPO comprises a sequence of SEQ ID NO: 38, a variant, derivative, orthologue, paralogue or homologue thereof, in which: the amino acid at or corresponding to position 98 is Met, and the amino acid at or corresponding to position 392 is Ile.

In another preferred embodiment, the mutated PPO comprises a sequence of SEQ ID NO: 38, a variant, derivative, orthologue, paralogue or homologue thereof, in which: the amino acid at or corresponding to position 98 is Met, and the amino acid at or corresponding to position 392 is Met.

In another preferred embodiment, the mutated PPO comprises a sequence of SEQ ID NO: 38, a variant, derivative, orthologue, paralogue or homologue thereof, in which: the amino acid at or corresponding to position 98 is Tyr, and the amino acid at or corresponding to position 392 is Ala.

In another preferred embodiment, the mutated PPO comprises a sequence of SEQ ID NO: 38, a variant, derivative, orthologue, paralogue or homologue thereof, in which: the amino acid at or corresponding to position 98 is Tyr, and the amino acid at or corresponding to position 392 is Leu.

In another preferred embodiment, the mutated PPO comprises a sequence of SEQ ID NO: 38, a variant, derivative, orthologue, paralogue or homologue thereof, in which: the amino acid at or corresponding to position 98 is Tyr, and the amino acid at or corresponding to position 392 is Val.

In another preferred embodiment, the mutated PPO comprises a sequence of SEQ ID NO: 38, a variant, derivative, orthologue, paralogue or homologue thereof, in which: the amino acid at or corresponding to position 98 is Tyr, and the amino acid at or corresponding to position 392 is Ile.

In another preferred embodiment, the mutated PPO comprises a sequence of SEQ ID NO: 38, a variant, derivative, orthologue, paralogue or homologue thereof, in which: the amino acid at or corresponding to position 98 is Tyr, and the amino acid at or corresponding to position 392 is Met.

In another preferred embodiment, the mutated PPO comprises a sequence of SEQ ID NO: 38, a variant, derivative, orthologue, paralogue or homologue thereof, in which: the amino acid at or corresponding to position 98 is Gly, and the amino acid at or corresponding to position 392 is Ala.

In another preferred embodiment, the mutated PPO comprises a sequence of SEQ ID NO: 38, a variant, derivative, orthologue, paralogue or homologue thereof, in which: the amino acid at or corresponding to position 98 is Gly, and the amino acid at or corresponding to position 392 is Leu.

In another preferred embodiment, the mutated PPO comprises a sequence of SEQ ID NO: 38, a variant, derivative, orthologue, paralogue or homologue thereof, in which: the amino acid at or corresponding to position 98 is Gly, and the amino acid at or corresponding to position 392 is Val.

In another preferred embodiment, the mutated PPO comprises a sequence of SEQ ID NO: 38, a variant, derivative, orthologue, paralogue or homologue thereof, in which: the amino acid at or corresponding to position 98 is Gly, and the amino acid at or corresponding to position 392 is Ile.

In another preferred embodiment, the mutated PPO comprises a sequence of SEQ ID NO: 38, a variant, derivative, orthologue, paralogue or homologue thereof, in which: the amino acid at or corresponding to position 98 is Gly, and the amino acid at or corresponding to position 392 is Met.

In another preferred embodiment, the mutated PPO comprises a sequence of SEQ ID NO: 38, a variant, derivative, orthologue, paralogue or homologue thereof, in which: the amino acid at or corresponding to position 98 is Asn, and the amino acid at or corresponding to position 392 is Ala.

In another preferred embodiment, the mutated PPO comprises a sequence of SEQ ID NO: 38, a variant, derivative, orthologue, paralogue or homologue thereof, in which: the amino acid at or corresponding to position 98 is Asn, and the amino acid at or corresponding to position 392 is Leu.

In another preferred embodiment, the mutated PPO comprises a sequence of SEQ ID NO: 38, a variant, derivative, orthologue, paralogue or homologue thereof, in which: the amino acid at or corresponding to position 98 is Asn, and the amino acid at or corresponding to position 392 is Val.

In another preferred embodiment, the mutated PPO comprises a sequence of SEQ ID NO: 38, a variant, derivative, orthologue, paralogue or homologue thereof, in which: the amino acid at or corresponding to position 98 is Asn, and the amino acid at or corresponding to position 392 is Ile.

In another preferred embodiment, the mutated PPO comprises a sequence of SEQ ID NO: 38, a variant, derivative, orthologue, paralogue or homologue thereof, in which:

the amino acid at or corresponding to position 98 is Asn, and the amino acid at or corresponding to position 392 is Met.

In another preferred embodiment, the mutated PPO comprises a sequence of SEQ ID NO: 38, a variant, derivative, orthologue, paralogue or homologue thereof, in which:
the amino acid at or corresponding to position 98 is Cys, and the amino acid at or corresponding to position 392 is Ala.

In another preferred embodiment, the mutated PPO comprises a sequence of SEQ ID NO: 38, a variant, derivative, orthologue, paralogue or homologue thereof, in which:
the amino acid at or corresponding to position 98 is Cys, and the amino acid at or corresponding to position 392 is Leu.

In another preferred embodiment, the mutated PPO comprises a sequence of SEQ ID NO: 38, a variant, derivative, orthologue, paralogue or homologue thereof, in which:
the amino acid at or corresponding to position 98 is Cys, and the amino acid at or corresponding to position 392 is Val.

In another preferred embodiment, the mutated PPO comprises a sequence of SEQ ID NO: 38, a variant, derivative, orthologue, paralogue or homologue thereof, in which:
the amino acid at or corresponding to position 98 is Cys, and the amino acid at or corresponding to position 392 is Ile.

In another preferred embodiment, the mutated PPO comprises a sequence of SEQ ID NO: 38, a variant, derivative, orthologue, paralogue or homologue thereof, in which:
the amino acid at or corresponding to position 98 is Cys, and the amino acid at or corresponding to position 392 is Met.

In another preferred embodiment, the mutated PPO comprises a sequence of SEQ ID NO: 38, a variant, derivative, orthologue, paralogue or homologue thereof, in which:
the amino acid at or corresponding to position 98 is Phe, and the amino acid at or corresponding to position 392 is Ala.

In another preferred embodiment, the mutated PPO comprises a sequence of SEQ ID NO: 38, a variant, derivative, orthologue, paralogue or homologue thereof, in which:
the amino acid at or corresponding to position 98 is Phe, and the amino acid at or corresponding to position 392 is Leu.

In another preferred embodiment, the mutated PPO comprises a sequence of SEQ ID NO: 38, a variant, derivative, orthologue, paralogue or homologue thereof, in which:
the amino acid at or corresponding to position 98 is Phe, and the amino acid at or corresponding to position 392 is Val.

In another preferred embodiment, the mutated PPO comprises a sequence of SEQ ID NO: 38, a variant, derivative, orthologue, paralogue or homologue thereof, in which:
the amino acid at or corresponding to position 98 is Phe, and the amino acid at or corresponding to position 392 is Ile.

In another preferred embodiment, the mutated PPO comprises a sequence of SEQ ID NO: 38, a variant, derivative, orthologue, paralogue or homologue thereof, in which:
the amino acid at or corresponding to position 98 is Phe, and the amino acid at or corresponding to position 392 is Met.

In another preferred embodiment, the mutated PPO comprises a sequence of SEQ ID NO: 38, a variant, derivative, orthologue, paralogue or homologue thereof, in which:
the amino acid at or corresponding to position 98 is Ser, and the amino acid at or corresponding to position 392 is Ala.

In another preferred embodiment, the mutated PPO comprises a sequence of SEQ ID NO: 38, a variant, derivative, orthologue, paralogue or homologue thereof, in which:
the amino acid at or corresponding to position 98 is Ser, and the amino acid at or corresponding to position 392 is Leu.

In another preferred embodiment, the mutated PPO comprises a sequence of SEQ ID NO: 38, a variant, derivative, orthologue, paralogue or homologue thereof, in which:
the amino acid at or corresponding to position 98 is Ser, and the amino acid at or corresponding to position 392 is Val.

In another preferred embodiment, the mutated PPO comprises a sequence of SEQ ID NO: 38, a variant, derivative, orthologue, paralogue or homologue thereof, in which:
the amino acid at or corresponding to position 98 is Ser, and the amino acid at or corresponding to position 392 is Ile.

In another preferred embodiment, the mutated PPO comprises a sequence of SEQ ID NO: 38, a variant, derivative, orthologue, paralogue or homologue thereof, in which:
the amino acid at or corresponding to position 98 is Ser, and the amino acid at or corresponding to position 392 is Met.

In another preferred embodiment, the mutated PPO comprises a sequence of SEQ ID NO: 38, a variant, derivative, orthologue, paralogue or homologue thereof, in which:
the amino acid at or corresponding to position 98 is Thr, and the amino acid at or corresponding to position 392 is Ala.

In another preferred embodiment, the mutated PPO comprises a sequence of SEQ ID NO: 38, a variant, derivative, orthologue, paralogue or homologue thereof, in which:
the amino acid at or corresponding to position 98 is Thr, and the amino acid at or corresponding to position 392 is Leu.

In another preferred embodiment, the mutated PPO comprises a sequence of SEQ ID NO: 38, a variant, derivative, orthologue, paralogue or homologue thereof, in which:
the amino acid at or corresponding to position 98 is Thr, and the amino acid at or corresponding to position 392 is Val.

In another preferred embodiment, the mutated PPO comprises a sequence of SEQ ID NO: 38, a variant, derivative, orthologue, paralogue or homologue thereof, in which:
the amino acid at or corresponding to position 98 is Thr, and the amino acid at or corresponding to position 392 is Ile.

In another preferred embodiment, the mutated PPO comprises a sequence of SEQ ID NO: 38, a variant, derivative, orthologue, paralogue or homologue thereof, in which:
the amino acid at or corresponding to position 98 is Thr, and the amino acid at or corresponding to position 392 is Met.

In another preferred embodiment, the mutated PPO comprises a sequence of SEQ ID NO: 38, a variant, derivative, orthologue, paralogue or homologue thereof, in which:
the amino acid at or corresponding to position 98 is Gin, and the amino acid at or corresponding to position 392 is Ala.

In another preferred embodiment, the mutated PPO comprises a sequence of SEQ ID NO: 38, a variant, derivative, orthologue, paralogue or homologue thereof, in which:
the amino acid at or corresponding to position 98 is Gin, and the amino acid at or corresponding to position 392 is Leu.

In another preferred embodiment, the mutated PPO comprises a sequence of SEQ ID NO: 38, a variant, derivative, orthologue, paralogue or homologue thereof, in which:

the amino acid at or corresponding to position 98 is Gln, and the amino acid at or corresponding to position 392 is Val.

In another preferred embodiment, the mutated PPO comprises a sequence of SEQ ID NO: 38, a variant, derivative, orthologue, paralogue or homologue thereof, in which:
the amino acid at or corresponding to position 98 is Gln, and the amino acid at or corresponding to position 392 is Ile.

In another preferred embodiment, the mutated PPO comprises a sequence of SEQ ID NO: 38, a variant, derivative, orthologue, paralogue or homologue thereof, in which:
the amino acid at or corresponding to position 98 is Gln, and the amino acid at or corresponding to position 392 is Met.

In another preferred embodiment, the mutated PPO comprises a sequence of SEQ ID NO: 38, a variant, derivative, orthologue, paralogue or homologue thereof, in which:
the amino acid at or corresponding to position 98 is His, and the amino acid at or corresponding to position 392 is Ala.

In another preferred embodiment, the mutated PPO comprises a sequence of SEQ ID NO: 38, a variant, derivative, orthologue, paralogue or homologue thereof, in which:
the amino acid at or corresponding to position 98 is His, and the amino acid at or corresponding to position 392 is Leu.

In another preferred embodiment, the mutated PPO comprises a sequence of SEQ ID NO: 38, a variant, derivative, orthologue, paralogue or homologue thereof, in which:
the amino acid at or corresponding to position 98 is His, and the amino acid at or corresponding to position 392 is Val.

In another preferred embodiment, the mutated PPO comprises a sequence of SEQ ID NO: 38, a variant, derivative, orthologue, paralogue or homologue thereof, in which:
the amino acid at or corresponding to position 98 is His, and the amino acid at or corresponding to position 392 is Ile.

In another preferred embodiment, the mutated PPO comprises a sequence of SEQ ID NO: 38, a variant, derivative, orthologue, paralogue or homologue thereof, in which:
the amino acid at or corresponding to position 98 is His, and the amino acid at or corresponding to position 392 is Met.

In another preferred embodiment, the mutated PPO comprises a sequence of SEQ ID NO: 46, a variant, derivative, orthologue, paralogue or homologue thereof, in which:
the amino acid at or corresponding to position 139 is Leu, Ala, Val, Ile, Met, Tyr, Gly, Asn, Cys, Phe, Ser, Thr, Gln, His, and the amino acid at or corresponding to position 465 is Ala, Leu, Val, Ile, Met.

In another preferred embodiment, the mutated PPO comprises a sequence of SEQ ID NO: 46, a variant, derivative, orthologue, paralogue or homologue thereof, in which:
the amino acid at or corresponding to position 139 is Leu, and the amino acid at or corresponding to position 465 is Ala.

In another preferred embodiment, the mutated PPO comprises a sequence of SEQ ID NO: 46, a variant, derivative, orthologue, paralogue or homologue thereof, in which:
the amino acid at or corresponding to position 139 is Leu, and the amino acid at or corresponding to position 465 is Leu.

In another preferred embodiment, the mutated PPO comprises a sequence of SEQ ID NO: 46, a variant, derivative, orthologue, paralogue or homologue thereof, in which:
the amino acid at or corresponding to position 139 is Leu, and the amino acid at or corresponding to position 465 is Val.

In another preferred embodiment, the mutated PPO comprises a sequence of SEQ ID NO: 46, a variant, derivative, orthologue, paralogue or homologue thereof, in which:
the amino acid at or corresponding to position 139 is Leu, and the amino acid at or corresponding to position 465 is Ile.

In another preferred embodiment, the mutated PPO comprises a sequence of SEQ ID NO: 46, a variant, derivative, orthologue, paralogue or homologue thereof, in which:
the amino acid at or corresponding to position 139 is Leu, and the amino acid at or corresponding to position 465 is Met.

In another preferred embodiment, the mutated PPO comprises a sequence of SEQ ID NO: 46, a variant, derivative, orthologue, paralogue or homologue thereof, in which:
the amino acid at or corresponding to position 139 is Ala, and the amino acid at or corresponding to position 465 is Ala.

In another preferred embodiment, the mutated PPO comprises a sequence of SEQ ID NO: 46, a variant, derivative, orthologue, paralogue or homologue thereof, in which:
the amino acid at or corresponding to position 139 is Ala, and the amino acid at or corresponding to position 465 is Leu.

In another preferred embodiment, the mutated PPO comprises a sequence of SEQ ID NO: 46, a variant, derivative, orthologue, paralogue or homologue thereof, in which:
the amino acid at or corresponding to position 139 is Ala, and the amino acid at or corresponding to position 465 is Val.

In another preferred embodiment, the mutated PPO comprises a sequence of SEQ ID NO: 46, a variant, derivative, orthologue, paralogue or homologue thereof, in which:
the amino acid at or corresponding to position 139 is Ala, and the amino acid at or corresponding to position 465 is Ile.

In another preferred embodiment, the mutated PPO comprises a sequence of SEQ ID NO: 46, a variant, derivative, orthologue, paralogue or homologue thereof, in which:
the amino acid at or corresponding to position 139 is Ala, and the amino acid at or corresponding to position 465 is Met.

In another preferred embodiment, the mutated PPO comprises a sequence of SEQ ID NO: 46, a variant, derivative, orthologue, paralogue or homologue thereof, in which:
the amino acid at or corresponding to position 139 is Val, and the amino acid at or corresponding to position 465 is Ala.

In another preferred embodiment, the mutated PPO comprises a sequence of SEQ ID NO: 46, a variant, derivative, orthologue, paralogue or homologue thereof, in which:
the amino acid at or corresponding to position 139 is Val, and the amino acid at or corresponding to position 465 is Leu.

In another preferred embodiment, the mutated PPO comprises a sequence of SEQ ID NO: 46, a variant, derivative, orthologue, paralogue or homologue thereof, in which:
the amino acid at or corresponding to position 139 is Val, and the amino acid at or corresponding to position 465 is Val.

In another preferred embodiment, the mutated PPO comprises a sequence of SEQ ID NO: 46, a variant, derivative, orthologue, paralogue or homologue thereof, in which:
the amino acid at or corresponding to position 139 is Val, and the amino acid at or corresponding to position 465 is Ile.

In another preferred embodiment, the mutated PPO comprises a sequence of SEQ ID NO: 46, a variant, derivative, orthologue, paralogue or homologue thereof, in which:
the amino acid at or corresponding to position 139 is Val, and the amino acid at or corresponding to position 465 is Met.

In another preferred embodiment, the mutated PPO comprises a sequence of SEQ ID NO: 46, a variant, derivative, orthologue, paralogue or homologue thereof, in which:
the amino acid at or corresponding to position 139 is Ile, and the amino acid at or corresponding to position 465 is Ala.

In another preferred embodiment, the mutated PPO comprises a sequence of SEQ ID NO: 46, a variant, derivative, orthologue, paralogue or homologue thereof, in which:
the amino acid at or corresponding to position 139 is Ile, and the amino acid at or corresponding to position 465 is Leu.

In another preferred embodiment, the mutated PPO comprises a sequence of SEQ ID NO: 46, a variant, derivative, orthologue, paralogue or homologue thereof, in which:
the amino acid at or corresponding to position 139 is Ile, and the amino acid at or corresponding to position 465 is Val.

In another preferred embodiment, the mutated PPO comprises a sequence of SEQ ID NO: 46, a variant, derivative, orthologue, paralogue or homologue thereof, in which:
the amino acid at or corresponding to position 139 is Ile, and the amino acid at or corresponding to position 465 is Ile.

In another preferred embodiment, the mutated PPO comprises a sequence of SEQ ID NO: 46, a variant, derivative, orthologue, paralogue or homologue thereof, in which:
the amino acid at or corresponding to position 139 is Ile, and the amino acid at or corresponding to position 465 is Met.

In another preferred embodiment, the mutated PPO comprises a sequence of SEQ ID NO: 46, a variant, derivative, orthologue, paralogue or homologue thereof, in which:
the amino acid at or corresponding to position 139 is Met, and the amino acid at or corresponding to position 465 is Ala.

In another preferred embodiment, the mutated PPO comprises a sequence of SEQ ID NO: 46, a variant, derivative, orthologue, paralogue or homologue thereof, in which:
the amino acid at or corresponding to position 139 is Met, and the amino acid at or corresponding to position 465 is Leu.

In another preferred embodiment, the mutated PPO comprises a sequence of SEQ ID NO: 46, a variant, derivative, orthologue, paralogue or homologue thereof, in which:
the amino acid at or corresponding to position 139 is Met, and the amino acid at or corresponding to position 465 is Val.

In another preferred embodiment, the mutated PPO comprises a sequence of SEQ ID NO: 46, a variant, derivative, orthologue, paralogue or homologue thereof, in which:
the amino acid at or corresponding to position 139 is Met, and the amino acid at or corresponding to position 465 is Ile.

In another preferred embodiment, the mutated PPO comprises a sequence of SEQ ID NO: 46, a variant, derivative, orthologue, paralogue or homologue thereof, in which:
the amino acid at or corresponding to position 139 is Met, and the amino acid at or corresponding to position 465 is Met.

In another preferred embodiment, the mutated PPO comprises a sequence of SEQ ID NO: 46, a variant, derivative, orthologue, paralogue or homologue thereof, in which:
the amino acid at or corresponding to position 139 is Tyr, and the amino acid at or corresponding to position 465 is Ala.

In another preferred embodiment, the mutated PPO comprises a sequence of SEQ ID NO: 46, a variant, derivative, orthologue, paralogue or homologue thereof, in which:
the amino acid at or corresponding to position 139 is Tyr, and the amino acid at or corresponding to position 465 is Leu.

In another preferred embodiment, the mutated PPO comprises a sequence of SEQ ID NO: 46, a variant, derivative, orthologue, paralogue or homologue thereof, in which:
the amino acid at or corresponding to position 139 is Tyr, and the amino acid at or corresponding to position 465 is Val.

In another preferred embodiment, the mutated PPO comprises a sequence of SEQ ID NO: 46, a variant, derivative, orthologue, paralogue or homologue thereof, in which:
the amino acid at or corresponding to position 139 is Tyr, and the amino acid at or corresponding to position 465 is Ile.

In another preferred embodiment, the mutated PPO comprises a sequence of SEQ ID NO: 46, a variant, derivative, orthologue, paralogue or homologue thereof, in which:
the amino acid at or corresponding to position 139 is Tyr, and the amino acid at or corresponding to position 465 is Met.

In another preferred embodiment, the mutated PPO comprises a sequence of SEQ ID NO: 46, a variant, derivative, orthologue, paralogue or homologue thereof, in which:
the amino acid at or corresponding to position 139 is Gly, and the amino acid at or corresponding to position 465 is Ala.

In another preferred embodiment, the mutated PPO comprises a sequence of SEQ ID NO: 46, a variant, derivative, orthologue, paralogue or homologue thereof, in which:
the amino acid at or corresponding to position 139 is Gly, and the amino acid at or corresponding to position 465 is Leu.

In another preferred embodiment, the mutated PPO comprises a sequence of SEQ ID NO: 46, a variant, derivative, orthologue, paralogue or homologue thereof, in which:
the amino acid at or corresponding to position 139 is Gly, and the amino acid at or corresponding to position 465 is Val.

In another preferred embodiment, the mutated PPO comprises a sequence of SEQ ID NO: 46, a variant, derivative, orthologue, paralogue or homologue thereof, in which:
the amino acid at or corresponding to position 139 is Gly, and the amino acid at or corresponding to position 465 is Ile.

In another preferred embodiment, the mutated PPO comprises a sequence of SEQ ID NO: 46, a variant, derivative, orthologue, paralogue or homologue thereof, in which:
the amino acid at or corresponding to position 139 is Gly, and the amino acid at or corresponding to position 465 is Met.

In another preferred embodiment, the mutated PPO comprises a sequence of SEQ ID NO: 46, a variant, derivative, orthologue, paralogue or homologue thereof, in which:
the amino acid at or corresponding to position 139 is Asn, and the amino acid at or corresponding to position 465 is Ala.

In another preferred embodiment, the mutated PPO comprises a sequence of SEQ ID NO: 46, a variant, derivative, orthologue, paralogue or homologue thereof, in which:
the amino acid at or corresponding to position 139 is Asn, and the amino acid at or corresponding to position 465 is Leu.

In another preferred embodiment, the mutated PPO comprises a sequence of SEQ ID NO: 46, a variant, derivative, orthologue, paralogue or homologue thereof, in which:
the amino acid at or corresponding to position 139 is Asn, and the amino acid at or corresponding to position 465 is Val.

In another preferred embodiment, the mutated PPO comprises a sequence of SEQ ID NO: 46, a variant, derivative, orthologue, paralogue or homologue thereof, in which:
the amino acid at or corresponding to position 139 is Asn, and the amino acid at or corresponding to position 465 is Ile.

In another preferred embodiment, the mutated PPO comprises a sequence of SEQ ID NO: 46, a variant, derivative, orthologue, paralogue or homologue thereof, in which:
the amino acid at or corresponding to position 139 is Asn, and the amino acid at or corresponding to position 465 is Met.

In another preferred embodiment, the mutated PPO comprises a sequence of SEQ ID NO: 46, a variant, derivative, orthologue, paralogue or homologue thereof, in which:
the amino acid at or corresponding to position 139 is Cys, and the amino acid at or corresponding to position 465 is Ala.

In another preferred embodiment, the mutated PPO comprises a sequence of SEQ ID NO: 46, a variant, derivative, orthologue, paralogue or homologue thereof, in which:
the amino acid at or corresponding to position 139 is Cys, and the amino acid at or corresponding to position 465 is Leu.

In another preferred embodiment, the mutated PPO comprises a sequence of SEQ ID NO: 46, a variant, derivative, orthologue, paralogue or homologue thereof, in which:
the amino acid at or corresponding to position 139 is Cys, and the amino acid at or corresponding to position 465 is Val.

In another preferred embodiment, the mutated PPO comprises a sequence of SEQ ID NO: 46, a variant, derivative, orthologue, paralogue or homologue thereof, in which:
the amino acid at or corresponding to position 139 is Cys, and the amino acid at or corresponding to position 465 is Ile.

In another preferred embodiment, the mutated PPO comprises a sequence of SEQ ID NO: 46, a variant, derivative, orthologue, paralogue or homologue thereof, in which:
the amino acid at or corresponding to position 139 is Cys, and the amino acid at or corresponding to position 465 is Met.

In another preferred embodiment, the mutated PPO comprises a sequence of SEQ ID NO: 46, a variant, derivative, orthologue, paralogue or homologue thereof, in which:
the amino acid at or corresponding to position 139 is Phe, and the amino acid at or corresponding to position 465 is Ala.

In another preferred embodiment, the mutated PPO comprises a sequence of SEQ ID NO: 46, a variant, derivative, orthologue, paralogue or homologue thereof, in which:
the amino acid at or corresponding to position 139 is Phe, and the amino acid at or corresponding to position 465 is Leu.

In another preferred embodiment, the mutated PPO comprises a sequence of SEQ ID NO: 46, a variant, derivative, orthologue, paralogue or homologue thereof, in which:
the amino acid at or corresponding to position 139 is Phe, and the amino acid at or corresponding to position 465 is Val.

In another preferred embodiment, the mutated PPO comprises a sequence of SEQ ID NO: 46, a variant, derivative, orthologue, paralogue or homologue thereof, in which:
the amino acid at or corresponding to position 139 is Phe, and the amino acid at or corresponding to position 465 is Ile.

In another preferred embodiment, the mutated PPO comprises a sequence of SEQ ID NO: 46, a variant, derivative, orthologue, paralogue or homologue thereof, in which:
the amino acid at or corresponding to position 139 is Phe, and the amino acid at or corresponding to position 465 is Met.

In another preferred embodiment, the mutated PPO comprises a sequence of SEQ ID NO: 46, a variant, derivative, orthologue, paralogue or homologue thereof, in which:
the amino acid at or corresponding to position 139 is Ser, and the amino acid at or corresponding to position 465 is Ala.

In another preferred embodiment, the mutated PPO comprises a sequence of SEQ ID NO: 46, a variant, derivative, orthologue, paralogue or homologue thereof, in which:
the amino acid at or corresponding to position 139 is Ser, and the amino acid at or corresponding to position 465 is Leu.

In another preferred embodiment, the mutated PPO comprises a sequence of SEQ ID NO: 46, a variant, derivative, orthologue, paralogue or homologue thereof, in which:
the amino acid at or corresponding to position 139 is Ser, and the amino acid at or corresponding to position 465 is Val.

In another preferred embodiment, the mutated PPO comprises a sequence of SEQ ID NO: 46, a variant, derivative, orthologue, paralogue or homologue thereof, in which:
the amino acid at or corresponding to position 139 is Ser, and the amino acid at or corresponding to position 465 is Ile.

In another preferred embodiment, the mutated PPO comprises a sequence of SEQ ID NO: 46, a variant, derivative, orthologue, paralogue or homologue thereof, in which:
the amino acid at or corresponding to position 139 is Ser, and the amino acid at or corresponding to position 465 is Met.

In another preferred embodiment, the mutated PPO comprises a sequence of SEQ ID NO: 46, a variant, derivative, orthologue, paralogue or homologue thereof, in which:
the amino acid at or corresponding to position 139 is Thr, and the amino acid at or corresponding to position 465 is Ala.

In another preferred embodiment, the mutated PPO comprises a sequence of SEQ ID NO: 46, a variant, derivative, orthologue, paralogue or homologue thereof, in which:
the amino acid at or corresponding to position 139 is Thr, and the amino acid at or corresponding to position 465 is Leu.

In another preferred embodiment, the mutated PPO comprises a sequence of SEQ ID NO: 46, a variant, derivative, orthologue, paralogue or homologue thereof, in which:
the amino acid at or corresponding to position 139 is Thr, and the amino acid at or corresponding to position 465 is Val.

In another preferred embodiment, the mutated PPO comprises a sequence of SEQ ID NO: 46, a variant, derivative, orthologue, paralogue or homologue thereof, in which:
the amino acid at or corresponding to position 139 is Thr, and the amino acid at or corresponding to position 465 is Ile.

In another preferred embodiment, the mutated PPO comprises a sequence of SEQ ID NO: 46, a variant, derivative, orthologue, paralogue or homologue thereof, in which:
the amino acid at or corresponding to position 139 is Thr, and the amino acid at or corresponding to position 465 is Met.

In another preferred embodiment, the mutated PPO comprises a sequence of SEQ ID NO: 46, a variant, derivative, orthologue, paralogue or homologue thereof, in which:
the amino acid at or corresponding to position 139 is Gln, and the amino acid at or corresponding to position 465 is Ala.

In another preferred embodiment, the mutated PPO comprises a sequence of SEQ ID NO: 46, a variant, derivative, orthologue, paralogue or homologue thereof, in which:
the amino acid at or corresponding to position 139 is Gln, and the amino acid at or corresponding to position 465 is Leu.

In another preferred embodiment, the mutated PPO comprises a sequence of SEQ ID NO: 46, a variant, derivative, orthologue, paralogue or homologue thereof, in which:
the amino acid at or corresponding to position 139 is Gln, and the amino acid at or corresponding to position 465 is Val.

In another preferred embodiment, the mutated PPO comprises a sequence of SEQ ID NO: 46, a variant, derivative, orthologue, paralogue or homologue thereof, in which:
the amino acid at or corresponding to position 139 is Gln, and the amino acid at or corresponding to position 465 is Ile.

In another preferred embodiment, the mutated PPO comprises a sequence of SEQ ID NO: 46, a variant, derivative, orthologue, paralogue or homologue thereof, in which:
the amino acid at or corresponding to position 139 is Gln, and the amino acid at or corresponding to position 465 is Met.

In another preferred embodiment, the mutated PPO comprises a sequence of SEQ ID NO: 46, a variant, derivative, orthologue, paralogue or homologue thereof, in which:
the amino acid at or corresponding to position 139 is His, and the amino acid at or corresponding to position 465 is Ala.

In another preferred embodiment, the mutated PPO comprises a sequence of SEQ ID NO: 46, a variant, derivative, orthologue, paralogue or homologue thereof, in which:
the amino acid at or corresponding to position 139 is His, and the amino acid at or corresponding to position 465 is Leu.

In another preferred embodiment, the mutated PPO comprises a sequence of SEQ ID NO: 46, a variant, derivative, orthologue, paralogue or homologue thereof, in which:
the amino acid at or corresponding to position 139 is His, and the amino acid at or corresponding to position 465 is Val.

In another preferred embodiment, the mutated PPO comprises a sequence of SEQ ID NO: 46, a variant, derivative, orthologue, paralogue or homologue thereof, in which:
the amino acid at or corresponding to position 139 is His, and the amino acid at or corresponding to position 465 is Ile.

In another preferred embodiment, the mutated PPO comprises a sequence of SEQ ID NO: 46, a variant, derivative, orthologue, paralogue or homologue thereof, in which:
the amino acid at or corresponding to position 139 is His, and the amino acid at or corresponding to position 465 is Met.

In another preferred embodiment, the mutated PPO comprises a sequence of SEQ ID NO: 48, a variant, derivative, orthologue, paralogue or homologue thereof, in which:
the amino acid at or corresponding to position 157 is Leu, Ala, Val, Ile, Met, Tyr, Gly, Asn, Cys, Phe, Ser, Thr, Gln, His, and the amino acid at or corresponding to position 439 is Ala, Leu, Val, Ile, Met.

In another preferred embodiment, the mutated PPO comprises a sequence of SEQ ID NO: 48, a variant, derivative, orthologue, paralogue or homologue thereof, in which:
the amino acid at or corresponding to position 157 is Leu, and the amino acid at or corresponding to position 439 is Ala.

In another preferred embodiment, the mutated PPO comprises a sequence of SEQ ID NO: 48, a variant, derivative, orthologue, paralogue or homologue thereof, in which:
the amino acid at or corresponding to position 157 is Leu, and the amino acid at or corresponding to position 439 is Leu.

In another preferred embodiment, the mutated PPO comprises a sequence of SEQ ID NO: 48, a variant, derivative, orthologue, paralogue or homologue thereof, in which:
the amino acid at or corresponding to position 157 is Leu, and the amino acid at or corresponding to position 439 is Val.

In another preferred embodiment, the mutated PPO comprises a sequence of SEQ ID NO: 48, a variant, derivative, orthologue, paralogue or homologue thereof, in which:
the amino acid at or corresponding to position 157 is Leu, and the amino acid at or corresponding to position 439 is Ile.

In another preferred embodiment, the mutated PPO comprises a sequence of SEQ ID NO: 48, a variant, derivative, orthologue, paralogue or homologue thereof, in which:
the amino acid at or corresponding to position 157 is Leu, and the amino acid at or corresponding to position 439 is Met.

In another preferred embodiment, the mutated PPO comprises a sequence of SEQ ID NO: 48, a variant, derivative, orthologue, paralogue or homologue thereof, in which:
the amino acid at or corresponding to position 157 is Ala, and the amino acid at or corresponding to position 439 is Ala.

In another preferred embodiment, the mutated PPO comprises a sequence of SEQ ID NO: 48, a variant, derivative, orthologue, paralogue or homologue thereof, in which:
the amino acid at or corresponding to position 157 is Ala, and the amino acid at or corresponding to position 439 is Leu.

In another preferred embodiment, the mutated PPO comprises a sequence of SEQ ID NO: 48, a variant, derivative, orthologue, paralogue or homologue thereof, in which:
the amino acid at or corresponding to position 157 is Ala, and the amino acid at or corresponding to position 439 is Val.

In another preferred embodiment, the mutated PPO comprises a sequence of SEQ ID NO: 48, a variant, derivative, orthologue, paralogue or homologue thereof, in which:
the amino acid at or corresponding to position 157 is Ala, and the amino acid at or corresponding to position 439 is Ile.

In another preferred embodiment, the mutated PPO comprises a sequence of SEQ ID NO: 48, a variant, derivative, orthologue, paralogue or homologue thereof, in which:
the amino acid at or corresponding to position 157 is Ala, and the amino acid at or corresponding to position 439 is Met.

In another preferred embodiment, the mutated PPO comprises a sequence of SEQ ID NO: 48, a variant, derivative, orthologue, paralogue or homologue thereof, in which:
the amino acid at or corresponding to position 157 is Val, and the amino acid at or corresponding to position 439 is Ala.

In another preferred embodiment, the mutated PPO comprises a sequence of SEQ ID NO: 48, a variant, derivative, orthologue, paralogue or homologue thereof, in which:

the amino acid at or corresponding to position 157 is Val, and the amino acid at or corresponding to position 439 is Leu.

In another preferred embodiment, the mutated PPO comprises a sequence of SEQ ID NO: 48, a variant, derivative, orthologue, paralogue or homologue thereof, in which:
the amino acid at or corresponding to position 157 is Val, and the amino acid at or corresponding to position 439 is Val.

In another preferred embodiment, the mutated PPO comprises a sequence of SEQ ID NO: 48, a variant, derivative, orthologue, paralogue or homologue thereof, in which:
the amino acid at or corresponding to position 157 is Val, and the amino acid at or corresponding to position 439 is Ile.

In another preferred embodiment, the mutated PPO comprises a sequence of SEQ ID NO: 48, a variant, derivative, orthologue, paralogue or homologue thereof, in which:
the amino acid at or corresponding to position 157 is Val, and the amino acid at or corresponding to position 439 is Met.

In another preferred embodiment, the mutated PPO comprises a sequence of SEQ ID NO: 48, a variant, derivative, orthologue, paralogue or homologue thereof, in which:
the amino acid at or corresponding to position 157 is Ile, and the amino acid at or corresponding to position 439 is Ala.

In another preferred embodiment, the mutated PPO comprises a sequence of SEQ ID NO: 48, a variant, derivative, orthologue, paralogue or homologue thereof, in which:
the amino acid at or corresponding to position 157 is Ile, and the amino acid at or corresponding to position 439 is Leu.

In another preferred embodiment, the mutated PPO comprises a sequence of SEQ ID NO: 48, a variant, derivative, orthologue, paralogue or homologue thereof, in which:
the amino acid at or corresponding to position 157 is Ile, and the amino acid at or corresponding to position 439 is Val.

In another preferred embodiment, the mutated PPO comprises a sequence of SEQ ID NO: 48, a variant, derivative, orthologue, paralogue or homologue thereof, in which:
the amino acid at or corresponding to position 157 is Ile, and the amino acid at or corresponding to position 439 is Ile.

In another preferred embodiment, the mutated PPO comprises a sequence of SEQ ID NO: 48, a variant, derivative, orthologue, paralogue or homologue thereof, in which:
the amino acid at or corresponding to position 157 is Ile, and the amino acid at or corresponding to position 439 is Met.

In another preferred embodiment, the mutated PPO comprises a sequence of SEQ ID NO: 48, a variant, derivative, orthologue, paralogue or homologue thereof, in which:
the amino acid at or corresponding to position 157 is Met, and the amino acid at or corresponding to position 439 is Ala.

In another preferred embodiment, the mutated PPO comprises a sequence of SEQ ID NO: 48, a variant, derivative, orthologue, paralogue or homologue thereof, in which:
the amino acid at or corresponding to position 157 is Met, and the amino acid at or corresponding to position 439 is Leu.

In another preferred embodiment, the mutated PPO comprises a sequence of SEQ ID NO: 48, a variant, derivative, orthologue, paralogue or homologue thereof, in which:
the amino acid at or corresponding to position 157 is Met, and the amino acid at or corresponding to position 439 is Val.

In another preferred embodiment, the mutated PPO comprises a sequence of SEQ ID NO: 48, a variant, derivative, orthologue, paralogue or homologue thereof, in which:
the amino acid at or corresponding to position 157 is Met, and the amino acid at or corresponding to position 439 is Ile.

In another preferred embodiment, the mutated PPO comprises a sequence of SEQ ID NO: 48, a variant, derivative, orthologue, paralogue or homologue thereof, in which:
the amino acid at or corresponding to position 157 is Met, and the amino acid at or corresponding to position 439 is Met.

In another preferred embodiment, the mutated PPO comprises a sequence of SEQ ID NO: 48, a variant, derivative, orthologue, paralogue or homologue thereof, in which:
the amino acid at or corresponding to position 157 is Tyr, and the amino acid at or corresponding to position 439 is Ala.

In another preferred embodiment, the mutated PPO comprises a sequence of SEQ ID NO: 48, a variant, derivative, orthologue, paralogue or homologue thereof, in which:
the amino acid at or corresponding to position 157 is Tyr, and the amino acid at or corresponding to position 439 is Leu.

In another preferred embodiment, the mutated PPO comprises a sequence of SEQ ID NO: 48, a variant, derivative, orthologue, paralogue or homologue thereof, in which:
the amino acid at or corresponding to position 157 is Tyr, and the amino acid at or corresponding to position 439 is Val.

In another preferred embodiment, the mutated PPO comprises a sequence of SEQ ID NO: 48, a variant, derivative, orthologue, paralogue or homologue thereof, in which:
the amino acid at or corresponding to position 157 is Tyr, and the amino acid at or corresponding to position 439 is Ile.

In another preferred embodiment, the mutated PPO comprises a sequence of SEQ ID NO: 48, a variant, derivative, orthologue, paralogue or homologue thereof, in which:
the amino acid at or corresponding to position 157 is Tyr, and the amino acid at or corresponding to position 439 is Met.

In another preferred embodiment, the mutated PPO comprises a sequence of SEQ ID NO: 48, a variant, derivative, orthologue, paralogue or homologue thereof, in which:
the amino acid at or corresponding to position 157 is Gly, and the amino acid at or corresponding to position 439 is Ala.

In another preferred embodiment, the mutated PPO comprises a sequence of SEQ ID NO: 48, a variant, derivative, orthologue, paralogue or homologue thereof, in which:
the amino acid at or corresponding to position 157 is Gly, and the amino acid at or corresponding to position 439 is Leu.

In another preferred embodiment, the mutated PPO comprises a sequence of SEQ ID NO: 48, a variant, derivative, orthologue, paralogue or homologue thereof, in which:
the amino acid at or corresponding to position 157 is Gly, and the amino acid at or corresponding to position 439 is Val.

In another preferred embodiment, the mutated PPO comprises a sequence of SEQ ID NO: 48, a variant, derivative, orthologue, paralogue or homologue thereof, in which:
the amino acid at or corresponding to position 157 is Gly, and the amino acid at or corresponding to position 439 is Ile.

In another preferred embodiment, the mutated PPO comprises a sequence of SEQ ID NO: 48, a variant, derivative, orthologue, paralogue or homologue thereof, in which:

the amino acid at or corresponding to position 157 is Gly, and the amino acid at or corresponding to position 439 is Met.

In another preferred embodiment, the mutated PPO comprises a sequence of SEQ ID NO: 48, a variant, derivative, orthologue, paralogue or homologue thereof, in which:
the amino acid at or corresponding to position 157 is Asn, and the amino acid at or corresponding to position 439 is Ala.

In another preferred embodiment, the mutated PPO comprises a sequence of SEQ ID NO: 48, a variant, derivative, orthologue, paralogue or homologue thereof, in which:
the amino acid at or corresponding to position 157 is Asn, and the amino acid at or corresponding to position 439 is Leu.

In another preferred embodiment, the mutated PPO comprises a sequence of SEQ ID NO: 48, a variant, derivative, orthologue, paralogue or homologue thereof, in which:
the amino acid at or corresponding to position 157 is Asn, and the amino acid at or corresponding to position 439 is Val.

In another preferred embodiment, the mutated PPO comprises a sequence of SEQ ID NO: 48, a variant, derivative, orthologue, paralogue or homologue thereof, in which:
the amino acid at or corresponding to position 157 is Asn, and the amino acid at or corresponding to position 439 is Ile.

In another preferred embodiment, the mutated PPO comprises a sequence of SEQ ID NO: 48, a variant, derivative, orthologue, paralogue or homologue thereof, in which:
the amino acid at or corresponding to position 157 is Asn, and the amino acid at or corresponding to position 439 is Met.

In another preferred embodiment, the mutated PPO comprises a sequence of SEQ ID NO: 48, a variant, derivative, orthologue, paralogue or homologue thereof, in which:
the amino acid at or corresponding to position 157 is Cys, and the amino acid at or corresponding to position 439 is Ala.

In another preferred embodiment, the mutated PPO comprises a sequence of SEQ ID NO: 48, a variant, derivative, orthologue, paralogue or homologue thereof, in which:
the amino acid at or corresponding to position 157 is Cys, and the amino acid at or corresponding to position 439 is Leu.

In another preferred embodiment, the mutated PPO comprises a sequence of SEQ ID NO: 48, a variant, derivative, orthologue, paralogue or homologue thereof, in which:
the amino acid at or corresponding to position 157 is Cys, and the amino acid at or corresponding to position 439 is Val.

In another preferred embodiment, the mutated PPO comprises a sequence of SEQ ID NO: 48, a variant, derivative, orthologue, paralogue or homologue thereof, in which:
the amino acid at or corresponding to position 157 is Cys, and the amino acid at or corresponding to position 439 is Ile.

In another preferred embodiment, the mutated PPO comprises a sequence of SEQ ID NO: 48, a variant, derivative, orthologue, paralogue or homologue thereof, in which:
the amino acid at or corresponding to position 157 is Cys, and the amino acid at or corresponding to position 439 is Met.

In another preferred embodiment, the mutated PPO comprises a sequence of SEQ ID NO: 48, a variant, derivative, orthologue, paralogue or homologue thereof, in which:
the amino acid at or corresponding to position 157 is Phe, and the amino acid at or corresponding to position 439 is Ala.

In another preferred embodiment, the mutated PPO comprises a sequence of SEQ ID NO: 48, a variant, derivative, orthologue, paralogue or homologue thereof, in which:
the amino acid at or corresponding to position 157 is Phe, and the amino acid at or corresponding to position 439 is Leu.

In another preferred embodiment, the mutated PPO comprises a sequence of SEQ ID NO: 48, a variant, derivative, orthologue, paralogue or homologue thereof, in which:
the amino acid at or corresponding to position 157 is Phe, and the amino acid at or corresponding to position 439 is Val.

In another preferred embodiment, the mutated PPO comprises a sequence of SEQ ID NO: 48, a variant, derivative, orthologue, paralogue or homologue thereof, in which:
the amino acid at or corresponding to position 157 is Phe, and the amino acid at or corresponding to position 439 is Ile.

In another preferred embodiment, the mutated PPO comprises a sequence of SEQ ID NO: 48, a variant, derivative, orthologue, paralogue or homologue thereof, in which:
the amino acid at or corresponding to position 157 is Phe, and the amino acid at or corresponding to position 439 is Met.

In another preferred embodiment, the mutated PPO comprises a sequence of SEQ ID NO: 48, a variant, derivative, orthologue, paralogue or homologue thereof, in which:
the amino acid at or corresponding to position 157 is Ser, and the amino acid at or corresponding to position 439 is Ala.

In another preferred embodiment, the mutated PPO comprises a sequence of SEQ ID NO: 48, a variant, derivative, orthologue, paralogue or homologue thereof, in which:
the amino acid at or corresponding to position 157 is Ser, and the amino acid at or corresponding to position 439 is Leu.

In another preferred embodiment, the mutated PPO comprises a sequence of SEQ ID NO: 48, a variant, derivative, orthologue, paralogue or homologue thereof, in which:
the amino acid at or corresponding to position 157 is Ser, and the amino acid at or corresponding to position 439 is Val.

In another preferred embodiment, the mutated PPO comprises a sequence of SEQ ID NO: 48, a variant, derivative, orthologue, paralogue or homologue thereof, in which:
the amino acid at or corresponding to position 157 is Ser, and the amino acid at or corresponding to position 439 is Ile.

In another preferred embodiment, the mutated PPO comprises a sequence of SEQ ID NO: 48, a variant, derivative, orthologue, paralogue or homologue thereof, in which:
the amino acid at or corresponding to position 157 is Ser, and the amino acid at or corresponding to position 439 is Met.

In another preferred embodiment, the mutated PPO comprises a sequence of SEQ ID NO: 48, a variant, derivative, orthologue, paralogue or homologue thereof, in which:
the amino acid at or corresponding to position 157 is Thr, and the amino acid at or corresponding to position 439 is Ala.

In another preferred embodiment, the mutated PPO comprises a sequence of SEQ ID NO: 48, a variant, derivative, orthologue, paralogue or homologue thereof, in which:
the amino acid at or corresponding to position 157 is Thr, and the amino acid at or corresponding to position 439 is Leu.

In another preferred embodiment, the mutated PPO comprises a sequence of SEQ ID NO: 48, a variant, derivative, orthologue, paralogue or homologue thereof, in which:

the amino acid at or corresponding to position 157 is Thr, and the amino acid at or corresponding to position 439 is Val.

In another preferred embodiment, the mutated PPO comprises a sequence of SEQ ID NO: 48, a variant, derivative, orthologue, paralogue or homologue thereof, in which:
the amino acid at or corresponding to position 157 is Thr, and the amino acid at or corresponding to position 439 is Ile.

In another preferred embodiment, the mutated PPO comprises a sequence of SEQ ID NO: 48, a variant, derivative, orthologue, paralogue or homologue thereof, in which:
the amino acid at or corresponding to position 157 is Thr, and the amino acid at or corresponding to position 439 is Met.

In another preferred embodiment, the mutated PPO comprises a sequence of SEQ ID NO: 48, a variant, derivative, orthologue, paralogue or homologue thereof, in which:
the amino acid at or corresponding to position 157 is Gin, and the amino acid at or corresponding to position 439 is Ala.

In another preferred embodiment, the mutated PPO comprises a sequence of SEQ ID NO: 48, a variant, derivative, orthologue, paralogue or homologue thereof, in which:
the amino acid at or corresponding to position 157 is Gin, and the amino acid at or corresponding to position 439 is Leu.

In another preferred embodiment, the mutated PPO comprises a sequence of SEQ ID NO: 48, a variant, derivative, orthologue, paralogue or homologue thereof, in which:
the amino acid at or corresponding to position 157 is Gin, and the amino acid at or corresponding to position 439 is Val.

In another preferred embodiment, the mutated PPO comprises a sequence of SEQ ID NO: 48, a variant, derivative, orthologue, paralogue or homologue thereof, in which:
the amino acid at or corresponding to position 157 is Gin, and the amino acid at or corresponding to position 439 is Ile.

In another preferred embodiment, the mutated PPO comprises a sequence of SEQ ID NO: 48, a variant, derivative, orthologue, paralogue or homologue thereof, in which:
the amino acid at or corresponding to position 157 is Gin, and the amino acid at or corresponding to position 439 is Met.

In another preferred embodiment, the mutated PPO comprises a sequence of SEQ ID NO: 48, a variant, derivative, orthologue, paralogue or homologue thereof, in which:
the amino acid at or corresponding to position 157 is His, and the amino acid at or corresponding to position 439 is Ala.

In another preferred embodiment, the mutated PPO comprises a sequence of SEQ ID NO: 48, a variant, derivative, orthologue, paralogue or homologue thereof, in which:
the amino acid at or corresponding to position 157 is His, and the amino acid at or corresponding to position 439 is Leu.

In another preferred embodiment, the mutated PPO comprises a sequence of SEQ ID NO: 48, a variant, derivative, orthologue, paralogue or homologue thereof, in which:
the amino acid at or corresponding to position 157 is His, and the amino acid at or corresponding to position 439 is Val.

In another preferred embodiment, the mutated PPO comprises a sequence of SEQ ID NO: 48, a variant, derivative, orthologue, paralogue or homologue thereof, in which:
the amino acid at or corresponding to position 157 is His, and the amino acid at or corresponding to position 439 is Ile.

In another preferred embodiment, the mutated PPO comprises a sequence of SEQ ID NO: 48, a variant, derivative, orthologue, paralogue or homologue thereof, in which:
the amino acid at or corresponding to position 157 is His, and the amino acid at or corresponding to position 439 is Met.

It will be within the knowledge of the skilled artisan to identify conserved regions and motifs shared between the homologues, orthologues and paralogues encoded by SEQ ID NO: 1, 3, 5, 7, 9, 11, 13, 15, 17, 19, 21, 23, 25, 27, 29, 31, 33, 35, 37, 39, 41, 43, 45, or 47, such as those depicted in Table 1. Having identified such conserved regions that may represent suitable binding motifs, amino acids corresponding to the amino acids listed in Table 3a and 3b, can be chosen to be substituted by any other amino acid, for example by conserved amino acids as shown in table 2, preferably by the amino acids of tables 3a and 3b.

Table 3c shows an overview of preferred mutation sites that are shared between homologues, orthologues and paralogues listed in Table 1.

TABLE 3c

| SEQ ID NO | Pos 1 | Pos 2 | Pos 3 | Pos 4 | Pos 5 | Pos 6 | Pos 7 | Pos 8 | Pos 9 | Pos 10 | Pos 11 | Pos 12 | Pos 13 | Pos 14 | Pos 15 |
|---|---|---|---|---|---|---|---|---|---|---|---|---|---|---|---|
| 2 | N126 | K127 | R128 | Y129 | I130 | A131 | S149 | I151 | A154 | P164 | K169 | E182 | S183 | E189 | F196 |
| 4 | N126 | K127 | R128 | Y129 | I130 | A131 | S149 | I151 | A154 | P164 | K169 | E182 | S183 | E189 | F196 |
| 6 | N126 | K127 | R128 | Y129 | I130 | A131 | S149 | I151 | A154 | P164 | K169 | E182 | S183 | E189 | F196 |
| 8 | N126 | K127 | R128 | Y129 | I130 | A131 | S149 | I151 | A154 | P164 | K169 | E182 | S183 | E189 | F196 |
| 10 | K145 | K146 | R147 | Y148 | I149 | V150 | S168 | V170 | T173 | P183 | K188 | E200 | S201 | Q207 | V214 |
| 12 | A153 | P154 | R155 | F156 | V157 | L158 | F176 | L178 | I181 | F189 | — | E203 | S204 | R210 | V217 |
| 14 | A160 | P161 | R162 | F163 | V164 | L165 | F183 | L185 | F188 | F196 | — | E210 | S211 | R217 | V224 |
| 16 | S167 | P168 | R169 | F170 | V171 | L172 | F190 | L192 | F195 | L203 | — | E217 | S218 | R224 | V231 |
| 18 | N125 | K126 | R127 | Y128 | I129 | A130 | S148 | I150 | A153 | P163 | K168 | E181 | S182 | E188 | F195 |
| 20 | A162 | P163 | R164 | F165 | V166 | L167 | F185 | L187 | I190 | F198 | — | E212 | S213 | R219 | V226 |
| 22 | A140 | P141 | R142 | F143 | V144 | L145 | F163 | L165 | I168 | L176 | — | E190 | S191 | R197 | V204 |
| 24 | H128 | K129 | R130 | Y131 | I132 | V133 | S151 | V153 | T156 | P166 | T174 | E187 | S188 | E194 | V201 |
| 26 | A165 | P166 | R167 | F168 | V169 | W170 | F187 | L189 | I192 | L200 | — | E215 | S216 | R222 | V229 |
| 28 | L128 | P129 | R130 | W131 | I132 | L133 | — | L152 | T155 | V165 | — | E180 | S181 | R187 | I194 |
| 30 | H128 | K129 | R130 | Y131 | I132 | V133 | S151 | V153 | T156 | P166 | T174 | E187 | S188 | E194 | V201 |
| 32 | A141 | P142 | R143 | F144 | V145 | L146 | F164 | L166 | I169 | L177 | — | E191 | S192 | R198 | V205 |
| 34 | N96 | K97 | R98 | Y99 | I100 | A101 | S119 | I121 | A124 | P134 | K139 | E152 | S153 | E159 | F166 |
| 36 | A142 | P143 | R144 | F145 | V146 | L147 | F165 | L167 | I170 | F178 | — | E192 | S193 | R199 | V206 |
| 38 | N96 | K97 | R98 | Y99 | I100 | A101 | S119 | F121 | T124 | P134 | N139 | E150 | S151 | Q157 | V164 |
| 40 | H96 | K97 | R98 | Y99 | I100 | V101 | S119 | L121 | A124 | P134 | R139 | E152 | S153 | E159 | V166 |
| 42 | A28 | P29 | R30 | F31 | V32 | L33 | F51 | L53 | I56 | F64 | — | E78 | S79 | R85 | V92 |

TABLE 3c-continued

| | | | | | | | | | | | | | | |
|---|---|---|---|---|---|---|---|---|---|---|---|---|---|---|
| 44 | H93 | K94 | R95 | Y96 | I97 | V98 | S116 | V118 | T121 | P131 | R139 | E152 | S153 | C158 | V165 |
| 46 | H137 | K138 | R139 | Y140 | I141 | V142 | S160 | V162 | T165 | P175 | R183 | E196 | S197 | E203 | V210 |
| 48 | A155 | P156 | R157 | F158 | V159 | L160 | F178 | L180 | F183 | L191 | — | E205 | S206 | R212 | V219 |

| SEQ ID NO | Pos 16 | Pos 17 | Pos 18 | Pos 19 | Pos 20 | Pos 21 | Pos 22 | Pos 23 | Pos 24 | Pos 25 | Pos 26 | Pos 27 | Pos 28 | Pos 29 | Pos 30 |
|---|---|---|---|---|---|---|---|---|---|---|---|---|---|---|---|
| 2 | D202 | C209 | G210 | G211 | L216 | M218 | H219 | H220 | N227 | S234 | S246 | K259 | P260 | R261 | L295 |
| 4 | D202 | C209 | G210 | G211 | L216 | M218 | H219 | H220 | N227 | S234 | S246 | K259 | P260 | R261 | L295 |
| 6 | D202 | C209 | G210 | — | L215 | M217 | Y218 | H219 | N226 | S233 | S245 | K258 | P259 | R260 | L294 |
| 8 | D202 | C209 | G210 | — | L215 | M217 | Y218 | H219 | N226 | S233 | S245 | K258 | P259 | R260 | L294 |
| 10 | D220 | S227 | A228 | A229 | L234 | M236 | K237 | H238 | N245 | S249 | A261 | K276 | K277 | G278 | L312 |
| 12 | E223 | Y230 | A231 | G232 | L237 | M239 | K240 | A241 | K248 | G254 | E266 | K281 | P282 | K283 | S316 |
| 14 | E230 | Y237 | A238 | G239 | L244 | M246 | K247 | A248 | N255 | G261 | D273 | K288 | P289 | K290 | T323 |
| 16 | E237 | Y244 | A245 | G246 | L251 | M253 | K254 | A255 | V262 | G268 | E280 | K295 | P296 | K297 | S330 |
| 18 | D201 | S208 | G209 | G210 | L215 | M217 | R218 | H219 | N226 | S233 | S245 | K259 | P260 | R261 | L295 |
| 20 | E232 | Y239 | A240 | G241 | L246 | M248 | K249 | A250 | K257 | G263 | E275 | T290 | P291 | K292 | S325 |
| 22 | E210 | Y217 | A218 | G219 | L224 | M226 | K227 | A228 | R235 | G241 | E253 | K268 | P269 | K270 | T303 |
| 24 | D207 | S214 | A215 | G216 | L221 | I223 | R224 | H225 | N232 | S239 | A251 | R266 | R267 | N268 | L302 |
| 26 | E235 | Y242 | A243 | G244 | L249 | M251 | K252 | A253 | I260 | G266 | E278 | K294 | P295 | K296 | V329 |
| 28 | E200 | Y207 | A208 | G209 | L214 | M216 | R217 | A218 | E225 | G232 | N244 | S271 | S272 | S273 | L306 |
| 30 | D207 | S214 | A215 | G216 | L221 | I223 | C224 | H225 | N232 | S239 | A251 | R266 | R267 | N268 | L302 |
| 32 | E211 | Y218 | A219 | G220 | L225 | M227 | K228 | A229 | R236 | G242 | E254 | T269 | P270 | K271 | T304 |
| 34 | D172 | C179 | G180 | G181 | L186 | M188 | H189 | H190 | N197 | S204 | S216 | K230 | P231 | R232 | L266 |
| 36 | E212 | Y219 | A220 | G221 | L226 | M228 | H229 | A230 | K237 | G243 | E255 | K270 | P271 | Q272 | S305 |
| 38 | D170 | C177 | G178 | G179 | L184 | M186 | H187 | H188 | N195 | S202 | P214 | K229 | K230 | R231 | L265 |
| 40 | D172 | S179 | A180 | A181 | L186 | M188 | R189 | H190 | N197 | S204 | A216 | N231 | K232 | H233 | L267 |
| 42 | E98 | Y105 | A106 | G107 | L112 | M114 | K115 | A116 | R123 | G129 | E141 | K156 | P157 | S158 | S191 |
| 44 | D171 | S178 | G179 | G180 | L185 | I187 | R188 | H189 | N196 | S203 | T215 | G230 | P231 | N232 | L266 |
| 46 | D216 | S223 | G224 | G225 | L230 | I232 | R233 | H234 | N241 | S248 | T260 | G275 | R276 | N277 | L311 |
| 48 | E225 | Y232 | A233 | G234 | L239 | M241 | K242 | A243 | T250 | G256 | E268 | K283 | P284 | K285 | S318 |

| SEQ ID NO | Pos 31 | Pos 32 | Pos 33 | Pos 34 | Pos 35 | Pos 36 | Pos 37 | Pos 38 | Pos 39 | Pos 40 | Pos 41 | Pos 42 | Pos 43 | Pos 44 | Pos 45 |
|---|---|---|---|---|---|---|---|---|---|---|---|---|---|---|---|
| 2 | Q301 | G308 | S324 | R335 | G346 | F349 | L351 | D352 | T358 | L384 | L397 | F417 | T418 | T419 | F420 |
| 4 | Q301 | G308 | S324 | R335 | G346 | F349 | L351 | D352 | T358 | L384 | L397 | F417 | T418 | T419 | F420 |
| 6 | Q300 | G307 | S323 | R334 | G345 | F348 | L350 | D351 | T357 | L383 | L396 | F416 | T417 | T418 | F419 |
| 8 | Q300 | G307 | S323 | R334 | G345 | F348 | L350 | D351 | T357 | L383 | L396 | F416 | T417 | T418 | F419 |
| 10 | S318 | E323 | R337 | C348 | G359 | F362 | L364 | N365 | G371 | L397 | L410 | Y430 | T431 | T432 | F433 |
| 12 | E322 | — | Q340 | Y351 | A365 | L368 | N370 | F371 | G377 | L404 | L414 | L434 | L435 | N436 | Y437 |
| 14 | E329 | — | Q347 | Y358 | A372 | L375 | K377 | F378 | A384 | L411 | L421 | L441 | L442 | N443 | Y444 |
| 16 | S336 | — | R354 | Y365 | A379 | L382 | K384 | F385 | A391 | L418 | L428 | I448 | L449 | N450 | Y451 |
| 18 | H301 | E308 | P324 | E346 | F349 | L351 | D352 | S358 | L384 | L397 | Y417 | T418 | T419 | F420 | |
| 20 | E331 | — | R349 | Y360 | A374 | L377 | S379 | F380 | A386 | L413 | L423 | L443 | L444 | N445 | Y446 |
| 22 | D309 | — | Q327 | Y338 | A352 | L355 | R357 | F358 | A364 | L391 | L401 | L421 | L422 | N423 | Y424 |
| 24 | F308 | G315 | T336 | S347 | G358 | V361 | L363 | D364 | D370 | L396 | L410 | Y430 | T431 | T432 | F433 |
| 26 | A335 | — | F353 | Y364 | G376 | L379 | L381 | F383 | L390 | V418 | L428 | L448 | L449 | N450 | Y451 |
| 28 | Q312 | A319 | V362 | F373 | A388 | L391 | E393 | F394 | V400 | L430 | L440 | L460 | L461 | N462 | Y463 |
| 30 | L308 | G315 | T336 | S347 | G358 | F361 | L363 | D364 | D370 | L396 | L410 | Y430 | T431 | T432 | F433 |
| 32 | D310 | — | Q328 | Y339 | A353 | L356 | I358 | F359 | A365 | L392 | L402 | L422 | L423 | N424 | Y425 |
| 34 | Q272 | G279 | S295 | R306 | G317 | F320 | L322 | D323 | S329 | L355 | L368 | F388 | T389 | T390 | F391 |
| 36 | E311 | — | Q329 | H340 | A354 | L357 | K359 | F360 | A366 | L393 | L403 | L423 | L424 | N425 | Y426 |
| 38 | C271 | D278 | S296 | C307 | G318 | F321 | L323 | N324 | D330 | L356 | L369 | Y389 | T390 | T391 | F392 |
| 40 | H273 | Q280 | D294 | Y305 | G316 | F319 | L321 | N322 | S328 | L354 | L367 | Y387 | T388 | T389 | F390 |
| 42 | D197 | — | L215 | Y226 | A240 | L243 | K246 | F252 | L279 | L289 | L309 | L310 | N311 | Y312 | |
| 44 | C272 | G279 | S300 | S311 | G322 | F325 | L327 | D328 | D334 | L360 | L374 | Y394 | T395 | S396 | F397 |
| 46 | C317 | G324 | S345 | S356 | G367 | F370 | L372 | D373 | D379 | L405 | L419 | Y462 | T463 | S464 | F465 |
| 48 | L324 | — | R342 | Y353 | A367 | L370 | K372 | F373 | A379 | L406 | L416 | I436 | L437 | S438 | Y439 |

| SEQ ID NO | Pos 46 | Pos 47 | Pos 48 | Pos 49 | Pos 50 | Pos 51 | Pos 52 | Pos 53 | Pos 54 | Pos 55 | Pos 56 | Pos 57 | Pos 58 | Pos 59 |
|---|---|---|---|---|---|---|---|---|---|---|---|---|---|---|
| 2 | A432 | T434 | K438 | L449 | T451 | F462 | Y470 | S476 | V477 | D482 | Y493 | K498 | E515 | K528 |
| 4 | A432 | T434 | K438 | L449 | T451 | F462 | Y470 | S476 | V477 | D482 | Y493 | K498 | E515 | K528 |
| 6 | A431 | T433 | K437 | L448 | T450 | F461 | Y469 | S475 | V476 | D481 | Y492 | K497 | E514 | K527 |
| 8 | A431 | T433 | K437 | L448 | T450 | F461 | Y469 | C475 | V476 | D481 | Y492 | K497 | E514 | K527 |
| 10 | A445 | T447 | K451 | L462 | V464 | Y475 | Y483 | S489 | V490 | D495 | Y506 | R511 | D528 | K541 |
| 12 | K449 | E451 | V455 | K468 | K470 | V481 | F489 | D495 | T496 | K501 | L514 | V519 | S536 | — |
| 14 | K456 | E458 | V462 | R475 | D477 | V488 | F496 | D502 | I503 | K508 | L521 | V526 | A543 | — |
| 16 | K463 | K465 | A469 | N482 | N484 | V495 | F503 | D509 | L510 | K515 | L528 | K533 | A550 | — |
| 18 | A432 | T434 | K438 | L449 | T451 | Y462 | Y470 | S476 | V477 | E482 | Y493 | K498 | E515 | K525 |
| 20 | K458 | E460 | V464 | K477 | K479 | V490 | F498 | D504 | T505 | K510 | L523 | V528 | S545 | — |
| 22 | K436 | E438 | V442 | N455 | T457 | V468 | Y476 | D482 | L483 | K488 | L501 | V506 | S523 | — |
| 24 | A445 | T447 | K451 | L462 | V464 | Y475 | Y483 | S489 | V490 | E495 | Y506 | K511 | D528 | N541 |
| 26 | Q463 | T465 | V469 | K482 | D484 | V495 | F503 | E509 | Q510 | R515 | L528 | V533 | A550 | A563 |
| 28 | A475 | P477 | A481 | R495 | G497 | V508 | F516 | D522 | R523 | K528 | L545 | V550 | E567 | — |
| 30 | A445 | T447 | K451 | L462 | V464 | Y475 | Y483 | S489 | V490 | E495 | Y506 | K511 | D528 | N541 |
| 32 | K437 | E439 | V443 | N456 | K458 | V469 | F477 | D483 | H484 | K489 | L502 | V507 | S524 | — |

TABLE 3c-continued

| 34 | A403 | T405 | K409 | L420 | T422 | F433 | Y441 | S447 | V448 | D453 | Y464 | K469 | E486 | K499 |
| --- | --- | --- | --- | --- | --- | --- | --- | --- | --- | --- | --- | --- | --- | --- |
| 36 | K438 | E440 | V444 | — | — | — | F447 | D453 | I454 | K459 | L472 | V477 | I494 | — |
| 38 | A404 | R406 | K410 | L421 | A423 | Y434 | Y442 | S448 | V449 | D454 | Y465 | R470 | D487 | — |
| 40 | A402 | T404 | R408 | L419 | A421 | Y432 | Y440 | S446 | V447 | D452 | Y463 | K468 | D485 | T498 |
| 42 | Q324 | E326 | I330 | N343 | N345 | V356 | F364 | D370 | V371 | K376 | L389 | V394 | — | — |
| 44 | A409 | T411 | K415 | L426 | V428 | H439 | Y447 | L453 | V454 | A459 | Y470 | K475 | D492 | D505 |
| 46 | A477 | T479 | K483 | L494 | V496 | H507 | Y515 | L521 | V522 | A527 | Y538 | K543 | D560 | D573 |
| 48 | K451 | E453 | A457 | N470 | N472 | V483 | F491 | D497 | V498 | K503 | L516 | V521 | S538 | — |

In addition, the present invention refers to a method for identifying a PPO-inhibiting herbicide by using a mutated PPO encoded by a nucleic acid which comprises the nucleotide sequence of SEQ ID NO: 1, 3, 5, 7, 9, 11, 13, 15, 17, 19, 21, 23, 25, 27, 29, 31, 33, 35, 37, 39, 41, 43, 45, or 47, or a variant or derivative thereof.

Said method comprises the steps of:
a) generating a transgenic cell or plant comprising a nucleic acid encoding a mutated PPO, wherein the mutated PPO is expressed;
b) applying a PPO-inhibiting herbicide to the transgenic cell or plant of a) and to a control cell or plant of the same variety;
c) determining the growth or the viability of the transgenic cell or plant and the control cell or plant after application of said PPO-inhibiting herbicide, and
d) selecting "PPO-inhibiting herbicides" which confer reduced growth to the control cell or plant as compared to the growth of the transgenic cell or plant.

By "control cell" or "similar, wild-type, plant, plant tissue, plant cell or host cell" is intended a plant, plant tissue, plant cell, or host cell, respectively, that lacks the herbicide-resistance characteristics and/or particular polynucleotide of the invention that are disclosed herein. The use of the term "wild-type" is not, therefore, intended to imply that a plant, plant tissue, plant cell, or other host cell lacks recombinant DNA in its genome, and/or does not possess herbicide-resistant characteristics that are different from those disclosed herein.

Another object refers to a method of identifying a nucleotide sequence encoding a mutated PPO which is resistant or tolerant to a PPO-inhibiting herbicide, the method comprising:
a) generating a library of mutated PPO-encoding nucleic acids,
b) screening a population of the resulting mutated PPO-encoding nucleic acids by expressing each of said nucleic acids in a cell or plant and treating said cell or plant with a PPO-inhibiting herbicide,
c) comparing the PPO-inhibiting herbicide-tolerance levels provided by said population of mutated PPO encoding nucleic acids with the PPO-inhibiting herbicide-tolerance level provided by a control PPO-encoding nucleic acid,
d) selecting at least one mutated PPO-encoding nucleic acid that provides a significantly increased level of tolerance to a PPO-inhibiting herbicide as compared to that provided by the control PPO-encoding nucleic acid.

In a preferred embodiment, the mutated PPO-encoding nucleic acid selected in step d) provides at least 2-fold as much resistance or tolerance of a cell or plant to a PPO-inhibiting herbicide as compared to that provided by the control PPO-encoding nucleic acid.

In a further preferred embodiment, the mutated PPO-encoding nucleic acid selected in step d) provides at least 2-fold, at least 5-fold, at least 10-fold, at least 20-fold, at least 50-fold, at least 100-fold, at least 500-fold, as much resistance or tolerance of a cell or plant to a PPO-inhibiting herbicide as compared to that provided by the control PPO-encoding nucleic acid.

The resistance or tolerance can be determined by generating a transgenic plant or host cell, preferably a plant cell, comprising a nucleic acid sequence of the library of step a) and comparing said transgenic plant with a control plant or host cell, preferably a plant cell.

Another object refers to a method of identifying a plant or algae containing a nucleic acid comprising a nucleotide sequence encoding a wild-type or mutated PPO which is resistant or tolerant to a PPO-inhibiting herbicide, the method comprising:
a) identifying an effective amount of a PPO-inhibiting herbicide in a culture of plant cells or green algae that leads to death of said cells.
b) treating said plant cells or green algae with a mutagenizing agent,
c) contacting said mutagenized cells population with an effective amount of PPO-inhibiting herbicide, identified in a),
d) selecting at least one cell surviving these test conditions,
e) PCR-amplification and sequencing of PPO genes from cells selected in d) and comparing such sequences to wild-type PPO gene sequences, respectively.

In a preferred embodiment, said mutagenizing agent is ethylmethanesulfonate (EMS).

Many methods well known to the skilled artisan are available for obtaining suitable candidate nucleic acids for identifying a nucleotide sequence encoding a mutated PPO from a variety of different potential source organisms including microbes, plants, fungi, algae, mixed cultures etc. as well as environmental sources of DNA such as soil. These methods include inter alia the preparation of cDNA or genomic DNA libraries, the use of suitably degenerate oligonucleotide primers, the use of probes based upon known sequences or complementation assays (for example, for growth upon tyrosine) as well as the use of mutagenesis and shuffling in order to provide recombined or shuffled mutated PPO-encoding sequences.

Nucleic acids comprising candidate and control PPO encoding sequences can be expressed in yeast, in a bacterial host strain, in an alga or in a higher plant such as tobacco or Arabidopsis and the relative levels of inherent tolerance of the PPO encoding sequences screened according to a visible indicator phenotype of the transformed strain or plant in the presence of different concentrations of the selected PPO-inhibiting herbicide. Dose responses and relative shifts in dose responses associated with these indicator phenotypes (formation of brown color, growth inhibition, herbicidal effect etc) are conveniently expressed in terms, for example, of GR50 (concentration for 50% reduction of growth) or MIC (minimum inhibitory concentration) values where increases in values correspond to increases in inherent tolerance of the expressed PPO. For example, in a relatively rapid assay system based upon transformation of a bacterium such as *E. coli*, each mutated PPO encoding sequence may be expressed, for example, as a DNA sequence under expression control of a controllable promoter such as the lacZ promoter and taking suitable account, for example by the use of synthetic DNA, of such issues as codon usage in order to obtain as comparable a level of expression as possible of different PPO sequences. Such strains expressing nucleic acids comprising alternative candidate PPO sequences may be plated out on different concentrations of the selected PPO-inhibiting herbicide in, optionally, a tyrosine supplemented medium and the relative levels of inherent tolerance of the expressed PPO enzymes estimated on the basis of the extent and MIC for inhibition of the formation of the brown, ochronotic pigment.

In another embodiment, candidate nucleic acids are transformed into plant material to generate a transgenic plant, regenerated into morphologically normal fertile plants which are then measured for differential tolerance to selected PPO-inhibiting herbicides as described in the Example section hereinafter. Many suitable methods for transformation using suitable selection markers such as kanamycin, binary vectors such as from *Agrobacterium* and plant regeneration as, for example, from tobacco leaf discs are well known in the art. Optionally, a control population of plants is likewise transformed with a nucleic acid expressing the control PPO. Alternatively, an untransformed dicot plant such as *Arabidopsis* or Tobacco can be used as a control since this, in any case, expresses its own endogenous PPO. The average, and distribution, of herbicide tolerance levels of a range of primary plant transformation events or their progeny to PPO-inhibiting herbicides described supra are evaluated in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance of the expressed PPO. Herbicides can suitably be applied pre-emergence or post-emergence.

Another object of the present invention refers to an isolated nucleic acid encoding a mutated PPO as disclosed SUPRA, wherein the nucleic acid comprises the nucleotide sequence of SEQ ID NO: 1, 3, 5, 7, 9, 11, 13, 15, 17, 19, 21, 23, 25, 27, 29, 31, 33, 35, 37, 39, 41, 43, 45 or 47, or a variant or derivative thereof.

In one embodiment, the nucleic acid is identifiable by a method as defined above.

In a preferred embodiment, the encoded mutated PPO is a variant of SEQ ID NO: 2 or SEQ ID NO. 4, or an orthologue thereof, which includes one or more of the following: the amino acid at or corresponding to position 128 of SEQ ID NO:2 is other than Arginine; and/or the amino acid at or corresponding to position 420 of SEQ ID NO:2 is other than Phenylalanine.

In another embodiment, the invention refers to a plant cell transformed by a nucleic acid encoding a mutated PPO polypeptide according to the present invention or to a plant cell which has been mutated to obtain a plant expressing a nucleic acid encoding a mutated PPO polypeptide according to the present invention, wherein expression of the nucleic acid in the plant cell results in increased resistance or tolerance to a PPO-inhibiting herbicide as compared to a wild type variety of the plant cell. Preferably, the mutated PPO polypeptide encoding nucleic acid comprises a polynucleotide sequence selected from the group consisting of:

a) a polynucleotide as shown in SEQ ID NO: 1, 3, 5, 7, 9, 11, 13, 15, 17, 19, 21, 23, 25, 27, 29, 31, 33, 35, 37, 39, 41, 43, 45 or 47, or a variant or derivative thereof; b) a polynucleotide encoding a polypeptide as shown in SEQ ID NO: 2, 4, 6, 8, 10, 12, 14, 16, 18, 20, 22, 24, 26, 28, 30, 32, 34, 36, 38, 40, 42, 44, 46, or 48, or a variant or derivative thereof; c) a polynucleotide comprising at least 60 consecutive nucleotides of any of a) or b); and d) a polynucleotide complementary to the polynucleotide of any of a) through c).

The term "expression/expressing" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

To obtain the desired effect, i.e. plants that are tolerant or resistant to the PPO-inhibiting herbicide derivative herbicide of the present invention, it will be understood that the at least one nucleic acid is "over-expressed" by methods and means known to the person skilled in the art.

The term "increased expression" or "overexpression" as used herein means any form of expression that is additional to the original wild-type expression level. Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994)

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229). The genetically modified plant cells can be regenerated via all methods with which the skilled worker is familiar. Suitable methods can be found in the abovementioned publications by S. D. Kung and R. Wu, Potrykus or Hdfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the wild-type or mutated PPO nucleic acid comprises a polynucleotide sequence selected from the group consisting of: a) a polynucleotide as shown in SEQ ID NO: 1, 3, 5, 7, 9, 11, 13, 15, 17, 19, 21, 23, 25, 27, 29, 31, 33, 35, 37, 39, 41, 43, 45, or 47, or a variant or derivative thereof; b) a polynucleotide encoding a polypeptide as shown in SEQ ID NO: 2, 4, 6, 8, 10, 12, 14, 16, 18, 20, 22, 24, 26, 28, 30, 32, 34, 36, 38, 40, 42, 44, 46, or 48, or a variant or derivative thereof; c) a polynucleotide comprising at least 60 consecutive nucleotides of any of a) or b); and d) a polynucleotide complementary to the polynucleotide of any of a) through c).

Preferably, the expression of the nucleic acid in the plant results in the plant's increased resistance to PPO-inhibiting herbicide as compared to a wild type variety of the plant.

In another embodiment, the invention refers to a plant, preferably a transgenic plant, comprising a plant cell according to the present invention, wherein expression of the nucleic acid in the plant results in the plant's increased resistance to PPO-inhibiting herbicide as compared to a wild type variety of the plant.

The plants described herein can be either transgenic crop plants or non-transgenic plants.

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or
(b) genetic control sequence(s) which is operably linked with the nucleic acid sequence according to the invention, for example a promoter, or
(c) a) and b)

are not located in their natural genetic environment or have been modified by recombinant methods, it being possible for the modification to take the form of, for example, a substitution, addition, deletion, inversion or insertion of one or more nucleotide residues in order to allow for the expression of the mutated PPO of the present invention. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein. Furthermore, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

Plants containing mutations arising due to non-spontaneous mutagenesis and selective breeding are referred to herein as non-transgenic plants and are included in the present invention. In embodiments wherein the plant is transgenic and comprises multiple mutated PPO nucleic acids, the nucleic acids can be derived from different genomes or from the same genome. Alternatively, in embodiments wherein the plant is non-transgenic and comprises multiple mutated PPO nucleic acids, the nucleic acids are located on different genomes or on the same genome. As used herein, "mutagenized" refers to an organism or DNA thereof having alteration(s) in the biomolecular sequence of its native genetic material as compared to the sequence of the genetic material of a corresponding wild-type organism or DNA, wherein the alteration(s) in genetic material were induce and/or selected by human action. Methods of inducing mutations can induce mutations in random positions in the genetic material or can induce mutations in specific locations in the genetic material (i.e., can be directed mutagenesis techniques), such as by use of a genoplasty technique.

In certain embodiments, the present invention involves herbidicide-resistant plants that are produced by mutation breeding. Such plants comprise a polynucleotide encoding a mutated PPO and are tolerant to one or more PPO-inhibiting herbicides. Such methods can involve, for example, exposing the plants or seeds to a mutagen, particularly a chemical mutagen such as, for example, ethyl methanesulfonate (EMS) and selecting for plants that have enhanced tolerance to at least one or more PPO-inhibiting herbicide.

However, the present invention is not limited to herbicide-tolerant plants that are produced by a mutagenesis method involving the chemical mutagen EMS. Any mutagenesis method known in the art may be used to produce the herbicide-resistant plants of the present invention. Such mutagenesis methods can involve, for example, the use of any one or more of the following mutagens: radiation, such as X-rays, Gamma rays (e.g., cobalt 60 or cesium 137), neutrons, (e.g., product of nuclear fission by uranium 235 in an atomic reactor), Beta radiation (e.g., emitted from radio-isotopes such as phosphorus 32 or carbon 14), and ultraviolet radiation (preferably from 2500 to 2900 nm), and chemical mutagens such as base analogues (e.g., 5-bromo-uracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. Herbicide-resistant plants can also be produced by using tissue culture methods to select for plant cells comprising herbicide-resistance mutations and then regenerating herbicide-resistant plants therefrom. See, for example, U.S. Pat. Nos. 5,773,702 and 5,859,348, both of which are herein incorporated in their entirety by reference. Further details of mutation breeding can be found in "Principals of Cultivar Development" Fehr, 1993 Macmillan Publishing Company the disclosure of which is incorporated herein by reference In addition to the definition above, the term "plant" is intended to encompass crop plants at any stage of maturity or development, as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts, and the like.

The plant of the present invention comprises at least one mutated PPO nucleic acid or over-expressed wild-type PPO nucleic acid, and has increased tolerance to a PPO-inhibiting herbicide as compared to a wild-type variety of the plant. It is possible for the plants of the present invention to have multiple wild-type or mutated PPO nucleic acids from different genomes since these plants can contain more than one genome. For example, a plant contains two genomes, usually referred to as the A and B genomes. Because PPO is a required metabolic enzyme, it is assumed that each genome has at least one gene coding for the PPO enzyme (i.e. at least one PPO gene). As used herein, the term "PPO gene locus" refers to the position of an PPO gene on a genome, and the terms "PPO gene" and "PPO nucleic acid" refer to a nucleic acid encoding the PPO enzyme. The PPO nucleic acid on each genome differs in its nucleotide sequence from an PPO nucleic acid on another genome. One of skill in the art can determine the genome of origin of each PPO nucleic acid through genetic crossing and/or either sequencing methods or exonuclease digestion methods known to those of skill in the art.

The present invention includes plants comprising one, two, three, or more mutated PPO alleles, wherein the plant has increased tolerance to a PPO-inhibiting herbicide as compared to a wild-type variety of the plant. The mutated PPO alleles can comprise a nucleotide sequence selected from the group consisting of a polynucleotide as defined in SEQ ID NO: 1, 3, 5, 7, 9, 11, 13, 15, 17, 19, 21, 23, 25, 27, 29, 31, 33, 35, 37, 39, 41, 43, 45, or 47, or a variant or derivative thereof, a polynucleotide encoding a polypeptide as defined in SEQ ID NO: 2, 4, 6, 8, 10, 12, 14, 16, 18, 20, 22, 24, 26, 28, 30, 32, 34, 36, 38, 40, 42, 44, 46, or 48, or a variant or derivative, homologue, orthologue, paralogue thereof, a polynucleotide comprising at least 60 consecutive nucleotides of any of the aforementioned polynucleotides; and a polynucleotide complementary to any of the aforementioned polynucleotides.

"Alleles" or "allelic variants" are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms The term "variety" refers to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. The terms "breeding line" or "line" refer to a group of plants within a cultivar defined by the sharing of a common set of characteristics or traits accepted by those skilled in the art as sufficient to distinguish one breeding line or line from another breeding line or line. There is no implication in either term that all plants of any given breeding line or line will be genetically identical at either the whole gene or molecular level or that any given plant will be homozygous at all loci. A breeding line or line is considered "true breeding" for a particular trait if, when the true-breeding line or breeding line is self-pollinated, all of the progeny contain the trait. In the present invention, the trait arises from a mutation in a PPO gene of the plant or seed.

In some embodiments, traditional plant breeding is employed whereby the PPO-inhibiting herbicides-tolerant trait is introduced in the progeny plant resulting therefrom. In one embodiment, the present invention provides a method for producing a PPO-inhibiting herbicides-tolerant progeny plant, the method comprising: crossing a parent plant with a PPO-inhibiting herbicides-tolerant plant to introduce the PPO-inhibiting herbicides-tolerance characteristics of the PPO-inhibiting herbicides-tolerant plant into the germplasm of the progeny plant, wherein the progeny plant has increased tolerance to the PPO-inhibiting herbicides relative to the parent plant. In other embodiments, the method further comprises the step of introgressing the PPO-inhibiting herbicides-tolerance characteristics through traditional plant breeding techniques to obtain a descendent plant having the PPO-inhibiting herbicides-tolerance characteristics The herbicide-resistant plants of the invention that comprise polynucleotides encoding mutated PPO polypeptides also find use in methods for increasing the herbicide-resistance of a plant through conventional plant breeding involving sexual reproduction. The methods comprise crossing a first plant that is a herbicide-resistant plant of the invention to a second plant that may or may not be resistant to the same herbicide or herbicides as the first plant or may be resistant to different herbicide or herbicides than the first plant. The second plant can be any plant that is capable of producing viable progeny plants (i.e., seeds) when crossed with the first plant. Typically, but not necessarily, the first and second plants are of the same species. The methods can optionally involve selecting for progeny plants that comprise the mutated PPO polypeptides of the first plant and the herbicide resistance characteristics of the second plant. The progeny plants produced by this method of the present invention have increased resistance to a herbicide when compared to either the first or second plant or both. When the first and second plants are resistant to different herbicides, the progeny plants will have the combined herbicide tolerance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The present invention also provides plants, plant organs, plant tissues, plant cells, seeds, and non-human host cells that are transformed with the at least one polynucleotide molecule, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

In other aspects, plants of the invention include those plants which, in addition to being tolerant to PPO-inhibiting herbicides, have been subjected to further genetic modifications by breeding, mutagenesis or genetic engineering, e.g. have been rendered tolerant to applications of specific other classes of herbicides, such as AHAS inhibitors; auxinic herbicides; bleaching herbicides such as hydroxyphenylpyruvate dioxygenase (HPPD) inhibitors or phytoene desaturase (PDS) inhibitors; EPSPS inhibitors such as glyphosate; glutamine synthetase (GS) inhibitors such as glufosinate; lipid biosynthesis inhibitors such as acetyl CoA carboxylase (ACCase) inhibitors; or oxynil {i.e. bromoxynil or ioxynil} herbicides as a result of conventional methods of breeding or genetic engineering, Thus, PPO-inhibiting herbicides-tolerant plants of the invention can be made resistant to multiple classes of herbicides through multiple genetic modifications, such as resistance to both glyphosate and glufosinate or to both glyphosate and a herbicide from another class such as HPPD inhibitors, AHAS inhibitors, or ACCase inhibitors. These herbicide resistance technologies are, for example, described in Pest Management Science (at volume, year, page): 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. For example, PPO-inhibiting herbicides-tolerant plants of the invention, in some embodiments, may be tolerant to ACCase inhibitors, such as "dims" {e.g., cycloxydim, sethoxydim, clethodim, or tepraloxydim), "fops" {e.g., clodinafop, diclofop, fluazifop, haloxyfop, or quizalofop), and "dens" (such as pinoxaden); to auxinic herbicides, such as dicamba; to EPSPS inhibitors, such as glyphosate; to other PPO inhibitors; and to GS inhibitors, such as glufosinate.

In addition to these classes of inhibitors, PPO-inhibiting herbicides-tolerant plants of the invention may also be tolerant to herbicides having other modes of action, for example, chlorophyll/carotenoid pigment inhibitors, cell membrane disrupters, photosynthesis inhibitors, cell division inhibitors, root inhibitors, shoot inhibitors, and combinations thereof.

Such tolerance traits may be expressed, e.g.: as mutant or wildtype PPO proteins, as mutant AHASL proteins, mutant ACCase proteins, mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or CYP450s proteins having an herbicide-degrading activity.

PPO-inhibiting herbicides-tolerant plants hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, in other embodiments, PPO-inhibiting herbicides-tolerant plants are also covered which are, by the use of recombinant DNA techniques and/or by breeding and/or otherwise selected for such characteristics, rendered able to synthesize one or more insecticidal proteins, especially those known from the bacterial genus *Bacillus*, particularly from *Bacillus thuringiensis*, such as [delta]-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such streptomycete toxins; plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda).

In some embodiments, expression of one or more protein toxins (e.g., insecticidal proteins) in the PPO-inhibiting herbicides-tolerant plants is effective for controlling organisms that include, for example, members of the classes and orders: Coleoptera such as the American bean weevil *Acanthoscelides obtectus*; the leaf beetle *Agelastica alni*; click beetles (*Agriotes lineatus, Agriotes obscurus, Agriotes bicolor*); the grain beetle *Ahasverus advena*; the summer schafer *Amphimallon solstitialis*; the furniture beetle *Anobium punctatum; Anthonomus* spp. (weevils); the Pygmy mangold beetle *Atomaria linearis*; carpet beetles (*Anthrenus* spp., *Attagenus* spp.); the cowpea weevil *Callosobruchus maculates*; the fried fruit beetle *Carpophilus hemipterus*; the cabbage seedpod weevil *Ceutorhynchus assimilis*; the rape winter stem weevil *Ceutorhynchus picitarsis*; the wireworms *Conoderus vespertinus* and *Conoderus falli*; the banana weevil *Cosmopolites sordidus*; the New Zealand grass grub *Costelytra zealandica*; the June beetle *Cotinis nitida*; the sunflower stem weevil *Cylindrocopturus adspersus*; the larder beetle *Dermestes lardarius*; the corn rootworms *Diabrotica virgifera, Diabrotica virgifera virgifera*, and *Diabrotica barberi*; the Mexican bean beetle *Epilachna varivestis*; the old house borer *Hylotropes bajulus*; the lucerne weevil *Hypera postica*; the shiny spider beetle *Gibbium psylloides*; the cigarette beetle *Lasioderma serricorne*; the Colorado potato beetle *Leptinotarsa decemlineata; Lyctus* beetles {*Lyctus* spp., the pollen beetle *Meligethes aeneus*; the common cockshafer *Melolontha melolontha*; the American spider beetle *Mezium americanum*; the golden spider beetle *Niptus hololeucs*; the grain beetles *Oryzaephilus surinamensis* and *Oryzaephilus Mercator*; the black vine weevil *Otiorhynchus sulcatus*; the mustard beetle *Phaedon cochleariae*, the crucifer flea beetle *Phyllotreta cruciferae*; the striped flea beetle *Phyllotreta striolata*; the cabbage steam flea beetle *Psylliodes chrysocephala; Ptinus* spp. (spider beetles); the lesser grain borer *Rhizopertha dominica*; the pea and been weevil *Sitona lineatus*; the rice and granary beetles *Sitophilus oryzae* and *Sitophilus granaries*; the red sunflower seed weevil *Smicronyx fulvus*; the drugstore beetle *Stegobium paniceum*; the yellow mealworm beetle *Tenebrio molitor*, the flour beetles *Tribolium castaneum* and *Tribolium confusum*; warehouse and cabinet beetles {*Trogoderma* spp.); the sunflower beetle *Zygogramma exclamationis*; Dermaptera (earwigs) such as the European earwig *Forficula auricularia* and the striped earwig *Labidura riparia*; Dictyoptera such as the oriental cockroach *Blatta orientalis*; the greenhouse millipede *Oxidus gracilis*; the beet fly *Pegomyia betae*; the frit fly *Oscinella frit*; fruitflies (*Dacus* spp., *Drosophila* spp.); Isoptera (termites) including species from the familes Hodotermitidae, Kalotermitidae, Mastotermitidae, Rhinotermitidae, Serritermitidae, Termitidae, Termopsidae; the tarnished plant bug *Lygus lineolaris*; the black bean aphid *Aphis fabae*; the cotton or melon aphid *Aphis gossypii*; the green apple aphid *Aphis pomi*; the citrus spiny whitefly Aleurocanthus spiniferus; the sweet potato whitefly *Bemesia tabaci*; the cabbage aphid *Brevicoryne brassicae*; the pear psylla *Cacopsylla pyricola*; the currant aphid *Cryptomyzus ribis*; the grape phylloxera *Daktulosphaira vitifoliae*; the citrus psylla *Diaphorina citri*; the potato leafhopper *Empoasca fabae*; the bean leafhopper *Empoasca Solana*; the vine leafhopper *Empoasca vitis*; the woolly aphid *Eriosoma lanigerum*; the European fruit scale *Eulecanium corni*; the mealy plum aphid *Hyalopterus arundinis*; the small brown planthopper *Laodelphax striatellus*; the potato aphid *Macrosiphum euphorbiae*; the green peach aphid *Myzus persicae*; the green rice leafhopper *Nephotettix cinticeps*; the brown planthopper *Nilaparvata lugens*; the hop aphid *Phorodon humuli*; the bird-cherry aphid *Rhopalosiphum padi*; the grain aphid *Sitobion avenae*; Lepidoptera such as *Adoxophyes orana* (summer fruit *tortrix* moth); *Archips podana* (fruit tree *tortrix* moth); *Bucculatrix pyrivorella* (pear leafminer); *Bucculatrix thurberiella* (cotton leaf perforator); *Bupalus piniarius* (pine looper); *Carpocapsa pomonella* (codling moth); *Chilo suppressalis* (striped rice borer); *Choristoneura fumiferana* (eastern spruce budworm); *Cochylis hospes* (banded sunflower moth); *Diatraea grandiosella* (southwestern corn borer); *Eupoecilia ambiguella* (European grape berry moth); *Helicoverpa armigera* (cotton bollworm); *Helicoverpa zea* (cotton bollworm); *Heliothis vires cens* (tobacco budworm), *Homeosoma electellum* (sunflower moth); *Homona magnanima* (oriental tea tree *tortrix* moth); *Lithocolletis blancardella* (spotted tentiform leafminer); *Lymantria dispar* (gypsy moth); *Malacosoma neustria* (tent caterpillar); *Mamestra brassicae* (cabbage armyworm); *Mamestra configurata* (Bertha armyworm); *Operophtera brumata* (winter moth); *Ostrinia nubilalis* (European corn borer), *Panolis flammea* (pine beauty moth), *Phyllocnistis citrella* (citrus leafminer); *Pieris brassicae* (cabbage white butterfly); *Rachiplusia ni* (soybean looper); *Spodoptera exigua* (beet armyworm); *Spodoptera littoralis* (cotton leafworm); Sylepta derogata (cotton leaf roller); *Trichoplusia ni* (cabbage looper); Orthoptera such as the common cricket *Acheta domesticus*, tree locusts (Anacridium spp.), the migratory locust *Locusta migratoria*, the twostriped grasshopper *Melanoplus bivittatus*, the differential grasshopper *Melanoplus differ entialis*, the redlegged grasshopper *Melanoplus femurrubrum*, the migratory grasshopper *Melanoplus sanguinipes*, the northern mole cricket *Neocurtilla hexadectyla*, the red locust *Nomadacris septemfasciata*, the shortwinged mole cricket *Scapteriscus abbreviatus*, the southern mole cricket *Scapteriscus borellii*, the tawny mole cricket *Scapteriscus vicinus*, and the desert locust *Schistocerca gregaria*; Symphyla such as the garden symphylan *Scutigerella immaculata*; Thysanoptera such as the tobacco *thrips Frankliniella fusca*, the flower *thrips Frankliniella intonsa*, the western flower *thrips Frankliniella occidentalism* the cotton bud *thrips Frankliniella schultzei*, the banded greenhouse *thrips Hercinothrips femoralis*, the soybean *thrips Neohydatothrips variabilis*, Kelly's citrus *thrips Pezothrips kellyanus*, the avocado *thrips Scirtothrips perseae*, the melon *thrips Thrips palmi*, and the onion *thrips Thrips tabaci*; and the like, and combinations comprising one or more of the foregoing organisms.

In some embodiments, expression of one or more protein toxins (e.g., insecticidal proteins) in the PPO-inhibiting herbicides-tolerant plants is effective for controlling flea beetles, i.e. members of the flea beetle tribe of family Chrysomelidae, preferably against *Phyllotreta* spp., such as *Phyllotreta cruciferae* and/or *Phyllotreta triolata*. In other embodiments, expression of one or more protein toxins {e.g., insecticidal proteins) in the PPO-inhibiting herbicides-tolerant plants is effective for controlling cabbage seedpod weevil, the Bertha armyworm, *Lygus* bugs, or the diamondback moth. Furthermore, in one embodiment, PPO-inhibiting herbicides-tolerant plants are also covered which are, e.g. by the use of recombinant DNA techniques and/or by breeding and/or otherwise selected for such traits, rendered able to synthesize one or more proteins to increase the resistance or tolerance of those plants to bacterial, viral or fungal pathogens. The methods for producing such genetically modified plants are generally known to the person skilled in the art.

Furthermore, in another embodiment, PPO-inhibiting herbicides-tolerant plants are also covered which are, e.g. by the use of recombinant DNA techniques and/or by breeding and/or otherwise selected for such traits, rendered able to synthesize one or more proteins to increase the productivity (e.g. oil content), tolerance to drought, salinity or other growth-limiting environmental factors or tolerance to pests and fungal, bacterial or viral pathogens of those plants.

Furthermore, in other embodiments, PPO-inhibiting herbicides-tolerant plants are also covered which are, e.g. by the use of recombinant DNA techniques and/or by breeding and/or otherwise selected for such traits, altered to contain a modified amount of one or more substances or new substances, for example, to improve human or animal nutrition, e.g. oil crops that produce health-promoting long-chain omega-3 fatty acids or unsaturated omega-9 fatty acids (e.g. Nexera® rape, Dow Agro Sciences, Canada).

Furthermore, in some embodiments, PPO-inhibiting herbicides-tolerant plants are also covered which are, e.g. by the use of recombinant DNA techniques and/or by breeding and/or otherwise selected for such traits, altered to contain increased amounts of vitamins and/or minerals, and/or improved profiles of nutraceutical compounds.

In one embodiment, PPO-inhibiting herbicides-tolerant plants of the present invention, relative to a wild-type plant, comprise an increased amount of, or an improved profile of, a compound selected from the group consisting of: glucosinolates (e.g., glucoraphanin (4-methylsulfinylbutyl-glucosinolate), sulforaphane, 3-indolylmethyl-glucosinolate (glucobrassicin), I-methoxy-3-indolylmethyl-glucosinolate (neoglucobrassicin)); phenolics (e.g., flavonoids (e.g., quercetin, kaempferol), hydroxycinnamoyl derivatives (e.g., 1,2,2'-trisinapoylgentiobiose, 1,2-diferuloylgentiobiose, I,2'-disinapoyl-2-feruloylgentiobiose, 3-0-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, PPO-inhibiting herbicides-tolerant plants of the present invention, relative to a wild-type plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavans/tannins (such as the procyanidins comprising coumarin, proanthocyanidins, catechins, and anthocyanins); flavones; phytoestrogens such as coumestans, lignans, resveratrol, isoflavones e.g. genistein, daidzein, and glycitein; resorcyclic acid lactones; organosulphur compounds; phytosterols; terpenoids such as carnosol, rosmarinic acid, glycyrrhizin and saponins; chlorophyll; chlorphyllin, sugars, anthocyanins, and vanilla. In other embodiments, PPO-inhibiting herbicides-tolerant plants of the present invention, relative to a wild-type plant, comprise an increased amount of, or an improved profile of, a compound selected from the group consisting of: vincristine, vinblastine, taxanes (e.g., taxol (paclitaxel), baccatin III, 10-desacetylbaccatin III, 10-desacetyl taxol, xylosyl taxol, 7-epitaxol, 7-epibaccatin III, 10-desacetylcephalomannine, 7-epicephalomannine, taxotere, cephalomannine, xylosyl cephalomannine, taxagifine, 8-benxoyloxy taxagifine, 9-acetyloxy taxusin, 9-hydroxy taxusin, taiwanxam, taxane Ia, taxane Ib, taxane Ic, taxane Id, GMP paclitaxel, 9-dihydro 13-acetylbaccatin III, 10-desacetyl-7-epitaxol, tetrahydrocannabinol (THC), cannabidiol (CBD), genistein, diadzein, codeine, morphine, quinine, shikonin, ajmalacine, serpentine, and the like.

It is to be understood that the plant of the present invention can comprise a wild type PPO nucleic acid in addition to a mutated PPO nucleic acid. It is contemplated that the PPO-inhibiting herbicide tolerant lines may contain a mutation in only one of multiple PPO isoenzymes. Therefore, the present invention includes a plant comprising one or more mutated PPO nucleic acids in addition to one or more wild type PPO nucleic acids.

In another embodiment, the invention refers to a seed produced by a transgenic plant comprising a plant cell of the present invention, wherein the seed is true breeding for an increased resistance to a PPO-inhibiting herbicide as compared to a wild type variety of the seed.

In another embodiment, the invention refers to a method of producing a transgenic plant cell with an increased resistance to a PPO-inhibiting herbicide as compared to a wild type variety of the plant cell comprising, transforming the plant cell with an expression cassette comprising a mutated PPO nucleic acid.

In another embodiment, the invention refers to a method of producing a transgenic plant comprising, (a) transforming a plant cell with an expression cassette comprising a mutated PPO nucleic acid, and (b) generating a plant with an increased resistance to PPO-inhibiting herbicide from the plant cell.

Consequently, mutated PPO nucleic acids of the invention are provided in expression cassettes for expression in the plant of interest. The cassette will include regulatory sequences operably linked to a mutated PPO nucleic acid sequence of the invention. The term "regulatory element" as used herein refers to a polynucleotide that is capable of regulating the transcription of an operably linked polynucleotide. It includes, but not limited to, promoters, enhancers, introns, 5' UTRs, and 3' UTRs.

By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the mutated PPO nucleic acid sequence to be under the transcriptional regulation of the regulatory regions. The expression cassette may additionally contain selectable marker genes.

The expression cassette of the present invention will include in the 5'-3' direction of transcription, a transcriptional and translational initiation region (i.e., a promoter), a mutated PPO encoding nucleic acid sequence of the invention, and a transcriptional and translational termination region (i.e., termination region) functional in plants. The promoter may be native or analogous, or foreign or heterologous, to the plant host and/or to the mutated PPO nucleic acid sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the mutated PPO nucleic acid sequence of the invention, it is intended that the promoter is not the native or naturally occurring promoter for the operably linked mutated PPO nucleic acid sequence of the invention. As used herein, a chimeric gene comprises a coding sequence operably linked to a transcription initiation region that is heterologous to the coding sequence.

While it may be preferable to express the mutated PPO nucleic acids of the invention using heterologous promoters, the native promoter sequences may be used. Such constructs would change expression levels of the mutated PPO protein in the plant or plant cell. Thus, the phenotype of the plant or plant cell is altered.

The termination region may be native with the transcriptional initiation region, may be native with the operably linked mutated PPO sequence of interest, may be native with the plant host, or may be derived from another source (i.e., foreign or heterologous to the promoter, the mutated PPO nucleic acid sequence of interest, the plant host, or any combination thereof). Convenient termination regions are available from the Ti-plasmid of *A. tumefaciens*, such as the octopine synthase and nopaline synthase termination regions. See also Guerineau et al. (1991) Mol. Gen. Genet. 262: 141-144; Proudfoot (1991) Cell 64:671-674; Sanfacon et al. (1991) Genes Dev. 5: 141-149; Mogen et al. (1990) Plant Cell 2: 1261-1272; Munroe et al. (1990) Gene 91: 151-158; Ballas t al. (1989) Nucleic Acids Res. 17:7891-7903; and Joshi et al. (1987) Nucleic Acid Res. 15:9627-9639. Where appropriate, the gene(s) may be optimized for increased expression in the transformed plant. That is, the genes can be synthesized using plant-preferred codons for improved expression. See, for example, Campbell and Gowri (1990) Plant Physiol. 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. Nucleotide sequences for enhancing gene expression can also be used in the plant expression vectors. These include the introns of the maize AdhI, intronI gene (Callis et al. Genes and Development 1: 1183-1200, 1987), and leader sequences, (W-sequence) from the Tobacco Mosaic virus (TMV), Maize Chlorotic Mottle Virus and Alfalfa Mosaic Virus (Gallie et al. Nucleic Acid Res. 15:8693-8711, 1987 and Skuzeski et al. Plant Mol. Biol. 15:65-79, 1990). The first intron from the shrunken-1 locus of maize, has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize mutated PPO gene expression, the plant expression vectors of the invention may also contain DNA sequences containing matrix attachment regions (MARs). Plant cells transformed with such modified expression systems, then, may exhibit overexpression or constitutive expression of a nucleotide sequence of the invention.

The expression cassettes of the present invention may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. ScL USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and trans versions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2: 163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced mutated PPO expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) Plant J. 12(2):255-265; Kawamata et al. (1997) Plant Cell Physiol. 38(7):792-803; Hansen et al. (1997) Mol. Gen Genet. 254(3):337-343; Russell et al. (1997) Transgenic Res. 6(2): 157-168; Rinehart et al. (1996) Plant Physiol. 112(3): 1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20: 181-196; Orozco et al. (1993) Plant Mol Biol. 23(6): 1129-1138; Matsuoka e/[alpha]/. (1993) Proc Natl. Acad. Sci. USA 90(20):9586-9590; and Guevara-Garcia et al. (1993) Plant J. 4(3):495-505. Such promoters can be modified, if necessary, for weak expression. In one embodiment, the nucleic acids of interest are targeted to the chloroplast for expression.

In this manner, where the nucleic acid of interest is not directly inserted into the chloroplast, the expression cassette will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, "operably linked" means that the nucleic acid sequence encoding a transit peptide (i.e., the chloroplast-targeting sequence) is linked to the mutated PPO nucleic acid of the invention such that the two sequences are contiguous and in the same reading frame. See, for example, Von Heijne et al. (1991) Plant Mol. Biol. Rep. 9: 104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481. While the mutated PPO proteins of the invention include a native chloroplast transit peptide, any chloroplast transit peptide known in the art can be fused to the amino acid sequence of a mature mutated PPO protein of the invention by operably linking a chloroplast-targeting sequence to the 5'-end of a nucleotide sequence encoding a mature mutated PPO protein of the invention. Chloroplast targeting sequences are known in the art and include the chloroplast small subunit of ribulose-1,5-bisphosphate carboxylase (Rubisco) (de Castro Silva Filho et al. (1996) Plant Mol. Biol. 30:769-780; Schnell et al. (1991) J. Biol. Chem. 266(5):3335-3342); 5-(enolpyruvyl)shikimate-3-phosphate synthase (EPSPS) (Archer et al. (1990) J. Bioenerg. Biomemb. 22(6):789-810); tryptophan synthase (Zhao et al. (1995) J. Biol. Chem. 270(11):6081-6087); plastocyanin (Lawrence et al. (1997) J. Biol. Chem. 272(33):20357-20363); chorismate synthase (Schmidt et al. (1993) J. Biol. Chem. 268(36):27447-27457); and the light harvesting chlorophyll a/b binding protein (LHBP) (Lamppa et al. (1988) J. Biol. Chem. 263: 14996-14999). See also Von Heijne et al. (1991) Plant Mol. Biol. Rep. 9: 104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196: 1414-1421; and Shah et al. (1986) Science 233:478-481.

In a preferred embodiment, the targeting sequence comprises a nucleotide sequence that encodes a transit peptide comprising the amino acid sequence of SEQ ID NO: 49, 50, 51, 52, or 53 (Ferredoxin transit peptide Fdxtp). Preferably, the transit peptide encoding nucleic acid is operably linked such that the transit peptide is fused to the valine at position 46 in SEQ ID NO: 2 or 4.

In another preferred embodiment, the transit peptide encoding nucleic acid is operably linked such that the transit peptide is fused to the aspartic acid at position 71 in SEQ ID NO: 48.

In a particularly preferred embodiment, the nucleic acid sequence encoding a transit peptide comprises the sequence of SEQ ID NO: 54 (for expression in corn codon-optimized nucleic acid encoding the Ferredoxin transit peptide of *Silene pratensis*) or SEQ ID NO: 55 (for expression in soy codon-optimized nucleic acid encoding the Ferredoxin transit peptide of *Silene pratensis*).

Methods for transformation of chloroplasts are known in the art. See, for example, Svab et al. (1990) Proc. Natl. Acad. ScL USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305. The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

In a preferred embodiment, the mutated PPO nucleic acid comprises a polynucleotide sequence selected from the group consisting of: a) a polynucleotide as shown in SEQ ID NO: 1, 3, 5, 7, 9, 11, 13, 15, 17, 19, 21, 23, 25, 27, 29, 31, 33, 35, 37, 39, 41, 43, 45, or 47, or a variant or derivative thereof; b) a polynucleotide encoding a polypeptide as shown in SEQ ID NO: 2, 4, 6, 8, 10, 12, 14, 16, 18, 20, 22, 24, 26, 28, 30, 32, 34, 36, 38, 40, 42, 44, 46, or 48, or a variant or derivative thereof; c) a polynucleotide comprising at least 60 consecutive nucleotides of any of a) or c); and d) a polynucleotide complementary to the polynucleotide of any of a) through c)

Preferably, the expression cassette of the present invention further comprises a transcription initiation regulatory region and a translation initiation regulatory region that are functional in the plant.

While the polynucleotides of the invention find use as selectable marker genes for plant transformation, the expression cassettes of the invention can include another selectable marker gene for the selection of transformed cells. Selectable marker genes, including those of the present invention, are utilized for the selection of transformed cells or tissues. Marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christophers on et al (1992) Proc. Natl. Acad. ScL USA 89:6314-6318; Yao et al. (1992) Cell 71:63-72; Reznikoff (1992) Mol Microbiol 6:2419-2422; Barkley et al (1980) in The Operon, pp. 177-220; Hu et al (1987) Cell 48:555-566; Brown et al (1987) Cell 49:603-612; Figge et al (1988) Cell 52:713-722; Deuschle et al (1989) Proc. Natl Acad. AcL USA 86:5400-5404; Fuerst et al (1989) Proc. Natl Acad. ScL USA 86:2549-2553; Deuschle et al (1990) Science 248:480-483; Gossen (1993) Ph.D. Thesis, University of Heidelberg; Reines et al (1993) Proc. Natl Acad. ScL USA 90: 1917-1921; Labow et al (1990) Mol Cell Biol 10:3343-3356; Zambretti et al (1992) Proc. Natl Acad. ScL USA 89:3952-3956; Bairn et al (1991) Proc. Natl Acad. ScL USA 88:5072-5076; Wyborski et al (1991) Nucleic Acids Res. 19:4647-4653; Hillenand-Wissman (1989) Topics Mol Struc. Biol 10: 143-162; Degenkolb et al (1991) Antimicrob. Agents Chemother. 35: 1591-1595; Kleinschnidt et al (1988) Biochemistry 27: 1094-1104; Bonin (1993) Ph.D. Thesis, University of Heidelberg; Gossen et al (1992) Proc. Natl Acad. ScL USA 89:5547-5551; Oliva et al (1992) Antimicrob. Agents Chemother. 36:913-919; Hlavka et al (1985) Handbook of Experimental Pharmacology, Vol. 78 (Springer-Verlag, Berlin); Gill et al (1988) Nature 334:721-724. Such disclosures are herein incorporated by reference. The above list of selectable marker genes is not meant to be limiting. Any selectable marker gene can be used in the present invention.

The invention further provides an isolated recombinant expression vector comprising the expression cassette containing a mutated PPO nucleic acid as described above, wherein expression of the vector in a host cell results in increased tolerance to a PPO-inhibiting herbicide as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., mutated PPO polypeptides, fusion polypeptides, etc.).

In a preferred embodiment of the present invention, the mutated PPO polypeptides are expressed in plants and plants cells such as unicellular plant cells (such as algae) (See Falciatore et al., 1999, Marine Biotechnology 1(3):239-251 and references therein) and plant cells from higher plants (e.g., the spermatophytes, such as crop plants). A mutated PPO polynucleotide may be "introduced" into a plant cell by any means, including transfection, transformation or transduction, electroporation, particle bombardment, agroinfection, biolistics, and the like.

Suitable methods for transforming or transfecting host cells including plant cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J. As increased tolerance to PPO-inhibiting herbicides is a general trait wished to be inherited into a wide variety of plants like maize, wheat, rye, oat, triticale, rice, barley, soybean, peanut, cotton, rapeseed and canola, manihot, pepper, sunflower and *tagetes*, solanaceous plants like potato, tobacco, eggplant, and tomato, *Vicia* species, pea, alfalfa, bushy plants (coffee, cacao, tea), *Salix* species, trees (oil palm, coconut), perennial grasses, and forage crops, these crop plants are also preferred target plants for a genetic engineering as one further embodiment of the present invention. In a preferred embodiment, the plant is a crop plant. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of a mutated PPO polynucleotide into a plant is achieved by *Agrobacterium* mediated gene transfer. One transformation method known to those of skill in the art is the dipping of a flowering plant into an Agrobacteria solution, wherein the Agrobacteria contains the mutated PPO nucleic acid, followed by breeding of the transformed gametes. *Agrobacterium* mediated plant transformation can be performed using for example the GV3101(pMP90) (Koncz and Schell, 1986, Mol. Gen. Genet. 204:383-396) or LBA4404 (Clontech) *Agrobacterium tumefaciens* strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, 2nd Ed.—Dordrecht:

Kluwer Academic Publ., 1995.—in Sect., Ringbuc Zentrale Signatur: BT11-P ISBN 0-7923-2731-4; Glick, Bernard R. and Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced mutated PPO polynucleotide may be maintained in the plant cell stably if it is incorporated into a non-chromosomal autonomous replicon or integrated into the plant chromosomes. Alternatively, the introduced mutated PPO polynucleotide may be present on an extra-chromosomal non-replicating vector and be transiently expressed or transiently active. In one embodiment, a homologous recombinant microorganism can be created wherein the mutated PPO polynucleotide is integrated into a chromosome, a vector is prepared which contains at least a portion of an PPO gene into which a deletion, addition, or substitution has been introduced to thereby alter, e.g., functionally disrupt, the endogenous PPO gene and to create a mutated PPO gene. To create a point mutation via homologous recombination, DNA-RNA hybrids can be used in a technique known as chimeraplasty (Cole-Strauss et al., 1999, Nucleic Acids Research 27(5):1323-1330 and Kmiec, 1999, Gene therapy American Scientist 87(3):240-247). Other homologous recombination procedures in *Triticum* species are also well known in the art and are contemplated for use herein.

In the homologous recombination vector, the mutated PPO gene can be flanked at its 5' and 3' ends by an additional nucleic acid molecule of the PPO gene to allow for homologous recombination to occur between the exogenous mutated PPO gene carried by the vector and an endogenous PPO gene, in a microorganism or plant. The additional flanking PPO nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987, Cell 51:503 for a description of homologous recombination vectors or Strepp et al., 1998, PNAS, 95(8):4368-4373 for cDNA based recombination in *Physcomitrella patens*). However, since the mutated PPO gene normally differs from the PPO gene at very few amino acids, a flanking sequence is not always necessary. The homologous recombination vector is introduced into a microorganism or plant cell (e.g., via polyethylene glycol mediated DNA), and cells in which the introduced mutated PPO gene has homologously recombined with the endogenous PPO gene are selected using art-known techniques.

In another embodiment, recombinant microorganisms can be produced that contain selected systems that allow for regulated expression of the introduced gene. For example, inclusion of a mutated PPO gene on a vector placing it under control of the lac operon permits expression of the mutated PPO gene only in the presence of IPTG. Such regulatory systems are well known in the art.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a mutated PPO polynucleotide can be expressed in bacterial cells such as *C. glutamicum*, insect cells, fungal cells, or mammalian cells (such as Chinese hamster ovary cells (CHO) or COS cells), algae, ciliates, plant cells, fungi or other microorganisms like *C. glutamicum*. Other suitable host cells are known to those skilled in the art.

A host cell of the invention, such as a prokaryotic or eukaryotic host cell in culture, can be used to produce (i.e., express) a mutated PPO polynucleotide. Accordingly, the invention further provides methods for producing mutated PPO polypeptides using the host cells of the invention. In one embodiment, the method comprises culturing the host cell of invention (into which a recombinant expression vector encoding a mutated PPO polypeptide has been introduced, or into which genome has been introduced a gene encoding a wild-type or mutated PPO polypeptide) in a suitable medium until mutated PPO polypeptide is produced. In another embodiment, the method further comprises isolating mutated PPO polypeptides from the medium or the host cell. Another aspect of the invention pertains to isolated mutated PPO polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of mutated PPO polypeptide in which the polypeptide is separated from some of the cellular components of the cells in which it is naturally or recombinantly produced. In one embodiment, the language "substantially free of cellular material" includes preparations of a mutated PPO polypeptide having less than about 30% (by dry weight) of non-mutated PPO material (also referred to herein as a "contaminating polypeptide"), more preferably less than about 20% of non-mutated PPO material, still more preferably less than about 10% of non-mutated PPO material, and most preferably less than about 5% non-mutated PPO material.

When the mutated PPO polypeptide, or biologically active portion thereof, is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of mutated PPO polypeptide in which the polypeptide is separated from chemical precursors or other chemicals that are involved in the synthesis of the polypeptide. In one embodiment, the language "substantially free of chemical precursors or other chemicals" includes preparations of a mutated PPO polypeptide having less than about 30% (by dry weight) of chemical precursors or non-mutated PPO chemicals, more preferably less than about 20% chemical precursors or non-mutated PPO chemicals, still more preferably less than about 10% chemical precursors or non-mutated PPO chemicals, and most preferably less than about 5% chemical precursors or non-mutated PPO chemicals. In preferred embodiments, isolated polypeptides, or biologically active portions thereof, lack contaminating polypeptides from the same organism from which the mutated PPO polypeptide is derived. Typically, such polypeptides are produced by recombinant expression of, for example, a mutated PPO polypeptide in plants other than, or in microorganisms such as *C. glutamicum*, ciliates, algae, or fungi.

In other aspects, a method for treating a plant of the present invention is provided.

In some embodiments, the method comprises contacting the plant with an agronomically acceptable composition.

In another aspect, the present invention provides a method for preparing a descendent seed.

The method comprises planting a seed of or capable of producing a plant of the present invention. In one embodiment, the method further comprises growing a descendent plant from the seed; and harvesting a descendant seed from the descendent plant. In other embodiments, the method further comprises applying a PPO-inhibiting herbicides herbicidal composition to the descendent plant.

In another embodiment, the invention refers to harvestable parts of the transgenic plant according to the present invention. Preferably, the harvestable parts comprise the PPO nucleic acid or PPO protein of the present invention. The harvestable parts may be seeds, roots, leaves and/or flowers comprising the PPO nucleic acid or PPO protein or parts thereof. Preferred parts of soy plants are soy beans comprising the PPO nucleic acid or PPO protein.

In another embodiment, the invention refers to products derived from a plant according to the present invention, parts thereof or harvestable parts thereof. A preferred plant product is fodder, seed meal, oil, or seed-treatment-coated seeds. Preferably, the meal and/or oil comprises the mutated PPO nucleic acids or PPO proteins of the present invention.

In another embodiment, the invention refers to a method for the production of a product, which method comprises
a) growing the plants of the invention or obtainable by the methods of invention and
b) producing said product from or by the plants of the invention and/or parts, e.g. seeds, of these plants.

In a further embodiment the method comprises the steps
a) growing the plants of the invention,
b) removing the harvestable parts as defined above from the plants and
c) producing said product from or by the harvestable parts of the invention.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

As described above, the present invention teaches compositions and methods for increasing the PPO-inhibiting tolerance of a crop plant or seed as compared to a wild-type variety of the plant or seed. In a preferred embodiment, the PPO-inhibiting tolerance of a crop plant or seed is increased such that the plant or seed can withstand a PPO-inhibiting herbicide application of preferably approximately 1-1000 g ai ha$^{-1}$, more preferably 1-200 g ai ha$^{-1}$, even more preferably 5-150 g ai ha$^{-1}$, and most preferably 10-100 g ai ha$^{-1}$. As used herein, to "withstand" a PPO-inhibiting herbicide application means that the plant is either not killed or only moderately injured by such application. It will be understood by the person skilled in the art that the application rates may vary, depending on the environmental conditions such as temperature or humidity, and depending on the chosen kind of herbicide (active ingredient ai).

Furthermore, the present invention provides methods that involve the use of at least one PPO-inhibiting herbicide, optionally in combination with one or more herbicidal compounds B, and, optionally, a safener C, as described in detail supra.

In these methods, the PPO-inhibiting herbicide can be applied by any method known in the art including, but not limited to, seed treatment, soil treatment, and foliar treatment. Prior to application, the PPO-inhibiting herbicide can be converted into the customary formulations, for example solutions, emulsions, suspensions, dusts, powders, pastes and granules. The use form depends on the particular intended purpose; in each case, it should ensure a fine and even distribution of the compound according to the invention.

By providing plants having increased tolerance to PPO-inhibiting herbicide, a wide variety of formulations can be employed for protecting plants from weeds, so as to enhance plant growth and reduce competition for nutrients. A PPO-inhibiting herbicide can be used by itself for pre-emergence, post-emergence, pre-planting, and at-planting control of weeds in areas surrounding the crop plants described herein, or a PPO-inhibiting herbicide formulation can be used that contains other additives. The PPO-inhibiting herbicide can also be used as a seed treatment. Additives found in a PPO-inhibiting herbicide formulation include other herbicides, detergents, adjuvants, spreading agents, sticking agents, stabilizing agents, or the like. The PPO-inhibiting herbicide formulation can be a wet or dry preparation and can include, but is not limited to, flowable powders, emulsifiable concentrates, and liquid concentrates. The PPO-inhibiting herbicide and herbicide formulations can be applied in accordance with conventional methods, for example, by spraying, irrigation, dusting, or the like.

Suitable formulations are described in detail in PCT/EP2009/063387 and PCT/EP2009/063386, which are incorporated herein by reference.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1: Site-Directed Mutagenesis of *Amaranthus* PPO

All nucleic acid coding sequence and all single and double mutants based on SEQ ID NO: 1, 3, 5, 7, 9, 15, 17, 19, 21, 23, 25, 27, 29, 31, 33, 35, 37, 39, 41, 43, 45, 47, were synthesized and cloned by Geneart (Geneart AG, Regensburg, Germany). Rational design mutants were synthesized by Geneart. Random PPO gene libraries were synthesized by Geneart. Plasmids were isolated from *E. coli* TOP10 by performing a plasmid minpreparation and confirmed by DNA sequencing.

Example 2: Expression and Purification of Recombinant Wildtype and Mutant PPO (Taken from: Franck E. Dayan, Pankaj R. Daga, Stephen O. Duke, Ryan M. Lee, Patrick J. Tranel, Robert J. Doerksen. Biochemical and structural consequences of a glycine deletion in the α-8 helix of protoporphyrinogen oxidase. Biochimica et Biophysica Acta 1804 (2010), 1548-56) Clones in pRSET vector were transformed into BL21(DE3)-pLysS strain of *E. coli*. Cells were grown in 250 mL of LB with 100 μgmL-1 of carbenicillin, shaking overnight at 37° C. Cultures were diluted in 1 L of LB with antibiotic and grown at 37° C. shaking for 2 h, induced with 1 mM IPTG and grown at 25° C. shaking for 5 more hours. The cells were harvested by centrifugation at 1600×g, washed with 0.09% NaCl, and stored at −80° C. Cells were lysed using a French press at 140 MPa in 50 mM sodium phosphate pH 7.5, 1 M NaCl, 5 mM imidazole, 5% glycerol, and 1 μg mL-1 leupeptin. Following lysis, 0.5 U of benzonase (Novagen, EMD Chemicals, Inc., Gibbstown, N.J.) and PMSF (final concentration of 1 mM) were added. Cell debris was removed by centrifugation at 3000×g. His-tagged PPO proteins were purified on a nickel activated Hitrap Chelating HP column (GE Healthcare Bio-Sciences Corp., Piscataway, N.J.) equilibrated with 20 mM sodium phosphate pH 8.0, 50 mM NaCl, 5 mM imidazole, 5 mM MgCl2, 0.1 mM EDTA, and 17% glycerol. PPO is eluted with 250 mM imidazole. The active protein was desalted on a PD-10 column (GE Healthcare Bio-Sciences Corp., Piscataway, N.J.) equilibrated with a 20 mM sodium phosphate buffer, pH 7.5, 5 mM MgCl2, 1 mM EDTA and 17% glycerol. Each liter of culture provided approximately 10 mg of pure PPO, which was stored at −20° C. until being used in assays.

Example 3: PPO Enzyme Assay (Non-Recombinant)

PPO protein (EC 1.3.3.4) was extracted from coleoptiles or shoots (150 g fresh weight) of dark-grown corn, black nightshade, morning glory, and velvetleaf seedlings as described previously (Grossmann et al. 2010). Before harvesting, the seedlings were allowed to green for 2 hours in the light in order to achieve the highest specific enzyme activities in the thylakoid fractions at low chlorophyll concentrations. At high chlorophyll concentrations significant quenching of fluorescence occurs, which limits the amount of green thylakoids that can be used in the test. Plant materials were homogenized in the cold with a Braun blender using a fresh-weight-to-volume ratio of 1:4. Homogenization buffer consisted of tris(hydroxymethyl)aminomethane (Tris)-HCl (50 mM; pH 7.3), sucrose (0.5 M), magnesium chloride (1 mM), ethylenediaminetetraacetic acid (EDTA) (1 mM) and bovine serum albumin (2 g $L^{-1}$). After filtration through four layers of Miracloth, crude plastid preparations were obtained after centrifugation at 10 000×g for 5 min and resuspension in homogenization buffer before centrifugation at 150×g for 2 min to remove crude cell debris. The supernatant was centrifuged at 4000×g for 15 min and the pellet fraction was resuspended in 1 ml of a buffer containing Tris-HCl (50 mM; pH 7.3), EDTA (2 mM), leupeptin (2 μM), pepstatin (2 μM) and glycerol (200 ml $L^{-1}$) and stored at −80° C. until use. Protein was determined in the enzyme extract with bovine serum albumin as a standard. PPO activity was assayed fluorometrically by monitoring the rate of Proto formation from chemically reduced protoporphyrinogen IX under initial velocity conditions. The assay mixture consisted of Tris-HCl (100 mM; pH 7.3), EDTA (1 mM), dithiothreitol (5 mM), Tween 80 (0.085%), protoporphyrinogen IX (2 μM), and 40 μg extracted protein in a total volume of 200 μl. The reaction was initiated by addition of substrate protoporphyrinogen IX at 22° C. saflufenacil, 1,5-dimethyl-6-thioxo-3-(2,2,7-trifluoro-3-oxo-4-(prop-2-ynyl)-3,4-dihydro-2H-benzo[b][1,4] oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control were prepared in dimethyl sulfoxide (DMSO) solution (0.1 mM concentration of DMSO in the assay) and added to the assay mixture in concentrations of 0.005 pM to 5 μM before incubation. Fluorescence was monitored directly from the assay mixture using a POLARstar Optima/Galaxy (BMG) with excitation at 405 nm and emission monitored at 630 nm. Non-enzymatic activity in the presence of heat-inactivated extract was negligible. Inhibition of enzyme activity induced by the herbicide was expressed as percentage inhibition relative to untreated controls. Molar concentrations of compound required for 50% enzyme inhibition ($IC_{50}$ values) were calculated by fitting the values to the dose-response equation using non-linear regression analysis.

Example 4: PPO Enzyme Assay (Recombinant)

Proto was purchased from Sigma-Aldrich (Milwaukee, Wis.). Protogen was prepared according to Jacobs and Jacobs (N. J. Jacobs, J. M. Jacobs, Assay for enzymatic protoporphyrinogen oxidation, a late step in heme synthesis, Enzyme 28 (1982) 206-219). Assays were conducted in 100 mM sodium phosphate pH 7.4 with 0.1 mM EDTA, 0.1% Tween 20, 5 μM FAD, and 500 mM imidazole. Dose-response curves with the PPO inhibitors saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control, and MC-15608 were obtained in the presence of 150 μM Protogen. Dose response was measured between the inhibitor concentration range of 1.00E-05 M to 1.00E-12 M. The excitation and emission bandwidths were set at 1.5 and 30 nm, respectively. All assays were made in duplicates or triplicates and measured using a POLARstar Optima/Galaxy (BMG) with excitation at 405 nm and emission monitored at 630 nm. Molar concentrations of compound required for 50% enzyme inhibition ($IC_{50}$ values) were calculated by fitting the values to the dose-response equation using non-linear regression analysis. The results are shown in Table 4.

TABLE 4a

IC50 values for various mutated PPO (mutated PPO)

| Amino Acid Substitution | SEQ. ID NO. | Relative Ezyme Activity (FU/min) | Saflufenacil | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione IC50 (M) |
|---|---|---|---|---|
| PPO herbicide sensitive PPO2 WC | 2 | 1000 | 1.86E−09 | 5.17E−10 |
| PPO herbicide sensitive PPO2 AC | 4 | 800 | 1.78E−10 | 5.96E−11 |
| dG210 | 6 & 8 | 80 | 1.60E−06 | 2.12E−09 |
| R128L | 2 | 700 | 2.22E−07 | 7.73E−10 |
| R128L | 2 | 700 | 2.22E−07 | 7.73E−10 |
| R128A | 2 | 730 | 1.29E−07 | 1.40E−10 |
| R128C | 4 | 515 | 5.57E−07 | 1.16E−10 |
| R128D | 4 | ND | ND | ND |
| R128E | 4 | ND | ND | ND |
| R128F | 4 | 280 | 5.25E−07 | 2.21E−10 |
| R128G | 4 | 440 | 9.91E−07 | 4.71E−11 |
| R128H | 4 | 640 | 1.02E−08 | 6.15E−11 |
| R128I | 4 | 250 | 3.65E−07 | 9.80E−11 |
| R128K | 4 | 180 | 9.65E−11 | ND |
| R128L | 4 | 280 | 3.88E−07 | 1.01E−10 |
| R128M | 4 | 200 | 6.97E−07 | 3.56E−11 |
| R128N | 4 | 420 | 5.79E−07 | 4.33E−11 |
| R128P | 4 | ND | ND | ND |
| R128Q | 4 | 480 | 1.94E−07 | 1.09E−11 |
| R128S | 4 | 490 | 2.46E−07 | 1.12E−11 |
| R128T | 4 | 510 | 2.11E−07 | 3.79E−11 |
| R128V | 4 | 600 | 2.49E−07 | 6.70E−11 |
| R128W | 4 | ND | ND | ND |
| R128Y | 4 | 230 | 2.19E−06 | 5.77E−11 |
| F420A | 4 | ND | ND | ND |
| F420V | 2 | 200 | 1.59E−06 | 1.61E−09 |
| F420V | 2 | 330 |  | 1.61E−09 |
| F420M | 2 | 350 | 6.77E−07 | 2.75E−10 |
| F420M | 2 | 700 |  | 2.18E−10 |
| F420L | 2 | 200 | 7.20E−06 | 9.93E−10 |
| F420I | 2 | 200 | 9.19E−07 | 4.95E−10 |
| R128A, F420V | 2 | 510 | >0.00001 | 2.50E−08 |
| R128A + F420M | 2 | 400 | >0.00001 | 6.24E−09 |
| R128A + F420L | 2 | 300 | >0.00001 | 1.62E−08 |
| R128A + F420I | 2 | 330 | >0.00001 | 2.46E−08 |
| R128A__F420A | 4 | ND | ND | ND |
| R128L__F420A | 4 | ND | ND | ND |
| R128L__F420L | 4 | 300 | >0.00001 | 1.71E−06 |
| R128L__F420I | 4 | 450 | >0.00001 | 1.23E−06 |
| R128L__F420V | 4 | 300 | >0.00001 | 1.51E−06 |
| R128L__F420M | 4 | 400 | >0.00001 | 2.46E−07 |
| R128I__F420A | 4 | ND | ND | ND |
| R128I__F420L | 4 | 200 | >0.00001 | 4.66E−07 |
| R128I__F420I | 4 | 100 | >0.00001 | 4.33E−07 |
| R128I__F420V | 4 | 470 | >0.00001 | 4.24E−07 |
| R128I__F420M | 4 | 500 | >0.00001 | 5.82E−08 |
| R128V__F420A | 4 | ND | ND | ND |
| R128V__F420L | 4 | 370 | >0.00001 | 4.41E−07 |
| R128V__F420I | 4 | 300 | >0.00001 | 2.23E−07 |
| R128V__F420V | 4 | 300 | >0.00001 | 4.46E−07 |
| R128V__F420M | 4 | 460 | >0.00001 | 4.27E−08 |
| R128M__F420A | 4 | ND | ND | ND |
| R128M__F420L | 4 | 300 | >0.00001 | 6.95E−07 |
| R128M__F420I | 4 | 350 | >0.00001 | 4.45E−07 |

TABLE 4a-continued

IC50 values for various mutated PPO (mutated PPO)

| Amino Acid Substitution | SEQ. ID NO. | Relative Ezyme Activity (FU/min) | Saflufenacil | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione IC50 (M) |
|---|---|---|---|---|
| R128M_F420V | 4 | 270 | >0.00001 | 7.04E−07 |
| R128M_F420M | 4 | 480 | >0.00001 | 7.05E−08 |

TABLE 4b

IC50 values for various mutated PPO (mutated PPO)

| Construct | SEQ. ID NO. | rate (FU/min) | Saflufenacil | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione IC50 (M) |
|---|---|---|---|---|
| PPO herbicide sensitive PPO2 WC | 2 | 1000 | 1.86E−09 | 5.17E−10 |
| PPO herbicide sensitive PPO2 AC | 4 | 800 | 1.78E−10 | 5.96E−11 |
| dG210 | 6 & 8 | 80 | 1.60E−06 | 2.12E−09 |
| R128L | 2 | 700 | 2.22E−07 | 7.73E−10 |
| R128K | 4 | 180 | 9.65E−11 | not determined |
| R128Q | 4 | 481 | 1.94E−07 | 1.09E−11 |
| R128S | 4 | 491 | 2.46E−07 | 1.13E−11 |
| R128M | 4 | 200 | 6.97E−07 | 3.56E−11 |
| R128T | 4 | 721 | 2.11E−07 | 3.79E−11 |
| R128N | 4 | 421 | 5.79E−07 | 4.33E−11 |
| R128G | 4 | 436 | 9.91E−07 | 4.71E−11 |
| R128Y | 4 | 230 | 2.19E−06 | 5.77E−11 |
| R128H | 4 | 636 | 1.02E−08 | 6.15E−11 |
| R128V | 4 | 923 | 2.49E−07 | 7.00E−11 |
| R128I | 4 | 250 | 3.65E−07 | 9.80E−11 |
| R128C | 4 | 933 | 5.57E−07 | 1.16E−10 |
| R128A | 4 | 731 | 1.29E−07 | 1.40E−10 |
| R128F | 4 | 278 | 5.25E−07 | 2.21E−10 |
| R128L | 4 | 700 | 2.22E−07 | 7.73E−10 |
| R128A, L397D | 2 | 98 | ≥1.00E−5 | 5.90E−09 |
| R128A, F420M | 2 | 378 | ≥1.00E−5 | 6.24E−09 |
| R128Q, F420M | 4 | 473 | ≥1.00E−5 | 1.54E−08 |
| R128A, F420L | 2 | 281 | ≥1.00E−5 | 1.62E−08 |
| R128S, F420M | 4 | 310 | ≥1.00E−5 | 1.77E−08 |
| R128C, F420M | 4 | 329 | ≥1.00E−5 | 2.30E−08 |
| R128A, F420I | 2 | 330 | ≥1.00E−5 | 2.46E−08 |
| R128A, F420V | 2 | 512 | ≥1.00E−5 | 2.50E−08 |
| R128H, F420M | 4 | 252 | ≥1.00E−5 | 2.92E−08 |
| R128G, F420M | 4 | 100 | ≥1.00E−5 | 3.02E−08 |
| R128V, F420M | 4 | 666 | ≥1.00E−5 | 4.27E−08 |
| R128S, F420I | 4 | 150 | ≥1.00E−5 | 4.64E−08 |
| R128Q, F420I | 4 | 202 | ≥1.00E−5 | 5.43E−08 |
| R128T, F420M | 4 | 303 | ≥1.00E−5 | 5.54E−08 |
| R128I, F420M | 4 | 497 | ≥1.00E−5 | 5.82E−08 |
| R128S, F420L | 4 | 110 | ≥1.00E−5 | 6.24E−08 |
| R128Q, F420L | 4 | 150 | ≥1.00E−5 | 6.90E−08 |
| R128M, F420M | 4 | 479 | ≥1.00E−5 | 7.05E−08 |
| R128F, F420M | 4 | 120 | ≥1.00E−5 | 7.84E−08 |
| R128M, F420M | 4 | 306 | ≥1.00E−5 | 8.26E−08 |
| R128N, F420M | 4 | 208 | ≥1.00E−5 | 1.01E−07 |
| R128C, F420I | 4 | 204 | ≥1.00E−5 | 1.20E−07 |
| R128M, F420I | 4 | 250 | ≥1.00E−5 | 1.44E−07 |
| R128H, F420I | 4 | 195 | ≥1.00E−5 | 1.47E−07 |
| R128T, F420V | 4 | 120 | ≥1.00E−5 | 1.50E−07 |
| R128Y, F420M | 4 | 200 | ≥1.00E−5 | 1.61E−07 |
| R128H, F420L | 4 | 185 | ≥1.00E−5 | 1.69E−07 |
| R128N, F420I | 4 | 100 | ≥1.00E−5 | 1.75E−07 |
| R128H, F420V | 4 | 74 | ≥1.00E−5 | 1.82E−07 |
| R128C, F420L | 4 | 217 | ≥1.00E−5 | 1.89E−07 |
| R128Q, F420V | 4 | 113 | ≥1.00E−5 | 2.02E−07 |

TABLE 4b-continued

IC50 values for various mutated PPO (mutated PPO)

| Construct | SEQ. ID NO. | rate (FU/min) | Saflufenacil | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione IC50 (M) |
|---|---|---|---|---|
| R128N, F420L | 4 | 100 | ≥1.00E−5 | 2.10E−07 |
| R128C, F420V | 4 | 223 | ≥1.00E−5 | 2.16E−07 |
| R128V, F420I | 4 | 300 | ≥1.00E−5 | 2.23E−07 |
| R128T, F420I | 4 | 238 | ≥1.00E−5 | 2.29E−07 |
| R128L, F420M | 4 | 518 | ≥1.00E−5 | 2.46E−07 |
| R128M, F420L | 4 | 211 | ≥1.00E−5 | 2.49E−07 |
| R128T, F420L | 4 | 157 | ≥1.00E−5 | 3.97E−07 |
| R128M, F420V | 4 | 127 | ≥1.00E−5 | 4.00E−07 |
| R128I, F420V | 4 | 464 | ≥1.00E−5 | 4.24E−07 |
| R128I, F420I | 4 | 128 | ≥1.00E−5 | 4.33E−07 |
| R128V, F420L | 4 | 365 | ≥1.00E−5 | 4.41E−07 |
| R128M, F420I | 4 | 343 | ≥1.00E−5 | 4.45E−07 |
| R128V, F420V | 4 | 300 | ≥1.00E−5 | 4.47E−07 |
| R128I, F420L | 4 | 281 | ≥1.00E−5 | 4.66E−07 |
| R128Y, F420I | 4 | 90 | ≥1.00E−5 | 6.11E−07 |
| R128A, ΔG210 | 4 | 170 | ≥1.00E−5 | 6.57E−07 |
| R128M, F420L | 4 | 300 | ≥1.00E−5 | 6.95E−07 |
| R128M, F420V | 4 | 261 | ≥1.00E−5 | 7.04E−07 |
| R128F, F420L | 4 | 101 | ≥1.00E−5 | 8.68E−07 |
| R128L, F420I | 4 | 453 | ≥1.00E−5 | 1.23E−06 |
| R128L, F420V | 4 | 289 | ≥1.00E−5 | 1.51E−06 |
| R128L, F420L | 4 | 300 | ≥1.00E−5 | 1.71E−06 |
| R128D | 4 | Low or no enzyme activity measured | | |
| R128E | 4 | Low or no enzyme activity measured | | |
| R128P | 4 | Low or no enzyme activity measured | | |
| R128W | 4 | Low or no enzyme activity measured | | |
| R128A, F420A | 2 | Low or no enzyme activity measured | | |
| R128L, F420A | 4 | Low or no enzyme activity measured | | |
| R128I, F420A | 4 | Low or no enzyme activity measured | | |
| R128V, F420A | 4 | Low or no enzyme activity measured | | |
| R128M, F420A | 4 | Low or no enzyme activity measured | | |
| R128M, F420A | 4 | Low or no enzyme activity measured | | |
| R128N, F420A | 4 | Low or no enzyme activity measured | | |

TABLE 4b-continued

IC50 values for various mutated PPO (mutated PPO)

| Construct | SEQ. ID NO. | rate (FU/min) | Saflufenacil | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione IC50 (M) |
|---|---|---|---|---|
| R128Y, F420A | 4 | Low or no enzyme activity measured | | |
| R128Y, F420L | 4 | Low or no enzyme activity measured | | |
| R128Y, F420V | 4 | Low or no enzyme activity measured | | |
| R128G, F420A | 4 | Low or no enzyme activity measured | | |
| R128G, F420L | 4 | Low or no enzyme activity measured | | |
| R128G, F420I | 4 | Low or no enzyme activity measured | | |
| R128G, F420V | 4 | Low or no enzyme activity measured | | |
| R128H, F420A | 4 | Low or no enzyme activity measured | | |
| R128N, F420V | 4 | Low or no enzyme activity measured | | |
| R128C, F420A | 4 | Low or no enzyme activity measured | | |
| R128F, F420A | 4 | Low or no enzyme activity measured | | |
| R128F, F420I | 4 | Low or no enzyme activity measured | | |
| R128F, F420V | 4 | Low or no enzyme activity measured | | |
| R128S, F420A | 4 | Low or no enzyme activity measured | | |
| R128S, F420V | 4 | Low or no enzyme activity measured | | |

TABLE 4b-continued

IC50 values for various mutated PPO (mutated PPO)

| Construct | SEQ. ID NO. | rate (FU/min) | Saflufenacil | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione IC50 (M) |
|---|---|---|---|---|
| R128T, F420A | 4 | Low or no enzyme activity measured | | |
| R128Q, F420A | 4 | Low or no enzyme activity measured | | |

IC50 (M): Concentration of inhibitor required for 50% inhibition of enzyme activity;

≥1.00E−5: indicates a very high IC50 over the measurement bounderies. which reflects very high in vitro tolerance.

TABLE 4c

| Common Name | IUPAC Name | SEQ ID | Mutation | rate (FU/min) | IC50 (M) | inhibition (%) at 1 × 10−5M |
|---|---|---|---|---|---|---|
| FOMESAFEN | | 2 or 4 | WT | 650 | 1.32E−09 | |
| FOMESAFEN | | 4 | R128A, F420M | 362 | 6.60E−06 | |
| FOMESAFEN | | 4 | R128A, F420L | 316 | 9.91E−06 | |
| FOMESAFEN | | 4 | R128A, F420V | 478 | 1.61E−06 | |
| FOMESAFEN | | 4 | R128I, F420L | 202 | ≥1.00E−05 | 38 |
| FOMESAFEN | | 4 | R128I, F420V | 292 | 2.79E−06 | |
| FOMESAFEN | | 4 | R128V, F420M | 413 | ≥1.00E−05 | 47 |
| FOMESAFEN | | 4 | R128M, F420M | 289 | ≥1.00E−05 | 48 |
| FOMESAFEN | | 4 | R128Y, F420I | 99 | 2.15E−05 | |
| FOMESAFEN | | 4 | R128Y, F420M | 174 | ≥1.00E−05 | 28 |
| FOMESAFEN | | 4 | R128N, F420M | 153 | 1.07E−05 | |
| FOMESAFEN | | 4 | R128C, F420L | 192 | ≥1.00E−05 | 42 |
| FOMESAFEN | | 4 | R128C, F420V | 160 | 2.36E−06 | |
| FOMESAFEN | | 4 | R128C, F420M | 277 | 1.10E−05 | |
| FOMESAFEN | | 4 | R128H, F420M | 184 | 2.91E−06 | |
| LACTOFEN | (2-ethoxy-1-methyl-2-oxo-ethyl) 5-[2-chloro-4-(trifluoromethyl)phenoxy]-2-nitro-benzoate | 2 or 4 | WT | 650 | 2.93E−10 | |
| LACTOFEN | (2-ethoxy-1-methyl-2-oxo-ethyl) 5-[2-chloro-4-(trifluoromethyl)phenoxy]-2-nitro-benzoate | 4 | R128A, F420M | 362 | 4.57E−08 | |
| LACTOFEN | (2-ethoxy-1-methyl-2-oxo-ethyl) 5-[2-chloro-4-(trifluoromethyl)phenoxy]-2-nitro-benzoate | 4 | R128A, F420L | 316 | 6.88E−08 | |
| LACTOFEN | (2-ethoxy-1-methyl-2-oxo-ethyl) 5-[2-chloro-4-(trifluoromethyl)phenoxy]-2-nitro-benzoate | 4 | R128A, F420V | 478 | 8.45E−09 | |
| LACTOFEN | (2-ethoxy-1-methyl-2-oxo-ethyl) 5-[2-chloro-4-(trifluoromethyl)phenoxy]-2-nitro-benzoate | 4 | R128I, F420L | 202 | 1.30E−07 | |
| LACTOFEN | (2-ethoxy-1-methyl-2-oxo-ethyl) 5-[2-chloro-4-(trifluoromethyl)phenoxy]-2-nitro-benzoate | 4 | R128I, F420V | 292 | 1.40E−08 | |
| LACTOFEN | (2-ethoxy-1-methyl-2-oxo-ethyl) 5-[2-chloro-4-(trifluoromethyl)phenoxy]-2-nitro-benzoate | 4 | R128V, F420M | 413 | 9.41E−08 | |
| LACTOFEN | (2-ethoxy-1-methyl-2-oxo-ethyl) 5-[2-chloro-4-(trifluoromethyl)phenoxy]-2-nitro-benzoate | 4 | R128M, F420M | 289 | 1.31E−07 | |
| LACTOFEN | (2-ethoxy-1-methyl-2-oxo-ethyl) 5-[2-chloro-4-(trifluoromethyl)phenoxy]-2-nitro-benzoate | 4 | R128Y, F420I | 99 | 4.80E−08 | |
| LACTOFEN | (2-ethoxy-1-methyl-2-oxo-ethyl) 5-[2-chloro-4-(trifluoromethyl)phenoxy]-2-nitro-benzoate | 4 | R128Y, F420M | 174 | 1.43E−07 | |
| LACTOFEN | (2-ethoxy-1-methyl-2-oxo-ethyl) 5-[2-chloro-4-(trifluoromethyl)phenoxy]-2-nitro-benzoate | 4 | R128N, F420M | 153 | 1.67E−07 | |

TABLE 4c-continued

| Common Name | IUPAC Name | SEQ ID | Mutation | rate (FU/min) | IC50 (M) | inhibition (%) at 1 × 10−5M |
|---|---|---|---|---|---|---|
| LACTOFEN | (2-ethoxy-1-methyl-2-oxo-ethyl) 5-[2-chloro-4-(trifluoromethyl)phenoxy]-2-nitro-benzoate | 4 | R128C, F420L | 192 | 1.42E−07 | |
| LACTOFEN | (2-ethoxy-1-methyl-2-oxo-ethyl) 5-[2-chloro-4-(trifluoromethyl)phenoxy]-2-nitro-benzoate | 4 | R128C, F420V | 160 | 1.50E−08 | |
| LACTOFEN | (2-ethoxy-1-methyl-2-oxo-ethyl) 5-[2-chloro-4-(trifluoromethyl)phenoxy]-2-nitro-benzoate | 4 | R128C, F420M | 277 | 6.39E−08 | |
| LACTOFEN | (2-ethoxy-1-methyl-2-oxo-ethyl) 5-[2-chloro-4-(trifluoromethyl)phenoxy]-2-nitro-benzoate | 4 | R128H, F420M | 184 | 6.13E−08 | |
| BUTAFENACIL | | 2 or 4 | WT | 650 | 1.38E−10 | |
| BUTAFENACIL | | 4 | R128A, F420M | 362 | 1.40E−08 | |
| BUTAFENACIL | | 4 | R128A, F420L | 316 | 9.17E−08 | |
| BUTAFENACIL | | 4 | R128A, F420V | 478 | 2.51E−08 | |
| BUTAFENACIL | | 4 | R128I, F420L | 202 | 8.02E−08 | |
| BUTAFENACIL | | 4 | R128I, F420V | 292 | 2.56E−08 | |
| BUTAFENACIL | | 4 | R128V, F420M | 413 | 1.05E−08 | |
| BUTAFENACIL | | 4 | R128M, F420M | 289 | 4.38E−08 | |
| BUTAFENACIL | | 4 | R128Y, F420I | 99 | 5.47E−08 | |
| BUTAFENACIL | | 4 | R128Y, F420M | 174 | 5.04E−08 | |
| BUTAFENACIL | | 4 | R128N, F420M | 153 | 2.84E−08 | |
| BUTAFENACIL | | 4 | R128C, F420L | 192 | 1.10E−07 | |
| BUTAFENACIL | | 4 | R128C, F420V | 160 | 6.69E−08 | |
| BUTAFENACIL | | 4 | R128C, F420M | 277 | 2.31E−08 | |
| BUTAFENACIL | | 4 | R128H, F420M | 184 | 1.28E−08 | |
| CARFENTRAZONE-ETHYL | | 2 or 4 | WT | 650 | 1.03E−09 | |
| CARFENTRAZONE-ETHYL | | 4 | R128A, F420M | 362 | 6.72E−08 | |
| CARFENTRAZONE-ETHYL | | 4 | R128A, F420L | 316 | 4.29E−07 | |
| CARFENTRAZONE-ETHYL | | 4 | R128A, F420V | 478 | 7.97E−07 | |
| CARFENTRAZONE-ETHYL | | 4 | R128I, F420L | 202 | 1.61E−07 | |
| CARFENTRAZONE-ETHYL | | 4 | R128I, F420V | 292 | 2.07E−07 | |
| CARFENTRAZONE-ETHYL | | 4 | R128V, F420M | 413 | 2.29E−08 | |
| CARFENTRAZONE-ETHYL | | 4 | R128M, F420M | 289 | 7.86E−08 | |
| CARFENTRAZONE-ETHYL | | 4 | R128Y, F420I | 99 | 2.82E−07 | |
| CARFENTRAZONE-ETHYL | | 4 | R128Y, F420M | 174 | 8.52E−08 | |
| CARFENTRAZONE-ETHYL | | 4 | R128N, F420M | 153 | 1.88E−07 | |
| CARFENTRAZONE-ETHYL | | 4 | R128C, F420L | 192 | 3.08E−07 | |
| CARFENTRAZONE-ETHYL | | 4 | R128C, F420V | 160 | 3.96E−07 | |
| CARFENTRAZONE-ETHYL | | 4 | R128C, F420M | 277 | 2.99E−08 | |
| CARFENTRAZONE-ETHYL | | 4 | R128H, F420M | 184 | 1.21E−07 | |
| ACIFLUORFEN | 5-(2-CHLORO-4-TRIFLUOROMETHYL-PHENOXY)-2-NITRO-BENZOIC ACID | 2 or 4 | WT | 650 | 3.36E−08 | |
| ACIFLUORFEN | 5-(2-CHLORO-4-TRIFLUOROMETHYL-PHENOXY)-2-NITRO-BENZOIC ACID | 4 | R128A, F420M | 362 | ≥1.00E−05 | 27 |
| ACIFLUORFEN | 5-(2-CHLORO-4-TRIFLUOROMETHYL-PHENOXY)-2-NITRO-BENZOIC ACID | 4 | R128A, F420L | 316 | ≥1.00E−05 | 20 |
| ACIFLUORFEN | 5-(2-CHLORO-4-TRIFLUOROMETHYL-PHENOXY)-2-NITRO-BENZOIC ACID | 4 | R128A, F420V | 478 | 6.67E−06 | |
| ACIFLUORFEN | 5-(2-CHLORO-4-TRIFLUOROMETHYL-PHENOXY)-2-NITRO-BENZOIC ACID | 4 | R128I, F420L | 202 | ≥1.00E−05 | 16 |
| ACIFLUORFEN | 5-(2-CHLORO-4-TRIFLUOROMETHYL-PHENOXY)-2-NITRO-BENZOIC ACID | 4 | R128I, F420V | 292 | 1.21E−05 | |
| ACIFLUORFEN | 5-(2-CHLORO-4-TRIFLUOROMETHYL-PHENOXY)-2-NITRO-BENZOIC ACID | 4 | R128V, F420M | 413 | ≥1.00E−05 | 17 |
| ACIFLUORFEN | 5-(2-CHLORO-4-TRIFLUOROMETHYL-PHENOXY)-2-NITRO-BENZOIC ACID | 4 | R128M, F420M | 289 | ≥1.00E−05 | 21 |
| ACIFLUORFEN | 5-(2-CHLORO-4-TRIFLUOROMETHYL-PHENOXY)-2-NITRO-BENZOIC ACID | 4 | R128Y, F420I | 99 | ≥1.00E−05 | 21 |
| ACIFLUORFEN | 5-(2-CHLORO-4-TRIFLUOROMETHYL-PHENOXY)-2-NITRO-BENZOIC ACID | 4 | R128Y, F420M | 174 | ≥1.00E−05 | 15 |
| ACIFLUORFEN | 5-(2-CHLORO-4-TRIFLUOROMETHYL-PHENOXY)-2-NITRO-BENZOIC ACID | 4 | R128N, F420M | 153 | ≥1.00E−05 | 39 |
| ACIFLUORFEN | 5-(2-CHLORO-4-TRIFLUOROMETHYL-PHENOXY)-2-NITRO-BENZOIC ACID | 4 | R128C, F420L | 192 | ≥1.00E−05 | 17 |
| ACIFLUORFEN | 5-(2-CHLORO-4-TRIFLUOROMETHYL-PHENOXY)-2-NITRO-BENZOIC ACID | 4 | R128C, F420V | 160 | 6.72E−06 | |
| ACIFLUORFEN | 5-(2-CHLORO-4-TRIFLUOROMETHYL-PHENOXY)-2-NITRO-BENZOIC ACID | 4 | R128C, F420M | 277 | ≥1.00E−05 | 33 |
| ACIFLUORFEN | 5-(2-CHLORO-4-TRIFLUOROMETHYL-PHENOXY)-2-NITRO-BENZOIC ACID | 4 | R128H, F420M | 184 | ≥1.00E−05 | 48 |
| FLUMIOXAZIN | 2-(7-fluoro-3-oxo-4-prop-2-ynyl-1,4-benzoxazin-6-yl)-4,5,6,7-tetrahydroisoindole-1,3-dione | 2 or 4 | WT | 650 | 9.58E−11 | |

TABLE 4c-continued

| Common Name | IUPAC Name | SEQ ID | Mutation | rate (FU/min) | IC50 (M) | inhibition (%) at 1 × 10−5M |
|---|---|---|---|---|---|---|
| FLUMIOXAZIN | 2-(7-fluoro-3-oxo-4-prop-2-ynyl-1,4-benzoxazin-6-yl)-4,5,6,7-tetrahydroisoindole-1,3-dione | 4 | R128A, F420M | 362 | 8.43E−06 | |
| FLUMIOXAZIN | 2-(7-fluoro-3-oxo-4-prop-2-ynyl-1,4-benzoxazin-6-yl)-4,5,6,7-tetrahydroisoindole-1,3-dione | 4 | R128A, F420L | 316 | ≥1.00E−05 | −8 |
| FLUMIOXAZIN | 2-(7-fluoro-3-oxo-4-prop-2-ynyl-1,4-benzoxazin-6-yl)-4,5,6,7-tetrahydroisoindole-1,3-dione | 4 | R128A, F420V | 478 | 6.34E−06 | |
| FLUMIOXAZIN | 2-(7-fluoro-3-oxo-4-prop-2-ynyl-1,4-benzoxazin-6-yl)-4,5,6,7-tetrahydroisoindole-1,3-dione | 4 | R128I, F420L | 202 | ≥1.00E−05 | 9 |
| FLUMIOXAZIN | 2-(7-fluoro-3-oxo-4-prop-2-ynyl-1,4-benzoxazin-6-yl)-4,5,6,7-tetrahydroisoindole-1,3-dione | 4 | R128I, F420V | 292 | ≥1.00E−05 | 41 |
| FLUMIOXAZIN | 2-(7-fluoro-3-oxo-4-prop-2-ynyl-1,4-benzoxazin-6-yl)-4,5,6,7-tetrahydroisoindole-1,3-dione | 4 | R128V, F420M | 413 | ≥1.00E−05 | 34 |
| FLUMIOXAZIN | 2-(7-fluoro-3-oxo-4-prop-2-ynyl-1,4-benzoxazin-6-yl)-4,5,6,7-tetrahydroisoindole-1,3-dione | 4 | R128M, F420M | 289 | ≥1.00E−05 | 21 |
| FLUMIOXAZIN | 2-(7-fluoro-3-oxo-4-prop-2-ynyl-1,4-benzoxazin-6-yl)-4,5,6,7-tetrahydroisoindole-1,3-dione | 4 | R128Y, F420I | 99 | ≥1.00E−05 | 19 |
| FLUMIOXAZIN | 2-(7-fluoro-3-oxo-4-prop-2-ynyl-1,4-benzoxazin-6-yl)-4,5,6,7-tetrahydroisoindole-1,3-dione | 4 | R128Y, F420M | 174 | ≥1.00E−05 | −2 |
| FLUMIOXAZIN | 2-(7-fluoro-3-oxo-4-prop-2-ynyl-1,4-benzoxazin-6-yl)-4,5,6,7-tetrahydroisoindole-1,3-dione | 4 | R128N, F420M | 153 | 6.15E−06 | |
| FLUMIOXAZIN | 2-(7-fluoro-3-oxo-4-prop-2-ynyl-1,4-benzoxazin-6-yl)-4,5,6,7-tetrahydroisoindole-1,3-dione | 4 | R128C, F420L | 192 | ≥1.00E−05 | −11 |
| FLUMIOXAZIN | 2-(7-fluoro-3-oxo-4-prop-2-ynyl-1,4-benzoxazin-6-yl)-4,5,6,7-tetrahydroisoindole-1,3-dione | 4 | R128C, F420V | 160 | 7.28E−06 | |
| FLUMIOXAZIN | 2-(7-fluoro-3-oxo-4-prop-2-ynyl-1,4-benzoxazin-6-yl)-4,5,6,7-tetrahydroisoindole-1,3-dione | 4 | R128C, F420M | 277 | ≥1.00E−05 | 48 |
| FLUMIOXAZIN | 2-(7-fluoro-3-oxo-4-prop-2-ynyl-1,4-benzoxazin-6-yl)-4,5,6,7-tetrahydroisoindole-1,3-dione | 4 | R128H, F420M | 184 | ≥1.00E−05 | 30 |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 2 or 4 | WT | 650 | 6.69E−10 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 4 | R128A, F420M | 362 | 1.60E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 4 | R128A, F420L | 316 | ≥1.00E−05 | 48 |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 4 | R128A, F420V | 478 | 5.43E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 4 | R128I, F420L | 202 | 9.51E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 4 | R128I, F420V | 292 | 4.72E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 4 | R128V, F420M | 413 | 1.78E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 4 | R128M, F420M | 289 | 3.84E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 4 | R128Y, F420I | 99 | ≥1.00E−05 | 38 |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 4 | R128Y, F420M | 174 | 1.08E−05 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 4 | R128N, F420M | 153 | ≥1.00E−05 | 48 |

TABLE 4c-continued

| Common Name | IUPAC Name | SEQ ID | Mutation | rate (FU/min) | IC50 (M) | inhibition (%) at 1 × 10−5M |
|---|---|---|---|---|---|---|
| CINIDON-ETHYL | ethyl (Z)-2-chloro-3-[2-chloro-5-(1,3-dioxo-4,5,6,7-tetrahydroisoindol-2-yl)phenyl]prop-2-enoate | 4 | R128C, F420L | 192 | ≥1.00E−05 | 42 |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 4 | R128C, F420V | 160 | 9.43E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 4 | R128C, F420M | 277 | 2.45E−06 | |
| CINIDON-ETHYL | ethyl (Z)-2-chloro-3-[2-chloro-5-(1,3-dioxo-4,5,6,7-tetrahydroisoindol-2-yl)phenyl]prop-2-enoate | 4 | R128H, F420M | 184 | ≥1.00E−05 | 41 |
| OXIFLUORFEN | 2-CHLORO-1-(3-ETHOXY-4-NITROPHENOXY)-4-(TRIFLUOROMETHYL)BENZENE | 2 or 4 | WT | 650 | 1.04E−09 | |
| OXIFLUORFEN | 2-CHLORO-1-(3-ETHOXY-4-NITROPHENOXY)-4-(TRIFLUOROMETHYL)BENZENE | 4 | R128A, F420M | 365 | 2.17E−07 | |
| OXIFLUORFEN | 2-CHLORO-1-(3-ETHOXY-4-NITROPHENOXY)-4-(TRIFLUOROMETHYL)BENZENE | 4 | R128A, F420L | 343 | 5.58E−07 | |
| OXIFLUORFEN | 2-CHLORO-1-(3-ETHOXY-4-NITROPHENOXY)-4-(TRIFLUOROMETHYL)BENZENE | 4 | R128A, F420V | 550 | 2.35E−08 | |
| OXIFLUORFEN | 2-CHLORO-1-(3-ETHOXY-4-NITROPHENOXY)-4-(TRIFLUOROMETHYL)BENZENE | 4 | R128I, F420L | 196 | 4.21E−06 | |
| OXIFLUORFEN | 2-CHLORO-1-(3-ETHOXY-4-NITROPHENOXY)-4-(TRIFLUOROMETHYL)BENZENE | 4 | R128I, F420V | 326 | 1.98E−07 | |
| OXIFLUORFEN | 2-CHLORO-1-(3-ETHOXY-4-NITROPHENOXY)-4-(TRIFLUOROMETHYL)BENZENE | 4 | R128V, F420M | 482 | 1.05E−06 | |
| OXIFLUORFEN | 2-CHLORO-1-(3-ETHOXY-4-NITROPHENOXY)-4-(TRIFLUOROMETHYL)BENZENE | 4 | R128M, F420M | 323 | 7.36E−07 | |
| OXIFLUORFEN | 2-CHLORO-1-(3-ETHOXY-4-NITROPHENOXY)-4-(TRIFLUOROMETHYL)BENZENE | 4 | R128Y, F420I | 75 | 1.17E−06 | |
| OXIFLUORFEN | 2-CHLORO-1-(3-ETHOXY-4-NITROPHENOXY)-4-(TRIFLUOROMETHYL)BENZENE | 4 | R128Y, F420M | 175 | 1.13E−06 | |
| OXIFLUORFEN | 2-CHLORO-1-(3-ETHOXY-4-NITROPHENOXY)-4-(TRIFLUOROMETHYL)BENZENE | 4 | R128N, F420M | 174 | 3.91E−07 | |
| OXIFLUORFEN | 2-CHLORO-1-(3-ETHOXY-4-NITROPHENOXY)-4-(TRIFLUOROMETHYL)BENZENE | 4 | R128C, F420L | 188 | 1.49E−06 | |
| OXIFLUORFEN | 2-CHLORO-1-(3-ETHOXY-4-NITROPHENOXY)-4-(TRIFLUOROMETHYL)BENZENE | 4 | R128C, F420V | 225 | 6.52E−08 | |
| OXIFLUORFEN | 2-CHLORO-1-(3-ETHOXY-4-NITROPHENOXY)-4-(TRIFLUOROMETHYL)BENZENE | 4 | R128C, F420M | 271 | 4.16E−07 | |
| OXIFLUORFEN | 2-CHLORO-1-(3-ETHOXY-4-NITROPHENOXY)-4-(TRIFLUOROMETHYL)BENZENE | 4 | R128H, F420M | 196 | 3.68E−07 | |
| OXADIARGYL | | 2 or 4 | WT | 650 | 3.64E−10 | |
| OXADIARGYL | | 4 | R128A, F420M | 365 | 1.97E−08 | |
| OXADIARGYL | | 4 | R128A, F420L | 343 | 1.37E−06 | |
| OXADIARGYL | | 4 | R128A, F420V | 550 | 4.38E−08 | |
| OXADIARGYL | | 4 | R128I, F420L | 196 | 8.64E−07 | |
| OXADIARGYL | | 4 | R128I, F420V | 326 | 2.76E−08 | |
| OXADIARGYL | | 4 | R128V, F420M | 482 | 3.40E−08 | |
| OXADIARGYL | | 4 | R128M, F420M | 323 | 3.33E−08 | |
| OXADIARGYL | | 4 | R128Y, F420I | 75 | 1.73E−07 | |
| OXADIARGYL | | 4 | R128Y, F420M | 175 | 3.60E−08 | |
| OXADIARGYL | | 4 | R128N, F420M | 174 | 1.28E−07 | |
| OXADIARGYL | | 4 | R128C, F420L | 188 | 3.01E−06 | |
| OXADIARGYL | | 4 | R128C, F420V | 225 | 1.46E−07 | |
| OXADIARGYL | | 4 | R128C, F420M | 271 | 6.24E−08 | |
| OXADIARGYL | | 4 | R128H, F420M | 196 | 1.32E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 2 or 4 | WT | 650 | 1.35E−10 | |

TABLE 4c-continued

| Common Name | IUPAC Name | SEQ ID | Mutation | rate (FU/min) | IC50 (M) | inhibition (%) at 1 × 10−5M |
|---|---|---|---|---|---|---|
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 4 | R128A, F420M | 365 | 3.71E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 4 | R128A, F420L | 343 | 2.77E−07 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 4 | R128A, F420V | 550 | 4.75E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 4 | R128I, F420L | 196 | 2.01E−07 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 4 | R128I, F420V | 326 | 4.38E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 4 | R128V, F420M | 482 | 3.58E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 4 | R128M, F420M | 323 | 4.83E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 4 | R128Y, F420I | 75 | 4.64E−07 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 4 | R128Y, F420M | 175 | 8.92E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 4 | R128N, F420M | 174 | 1.92E−07 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 4 | R128C, F420L | 188 | 6.81E−07 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 4 | R128C, F420V | 225 | 1.24E−07 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 4 | R128C, F420M | 271 | 6.95E−08 | |
| S-3100 | ethyl 2-[[3-[2-chloro-4-fluoro-5-[3-methyl-2,6-dioxo-4-(trifluoromethyl)pyrimidin-1-yl]phenoxy]-2-pyridyl]oxy]acetate | 4 | R128H, F420M | 196 | 4.18E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 2 or 4 | WT | 650 | 5.17E−10 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128A, F420M | 321 | 7.02E−09 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128A, F420M | 362 | 7.95E−09 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128A, F420M | 365 | 6.10E−09 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128A, F420L | 316 | 2.96E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128A, F420L | 343 | 1.56E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128A, F420V | 478 | 4.14E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128A, F420V | 550 | 2.13E−08 | |

TABLE 4c-continued

| Common Name | IUPAC Name | SEQ ID | Mutation | rate (FU/min) | IC50 (M) | inhibition (%) at 1 × 10−5M |
|---|---|---|---|---|---|---|
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128A, F420V | 555 | 3.99E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128I, F420L | 202 | 4.05E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128I, F420L | 196 | 2.45E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128I, F420I | 95 | 1.38E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128I, F420V | 292 | 2.14E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128I, F420V | 326 | 3.15E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128I, F420M | 328 | 6.10E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128V, F420M | 413 | 6.50E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128V, F420M | 482 | 4.86E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128M, F420M | 235 | 7.69E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128M, F420M | 289 | 7.07E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128M, F420M | 323 | 4.84E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128Y, F420I | 99 | 4.82E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128Y, F420I | 75 | 2.63E−06 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128Y, F420M | 174 | 2.85E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128Y, F420M | 175 | 1.02E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128G, F420M | 153 | 1.26E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128Q, F420M | 432 | 1.07E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128H, F420L | 193 | 7.98E−08 | |

TABLE 4c-continued

| Common Name | IUPAC Name | SEQ ID | Mutation | rate (FU/min) | IC50 (M) | inhibition (%) at 1 × 10−5M |
|---|---|---|---|---|---|---|
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128H, F420I | 191 | 8.22E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128N, F420M | 153 | 7.12E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128N, F420M | 174 | 4.97E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128C, F420L | 192 | 1.00E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128C, F420L | 188 | 1.83E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128C, F420V | 160 | 1.66E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128C, F420V | 225 | 2.66E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128C, F420M | 277 | 2.53E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128C, F420M | 271 | 2.33E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128F, F420L | 129 | 1.01E−06 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128F, F420M | 136 | 1.21E−07 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128S, F420M | 328 | 2.40E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128T, F420M | 275 | 4.33E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128H, F420V | 95 | 7.63E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128H, F420M | 184 | 2.64E−08 | |
| BAS 850H | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 4 | R128H, F420M | 196 | 2.13E−08 | |
| 850 analogon | 2-(2,2,7-trifluoro-3-oxo-4-prop-2-ynyl-1,4-benzoxazin-6-yl)-4,5,6,7-tetrahydroisoindole-1,3-dione | 2 or 4 | WT | 650 | 1.46E−10 | |
| 850 analogon | 2-(2,2,7-trifluoro-3-oxo-4-prop-2-ynyl-1,4-benzoxazin-6-yl)-4,5,6,7-tetrahydroisoindole-1,3-dione | 4 | R128A, F420M | 365 | 6.41E−07 | |
| 850 analogon | 2-(2,2,7-trifluoro-3-oxo-4-prop-2-ynyl-1,4-benzoxazin-6-yl)-4,5,6,7-tetrahydroisoindole-1,3-dione | 4 | R128A, F420L | 343 | 1.14E−05 | |
| 850 analogon | 2-(2,2,7-trifluoro-3-oxo-4-prop-2-ynyl-1,4-benzoxazin-6-yl)-4,5,6,7-tetrahydroisoindole-1,3-dione | 4 | R128A, F420V | 550 | 2.74E−07 | |

TABLE 4c-continued

| Common Name | IUPAC Name | SEQ ID | Mutation | rate (FU/min) | IC50 (M) | inhibition (%) at 1 × 10−5M |
|---|---|---|---|---|---|---|
| 850 analogon | 2-(2,2,7-trifluoro-3-oxo-4-prop-2-ynyl-1,4-benzoxazin-6-yl)-4,5,6,7-tetrahydroisoindole-1,3-dione | 4 | R128I, F420L | 196 | ≥1.00E−05 | 6 |
| 850 analogon | 2-(2,2,7-trifluoro-3-oxo-4-prop-2-ynyl-1,4-benzoxazin-6-yl)-4,5,6,7-tetrahydroisoindole-1,3-dione | 4 | R128I, F420V | 326 | 4.32E−06 | |
| 850 analogon | 2-(2,2,7-trifluoro-3-oxo-4-prop-2-ynyl-1,4-benzoxazin-6-yl)-4,5,6,7-tetrahydroisoindole-1,3-dione | 4 | R128V, F420M | 482 | 3.11E−06 | |
| 850 analogon | 2-(2,2,7-trifluoro-3-oxo-4-prop-2-ynyl-1,4-benzoxazin-6-yl)-4,5,6,7-tetrahydroisoindole-1,3-dione | 4 | R128M, F420M | 323 | ≥1.00E−05 | 48 |
| 850 analogon | 2-(2,2,7-trifluoro-3-oxo-4-prop-2-ynyl-1,4-benzoxazin-6-yl)-4,5,6,7-tetrahydroisoindole-1,3-dione | 4 | R128Y, F420I | 75 | ≥1.00E−05 | 32 |
| 850 analogon | 2-(2,2,7-trifluoro-3-oxo-4-prop-2-ynyl-1,4-benzoxazin-6-yl)-4,5,6,7-tetrahydroisoindole-1,3-dione | 4 | R128Y, F420M | 175 | ≥1.00E−05 | 41 |
| 850 analogon | 2-(2,2,7-trifluoro-3-oxo-4-prop-2-ynyl-1,4-benzoxazin-6-yl)-4,5,6,7-tetrahydroisoindole-1,3-dione | 4 | R128N, F420M | 174 | ≥1.00E−05 | 43 |
| 850 analogon | 2-(2,2,7-trifluoro-3-oxo-4-prop-2-ynyl-1,4-benzoxazin-6-yl)-4,5,6,7-tetrahydroisoindole-1,3-dione | 4 | R128C, F420L | 188 | ≥1.00E−05 | 11 |
| 850 analogon | 2-(2,2,7-trifluoro-3-oxo-4-prop-2-ynyl-1,4-benzoxazin-6-yl)-4,5,6,7-tetrahydroisoindole-1,3-dione | 4 | R128C, F420V | 225 | 3.70E−06 | |
| 850 analogon | 2-(2,2,7-trifluoro-3-oxo-4-prop-2-ynyl-1,4-benzoxazin-6-yl)-4,5,6,7-tetrahydroisoindole-1,3-dione | 4 | R128C, F420M | 271 | 3.57E−06 | |
| 850 analogon | 2-(2,2,7-trifluoro-3-oxo-4-prop-2-ynyl-1,4-benzoxazin-6-yl)-4,5,6,7-tetrahydroisoindole-1,3-dione | 4 | R128H, F420M | 196 | 3.07E−06 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 2 or 4 | WT | 650 | 3.15E−10 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 4 | R128A, F420M | 365 | 2.56E−09 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 4 | R128A, F420L | 343 | 1.62E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 4 | R128A, F420V | 550 | 6.33E−09 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 4 | R128I, F420L | 196 | 2.69E−07 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 4 | R128I, F420V | 326 | 9.01E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 4 | R128V, F420M | 482 | 4.65E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 4 | R128M, F420M | 323 | 4.94E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 4 | R128Y, F420I | 75 | 4.46E−07 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 4 | R128Y, F420M | 175 | 1.13E−07 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 4 | R128N, F420M | 174 | 5.94E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 4 | R128C, F420L | 188 | 6.72E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 4 | R128C, F420V | 225 | 2.60E−08 | |
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 4 | R128C, F420M | 271 | 1.11E−08 | |

TABLE 4c-continued

| Common Name | IUPAC Name | SEQ ID | Mutation | rate (FU/min) | IC50 (M) | inhibition (%) at 1 × 10−5M |
|---|---|---|---|---|---|---|
| 850 analogon | 1-methyl-6-(trifluoromethyl)-3-(2,2,7-trifluoro-3-oxo-4-prop-2-ynyl-1,4-benzoxazin-6-yl)pyrimidine-2,4-dione | 4 | R128H, F420M | 196 | 1.05E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 or 4 | WT | 650 | 4.11E−10 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128A, F420M | 321 | 8.19E−09 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128A, F420L | 343 | 4.70E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128A, F420V | 555 | 2.32E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128I, F420L | 196 | 7.13E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128I, F420I | 95 | 2.27E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128I, F420V | 326 | 1.71E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128I, F420M | 328 | 1.15E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128V, F420M | 482 | 1.49E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128M, F420M | 235 | 1.62E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128Y, F420I | 75 | 2.86E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128G, F420M | 153 | 4.76E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128Q, F420M | 432 | 7.14E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128H, F420L | 193 | 4.47E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128H, F420I | 191 | 7.54E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128N, F420M | 174 | 1.20E−07 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128C, F420V | 225 | 1.16E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128C, F420M | 271 | 1.16E−08 | |

TABLE 4c-continued

| Common Name | IUPAC Name | SEQ ID | Mutation | rate (FU/min) | IC50 (M) | inhibition (%) at 1 × 10−5M |
|---|---|---|---|---|---|---|
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128F, F420L | 129 | 4.84E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128F, F420M | 136 | 2.81E−09 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128S, F420M | 328 | 3.62E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128T, F420M | 275 | 2.79E−08 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128H, F420V | 95 | 6.93E−09 | |
| | methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128H, F420M | 196 | 1.76E−08 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 or 4 | WT | 650 | 3.80E−10 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128A, F420M | 321 | 1.51E−08 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128A, F420V | 555 | 2.92E−08 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128I, F420M | 328 | 1.39E−08 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128M, F420M | 235 | 2.24E−08 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128S, F420M | 328 | 4.68E−08 | |
| | 2-ethoxyethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128T, F420M | 275 | 2.93E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 or 4 | WT | 650 | 5.23E−10 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128A, F420M | 321 | 2.27E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128A, F420L | 343 | 9.37E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128A, F420V | 555 | 4.16E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128I, F420L | 196 | 1.07E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128I, F420I | 95 | 1.82E−06 | |

TABLE 4c-continued

| Common Name | IUPAC Name | SEQ ID | Mutation | rate (FU/min) | IC50 (M) | inhibition (%) at 1 × 10−5M |
|---|---|---|---|---|---|---|
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128I, F420V | 326 | 3.78E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128I, F420M | 328 | 1.06E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128V, F420M | 482 | 1.49E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128M, F420M | 235 | 3.22E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128Y, F420I | 75 | 6.82E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128G, F420M | 153 | 5.14E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128Q, F420M | 432 | 1.72E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128H, F420L | 193 | 6.93E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128H, F420I | 191 | 1.31E−06 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128N, F420M | 174 | 1.48E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128C, F420V | 225 | 1.01E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128C, F420M | 271 | 2.98E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128F, F420L | 129 | 1.18E−06 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128F, F420M | 136 | 6.26E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128S, F420M | 328 | 5.24E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128T, F420M | 275 | 1.17E−07 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128H, F420V | 95 | 9.06E−08 | |
| | cyclohexyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128H, F420M | 196 | 2.97E−07 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 or 4 | WT | 650 | 4.27E−10 | |

TABLE 4c-continued

| Common Name | IUPAC Name | SEQ ID | Mutation | rate (FU/min) | IC50 (M) | inhibition (%) at 1 × 10−5M |
|---|---|---|---|---|---|---|
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128A, F420M | 321 | 1.22E−08 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128A, F420V | 555 | 2.61E−08 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128I, F420M | 328 | 1.56E−08 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128M, F420M | 235 | 3.34E−08 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128S, F420M | 328 | 5.65E−08 | |
| | 4-pyridylmethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128T, F420M | 275 | 5.88E−08 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 or 4 | WT | 650 | 4.16E−10 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128A, F420M | 321 | 1.19E−08 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128A, F420V | 555 | 4.25E−08 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128I, F420M | 328 | 1.37E−08 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128M, F420M | 235 | 2.47E−08 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128S, F420M | 328 | 6.94E−08 | |
| | (1-methylcyclopropyl)methyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128T, F420M | 275 | 5.77E−08 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 2 or 4 | WT | 650 | 4.43E−10 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128A, F420M | 321 | 4.93E−08 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128A, F420V | 555 | 6.42E−08 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128I, F420M | 328 | 4.61E−08 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128M, F420M | 235 | 1.06E−07 | |
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128S, F420M | 328 | 9.94E−08 | |

TABLE 4c-continued

| Common Name | IUPAC Name | SEQ ID | Mutation | rate (FU/min) | IC50 (M) | inhibition (%) at 1 × 10−5M |
|---|---|---|---|---|---|---|
| | 2,2-difluoroethyl 2-[2-[2-chloro-4-fluoro-5-[3-methyl-2,6-dioxo-4-(trifluoromethyl)pyrimidin-1-yl]phenoxy]phenoxy]-2-methoxy-acetate | 4 | R128T, F420M | 275 | 1.50E−07 | |

IC50 (M): Concentration of inhibitor required for 50% inhibition of enzyme activity; ≥1.00E−5: indicates a very high IC50 over the measurement bounderies, which reflects very high in vitro tolerance.

Example 5: Engineering PPO-Derivative Herbicide Tolerant Plants Having Wildtype or Mutated PPO Sequences PPO-derivative herbicide tolerant soybean (*Glyceine max*), corn (*Zea mays*), and Canola (*Brassica napus* or *Brassica Rapa* var. or *Brassica campestris* L.) plants are produced by a method as described by Olhoft et al. (US patent 2009/0049567). For transformation of soybean or *Arabidopsis thaliana*, Wildtype or Mutated PPO sequences based on one of the following sequences SEQ ID NO: 1, 3, 5, 7, 9, 11, 13, 15, 17, 19, 21, 23, 25, 27, 29, 31, 33, 35, 37, 39, 41, 43, 45, 47, are cloned with standard cloning techniques as described in Sambrook et al. (Molecular cloning (2001) Cold Spring Harbor Laboratory Press) in a binary vector containing resistance marker gene cassette (AHAS) and mutated PPO sequence (marked as GOI) in between ubiquitin promoter (PcUbi) and nopaline synthase terminator (NOS) sequence. For corn transformation, Wildtype or Mutated PPO sequences are cloned with standard cloning techniques as described in Sambrook et al. (Molecular cloning (2001) Cold Spring Harbor Laboratory Press) in a binary vector containing resistance marker gene cassette (AHAS) and mutated PPO sequence (marked as GOI) in between corn ubiquitin promoter (ZmUbi) and nopaline synthase terminator (NOS) sequence. Binary plasmids are introduced to *Agrobacterium tumefaciens* for plant transformation. Plasmid constructs are introduced into soybean's axillary meristem cells at the primary node of seedling explants via *Agrobacterium*-mediated transformation. After inoculation and co-cultivation with Agrobacteria, the explants are transferred to shoot introduction media without selection for one week. The explants were subsequently transferred to a shoot induction medium with 1-3 µM imazapyr (Arsenal) for 3 weeks to select for transformed cells. Explants with healthy callus/shoot pads at the primary node are then transferred to shoot elongation medium containing 1-3 µM imazapyr until a shoot elongated or the explant died. Transgenic plantlets are rooted, subjected to TaqMan analysis for the presence of the transgene, transferred to soil and grown to maturity in greenhouse. Transformation of corn plants are done by a method described by McElver and Singh (WO 2008/124495). Plant transformation vector constructs containing mutated PPO sequences are introduced into maize immature embryos via *Agrobacterium*-mediated transformation.

Transformed cells were selected in selection media supplemented with 0.5-1.5 µM imazethapyr for 3-4 weeks. Transgenic plantlets were regenerated on plant regeneration media and rooted afterwards. Transgenic plantlets are subjected to TaqMan analysis for the presence of the transgene before being transplanted to potting mixture and grown to maturity in greenhouse. *Arabidopsis thaliana* are transformed with wildtype or mutated PPO sequences by floral dip method as described by McElver and Singh (WO 2008/124495). Transgenic *Arabidopsis* plants were subjected to TaqMan analysis for analysis of the number of integration loci. Transformation of *Oryza sativa* (rice) are done by protoplast transformation as described by Peng et al. (U.S. Pat. No. 6,653,529) T0 or T1 transgenic plant of soybean, corn, and rice containing mutated PPO sequences are tested for improved tolerance to PPO-derived herbicides in greenhouse studies and mini-plot studies with the following PPO-inhibiting herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control.

Transgenic *Arabidopsis thaliana* plants were assayed for improved tolerance to saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control in 48-well plates. Therefore, T2 seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v) Four to five seeds per well are plated on solid nutrient medium consisting of half-strength murashige skoog nutrient solution, pH 5.8 (Murashige and Skoog (1962) *Physiologia Plantarum* 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 µmol Phot*$m^{-2}$*$s^{-1}$ with 14:10 h light:dark photoperiod. Growth inhibition is evaluated seven to ten days after seeding in comparison to wild type plants.

Additionally, transgenic T1 *Arabidopsis* plants were tested for improved tolerance to PPO-inhibiting herbicides in greenhouse studies with the following PPO-inhibiting herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control.

Results are shown in Table 5:

TABLE 5a

Germination Assay
Tolerance trails with:
1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione

| Test Event | SEQ ID NO | Mutation | Tolerance Factor (non-transgenic *Arabidopsis* = 1) |
|---|---|---|---|
| 1 | 4 | R128A, F420V | 300 |
| 2 | 4 | R128A, F420V | 300 |

TABLE 5a-continued

Germination Assay
Tolerance trails with:
1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione

| Test Event | SEQ ID NO | Mutation | Tolerance Factor (non-transgenic Arabidopsis = 1) |
|---|---|---|---|
| 3 | 4 | R128A, F420V | 3 |
| 4 | 4 | R128A, F420V | 300 |
| 5 | 4 | R128A, F420V | 300 |
| 6 | 4 | R128A, F420V | 200 |
| 7 | 4 | R128A, F420V | 3 |
| 8 | 4 | R128A, F420V | 300 |
| 9 | 4 | R128A, F420V | 300 |
| 10 | 4 | R128A, F420V | 300 |
| 11 | 4 | R128A, F420V | 40 |
| 12 | 4 | R128A, F420V | 3 |
| 13 | 4 | R128A, F420V | 300 |
| 14 | 4 | R128A, F420V | 3 |
| 15 | 4 | R128A, F420V | 200 |
| 16 | 4 | R128A, F420V | 200 |
| 17 | 4 | R128A, F420V | 300 |
| 18 | 4 | R128A, F420V | 3 |
| 19 | 4 | R128A, F420V | 75 |
| 20 | 4 | R128A, F420V | 200 |
| 21 | 4 | R128A, F420V | 300 |
| 22 | 4 | R128A, F420V | 3 |
| 23 | 4 | R128A, F420V | 8 |
| 24 | 4 | R128A, F420V | 75 |
| 25 | 4 | R128A, F420V | 200 |
| 26 | 4 | R128A, F420V | 300 |
| 1 | 4 | F420V | 75 |
| 2 | 4 | F420V | 75 |
| 3 | 4 | F420V | 35 |
| 4 | 4 | F420V | 75 |
| 5 | 4 | F420V | 300 |
| 6 | 4 | F420V | 300 |
| 7 | 4 | F420V | 300 |
| 8 | 4 | F420V | 300 |
| 9 | 4 | F420V | 300 |
| 10 | 4 | F420V | 300 |
| 11 | 4 | F420V | 3 |
| 12 | 4 | F420V | 8 |
| 13 | 4 | F420V | 300 |
| 14 | 4 | F420V | 20 |
| 15 | 4 | F420V | 300 |
| 16 | 4 | F420V | 300 |
| 17 | 4 | F420V | 300 |
| 18 | 4 | F420V | 35 |
| 19 | 4 | F420V | 3 |
| 20 | 4 | F420V | 300 |
| 21 | 4 | F420V | 300 |
| 22 | 4 | F420V | 300 |
| 23 | 4 | F420V | 300 |
| 24 | 4 | F420V | 300 |

TABLE 5b

Relative tolerance rates of transgenic Arabidopsis plants as compared to a non-transgenic Arabidopsis plant (non-transgenic = 1.0), treated with various PPO inhibitors. Growth inhibition is evaluated seven to ten days after seeding in comparison to wild type plants.

| Mut PPO | Saflufenacil | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | Flumioxazin | Fomesafen | Lactofen | Sulfentrazon |
|---|---|---|---|---|---|---|
| AMATU_PPO2_wt | 10 | 13 | 17 | 19 | 8 | |
| AMATU_PPO2_dG210 | 100 | 33 | 107 | 29 | 19 | 203 |
| AMATU_PPO2_R128L | 160 | 23 | 126 | 27 | 22 | 186 |
| AMATU_PPO2_dG210_R128L | 1200 | 153 | 271 | 29 | 29 | 244 |
| AMATU_PPO2_F420I | 80 | 367 | 286 | 18 | 17 | 193 |
| AMATU_PPO2_F420M | 168 | 102 | 271 | 29 | 29 | 161 |
| AMATU_PPO2_F420L | 192 | 253 | 286 | 23 | 19 | 111 |
| AMATU_PPO2_R128A_F420I | 1200 | 333 | 286 | 29 | 27 | 621 |
| AMATU_PPO2_R128A_F420L | 1200 | 333 | 286 | 29 | 29 | 717 |
| AMATU_PPO2_R128A_F420M | 1160 | 204 | 286 | 29 | 29 | |

TABLE 5c

Phytotox values of transgenic *Arabidopsis* plants as compared to a non-transgenic *Arabidopsis* plant (non-transgenic = 100% damage), treated with 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione.

| Line | Assesment DAT (DAT = Days After Treatment) | SEQ_ID | Substitution | \multicolumn{3}{c}{Injury Rating 0-100% (0 = no injury, 100 = total control)} | | |
|---|---|---|---|---|---|---|
| | | | | 300 | 150 | 75 |
| | | | | \multicolumn{3}{c}{1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione g/Ha + 1% MSO} | | |
| 1 | 7 | 2 & 4 | R128A_F420V | 40 | 95 | 95 |
| 1 | 7 | 2 & 4 | R128A_F420V | 100 | 25 | 0 |
| 1 | 7 | 2 & 4 | R128A_F420V | 25 | 35 | 35 |
| 1 | 19 | 2 & 4 | R128A_F420V | 28 | 90 | 90 |
| 1 | 19 | 2 & 4 | R128A_F420V | 100 | 60 | 25 |
| 1 | 19 | 2 & 4 | R128A_F420V | 25 | 30 | 30 |
| 2 | 7 | 2 & 4 | F420V | 98 | 95 | 95 |
| 2 | 7 | 2 & 4 | F420V | 25 | 90 | 15 |
| 2 | 7 | 2 & 4 | F420V | 25 | 15 | 15 |
| 2 | 19 | 2 & 4 | F420V | 95 | 90 | 98 |
| 2 | 19 | 2 & 4 | F420V | 55 | 85 | 40 |
| 2 | 19 | 2 & 4 | F420V | 45 | 45 | 30 |

TABLE 5d

Relative tolerance rates of transgenic *Arabidopsis* plants as compared to a non-transgenic *Arabidopsis* plant on a scale from 0-100, were 100 is 100% damage, treated with single and mixtures of PPO inhibitors (e.g. Saflufenacil plus 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione). Plant growth injury is evaluated seven to ten days after application in comparison to wild type plants.

| PPO Herbicide (+1% MSO) | g ai/ha DAT | non-transgenic *Arabidopsis* POST 7 | non-transgenic *Arabidopsis* POST 7 | non-transgenic *Arabidopsis* POST 7 | Ø non-transgenic *Arabidopsis* POST 7 | Ø R128A, F420V 1 POST 7 | Ø R128A, F420V 2 POST 7 |
|---|---|---|---|---|---|---|---|
| Saflufenacil + 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 50 + 25 | 98 | 98 | 98 | 98 | 23 | 23 |
| | 25 + 50 | 98 | 98 | 98 | 98 | 16 | 19 |
| | 100 + 50 | 98 | 98 | 98 | 98 | 15 | 26 |
| | 50 + 100 | 98 | 98 | 98 | 98 | 10 | 20 |
| | 200 + 100 | 98 | 98 | 98 | 98 | 25 | 23 |
| | 100 + 200 | 98 | 98 | 98 | 98 | 30 | 29 |
| Saflufenacil | 75 | 98 | 98 | 98 | 98 | 16 | 22 |
| | 150 | 98 | 98 | 98 | 98 | 18 | 24 |
| | 300 | 98 | 98 | 98 | 98 | 22 | 22 |
| 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 75 | 98 | 98 | 98 | 98 | 18 | 24 |
| | 150 | 98 | 98 | 98 | 98 | 23 | 20 |
| | 300 | 98 | 98 | 98 | 98 | 26 | 33 |

| PPO Herbicide (+1% MSO) | Ø R128A, F420V 3 POST 7 | Ø F420V 1 POST 7 | Ø F420V 2 POST 7 | Ø F420V 3 POST 7 | Ø R128A, F420V 1 to 3 | Ø F420V 1 to 3 |
|---|---|---|---|---|---|---|
| Saflufenacil + 1,5-dimethyl-6-thioxo-3-(2,2,7-trifluoro-3-oxo-4-(prop-2-ynyl)-3,4-dihydro-2H-benzo[b][1,4]oxazin- | 21 | 33 | 33 | 27 | 22 | 31 |
| | 16 | 27 | 22 | 16 | 17 | 22 |
| | 23 | 55 | 47 | 43 | 21 | 48 |
| | 28 | 35 | 33 | 31 | 19 | 33 |

TABLE 5d-continued

Relative tolerance rates of transgenic *Arabidopsis* plants as compared to a non-transgenic *Arabidopsis* plant on a scale from 0-100, were 100 is 100% damage, treated with single and mixtures of PPO inhibitors (e.g. Saflufenacil plus 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione). Plant growth injury is evaluated seven to ten days after application in comparison to wild type plants.

| | | | | | | |
|---|---|---|---|---|---|---|
| 6-yl)-1,3,5-triazinane-2,4-dione | 28 | 63 | 60 | 66 | 25 | 63 |
| | 26 | 58 | 45 | 56 | 28 | 53 |
| Saflufenacil | 18 | 39 | 36 | 51 | 18 | 42 |
| | 18 | 60 | 55 | 66 | 20 | 60 |
| | 19 | 77 | 72 | 78 | 21 | 76 |
| 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 11 | 17 | 9 | 8 | 18 | 11 |
| | 30 | 28 | 11 | 12 | 24 | 17 |
| | 36 | 36 | 22 | 22 | 32 | 26 |

| | | ARBTH WT | AMATU_PPO2_R128A_F420V | AMATU_PPO2_R128A_F420V | AMATU_PPO2_R128A_F420V | AMATU_PPO2_L397D_F420V | AMATU_PPO2_L397D_F420V |
|---|---|---|---|---|---|---|---|
| | | | | | event | | |
| compound | g ai/ha | 1 | A | B | D | O | P |
| KIXOR + VALOR (Flumioxazin) + DESTINY HC | 75 + 400 + 3750 | 100 | 8 | 0 | 20 | 0 | 7 |
| | 50 + 200 + 3750 | 100 | 0 | 0 | 12 | 0 | 7 |
| | 25 + 100 + 3750 | 100 | 0 | 17 | 12 | 0 | 3 |
| KIXOR + SPOTLIGHT (Carfentrazone) + DESTINY HC | 75 + 120 + 3750 | 100 | 5 | 3 | 13 | 15 | 22 |
| | 50 + 60 + 3750 | 100 | 0 | 3 | 3 | 5 | 7 |
| | 25 + 30 + 3750 | 100 | 0 | 7 | 3 | 3 | 3 |
| KIXOR + BAS 850 00 H + DESTINY HC | 75 + 200 + 3750 | 100 | 3 | 8 | 22 | 13 | 15 |
| | 50 + 100 + 3750 | 100 | 0 | 7 | 13 | 10 | 10 |
| | 25 + 50 + 3750 | 100 | 0 | 15 | 15 | 7 | 7 |
| BAS 850 00 H + VALOR (Flumioxazin) + DESTINY HC | 200 + 400 + 3750 | 100 | 10 | 12 | 20 | 17 | 17 |
| | 100 + 200 + 3750 | 100 | 2 | 7 | 13 | 10 | 10 |
| | 50 + 100 + 3750 | 100 | 0 | 0 | 3 | 3 | 0 |
| BAS 850 00 H + SPOTLIGHT (Carfentrazone) + DESTINY HC | 200 + 120 + 3750 | 100 | 8 | 20 | 23 | 17 | 20 |
| | 100 + 60 + 3750 | 100 | 3 | 12 | 7 | 8 | 7 |
| | 50 + 30 + 3750 | 100 | 0 | 7 | 7 | 0 | 3 |

| compound | g ai/ha | ARBTH WT | AMATU_PPO2 F420V | | | | AMATU_PPO2 R128A_F420V | | | | AMATU_PPO2 L397D | | | | AMATU_PPO2 L397D_F420V | | | |
|---|---|---|---|---|---|---|---|---|---|---|---|---|---|---|---|---|---|
| | | | \multicolumn{16}{c}{repetition} |
| | | 1 | 1 | 2 | 1 | 2 | 1 | 2 | 1 | 2 | 1 | 2 | 1 | 2 | 1 | 2 | 1 | 2 |
| Kixor | 200 | 100 | 85 | 90 | 95 | 80 | 10 | 10 | 40 | 10 | 95 | 95 | 85 | 90 | 30 | 0 | 10 | 10 |
| | 100 | 100 | 65 | 70 | 70 | 65 | 10 | 0 | 10 | 10 | 85 | 85 | 80 | 80 | 10 | 0 | 20 | 10 |
| | 50 | 100 | 50 | 30 | 50 | 50 | 0 | 0 | 10 | 10 | 65 | 65 | 50 | 70 | 10 | 20 | 10 | 40 |
| BAS 850H | 300 | 100 | 70 | 50 | 40 | 50 | 20 | 30 | 20 | 30 | 90 | 100 | 70 | 85 | 10 | 20 | 50 | 10 |
| | 150 | 100 | 60 | 40 | 40 | 65 | 10 | 10 | 40 | 50 | 75 | 70 | 70 | 70 | 20 | 10 | 30 | 0 |
| | 75 | 100 | 30 | 40 | 30 | 40 | 0 | 0 | 10 | 20 | 70 | 80 | 60 | 65 | 10 | 10 | 40 | 10 |
| Carfentrazone | 200 | 100 | 40 | 10 | 50 | 20 | 30 | 40 | 10 | 10 | 65 | 60 | 50 | 65 | 20 | 20 | 20 | 10 |
| | 100 | 100 | 10 | 10 | 40 | 20 | 10 | 10 | 10 | 10 | 60 | 50 | 30 | 30 | 20 | 20 | 50 | 10 |
| | 50 | 100 | 10 | 10 | 40 | 10 | 10 | 10 | 30 | 0 | 30 | 60 | 20 | 30 | 30 | 10 | 50 | 20 |
| Kixor + Carfentrazone | 75 + 120 | 100 | 40 | 70 | 75 | 65 | 10 | 10 | 10 | 10 | 90 | 80 | 55 | 65 | 40 | 30 | 10 | 10 |
| | 37.5 + 60 | 100 | 30 | 65 | 70 | 50 | 10 | 30 | 0 | 0 | 70 | 80 | 55 | 50 | 10 | 10 | 10 | 10 |
| | 18.75 + 30 | 100 | 30 | 30 | 30 | 30 | 10 | 30 | 30 | 0 | 60 | 70 | 10 | 20 | 10 | 10 | 75 | 20 |

| compound | repetition g ai/ha | wild type | AMATU_PPO2_ F420M | | AMATU_PPO2_ R128A_F420M | | AMATU_PPO2_ R128A_F420V Event | | AMATU_PPO2_ L397D_F420V | | AMATU_PPO2_ L397D | |
|---|---|---|---|---|---|---|---|---|---|---|---|---|
| | | | A | B | A | B | A | D | O | A | E | O |
| Oxyfluorfen Kixor MSO 1% | 800 + 75 + 3750 | 100 | 70 | 73 | 15 | 5 | 75 | 55 | 7.5 | 75 | 78 | 73 |
| | 800 + 50 + 3750 | 100 | 65 | 63 | 18 | 10 | 50 | 53 | 23 | 83 | 78 | 68 |
| | 800 + 25 + 3750 | 100 | 65 | 58 | 13 | 13 | 63 | 43 | 5 | 83 | 68 | 53 |
| Oxyfluorfen Flumioxazin MSO 1% | 800 + 400 + 3750 | 100 | 60 | 60 | 13 | 20 | 63 | 60 | 20 | 83 | 63 | 43 |
| | 800 + 200 + 3750 | 100 | 65 | 55 | 25 | 23 | 73 | 43 | 35 | 80 | 60 | 38 |
| | 800 + 100 + 3750 | 100 | 63 | 53 | 40 | 35 | 70 | 40 | 5 | 85 | 50 | 38 |
| Oxyfluorfen BAS 850H MSO 1% | 800 + 200 + 3750 | 100 | 75 | 70 | 60 | 58 | 70 | 60 | 20 | 90 | 95 | 83 |
| | 800 + 100 + 3750 | 100 | 73 | 65 | 63 | 50 | 75 | 55 | 13 | 93 | 100 | 78 |
| | 800 + 50 + 3750 | 100 | 73 | 50 | 43 | 50 | 73 | 60 | 25 | 88 | 88 | 70 |
| Fomesafen BAS 850H MSO 1% | 300 + 200 + 3750 | 100 | 85 | 85 | 63 | 55 | 80 | 78 | 60 | 97 | 90 | 73 |
| | 300 + 100 + 3750 | 100 | 85 | 85 | 58 | 55 | 85 | 78 | 70 | 95 | 93 | 83 |
| | 300 + 50 + 3750 | 100 | 93 | 83 | 48 | 55 | 85 | 80 | 63 | 94 | 90 | 75 |
| Oxyfluorfen Fomesafen MSO 1% | 800 + 600 + 3750 | 100 | 85 | 95 | 60 | 50 | 90 | 83 | 58 | 93 | 68 | 40 |
| | 800 + 450 + 3750 | 100 | 88 | 85 | 58 | 48 | 80 | 80 | 50 | 94 | 58 | 35 |
| | 800 + 300 + 3750 | 100 | 80 | 80 | 60 | 43 | 80 | 80 | 65 | 97 | 58 | 45 |
| Flumioxazin Carfentrazone MSO 1% | 100 + 120 + 3750 | 100 | 68 | 70 | 58 | 55 | 45 | 28 | 0 | 78 | 80 | 60 |
| | 100 + 60 + 3750 | 100 | 60 | 60 | 50 | 43 | 40 | 45 | 0 | 83 | 73 | 60 |
| | 100 + 30 + 3750 | 100 | 65 | 60 | 45 | 43 | 53 | 43 | 5 | 97 | 70 | 60 |
| Oxyfluorfen Carfentrazone MSO 1% | 800 + 120 + 3750 | 100 | 45 | 43 | 43 | 35 | 65 | 68 | 25 | 88 | 68 | 53 |
| | 800 + 60 + 3750 | 100 | 38 | 25 | 10 | 33 | 58 | 60 | 35 | 88 | 58 | 53 |
| | 800 + 30 + 3750 | 100 | 38 | 18 | 10 | 25 | 65 | 58 | 30 | 95 | 55 | 30 |

Example 6: Tissue Culture Conditions

An in vivo tissue culture mutagenesis assay has been developed to isolate and characterize plant tissue (e.g., maize, rice tissue) that is tolerant to protoporphyrinogen oxidase inhibiting herbicides, (saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control). The assay utilizes the somaclonal variation that is found in in vitro tissue culture. Spontaneous mutations derived from somaclonal variation can be enhanced by chemical mutagenesis and subsequent selection in a stepwise manner, on increasing concentrations of herbicide.

The present invention provides tissue culture conditions for encouraging growth of friable, embryogenic maize or rice callus that is regenerable. Calli were initiated from 4 different maize or rice cultivars encompassing *Zea mays* and Japonica (Taipei 309, Nipponbare, Koshihikari) and Indica (Indica 1) varieties, respectively. Seeds were surface sterilized in 70% ethanol for approximately 1 min followed by 20% commercial Clorox bleach for 20 minutes. Seeds were rinsed with sterile water and plated on callus induction media. Various callus induction media were tested. The ingredient lists for the media tested are presented in Table 6.

acifluorfen, lactofen, bifenox, sulfentrazone, and photosynthesis inhibitor diuron as negative control in selection media, the tissues were selected in a step-wise fashion by increasing the concentration of the PPO inhibitor with each transfer until cells are recovered that grew vigorously in the presence of toxic doses. The resulting calli were further subcultured every 3-4 weeks to R001M with selective agent. Over 26,000 calli were subjected to selection for 4-5 subcultures until the selective pressure was above toxic levels as determined by kill curves and observations of continued culture. Alternatively, liquid cultures initiated from calli in MS711R with slow shaking and weekly subcultures. Once liquid cultures were established, selection agent was added directly to the flask at each subculture. Following 2-4 rounds

TABLE 6

| Ingredient | Supplier | R001M | R025M | R026M | R327M | R008M | MS711R |
|---|---|---|---|---|---|---|---|
| B5 Vitamins | Sigma | | | | | 1.0 X | |
| MS salts | Sigma | | | 1.0 X | 1.0 X | 1.0 X | 1.0 X |
| MS Vitamins | Sigma | | | 1.0 X | 1.0 X | | |
| N6 salts | Phytotech | 4.0 g/L | 4.0 g/L | | | | |
| N6 vitamins | Phytotech | 1.0 X | 1.0 X | | | | |
| L-Proline | Sigma | 2.9 g/L | 0.5 g/L | | | | 1.2 g/L |
| Casamino Acids | BD | 0.3 g/L | 0.3 g/L | 2 g/L | | | |
| Casein Hydrolysate | Sigma | | | | | | 1.0 g/L |
| L-Asp Monohydrate | Phytotech | | | | | | 150 mg/L |
| Nicotinic Acid | Sigma | | | | | | 0.5 mg/L |
| Pyridoxine HCl | Sigma | | | | | | 0.5 mg/L |
| Thiamine HCl | Sigma | | | | | | 1.0 mg/L |
| Myo-inositol | Sigma | | | | | | 100 mg/L |
| MES | Sigma | 500 mg/L | 500 mg/L | 500 mg/L | 500 mg/L | 500 mg/L | 500 mg/L |
| Maltose | VWR | 30 g/L | 30 g/L | 30 g/L | 30 g/L | | |
| Sorbitol | Duchefa | | | 30 g/L | | | |
| Sucrose | VWR | | | | | 10 g/L | 30 g/L |
| NAA | Duchefa | | | | | 50 µg/L | |
| 2,4-D | Sigma | 2.0 mg/L | | | | | 1.0 mg/L |
| MgCl$_2$•6H$_2$O | VWR | | | | | 750 mg/L | |
| →pH | | 5.8 | 5.8 | 5.8 | 5.8 | 5.8 | 5.7 |
| Gelrite | Duchefa | 4.0 g/L | | | | 2.5 g/L | |
| Agarose Type1 | Sigma | | 7.0 g/L | 10 g/L | 10 g/L | | |
| →Autoclave | | 15 min | 15 min | 15 min | 15 min | 15 min | 20 min |
| Kinetin | Sigma | | 2.0 mg/L | 2.0 mg/L | | | |
| NAA | Duchefa | | 1.0 mg/L | 1.0 mg/L | | | |
| ABA | Sigma | | 5.0 mg/L | | | | |
| Cefotaxime | Duchefa | | 0.1 g/L | 0.1 g/L | 0.1 g/L | | |
| Vancomycin | Duchefa | | 0.1 g/L | 0.1 g/L | 0.1 g/L | | |
| G418 Disulfate | Sigma | | 20 mg/L | 20 mg/L | 20 mg/L | | |

R001M callus induction media was selected after testing numerous variations. Cultures were kept in the dark at 30° C. Embryogenic callus was subcultured to fresh media after 10-14 days.

Example 7: Selection of Herbicide-Tolerant Calli

Once tissue culture conditions were determined, further establishment of selection conditions were established through the analysis of tissue survival in kill curves with saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control. Careful consideration of accumulation of the herbicide in the tissue, as well as its persistence and stability in the cells and the culture media was performed. Through these experiments, a sub-lethal dose has been established for the initial selection of mutated material. After the establishment of the starting dose of saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, of liquid selection, cultures were transferred to filters on solid R001M media for further growth.

Example 8: Regeneration of Plants

Tolerant tissue was regenerated and characterized molecularly for PPO gene sequence mutations and/or biochemically for altered PPO activity in the presence of the selective agent. In addition, genes involved directly and/or indirectly in tetrapyrrole biosynthesis and/or metabolism pathways were also sequenced to characterize mutations. Finally, enzymes that change the fate (e.g. metabolism, translocation, transportation) were also sequence to characterized mutations. Following herbicide selection, calli were regenerated using a media regime of R025M for 10-14 days, R026M for ca. 2 weeks, R327M until well formed shoots were developed, and R008S until shoots were well rooted for transfer to the greenhouse. Regeneration was carried out in the light. No selection agent was included during regeneration. Once strong roots were established, MO regenerants were transplant to the greenhouse in square or round pots. Transplants were maintained under a clear plastic cup until they were adapted to greenhouse conditions. The greenhouse was set to a day/night cycle of 27° C./21° C. (80° F./70° F.) with 600 W high pressure sodium lights supplementing light to maintain a 14 hour day length. Plants were watered according to need, depending in the weather and fertilized daily.

Example 9: Sequence Analysis

Leaf tissue was collected from clonal plants separated for transplanting and analyzed as individuals. Genomic DNA was extracted using a Wizard® 96 Magnetic DNA Plant System kit (Promega, U.S. Pat. Nos. 6,027,945 & 6,368,800) as directed by the manufacturer. Isolated DNA was PCR amplified using the appropriate forward and reverse primer.

PCR amplification was performed using Hotstar Taq DNA Polymerase (Qiagen) using touchdown thermocycling program as follows: 96° C. for 15 min, followed by 35 cycles (96° C., 30 sec; 58° C.-0.2° C. per cycle, 30 sec; 72° C., 3 min and 30 sec), 10 min at 72° C. PCR products were verified for concentration and fragment size via agarose gel electrophoresis. Dephosphorylated PCR products were analyzed by direct sequence using the PCR primers (DNA Landmarks, or Entelechon). Chromatogram trace files (.scf) were analyzed for mutation relative to the wild-type gene using Vector NTI Advance 10™ (Invitrogen). Based on sequence information, mutations were identified in several individuals. Sequence analysis was performed on the representative chromatograms and corresponding AlignX alignment with default settings and edited to call secondary peaks.

Example 10: Demonstration of Herbicide-Tolerance

T0 or T1 transgenic plant of soybean, corn, Canola varieties and rice containing PPO1 and or PPO2 sequences are tested for improved tolerance to herbicides in greenhouse studies and mini-plot studies with the following herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control. For the pre-emergence treatment, the herbicides are applied directly after sowing by means of finely distributing nozzles. The containers are irrigated gently to promote germination and growth and subsequently covered with transparent plastic hoods until the plants have rooted. This cover causes uniform germination of the test plants, unless this has been impaired by the herbicides. For post emergence treatment, the test plants are first grown to a height of 3 to 15 cm, depending on the plant habit, and only then treated with the herbicides. For this purpose, the test plants are either sown directly, and grown in the same containers or they are first grown separately and transplanted into the test containers a few days prior to treatment.

For testing of T0 plants, cuttings can be used. In the case of soybean plants, an optimal shoot for cutting is about 7.5 to 10 cm tall, with at least two nodes present. Each cutting is taken from the original transformant (mother plant) and dipped into rooting hormone powder (indole-3-butyric acid, IBA). The cutting is then placed in oasis wedges inside a bio-dome. Wild type cuttings are also taken simultaneously to serve as controls. The cuttings are kept in the bio-dome for 5-7 days and then transplanted to pots and then acclimated in the growth chamber for two more days. Subsequently, the cuttings are transferred to the greenhouse, acclimated for approximately 4 days, and then subjected to spray tests as indicated. Depending on the species, the plants are kept at 10-25° C. or 20-35° C. The test period extends over 3 weeks. During this time, the plants are tended and their response to the individual treatments is evaluated. Herbicide injury evaluations are taken at 2 and 3 weeks after treatment. Plant injury is rated on a scale of 0% to 100%, 0% being no injury and 100% being complete death.

Figure 2:
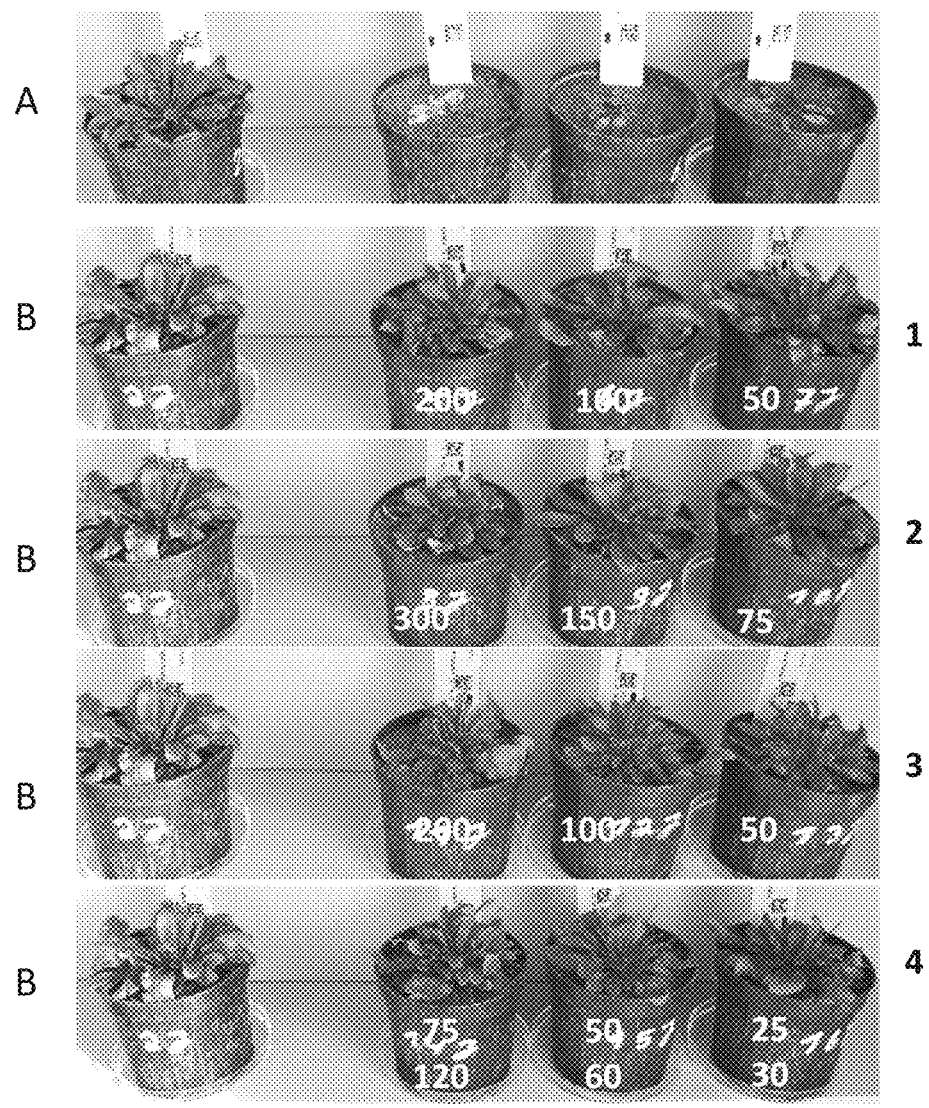
FIG. 2 shows wildtype and transgenic *Arabidopsis* plants comprising a nucleic encoding a mutated PPO polypeptide (based on SEQ ID NO:2; AMATU_PPO2_R128A_420V); 1=Kixor [saflufenacil]; 2=BAS 850H [1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione]; 3=Spotlight [fluroxypyr]; 4=Kixor+Spotlight; A=non-transgenic (for any PPOi treatment); B=AMATU_PPO2_R128A_420V transgenic plants)

Transgenic *Arabidopsis thaliana* plants were assayed for improved tolerance to saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control, in 48-well plates. Therefore, T2 seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v) Four to five seeds per well are plated on solid nutrient medium consisting of half-strength murashige skoog nutrient solution, pH 5.8 (Murashige and Skoog (1962) *Physiologia Plantarum* 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 µmol Phot$*m^{-2}*s^{-1}$ with 14:10 h light:dark photoperiod. Growth inhibition is evaluated seven to ten days after seeding in comparison to wild type plants. Additionally, transgenic T1 *Arabidopsis* plants were tested for improved tolerance to herbicides in greenhouse studies with the following herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control. Results are shown in Table 5 and FIG. 2.

Example 11: Herbicide Selection Using Tissue Culture

Media was selected for use and kill curves developed as specified above. For selection, different techniques were utilized. Either a step wise selection was applied, or an immediate lethal level of herbicide was applied. In either case, all of the calli were transferred for each new round of selection. Selection was 4-5 cycles of culture with 3-5 weeks for each cycle. Cali were placed onto nylon membranes to facilitate transfer (200 micron pore sheets, Biodesign, Saco, Me.). Membranes were cut to fit 100×20 mm Petri dishes and were autoclaved prior to use 25-35 calli (average weight/calli being 22 mg) were utilized in every plate. In addition, one set of calli were subjected to selection in liquid culture media with weekly subcultures followed by further selection on semi-solid media. Mutant lines were selected using saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, sulfentrazone, and photosynthesis inhibitor diuron as negative control. Efficiencies of obtaining mutants was high either based on a percentage of calli that gave rise to a regenerable, mutant line or the number of lines as determined by the gram of tissue utilized.

Figure 3:
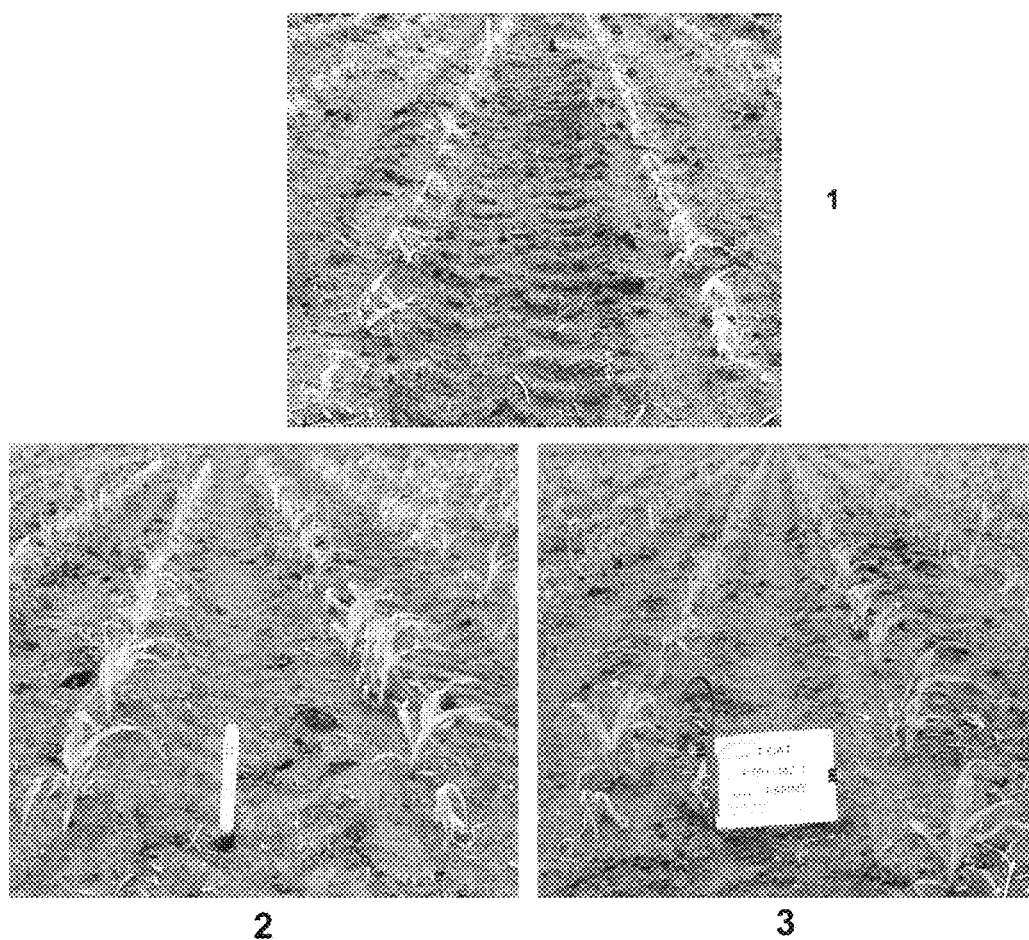
FIG. 3 shows T1 Transformed corn 7 days after treatment with 100 g saflufenacil+50 g ai/ha BAS 850H+1% (v/v) MSO. Plants were sprayed at the V2-V3 stage. 1=untransformed control; 2=Tp-Fdx_AmtuPPX2L_R128A_F420V (Transit peptide of *Silene pratensis* Ferredoxin fused to mutated PPO); 3=AmtuPPX2L_R128A_F420L
Figure 4:
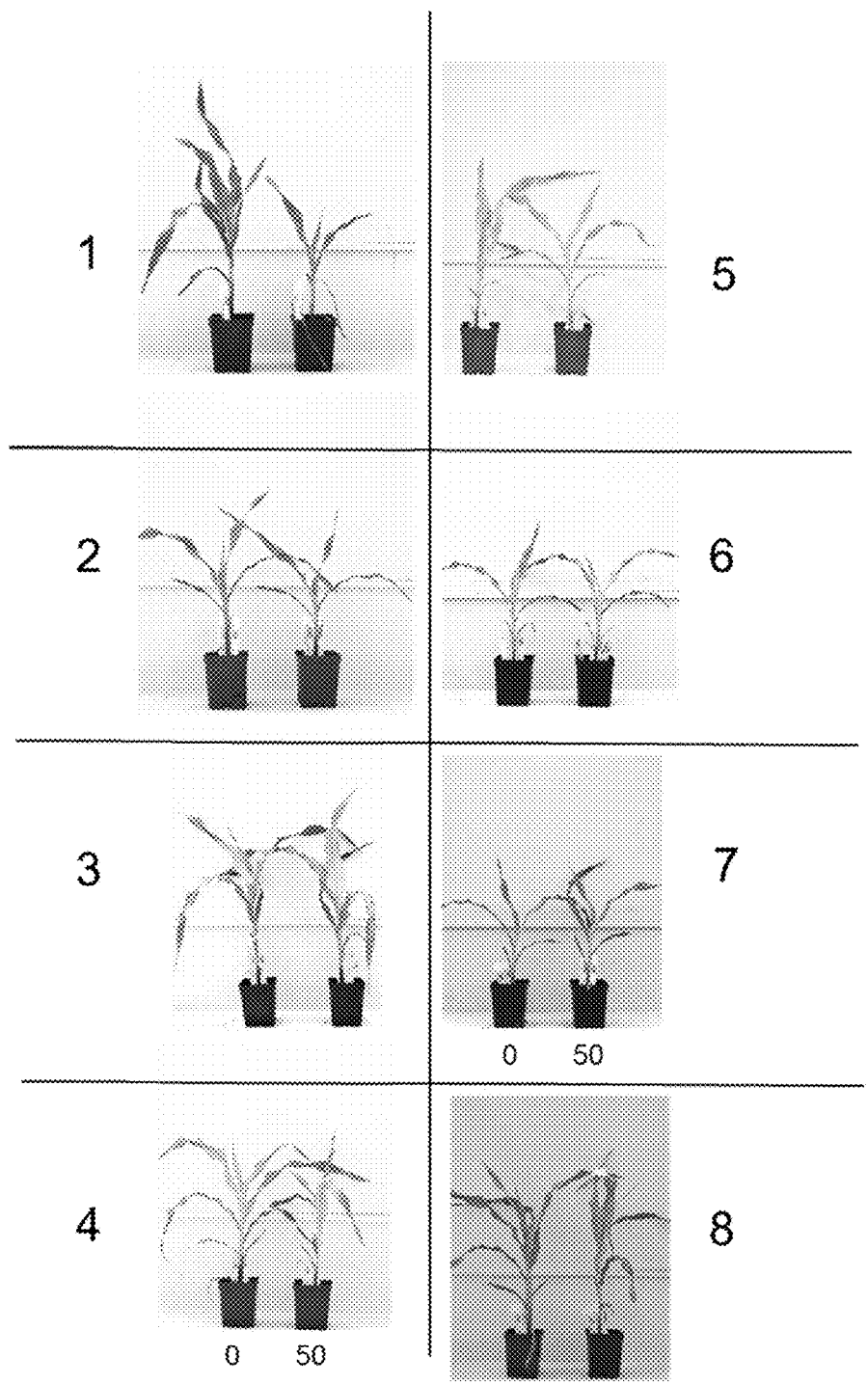
FIG. 4 shows T0 Transformed corn 3 days after treatment. Plants were sprayed with 0 or 50 g ai/ha BAS 850H+1%

Example 12: Maize Whole Plant Transformation and PPO Inhibitor Tolerance Testing Immature embryos were transformed according to the procedure outlined in Peng et al. (WO2006/136596). Plants were tested for the presence of the T-DNA by Taqman analysis with the target being the nos terminator which is present in all constructs. Healthy looking plants were sent to the greenhouse for hardening and subsequent spray testing. The plants were individually transplanted into MetroMix 360 soil in 4" pots. Once in the greenhouse (day/night cycle of 27° C./21° C. with 14 hour day length supported by 600 W high pressure sodium lights), they were allowed to grow for 14 days. They were then sprayed with a treatment of 25 to 200 g ai/ha saflufenacil+1.0% v/v methylated seed oil (MSO) and/or 25-200 g ai/ha 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) plus 1% MSO. Other PPO inhibiting herbicides were also tested in a similar fashion for confirming cross resistance: flumioxazin, butafenacil, acifluorfen, lactofen, bifenox, sulfentrazone, and photosynthesis inhibitor diuron as negative control. Herbicide injury evaluations were taken at 7, 14 and 21 days after treatment. Herbicide injury evaluations were taken 2, 7, 14 and 21 days post-spray to look for injury to new growth points and overall plant health. The top survivors were transplanted into gallon pots filled with MetroMix 360 for seed production. Results are shown in Table 7 and FIGS. 3, and 4.

Table 7a Transgenic T0 corn events were sprayed in the greenhouse with the indicated amount of compound+1% (v/v) MSO at V2 stage. Herbicide injury was evaluated 7 days after treatment with a 0 to 9 rating scale where 0 is no injury relative to an unsprayed wild type check and 9 is completely dead.

TABLE 7a

| SEQ ID | Event | BAS800H (g ai/ha) | | | BAS850H (g ai/ha) | | |
|---|---|---|---|---|---|---|---|
| | | 0 | 50 | 75 | 50 | 75 | 100 |
| AmtuPPX2L_R128A_F420V | 1 | 0 | | | | | |
| | 2 | 0 | | | | | |
| | 3 | 0 | | | | | |
| | 4 | 0 | | | | | |
| | 5 | 0 | | | | | |
| | 6 | 0 | | | | | |
| | 7 | 0 | | | | | |
| | 8 | 0 | | | | | |
| | 9 | | | | 4 | | |
| | 10 | | | | 4 | | |
| | 11 | | | | 4 | | |
| | 12 | | | | 4 | | |
| | 13 | | | | 3 | | |
| | 14 | | | | 4 | | |
| | 15 | | | | 4 | | |
| | 16 | | | | 3 | | |
| | 17 | | | | | 4 | |
| | 18 | | | | | 4 | |
| AmtuPPX2L_R128A_F420I | 1 | 1 | | | | | |
| | 2 | 1 | | | | | |
| | 3 | 1 | | | | | |
| | 4 | 0 | | | | | |
| | 5 | 0 | | | | | |
| | 6 | 2 | | | | | |
| | 7 | 0 | | | | | |
| | 8 | 1 | | | | | |
| | 9 | 1 | | | | | |
| | 10 | 1 | | | | | |
| | 11 | 8 | | | | | |
| | 12 | 1 | | | | | |
| | 13 | 4 | | | | | |
| | 14 | 1 | | | | | |
| | 15 | 0 | | | | | |
| | 16 | | | | 6 | | |
| | 17 | | | | 0 | | |
| | 18 | | | | 2 | | |
| | 19 | | | | 2 | | |
| | 20 | | | | 1 | | |
| | 21 | | | | | 5 | |
| | 22 | | | | | 1 | |
| | 23 | 0 | | | | | |
| | 24 | 0 | | | | | |
| | 25 | 0 | | | | | |
| | 26 | 0 | | | | | |
| | 27 | 0 | | | | | |
| | 28 | | 0 | | | | |
| | 29 | | 0 | | | | |
| | 30 | | | | 0 | | |
| | 31 | | | | 1 | | |
| | 32 | | | | 0 | | |
| | 33 | | | | 0 | | |
| | 34 | | | | 3 | | |
| | 35 | | | | | 1 | |
| | 36 | 0 | | | | | |
| | 37 | 0 | | | | | |
| | 38 | 0 | | | | | |
| | 39 | | | | | 4 | |
| | 40 | | | | 0 | | |
| | 41 | | | | 2 | | |
| | 42 | | | | 1 | | |
| | 43 | | | | | | 4 |
| AmtuPPX2L_R128A_F420L | 1 | 0 | | | | | |
| | 2 | | | | 3 | | |
| | 3 | | | | | | 2 |
| | 4 | 0 | | | | | |
| | 5 | | | | 2 | | |
| | 6 | | | | | | 2 |
| | 7 | 0 | | | | | |
| | 8 | | | | 2 | | |
| | 9 | 0 | | | | | |
| | 10 | | | | 2 | | |
| | 11 | 0 | | | | | |
| | 12 | | | | 3 | | |
| | 13 | 0 | | | | | |
| | 14 | | | | 3 | | |
| | 15 | 0 | | | | | |
| | 16 | | | | 2 | | |
| | 17 | 0 | | | | | |
| | 18 | | | | | | 2 |
| | 19 | 0 | | | | | |
| | 20 | | | | | | 2 |
| | 21 | 0 | | | | | |
| | 22 | 0 | | | | | |
| | 23 | 0 | | | | | |
| | 24 | 0 | | | | | |
| | 25 | 2 | | | | | |
| AmtuPPX2L_R128A_F420V | 1 | 0 | | | | | |
| | 2 | | | | 1 | | |
| | 3 | | | | | 1 | |
| | 4 | 0 | | | | | |
| | 5 | | | | 4 | | |
| | 6 | | | | | 5 | |
| | 7 | 0 | | | | | |
| | 8 | | | | 3 | | |
| | 9 | | | | | 1 | |
| | 10 | 0 | | | | | |
| | 11 | | | | 6 | | |
| | 12 | 0 | | | | | |
| | 13 | | | | 3 | | |
| | 14 | 0 | | | | | |

TABLE 7a-continued

| SEQ ID | Event | 0 | BAS800H (g ai/ha) 50 | BAS800H (g ai/ha) 75 | BAS850H (g ai/ha) 50 | BAS850H (g ai/ha) 75 | BAS850H (g ai/ha) 100 |
|---|---|---|---|---|---|---|---|
| | 15 | | | | 1 | | |
| | 16 | 0 | | | | | |
| | 17 | | | | 3 | | |
| | 18 | 0 | | | | | |
| | 19 | | | | | | 1 |
| | 20 | 0 | | | | | |
| | 21 | | | | 5 | | |
| | 22 | 0 | | | | | |
| | 23 | | | | 1 | | |
| | 24 | 0 | | | | | |
| | 25 | 3 | | | | | |
| | 26 | 1 | | | | | |
| | 27 | 1 | | | | | |
| Tp-Fdx::c-AmtuPPX2L_R128A_F420V | 1 | 0 | | | | | |
| | 2 | 0 | | | | | |
| | 3 | 0 | | | | | |
| | 4 | | | | 0 | | |
| | 5 | | | | 1 | | |
| | 6 | | | | 0 | | |
| | 7 | 0 | | | | | |
| | 8 | | | | 0 | | |
| | 9 | | | | | | 0 |
| | 10 | 0 | | | | | |
| | 11 | | | | 0 | | |
| | 12 | 0 | | | | | |
| | 13 | | | | 0 | | |
| | 14 | | | | | | 1 |
| | 15 | | | 2 | | | |
| AmtuPPX2L_R128L_F420M | 1 | 0 | | | 1 | | |
| | 2 | | | | 1 | | |
| | 3 | | | | 0 | | |
| | 4 | | | | 5 | | |
| | 5 | | | | 1 | | |
| | 6 | | | | 5 | | |
| | 7 | | | | 3 | | |
| | 8 | | | | 2 | | |
| | 9 | | | | 8 | | |
| | 10 | | | | 2 | | |
| | 11 | | | | 2 | | |
| | 12 | | | | 0 | | |
| | 13 | 0 | | | 0 | | |
| | 14 | 0 | | | 2 | | |
| | 15 | | | | 0 | | |
| | 16 | | | | 0 | | |
| | 17 | | | | 3 | | |
| | 18 | | | | 3 | | |
| | 19 | | | | 6 | | |
| | 20 | | | | 1 | | |
| | 21 | | | | 4 | | |
| | 22 | | | | 3 | | |
| | 23 | | | | 2 | | |
| | 24 | | | | 2 | | |
| | 25 | | | | 0 | | |
| | 26 | | | | 0 | | |
| | 27 | | | | 0 | | |
| | 28 | | | | 2 | | |
| | 29 | | | | 2 | | |
| | 30 | | | | 1 | | |
| | 31 | | | | 0 | | |
| | 32 | | | | 2 | | |
| | 33 | | | | 2 | | |
| | 34 | | | | 1 | | |
| | 35 | | | | 4 | | |
| | 36 | | | | 1 | | |
| | 37 | | | | 2 | | |
| AmtuPPX2L_R128M_F420I | 1 | 0 | | | 7 | | |
| | 2 | 0 | | | 0 | | |
| | 3 | 0 | | 0 | 1 | | 0 |
| | 4 | | | | 1 | | |
| | 5 | | | | 1 | | |
| | 6 | | | | 0 | | |
| | 7 | | | | 2 | | |
| | 8 | 0 | | | 1 | 0 | |
| | 9 | 0 | | | 0 | 1 | |
| | 10 | 0 | | | 0 | | |
| | 11 | 0 | | | 1 | | |
| | 12 | 0 | | | 1 | | |
| | 13 | 0 | | | 4 | | |
| | 14 | 0 | | | 0 | | |
| | 15 | 0 | | | 1 | | |
| | 16 | 0 | | | 1 | | |
| | 17 | | | | 2 | | |
| | 18 | | | | 4 | | |
| | 19 | | | | 2 | | |
| | 20 | | | | 0 | | |
| | 21 | | | | 0 | | |
| | 22 | | | | 0 | | |
| | 23 | | | | 0 | | |
| | 24 | | | | 1 | | |
| | 25 | | | | 4 | | |
| | 26 | | | | 0 | | |
| | 27 | | | | 0 | | |
| | 28 | | | | 0 | | |
| | 29 | | | | 2 | | |
| | 30 | | | | 3 | | |
| | 31 | 0 | | | 3 | | |
| | 32 | 0 | | | 1 | 2 | |
| | 33 | | | | 4 | | |
| | 34 | 0 | | | 3 | | |
| | 35 | 0 | | | 1 | | 2 |
| | 36 | | | | 4 | | |
| | 37 | | | | 1 | | |
| AmtuPPX2L_R128M_F420L | 1 | 1 | | | 1 | | |
| | 2 | | | | 0 | | |
| | 3 | | | | 4 | | |
| | 4 | | | | 0 | | |
| | 5 | 0 | | | 1 | 2 | |
| | 6 | 0 | | | 0 | | |
| | 7 | | | | 0 | | |
| | 8 | | | | 1 | | |
| | 9 | | | | 6 | | |
| | 10 | | | | 0 | | |
| | 11 | | | | 0 | | |
| | 12 | | | | 0 | | |
| | 13 | 0 | | | 1 | | |
| | 14 | 0 | | | 3 | | |
| | 15 | | | | 2 | | |
| | 16 | 0 | | | 1 | | |
| | 17 | 0 | | | 3 | | |
| | 18 | | | | 0 | | |
| AmtuPPX2L_R128M_F420V | 1 | 0 | | | 0 | | |
| | 2 | 0 | | | 3 | | |
| | 3 | 0 | | | 0 | | |
| | 4 | 0 | | | 0 | | |
| | 5 | 0 | | 1 | 0 | | 0 |
| | 6 | 0 | | | 5 | | |
| | 7 | | | | 6 | | |
| | 8 | | | | 1 | | |
| | 9 | | | | 5 | | |
| | 10 | | | | 1 | | |
| | 11 | | | | 0 | | |
| | 12 | | | | 0 | | |
| | 13 | | | | 0 | | |
| | 14 | 2 | | | 0 | | |
| | 15 | 0 | | | 0 | | |
| | 16 | 1 | | | 1 | | |
| | 17 | 0 | | | 0 | | 1 |
| | 18 | | | | 1 | | |
| | 19 | | | | 0 | | |
| | 20 | | | | 1 | | |
| | 21 | | | | 0 | | |
| | 22 | | | | 1 | | |
| | 23 | | | | 0 | | |
| | 24 | | | | 0 | | |
| | 25 | | | | 0 | | |
| | 26 | 2 | | | 0 | | |
| | 27 | 0 | | | 0 | | |
| | 28 | 1 | | | 1 | | |
| | 29 | 0 | | | 0 | | 1 |
| | 30 | | | | 1 | | |

TABLE 7a-continued

| SEQ ID | Event | BAS800H (g ai/ha) 0 | BAS800H (g ai/ha) 50 | BAS800H (g ai/ha) 75 | BAS850H (g ai/ha) 50 | BAS850H (g ai/ha) 75 | BAS850H (g ai/ha) 100 |
|---|---|---|---|---|---|---|---|
| | 31 | | 0 | | | | |
| | 32 | | 1 | | | | |
| | 33 | | 0 | | | | |
| | 34 | | 1 | | | | |
| | 35 | | 0 | | | | |
| | 36 | | 0 | | | | |
| | 37 | | 0 | | | | |
| | 38 | | 2 | | | | |
| | 39 | | 0 | | | | |
| | 40 | | 1 | | | | |

TABLE 7b

Transgenic T1 corn events were sprayed in the field with 100 g ai BAS800H and 50 g ai BAS850H + 1% (v/v) MSO at V2-V3 developmental stage. Herbicide injury was evaluated at 3, 7, 14, and 21 days after treatment (DAT) with a 0 to 100 rating scale where 0 is no injury relative to an unsprayed wild type check and 100 is completely dead

| Construct | SEQ ID | Event | 3 DAT | 7 DAT | 14 DAT | 21 DAT |
|---|---|---|---|---|---|---|
| RTP11136-1 | AmtuPPX2L_R128A_F420V | 1 | 20 | 30 | 0 | 0 |
| RTP11141-1 | AmtuPPX2L_R128A_F420I | 2 | 70 | 80 | 70 | 80 |
| RTP11141-1 | | 3 | 20 | 10 | 10 | 10 |
| RTP11141-1 | | 4 | 10 | 0 | 30 | 20 |
| RTP11141-1 | | 5 | 10 | 0 | 20 | 10 |
| RTP11141-1 | | 6 | 10 | 0 | 10 | 0 |
| RTP11141-1 | | 7 | 10 | 0 | 30 | 20 |
| RTP11141-1 | | 8 | 80 | 80 | 70 | 70 |
| RTP11141-1 | | 9 | 10 | 0 | 10 | 0 |
| RTP11141-1 | | 10 | 10 | 10 | 40 | 30 |
| RTP11141-1 | | 11 | 10 | 10 | 30 | 20 |
| RTP11142-2 | AmtuPPX2L_R128A_F420L | 12 | 10 | 30 | 10 | 10 |
| RTP11142-2 | | 13 | 10 | 10 | 30 | 20 |
| RTP11142-2 | | 14 | 10 | 10 | 20 | 20 |
| RTP11142-2 | | 15 | 10 | 10 | 30 | 20 |
| RTP11142-2 | | 16 | 20 | 30 | 40 | 20 |
| RTP11142-2 | | 17 | 10 | 0 | 20 | 0 |
| RTP11142-2 | | 18 | 10 | 10 | 10 | 0 |
| RTP11142-2 | | 19 | 20 | 10 | 10 | 0 |
| RTP11142-2 | | 20 | 10 | 10 | 10 | 0 |
| RTP11142-2 | | 21 | 10 | 10 | 10 | 0 |
| RTP11142-2 | | 22 | 10 | 0 | 10 | 0 |
| RTP11142-2 | | 23 | 20 | 40 | 50 | 50 |
| RTP11142-2 | | 24 | 50 | 80 | | |
| RTP11142-2 | | 25 | 10 | 10 | 0 | 0 |
| RTP11142-2 | | 26 | 0 | 10 | 10 | 0 |
| RTP11142-2 | | 27 | 10 | 20 | 20 | 0 |
| RTP11142-2 | | 28 | 10 | 20 | 20 | 10 |
| RTP11142-2 | | 29 | 10 | 20 | 30 | 10 |
| RTP11142-2 | | 30 | 10 | 40 | 40 | 20 |
| RTP11142-2 | | 31 | 0 | 30 | 40 | 20 |
| RTP11143-2 | AmtuPPX2L_R128A_F420V | 32 | 10 | 40 | 40 | 20 |
| RTP11143-2 | | 33 | 10 | 30 | 30 | 10 |
| RTP11143-2 | | 34 | 10 | 20 | 20 | 10 |
| RTP11143-2 | | 35 | 10 | 40 | 40 | 20 |
| RTP11143-2 | | 36 | 10 | 20 | 10 | 0 |
| RTP11144-2 | Tp-Fdx::c- | 37 | 20 | 10 | 10 | 0 |
| RTP11144-2 | AmtuPPX2L_R128A_F420V | 38 | 20 | 10 | 10 | 0 |
| RTP11144-2 | | 39 | 0 | 0 | 10 | 0 |
| RTP11144-2 | | 40 | 30 | 20 | 20 | 0 |
| RTP11144-2 | | 41 | 40 | 10 | 10 | 0 |
| RTP11144-2 | | 42 | 20 | 10 | 0 | 0 |
| RTP11144-2 | | 43 | 0 | 10 | 0 | 0 |
| RTP11144-2 | | 44 | 30 | 10 | 10 | 0 |
| RTP11144-2 | | 45 | 20 | 20 | 0 | 0 |

After regeneration, transformants were transplanted to soil in small pots, placed in growth chambers (16 hr day/8 hr night; 25° C. day/23° C. night; 65% relative humidity; 130-150 microE m−2 s−1) and subsequently tested for the presence of the T-DNA via Taqman analysis. After a few weeks, healthy, transgenic positive, single copy events were transplanted to larger pots and allowed to grow in the growth chamber. An optimal shoot for cutting was about 3-4 inches tall, with at least two nodes present. Each cutting was taken from the original transformant (mother plant) and dipped into rooting hormone powder (indole-3-butyric acid, IBA). The cutting was then placed in oasis wedges inside a bio-dome. The mother plant was taken to maturity in the greenhouse and harvested for seed. Wild type cuttings were also taken simultaneously to serve as negative controls. The cuttings were kept in the bio-dome for 5-7 days and then transplanted to 3 inch pots and then acclimated in the growth chamber for two more days. Subsequently, the cuttings were transferred to the greenhouse, acclimated for approximately 4 days, and then sprayed with a treatment of 0-200 g ai/ha

Example 13: Soybean Transformation and PPO Inhibitor Tolerance Testing

Figure 5:
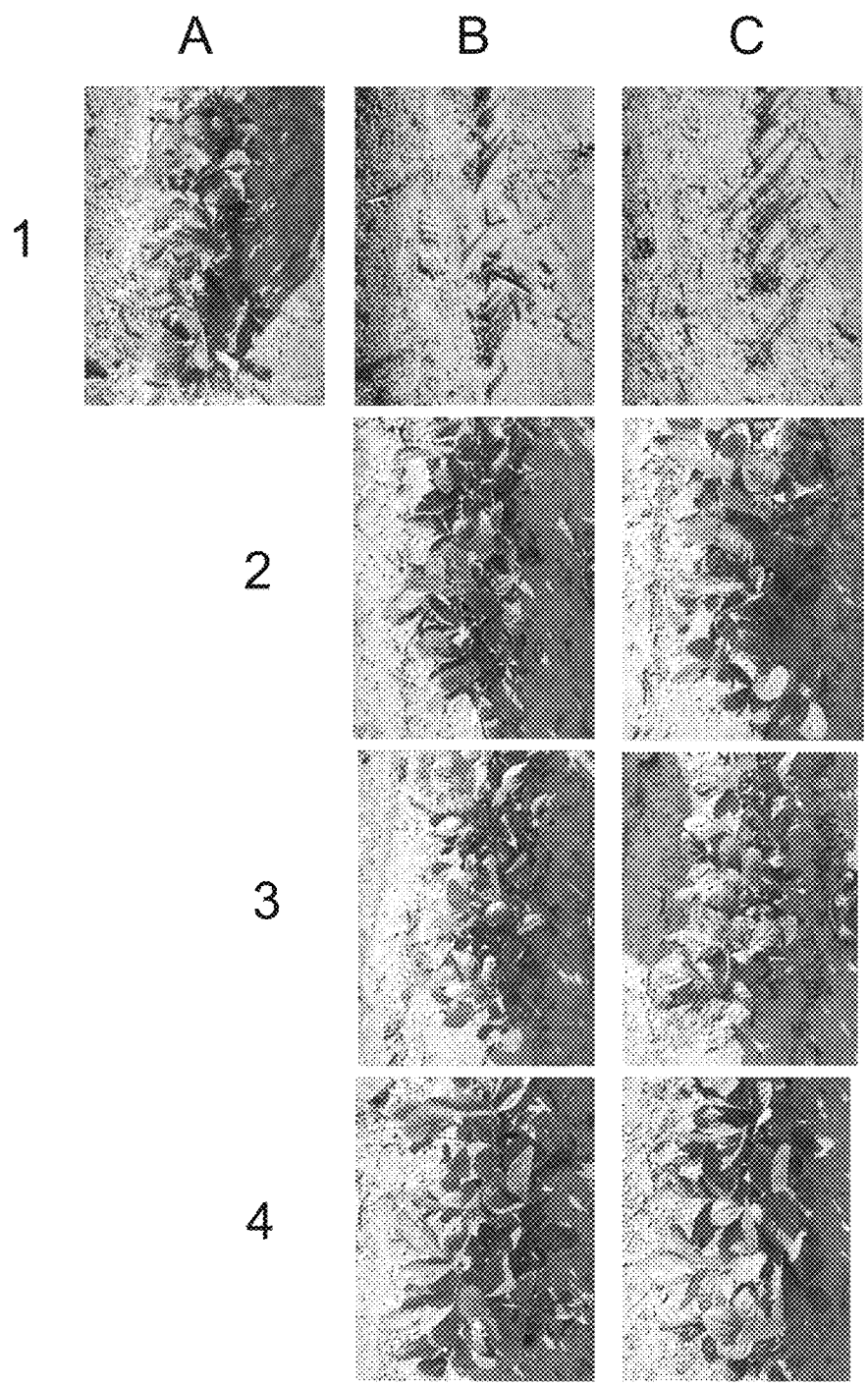
FIG. 5 shows T1 transformed soybean 7 days after treatment with the indicated herbicide+1% (v/v) MSO. Plants were sprayed at the V2-V3 stage; A=unsprayed; B=saflufenacil 150 g ai/ha; C=BAS 850H 100 g ai/ha; 1=wildtype control plant; 2=AmtuPPX2L_R128A_F420M; 3=AmtuPPX2L_R128A_F420I; 4=AmtuPPX2L_R128A_F420V.
Figure 6:
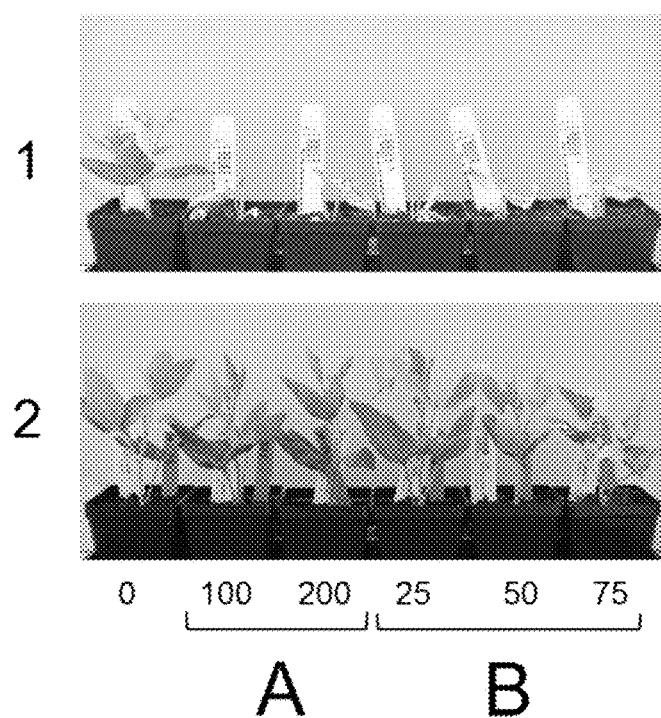
FIG. 6 shows T0 Transformed soybean clones 7 days after indicated treatment. Plants were sprayed at the V2-V3 stage; 1=wildtype control; 2=AmtuPPX2L_R128L_F420V; A=saflufenacil g ai/ha+1% MSO; B=BAS 850H g ai/ha+1% MSO
Figure 7:
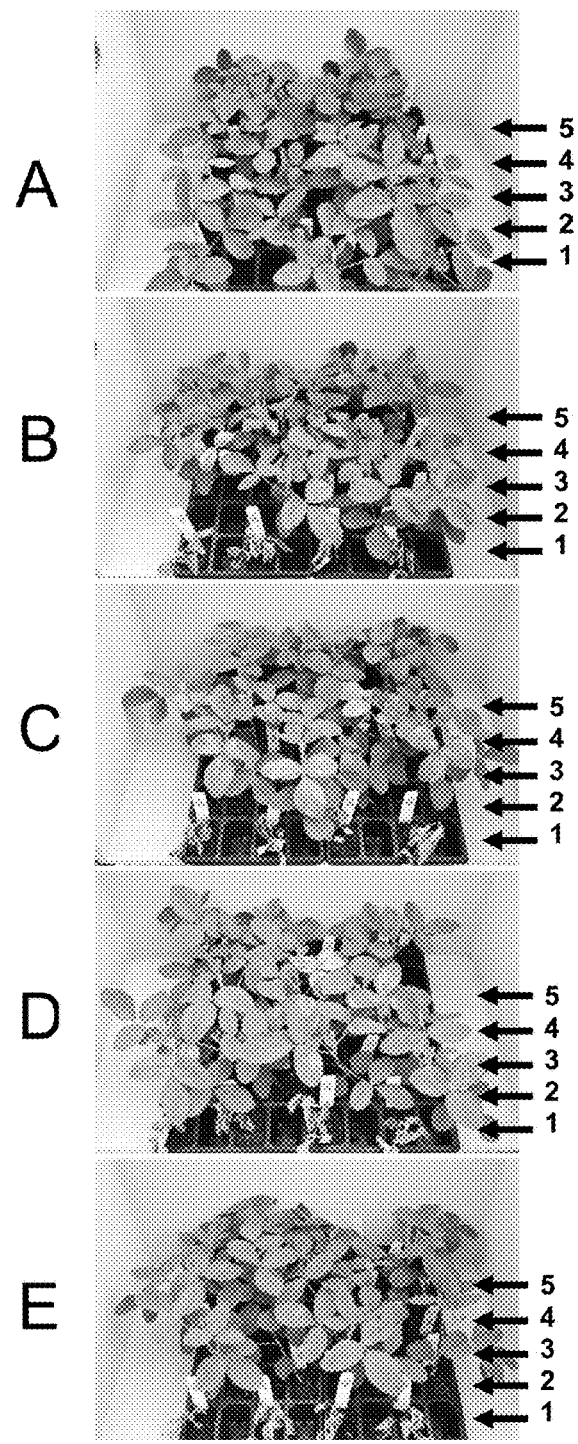
FIG. 7 shows T2 Transformed soybean 4 days after the indicated treatment. Plants were sprayed at the V2-V3 stage. Treatments contained 1% (v/v) MSO (methylated soy oil-based spray adjuvant; also known as Destiny HC); 1=wildtype; 2=AmtuPPX2L_R128A_F420V; 3=AmtuPPX2L_R128A_F420L; 4=AmtuPPX2L_R128A_F420M; 5=AmtuPPX2L_R128A_F420I; A=unsprayed; B=100 g ai/ha saflufenacil+50 g ai/ha BAS 850H; C=200 g ai/ha saflufenacil+100 g ai/ha BAS 850H; D=100 g ai/ha saflufenacil+140 g ai/ha flumioxazin; E=100 g ai/ha saflufenacil+560 g ai/ha sulfentrazone.

Soybean cv Jake was transformed as previously described by Siminszky et al., Phytochem Rev. 5:445-458 (2006).

saflufenacil plus 1% MSO and/or 25-200 g ai/ha 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4) plus 1% MSO. Other PPO inhibiting herbicides were also tested in a similar fashion for confirming cross resistance: flumioxazin, butafenacil, acifluorfen, lactofen, bifenox, sulfentrazone, and photosynthesis inhibitor diuron as negative control. Herbicide injury evaluations were taken at 2, 7, 14 and 21 days after treatment. Results are shown in Table 8, and FIGS. 5, 6, and 7.

TABLE 8a

Injury score from 0-9 taken 1 week after treatment of wildtype soybeans and soybeans expressing mutated PPO with either Kixor or 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione + 1% MSO
Data of T0 cuttings
Injury score from 0-9 taken 1 week after treatment with either Kixor or 1,5-dimethyl-6-thioxo-3- (2,2,7-trifluoro-3-oxo-4-(prop-2-ynyl)-3,4-dihydro-2H-benzo[b][1,4]oxazin-6-yl)-1,3,5-triazinane-2,4-dione + 1% MSO

| GOI | # events | Kixor | | | | | | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | | | |
|---|---|---|---|---|---|---|---|---|---|---|---|
| | | 0 | 12.5 | 25 | 50 | 100 | 200 | 12.5 | 25 | 50 | 75 |
| wild type Jake variety | | 0 | 9 | 9 | 9 | 9 | 9 | 7 | 8 | 9 | 9 |
| NitabPPX2 | 13 | 0 | 3 | 6 | 9 | * | * | 6 | 6 | * | * |
| NitabPPX2_R98A_F392V | 9 | 1 | * | * | 0 | 2 | 2 | * | 0 | 0 | * |
| AmtuPPX2L | 10 | 0 | 2 | 4 | 7 | * | * | 3 | 5 | * | * |
| AmtuPPX2L_dG210 | 13 | 0 | * | 1 | 2 | 1 | * | * | 1 | 3 | * |
| AmtuPPX2L_dG210_R128L | 12 | 0 | * | 0 | 1 | 1 | * | * | 2 | 3 | * |
| AmtuPPX2L_F420L | 7 | 0 | 1 | 0 | 0 | * | * | 2 | 1 | * | * |
| AmtuPPX2L_F420M | 8 | 0 | * | 0 | 3 | 3 | * | * | 1 | 2 | * |
| AmtuPPX2L_R128A_F420L | 6 | 0 | * | 0 | 1 | 1 | * | * | 0 | * | * |
| AmtuPPX2L_R128A_F420M | 7 | * | * | * | * | 2 | 2 | * | 3 | 3 | 4 |
| AmtuPPX2L_R128A_F420I | 9 | 0 | * | * | * | * | 1 | * | 2 | 2 | 3 |
| AmtuPPX2L_R128A_F420V | 14 | * | * | * | * | 2 | 2 | * | 2 | 2 | 3 |

TABLE 8b

| | | Greenhouse data - segregating T1 individuals. Rated for injury (0-9 point scale) 1 week after treatment | | | | | | | | |
|---|---|---|---|---|---|---|---|---|---|---|
| GOI Event | wild type | AmtuPPX2L R128A F420L SDS-10642 | AmtuPPX2L R128A F420L SDS-10787 | AmtuPPX2L R128A F420V SDS-11034 | AmtuPPX2L L397D F420V SDS-10652 | AmtuPPX2L R128A F420M SDS-10990 | AmtuPPX2L R128A F420M SDS-10985 | AmtuPPX2L R128A F420I SDS-10791 | AmtuPPX2L R128A F420I SDS-10648 |
| unsprayed | 0 | 0 | 0 | 0 | 0 | 0 | 0 | 0 | 0 |
| | 0 | 0 | 0 | 0 | 0 | 0 | 0 | 0 | 0 |
| | 0 | 0 | 0 | 0 | 0 | 0 | 0 | 0 | 0 |
| | 0 | 0 | 0 | 0 | 0 | 0 | 0 | 1 | 1 |
| Saflufenacil 150 g ai/ha | 1 | 0 | 0* | 0 | 0 | 0 | 0 | 0 | 0 |
| | 9 | 0 | 6 | 0 | 3 | 9 | 1 | 1 | 5 |
| | 9 | 5 | 5 | 0 | 5 | 3 | 0 | 0 | 5 |
| | 9 | 5 | 4 | 5 | 3 | 0 | * | 9 | 4 |
| | 9 | 5 | 4 | 1 | 4 | 1 | 3 | 9 | 6 |
| | 9 | 9 | 0 | 0 | 6 | 3 | 2 | 9 | 5 |
| | 9 | 1 | 4 | 0 | 4 | 3 | 0 | 1 | 3 |
| 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione 100 g ai/ha | 9 | 0 | 4 | 2 | 5 | 4 | 1 | 2 | 4 |
| | 9 | 6 | 4 | 4 | 9 | 9 | 9 | 3 | 4 |
| | 9 | 5 | 5 | 4 | 4 | 7 | 9 | 2 | 9 |
| | 9 | 5 | 9 | 4 | 4 | 6 | 6 | 4 | 4 |
| | 9 | 5 | 9 | 3 | 4 | 6 | 9 | 9 | 4 |
| | 8 | 9 | 5 | 2 | 4 | 9 | 6 | 3 | 5 |
| | 9 | 5 | 5 | 3 | 9 | 7 | 9 | 5 | 5 |
| | 9 | 4 | 6 | 2 | 4 | 6 | 9 | 4 | 3 |
| Fomesafen 600 g ai/ha | 5 | 0 | 1 | 2 | 1 | 1 | 3 | 6 | 5 |
| | 5 | 1 | 1 | 0 | 2 | 3 | 0 | 3 | 3 |
| | 4 | 0 | 0 | 0 | 0 | 0 | 0 | 3 | 3 |
| | 4 | 1 | 0 | 2 | 0 | 4 | 1 | 1 | 3 |
| | 4 | 0 | 2 | 0 | 1 | 5 | 3 | 4 | 3 |
| | 5 | 1 | 5 | 1 | 0 | 5 | 3 | 2 | 3 |
| Flumioxazin 150 g ai/ha | 4 | 2 | 2 | 1 | 2 | 0 | 1 | 1 | 4 |
| | 9 | 3 | 3 | 5 | 4 | 6 | 5 | 3 | 9 |
| | 9 | 3 | 9 | 4 | 9 | 5 | 9 | 9 | 9 |
| | 9 | 2 | 4 | 6 | 6 | 5 | 6 | 3 | 5 |
| | 9 | 1 | 5 | 5 | 6 | 6 | 4 | 1 | 9 |
| | 9 | 3 | 5 | 9 | 5 | 9 | 5 | 3 | 3 |
| | 9 | 9 | 9 | 3 | 4 | 3 | 9 | 1 | 3 |
| Sulfentrazone 350 g ai/ha | 9 | 1 | 5 | 1 | 6 | 6 | 3 | 3 | 3 |
| | 9 | 0 | 5 | 3 | 9* | 3 | 3 | 9 | 9 |
| | 7 | 3 | 4 | 3 | 6 | 4 | 8 | 9 | 3 |
| | 7 | 1 | 6 | 9 | 3 | 9 | 3 | 2 | 4 |
| | 8 | 2 | 9 | 0 | 5 | 4 | * | 1 | 5 |
| | 9 | 0 | 9 | 1 | 3 | 3 | 4 | 2 | 5 |

TABLE 8b-continued

Greenhouse data - segregating T1 individuals. Rated for injury (0-9 point scale) 1 week after treatment

| GOI Event | wild type | AmtuPPX2L R128A_F420L SDS-10642 | AmtuPPX2L R128A_F420L SDS-10787 | AmtuPPX2L R128A_F420V SDS-11034 | AmtuPPX2L L397D_F420V SDS-10652 | AmtuPPX2L R128A_F420M SDS-10990 | AmtuPPX2L R128A_F420M SDS-10985 | AmtuPPX2L R128A_F420I SDS10791 | AmtuPPX2L R128A_F420I SDS-10648 |
|---|---|---|---|---|---|---|---|---|---|
| Sulfentrazone 700 g ai/ha | 9 | 0 | 5 | 1 | 5 | 9 | 3 | 9 | 3 |
| | 9 | 3 | 5 | 1 | 6 | 3 | 1 | 9 | 8 |
| | 9 | 3 | 3 | 3 | 2 | 3 | 1 | 3 | 3 |
| | 9 | 1 | 4 | 3 | 3 | 4 | 9 | 3 | 2 |
| | 9 | 3 | 6 | 3 | 7 | 9 | 2 | 4 | 9 |
| | 9 | 2 | 4 | 2 | 7 | 4 | 3 | 9 | 3 |
| | 9 | 2 | 5 | 1 | 4 | 4 | 4 | 2 | 4 |
| | 9 | 2 | 6 | 3 | 6 | 9 | 3 | 9 | 4 |
| | 8 | 0 | 5 | 4 | 4 | 9 | 2 | 9 | 4 |
| | 7 | 2 | 6 | 2 | 6 | 4 | 9 | 4 | 5 |
| Oxyfluorfen 600 g ai/ha | 8 | 2 | 6 | 4 | 4 | 4 | 1 | 8 | 7 |
| | 9 | 3 | * | 9 | 5 | 8 | 3 | 4 | 6 |
| | 7 | 2 | 5 | 5 | 6 | 4 | 3 | 5 | 8 |
| | 8 | 8 | 8 | 4 | 6 | 3 | 4 | 5 | 6 |
| | 9 | 3 | 5 | 4 | 9 | 4 | 3 | 4 | 8 |
| | 7 | 2 | 6 | 5 | 4 | 5 | 4 | 3 | 9 |
| Oxyfluorfen 1200 g ai/ha | 9 | 3 | 6 | 5 | 5 | 9 | 9 | 9 | 3 |
| | 9 | 4 | 6 | 6 | 5 | 5 | 5 | 4 | 5 |
| | 9 | 3 | 5 | 6 | 4 | 4 | 4 | 5 | 9 |
| | 9 | 3 | 8 | 5 | 3 | 5 | 8 | 5 | 9 |
| | 8 | 2 | 5 | 6 | 4 | 5 | 8 | 5 | 4 |
| | 9 | 4 | 9 | 6 | 4 | 4 | 5 | 9 | 5 |
| | 9 | 3 | 5 | 5 | 4 | 4 | 4 | 5 | 9 |
| | 8 | 3 | 5 | 5 | 5 | 5 | 5 | 4 | 5 |

TABLE 8c

Field data - T1 generation. Rated for injury (1-5 point scale) 3 days after treatment.

| GOI Event | wild type | AmtuPPX2L R128A_F420M SDS-11052 | AmtuPPX2L R128A_F420I SDS-10648 | AmtuPPX2L R128A_F420I SDS-10791 | AmtuPPX2L R128A_F420I SDS-11014 | AmtuPPX2L R128A_F420V SDS-11035 | AmtuPPX2L L397D_F420V SDS-11034 |
|---|---|---|---|---|---|---|---|
| unsprayed | 1 | 1 | 1 | 1 | 1 | 1 | 1 |
| 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (="benzoxazin"; BAS 850H) 100 g ai/ha | 5 | 3 | 3 | 2 | 2 | 2 | 3 |
| benzoxazin 50 g ai/ha | 5 | 3 | 3 | 2 | 2 | 2 | 2 |
| Saflufenacil 150 g ai/ha | 5 | 2 | 2 | 2 | 2 | 2 | 2 |
| Saflufenacil 75 g ai/ha | 5 | 2 | 2 | 2 | 2 | 2 | 2 |

| Rating | Phenotype (phytotoxicity) of surviving plants |
|---|---|
| 1 | no obvious damage (no phytotoxicity) |
| 2 | minor amount of leaf damage, plant will survive |
| 3 | moderate amount of leaf damage, plant will survive |
| 4 | severe amount of leaf damage, plant will survive |
| 5 | no surviving plants - all plants dead/dying |

TABLE 8d

Field data - T1 generation soybeans rated for injury with 1-5 point scale.
Injury rating taken 3 days after treatment

| Genotype | GOI | Event | benzoxazin + Saflufenacil (100 gai/ha + 100 gai/ha) | benzoxazin + Saflufenacil (50 gai/ha + 50 gai/ha) | benzoxazin (100 gai/ha) | benzoxazin (50 gai/ha) | Saflufenacil (150 gai/ha) | Saflufenacil (75 gai/ha) |
|---|---|---|---|---|---|---|---|---|
| Wildtype | | Jake | 5 | 5 | 5 | 5 | 5 | 5 |
| LTM377-1 | AmtuPPX2L_dG210 | SDS-10656 | 4 | 4 | 4 | 4 | 3.5 | 3.5 |
| LTM377-1 | AmtuPPX2L_dG210 | SDS-10562 | * | * | 3 | 3 | 4 | 4 |
| LTM377-1 | AmtuPPX2L_dG210 | SDS-10566 | * | * | 3 | 3 | 4 | 4 |
| LTM387-1 | AmtuPPX2L_R128A_F420V | SDS-11034 | * | * | 2 | 2 | 2 | 3 |
| LTM387-1 | AmtuPPX2L_R128A_F420V | SDS-11035 | * | * | 2 | 2 | 2 | 2 |
| LTM387-1 | AmtuPPX2L_R128A_F420V | SDS-10998 | 2.5 | 2.5 | 2.5 | 2.5 | 2 | 2 |
| LTM387-1 | AmtuPPX2L_R128A_F420V | SDS-11105 | 3.5 | 3 | 3 | 3 | 2.5 | 2.5 |
| LTM387-1 | AmtuPPX2L_R128A_F420V | SDS-11110 | 3.5 | 3 | 3 | 3 | 2.5 | 2.5 |

TABLE 8e

Field data - T1 generation soybeans rated for injury with 1-5 point scale.
Injury rating taken 3 days after treatment

| Genotype | GOI | Event | Saflufenacil (150 gai/ha) | Saflufenacil (75 gai/ha) |
|---|---|---|---|---|
| Wildtype | | Jake | 5 | 5 |
| LTM382-2 | AmtuPPX2L__F420L | SDS-10533 | 2.5 | 2.5 |
| LTM382-2 | AmtuPPX2L__F420L | SDS-10544 | 2.5 | 2.5 |
| LTM382-2 | AmtuPPX2L__F420L | SDS-10558 | 2 | 2.5 |
| LTM383-1 | AmtuPPX2L__F420M | SDS-10645 | 3 | 4 |
| LTM383-1 | AmtuPPX2L__F420M | SDS-10761 | 3 | 3 |
| LTM383-1 | AmtuPPX2L__F420M | SDS-10633 | 3 | 3 |
| LTM383-1 | AmtuPPX2L__F420M | SDS-10635 | 3.5 | 3.5 |

TABLE 8e-continued

Field data - T1 generation soybeans rated for injury with 1-5 point scale.
Injury rating taken 3 days after treatment

| Genotype | GOI | Event | Saflufenacil (150 gai/ha) Rating | Saflufenacil (75 gai/ha) Rating |
|---|---|---|---|---|
| LTM383-1 | AmtuPPX2L__F420M | SDS-10646 | 2.5 | 2.5 |
| LTM384-1 | AmtuPPX2L__R128A__F420L | SDS-10642 | 2 | 2 |
| LTM384-1 | AmtuPPX2L__R128A__F420L | SDS-10787 | 2.5 | 3 |
| LTM385-1 | AmtuPPX2L__R128A__F420M | SDS-11052 | 3 | 3 |
| LTM385-1 | AmtuPPX2L__R128A__F420M | SDS-10985 | 2 | 2 |
| LTM385-1 | AmtuPPX2L__R128A__F420M | SDS-10990 | 2.5 | 2.5 |
| LTM385-1 | AmtuPPX2L__R128A__F420M | SDS-11011 | 2 | 2 |
| LTM386-1 | AmtuPPX2L__R128A__F420I | SDS-10648 | 3 | 3 |
| LTM386-1 | AmtuPPX2L__R128A__F420I | SDS-10791 | 2 | 2 |
| LTM386-1 | AmtuPPX2L__R128A__F420I | SDS-11014 | 2 | 2 |
| LTM386-1 | AmtuPPX2L__R128A__F420I | SDS-10658 | 3.5 | 3.5 |
| LTM386-1 | AmtuPPX2L__R128A__F420I | SDS-10776 | 2.5 | 2 |
| LTM386-1 | AmtuPPX2L__R128A__F420I | SDS-11036 | 2.5 | 2.5 |
| LTM386-1 | AmtuPPX2L__R128A__F420I | SDS-11111 | 2.5 | 2.5 |
| LTM386-1 | AmtuPPX2L__R128A__F420I | SDS-11118 | 2 | 2 |

TABLE 8f

Soy T0 plants greenhouse data

Herbicide treatment g ai/ha & injury scores 1 WAT

| SEQ ID | event number | Saflufenacil 0 | Saflufenacil 100 | Saflufenacil 200 | 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione 25 | 50 | 75 |
|---|---|---|---|---|---|---|---|
| AmtuPPX2L_R128L_F420V | 1 | 0 | 4 | 6 | 3 | 4 | 5 |
|  | 2 | 0 | 1 | 2 | 0 | 1 | 3 |

TABLE 8g

Field data - T1 generation. Rated for injury (1-5 point scale) 7 or 14 days after treatment (DAT) 1. Herbicide treatment 1 occurred at the V3-V4 stage and herbicide treatment 2 occurred 10 days later at ~V6 stage.

| | | saflufenacil + BAS 850H | saflufenacil + BAS 850H | BAS 850H | BAS 850H | saflufenacil | saflufenacil |
|---|---|---|---|---|---|---|---|
| | Herbicide treatment 1 | 150 g ai/ha + 100 g ai/ha | 300 g ai/ha + 300 g ai/ha | 100 g ai/ha | 300 g ai/ha | 150 g ai/ha | 300 g ai/ha |
| | Herbicide treatment 2 | 0 | 300 g ai/ha + 300 g ai/ha | 0 | 300 g ai/ha | 0 | 300 g ai/ha |
| | Timing of injury rating | 7 DAT | 14 DAT | 7DAT | 14 DAT | 7 DAT | 14 DAT |
| SEQ ID 2 or 4 | Event # | Injury rating | | | | | |
| | wild type | 5 | 5 | 5 | 5 | 5 | 5 |
| AmtuPPX2L_R128A_F420L | 1 | 2.5 | 3 | 2.5 | 3 | 1 | 1 |
| AmtuPPX2L_R128A_F420L | 2 | 3 | 3.5 | 3.5 | 3.5 | 3 | 2 |
| AmtuPPX2L_R128A_F420M | 3 | 2 | 3 | 3 | 3.5 | 1.5 | 1.5 |
| AmtuPPX2L_R128A_F420M | 4 | 2 | 3 | 3 | 3.5 | 1.5 | 1 |
| AmtuPPX2L_R128A_F420I | 5 | 2.5 | 3 | 3 | 3.5 | 1.5 | 1 |
| AmtuPPX2L_R128A_F420I | 6 | 3 | 3.5 | 3 | 3.5 | 3 | 3 |
| AmtuPPX2L_R128A_F420I | 7 | 2 | 3 | 3 | 3.5 | 1.5 | 1.5 |
| AmtuPPX2L_R128A_F420I | 8 | 1 | 2 | 2.5 | 2.5 | 1 | 2 |
| AmtuPPX2L_R128A_F420I | 9 | 1 | 1 | 2.5 | 1.5 | 1 | 1 |
| AmtuPPX2L_R128A_F420V | 10 | 3 | 3 | 3.5 | 3 | 3 | 3 |

TABLE 8h

Greenhouse data - T2 generation; Data are the average injury score (0-9 scale) of up to 4 individuals per homozygous T2 event. Injury was evaluated 1 week after treatment in the greenhouse. BAS800H refers to Saflufenacil/Kixor; BAS 850H refers to 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (or "Benzoxazin"), BAS850-Analog refers to 1-methyl-6-(trifluoromethyl)-3-(2,2,7-trifluoro-3-oxo-4-prop-2-ynyl-1,4-benzoxazin-6-yl)pyrimidine-2,4-dione (described in detail in WO2011/57935)

| Herbicide | g ai/ha | WT | AmtuPPX2L_R128A_F420L | AmtuPPX2L_R128A_F420M | AmtuPPX2L_R128A_F420I | AmtuPPX2L_R128A_F420V |
|---|---|---|---|---|---|---|
| unsprayed check | 0 | 0.5 | 1.3 | 1.0 | 1.0 | 1.3 |
| saflufenacil BAS 850H 1% (v/v) MSO | 100 50 | 9.0 | 4.3 | 4.0 | 2.0 | 2.7 |
| saflufenacil BAS 850H 1% (v/v) MSO | 200 100 | 9.0 | 4.5 | 5.0 | 1.8 | 2.8 |
| saflufenacil flumioxazin 1% (v/v) MSO | 100 140 | 9.0 | 4.8 | 5.0 | 0.5 | 2.0 |
| saflufenacil sulfentrazone 1% (v/v) MSO | 100 560 | 9.0 | 0.7 | 1.0 | 0.3 | 1.0 |
| saflufenacil BAS 850-Analog 1% (v/v) MSO | 100 50 | 9.0 | 5.0 | 6.0 | 5.0 | 4.7 |

25

TABLE 8i

Greenhouse data - T2 generation; Various mixture ratios of saflufenacil and 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione. Data are the average injury score (0-9 scale) of up to 4 individuals per homozygous T2 event. Injury was evaluated 1 week after treatment in the greenhouse. BAS800H refers to Saflufenacil/Kixor; BAS 850H refers to 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione ("Benzoxazin"), all mutants based on AmtuPPX2L (SEQ ID NO: 2 or 4)

| Herbicide | g ai/ha | wild type | R128A_F420L (event a) | R128A_F420L (event b) | R128A_F420V (event a) | R128A_F420V (event b) | R128A_F420V (event c) |
|---|---|---|---|---|---|---|---|
| saflufenacil + BAS 850H | unsprayed | 0.3 | 0.3 | 1.3 | 2.0 | 0.8 | 1.0 |
| | 6.25 + 3.125 | 8.3 | 4.0 | 6.0 | 0.5 | 0.3 | 0.0 |
| | 12.5 + 6.25 | 9.0 | 0.7 | 6.0 | 1.0 | 0.3 | 1.0 |
| | 25 + 12.5 | 9.0 | 1.5 | 7.5 | 1.7 | 1.0 | 3.5 |
| | 50 + 25 | 9.0 | 2.8 | 7.5 | 1.0 | 2.5 | 2.0 |
| | 100 + 50 | 9.0 | 5.0 | 6.0 | 2.3 | 2.3 | 4.0 |
| | 200 + 100 | 9.0 | 5.0 | 6.7 | 3.5 | 3.5 | 4.5 |
| | 400 + 200 | 9.0 | 4.7 | 8.5 | 3.3 | 2.8 | 4.3 |
| | 800 + 400 | 9.0 | 5.3 | 8.5 | 3.0 | 3.8 | 4.3 |

| Rating | Phenotype (phytotoxicity) of surviving plants |
|---|---|
| 1 | no obvious damage (no phytotoxicity) |
| 2 | minor amount of leaf damage, plant will survive |
| 3 | moderate amount of leaf damage, plant will survive |
| 4 | severe amount of leaf damage, plant will survive |
| 5 | no surviving plants - all plants dead/dying |

The following gives a definition of the injury scores measured above:

| Score | Description of injury |
|---|---|
| 0 | No Injury |
| 1 | Minimal injury, only a few patches of leaf injury or chlorosis. |
| 2 | Minimal injury with slightly stronger chlorosis, Overall growth points remain undamaged. |
| 3 | Slightly stronger injury on secondary leaf tissue, but primary leaf and growth points are still undamaged. |
| 4 | Overall plant morphology is slightly different, some chlorosis and necrosis in secondary growth points and leaf tissue. Stems are intact. Regrowth is highly probable within 1 week. |
| 5 | Overall plant morphology is clearly different, some chlorosis and necrosis on a few leaves and growth points, but primary growth point is intact. Stem tissue is still green. Regrowth is highly probably within 1 week. |

| Score | Description of injury |
|---|---|
| 6 | Strong injury can be seen on the new leaflet growth. Plant has a high probability to survive only through regrowth at different growth points. Most of the leaves are chlorotic/necrotic but stem tissue is still green. May have regrowth but with noticeable injured appearance. |
| 7 | Most of the active growth points are necrotic. There may be a single growth point that could survive and may be partially chlorotic or green and partially necrotic. Two leaves may still be chlorotic with some green; the rest of the plant including stem is necrotic. |
| 8 | Plant will likely die, and all growth points are necrotic. One leaf may still be chlorotic with some green. The remainder of the plant is necrotic. |
| 9 | Plant is dead. |
| * | Not tested |

The invention claimed is:

1. A method for controlling undesired vegetation at a plant cultivation site, the method comprising the steps of:
   a) providing, at said site, a plant that comprises at least one nucleic acid comprising a nucleotide sequence encoding a mutated protoporphyrinogen oxidase (PPO) which is resistant or tolerant to a PPO inhibiting herbicide and
   b) applying to said site an effective amount of said herbicide,
   wherein the mutated PPO comprises a sequence of SEQ ID NO: 2, a variant, derivative, orthologue, paralogue or homologue thereof, in which the amino acid at or corresponding to position 128 of SEQ ID NO:2 is Leu, Ala, Val, Ile, Met, Tyr, Gly, Asn, Cys, Phe, Ser, Thr, Gln, or His, and the amino acid at or corresponding to position 420 of SEQ ID NO:2 is Val.

2. The method according to claim 1, wherein the nucleotide sequence of a) comprises the sequence of SEQ ID NO: 1, 3, 5, 7, 9, 11, 13, 15, 17, 19, 21, 23, 25, 27, 29, 31, 33, 35, 37, 39, 41, 43, 45 or 47, or a variant or derivative thereof.

3. The method according to claim 1, wherein the plant comprises at least one additional heterologous nucleic acid comprising a nucleotide sequence encoding a herbicide tolerance enzyme.

4. The method according to claim 1, wherein the PPO inhibiting herbicide is applied in conjunction with one or more additional herbicides.

5. An isolated and/or recombinant and/or synthetic nucleic acid encoding a mutated PPO polypeptide, wherein the nucleic acid comprises the nucleotide sequence of SEQ ID NO: 1, 3, 5, 7, 9, 11, 13, 15, 17, 19, 21, 23, 25, 27, 29, 31, 33, 35, 37, 39, 41, 43, 45 or 47, or a variant or derivative thereof, wherein the mutated PPO comprises a sequence of SEQ ID NO: 2, a variant, derivative, orthologue, paralogue or homologue thereof, in which the amino acid at or corresponding to position 128 of SEQ ID NO:2 is Leu, Ala, Val, Ile, Met, Tyr, Gly, Asn, Cys, Phe, Ser, Thr, Gln, or His; and the amino acid at or corresponding to position 420 of SEQ ID NO: 2 is Val.

6. A mutated PPO polypeptide comprising a sequence of SEQ ID NO: 2, a variant, derivative, orthologue, paralogue or homologue thereof, in which the amino acid at or corresponding to position 128 of SEQ ID NO:2 is Leu, Ala, Val, Ile, Met, Tyr, Gly, Asn, Cys, Phe, Ser, Thr, Gln, or His, and the amino acid at or corresponding to position 420 of SEQ ID NO:2 is Val, wherein said mutated PPO polypeptide confers increased resistance or tolerance to a PPO inhibiting herbicide when expressed in a plant as compared to a wild type plant.

7. A transgenic plant cell transformed by and expressing a nucleic acid encoding a mutated PPO polypeptide as defined in claim 6, wherein expression of the nucleic acid in the plant cell results in increased resistance or tolerance to a PPO inhibiting herbicide as compared to a wild type variety of the plant cell.

8. The transgenic plant cell of claim 7, wherein the mutated PPO polypeptide encoding nucleic acid comprises a polynucleotide sequence selected from the group consisting of: a) a polynucleotide as shown in SEQ ID NO: 1, 3, 5, 7, 9, 11, 13, 15, 17, 19, 21, 23, 25, 27, 29, 31, 33, 35, 37, 39, 41, 43, 45 or 47, or a variant or derivative thereof; b) a polynucleotide encoding a polypeptide as shown in SEQ ID NO: 2, 4, 6, 8, 10, 12, 14, 16, 18, 20, 22, 24, 26, 28, 30, 32, 34, 36, 38, 40, 42, 44, 46, or 48, or a variant or derivative thereof; and c) a polynucleotide comprising at least 60 consecutive nucleotides of any of a) or b).

9. A transgenic plant comprising a plant cell of claim 7, wherein expression of the mutated PPO polypeptide encoding nucleic acid in the plant results in the plant's increased resistance to PPO inhibiting herbicide as compared to a wild type plant.

10. A plant cell mutagenized to obtain a plant cell which expresses a nucleic acid encoding a mutated PPO polypeptide of claim 6.

11. A plant that expresses a mutagenized or recombinant mutated PPO polypeptide of claim 6, and wherein said mutated PPO confers upon the plant increased herbicide tolerance as compared to the corresponding wild-type variety of the plant when expressed therein.

12. A method for growing a plant of claim 11 while controlling weeds in the vicinity of said plant, said method comprising the steps of:
  a) growing said plant; and
  b) applying a herbicide composition comprising a PPO-inhibiting herbicide to the plant and weeds, wherein the herbicide normally inhibits protoporphyrinogen oxidase, at a level of the herbicide that would inhibit the growth of a corresponding wild-type plant.

13. A seed produced by a plant of claim 11, wherein the seed is true breeding for an increased resistance to a PPO inhibiting herbicide as compared to a wild type variety of the seed.

14. A method of producing a transgenic plant cell with an increased resistance to a PPO inhibiting herbicide as compared to a wild type variety of the plant cell comprising, transforming the plant cell with an expression cassette comprising a nucleic acid encoding a mutated PPO polypeptide as defined in claim 6.

15. A method of producing a transgenic plant comprising, (a) transforming a plant cell with an expression cassette comprising a nucleic acid encoding a mutated PPO polypeptide as defined in claim 6, and (b) generating a plant with an increased resistance to PPO inhibiting herbicide from the plant cell.

16. The method of claim 14, wherein the nucleic acid encoding the mutated PPO polypeptide comprises a polynucleotide sequence selected from the group consisting of: a) a polynucleotide as shown in SEQ ID NO: 1, 3, 5, 7, 9, 11, 13, 15, 17, 19, 21, 23, 25, 27, 29, 31, 33, 35, 37, 39, 41, 43, 45 or 47, or a variant or derivative thereof; b) a polynucleotide encoding a polypeptide as shown in SEQ ID NO: 2, 4, 6, 8, 10, 12, 14, 16, 18, 20, 22, 24, 26, 28, 30, 32, 34, 36, 38, 40, 42, 44, 46, or 48, or a variant or derivative thereof; and c) a polynucleotide comprising at least 60 consecutive nucleotides of any of a) or b).

17. The method of claim 14, wherein the expression cassette further comprises a transcription initiation regulatory region and a translation initiation regulatory region that are functional in the plant.

18. An expression cassette comprising a nucleic acid encoding a mutated PPO polypeptide as defined in claim 6, a transcription initiation regulatory region and a translation initiation regulatory region that are functional in the plant, and a chloroplast-targeting sequence comprising a nucleotide sequence that encodes a chloroplast transit peptide.

19. The expression cassette of claim 18, wherein the targeting sequence comprises a nucleotide sequence that encodes a transit peptide comprising the amino acid sequence of SEQ ID NO: 49, 50, 51, 52, or 53.

20. A method of identifying or selecting a transformed plant cell, plant tissue, plant or part thereof comprising: i) providing a transformed plant cell, plant tissue, plant or part thereof, wherein said transformed plant cell, plant tissue, plant or part thereof comprises a polynucleotide as shown in SEQ ID NO: 1, 3, 5, 7, 9, 11, 13, 15, 17, 19, 21, 23, 25, 27, 29, 31, 33, 35, 37, 39, 41, 43, 45 or 47, or a variant or derivative thereof, wherein the polynucleotide encodes a mutated PPO polypeptide as defined in claim 7 that is used as a selection marker, and wherein said transformed plant cell, plant tissue, plant or part thereof may comprise a further isolated polynucleotide; ii) contacting the transformed plant cell, plant tissue, plant or part thereof with at least one PPO inhibiting compound; iii) determining whether the plant cell, plant tissue, plant or part thereof is affected by the PPO inhibiting compound; and iv) identifying or selecting the transformed plant cell, plant tissue, plant or part thereof.

21. The method of claim 1, wherein the amino acid at or corresponding to position 128 of SEQ ID NO:2 is Ala and the amino acid at or corresponding to position 420 of SEQ ID NO:2 is Val.

22. The method of claim 1, wherein mutated PPO comprises an amino acid sequence of SEQ ID NO:2 with the following amino acid substitutions: Arg128Ala and Phe420Val.

23. The nucleic acid of claim 5, wherein the amino acid at or corresponding to position 128 of SEQ ID NO:2 is Ala and the amino acid at or corresponding to position 420 of SEQ ID NO:2 is Val.

24. The nucleic acid of claim 5, wherein mutated PPO comprises an amino acid sequence of SEQ ID NO:2 with the following amino acid substitutions: Arg128Ala and Phe420Val.

25. The mutated PPO polypeptide of claim 6, wherein the amino acid at or corresponding to position 128 of SEQ ID NO:2 is Ala and the amino acid at or corresponding to position 420 of SEQ ID NO:2 is Val.

26. The mutated PPO polypeptide of claim 6, wherein mutated PPO polypeptide comprises an amino acid sequence of SEQ ID NO:2 with the following amino acid substitutions: Arg128Ala and Phe420Val.

27. The transgenic plant cell of claim 7, wherein the amino acid at or corresponding to position 128 of SEQ ID NO:2 is Ala and the amino acid at or corresponding to position 420 of SEQ ID NO:2 is Val.

28. The transgenic plant cell of claim 7, wherein mutated PPO polypeptide comprises an amino acid sequence of SEQ ID NO:2 with the following amino acid substitutions: Arg128Ala and Phe420Val.

* * * * *

SEQUENCE LISTING

<160> NUMBER OF SEQ ID NOS: 56

<210> SEQ ID NO 1
<211> LENGTH: 1605
<212> TYPE: DNA
<213> ORGANISM: Amaranthus tuberculatus

<400> SEQUENCE: 1

```
atggtaattc aatccattac ccacctttca ccaaaccttg cattgccatc gccattgtca      60
gtttcaacca agaactaccc agtagctgta atgggcaaca tttctgagcg ggaagaaccc     120
acttctgcta aaagggttgc tgttgttggt gctggagtta gtggacttgc tgctgcatat     180
aagctaaaat cccatggttt gagtgtgaca ttgtttgaag ctgattctag agctggaggc     240
aaacttaaaa ctgttaaaaa agatggtttt atttgggatg aggggcaaa tactatgaca      300
gaaagtgagg cagaggtctc gagtttgatc gatgatcttg ggcttcgtga gaagcaacag     360
ttgccaattt cacaaaataa aagatacata gctagagacg tcttcctgt gctactacct      420
tcaaatcccg ctgcactact cacgagcaat atcctttcag caaaatcaaa gctgcaaatt     480
atgttggaac catttctctg gagaaaacac aatgctactg aacttctga tgagcatgtt      540
caggaaagcg ttggtgaatt ttttgagcga cattttggga aagagtttgt tgattatgtt     600
atcgacccctt ttgttgcggg tacatgtggt ggagatcctc aatcgctttc catgcaccat   660
acatttccag aagtatggaa tattgaaaaa aggtttggct ctgtgtttgc tggactaatt    720
caatcaacat tgttatctaa gaaggaaaag ggtggagaaa atgcttctat taagaagcct    780
cgtgtacgtg ttcattttc atttcaaggt ggaatgcaga cacttgttga cacaatgtgc    840
aaacagcttg gtgaagatga actcaaactc cagtgtgagg tgctgtcctt gtcatataac    900
cagaagggga tcccctcatt agggaattgg tcagtctctt ctatgtcaaa taataccagt    960
gaagatcaat cttatgatgc tgtggttgtc actgctccaa ttcgcaatgt caaagaaatg  1020
aagattatga aatttggaaa tccattttca cttgacttta ttccagaggt gacgtacgta  1080
ccccttttccg ttatgattac tgcattcaaa aaggataaag tgaagagacc tcttgagggc  1140
ttcggagttc ttatccctc taaagagcaa cataatggac tgaagactct tggtacttta  1200
ttttcctcca tgatgtttcc tgatcgtgct ccatctgaca tgtgtctctt tactacattt  1260
gtcggaggaa gcagaaatag aaaacttgca aacgcttcaa cggatgaatt gaagcaaata  1320
gtttcttctg accttcagca gctgttgggc actgaggacg aaccttcatt tgtcaatcat  1380
ctcttttgga gcaacgcatt cccattgtat ggacacaatt acgattctgt tttgagagcc  1440
atagacaaga tggaaaagga tcttcctgga ttttttttatg caggtaacca taagggtgga  1500
```

```
ctttcagtgg gaaaagcgat ggcctccgga tgcaaggctg cggaacttgt aatatcctat    1560
ctggactctc atatatacgt gaagatggat gagaagaccg cgtaa                   1605
```

<210> SEQ ID NO 2
<211> LENGTH: 534
<212> TYPE: PRT
<213> ORGANISM: Amaranthus tuberculatum

<400> SEQUENCE: 2

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Leu Pro Ile Ser Gln Asn Lys Arg
            115                 120                 125

Tyr Ile Ala Arg Asp Gly Leu Pro Val Leu Leu Pro Ser Asn Pro Ala
130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
            195                 200                 205

Cys Gly Gly Asp Pro Gln Ser Leu Ser Met His His Thr Phe Pro Glu
        210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
            275                 280                 285

Lys Leu Gln Cys Glu Val Leu Ser Leu Ser Tyr Asn Gln Lys Gly Ile
290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Thr Ala Pro Ile Arg Asn
                325                 330                 335

Val Lys Glu Met Lys Ile Met Lys Phe Gly Asn Pro Phe Ser Leu Asp
            340                 345                 350

Phe Ile Pro Glu Val Thr Tyr Val Pro Leu Ser Val Met Ile Thr Ala
```

```
                355             360              365
Phe Lys Lys Asp Lys Val Lys Arg Pro Leu Glu Gly Phe Gly Val Leu
    370             375             380

Ile Pro Ser Lys Glu Gln His Asn Gly Leu Lys Thr Leu Gly Thr Leu
385             390             395              400

Phe Ser Ser Met Met Phe Pro Asp Arg Ala Pro Ser Asp Met Cys Leu
            405             410             415

Phe Thr Thr Phe Val Gly Gly Ser Arg Asn Arg Lys Leu Ala Asn Ala
            420             425             430

Ser Thr Asp Glu Leu Lys Gln Ile Val Ser Ser Asp Leu Gln Gln Leu
            435             440             445

Leu Gly Thr Glu Asp Glu Pro Ser Phe Val Asn His Leu Phe Trp Ser
    450             455             460

Asn Ala Phe Pro Leu Tyr Gly His Asn Tyr Asp Ser Val Leu Arg Ala
465             470             475              480

Ile Asp Lys Met Glu Lys Asp Leu Pro Gly Phe Phe Tyr Ala Gly Asn
            485             490             495

His Lys Gly Gly Leu Ser Val Gly Lys Ala Met Ala Ser Gly Cys Lys
            500             505             510

Ala Ala Glu Leu Val Ile Ser Tyr Leu Asp Ser His Ile Tyr Val Lys
            515             520             525

Met Asp Glu Lys Thr Ala
    530
```

<210> SEQ ID NO 3
<211> LENGTH: 1605
<212> TYPE: DNA
<213> ORGANISM: Amaranthus tuberculatus

<400> SEQUENCE: 3

```
atggtaattc aatccattac ccacctttca ccaaaccttg cattgccatc gccattgtca    60
gtttcaacca agaactaccc agtagctgta atgggcaaca tttctgagcg ggaagaaccc   120
acttctgcta aagggttgc tgttgttggt gctggagtta gtggacttgc tgctgcatat    180
aagctaaaat cccatggttt gagtgtgaca ttgtttgaag ctgattctag agctggaggc   240
aaacttaaaa ctgttaaaaa agatggtttt atttgggatg aggggggcaaa tactatgaca   300
gaaagtgagg cagaggtctc gagtttgatc gatgatcttg gcttcgtga aagcaacag    360
ttgccaattt cacaaaataa aagatacata gctagagccg tcttcctgt gctactacct    420
tcaaatcccg ctgcactact cacgagcaat atcctttcag caaaatcaaa gctgcaaatt    480
atgttggaac catttctctg gagaaaacac aatgctactg aactttctga tgagcatgtt    540
caggaaagcg ttggtgaatt ttttgagcga cattttggga aagagtttgt tgattatgtt    600
attgaccctt tgttgcggg tacatgtggt ggagatcctc aatcgctttc catgcaccat    660
acatttccag aagtatggaa tattgaaaaa ggtttggct ctgtgtttgc cggactaatt    720
caatcaacat tgttatctaa gaaggaaaag ggtggagaaa atgcttctat taagaagcct    780
cgtgtacgtg gttcatttc atttcaaggt ggaatgcaga cacttgttga cacaatgtgc    840
aaacagcttg gtgaagatga actcaaactc cagtgtgagg tgctgtcctt gtcatataac    900
cagaagggga tcccctcact agggaattgg tcagtctctt ctatgtcaaa taataccagt    960
gaagatcaat cttatgatgc tgtggttgtc actgctccaa ttcgcaatgt caaagaaatg   1020
aagattatga aatttggaaa tccatttca cttgactta ttccagaggt gacgtacgta   1080
```

-continued

```
ccccttttccg ttatgattac tgcattcaaa aaggataaag tgaagagacc tcttgagggc    1140
ttcggagttc ttatcccctc taaagagcaa cataatggac tgaagactct tggtacttta    1200
ttttcctcca tgatgtttcc tgatcgtgct ccatctgaca tgtgtctctt tactacattt    1260
gtcggaggaa gcagaaatag aaaacttgca aacgcttcaa cggatgaatt gaagcaaata    1320
gtttcttctg accttcagca gctgttgggc actgaggacg aaccttcatt tgtcaatcat    1380
ctctttggga gcaacgcatt cccattgtat ggacacaatt acgattctgt tttgagagcc    1440
atagacaaga tggaaaagga tcttcctgga tttttttatg caggtaacca taagggtgga    1500
ctttcagtgg gaaaagcgat ggcctccgga tgcaaggctg cggaacttgt aatatcctat    1560
ctggactctc atatatacgt gaagatggat gagaagaccg cgtaa                    1605
```

<210> SEQ ID NO 4
<211> LENGTH: 534
<212> TYPE: PRT
<213> ORGANISM: Amaranthus tuberculatum

<400> SEQUENCE: 4

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Ala Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Gln Ser Leu Ser Met His His Thr Phe Pro Glu
    210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
        275                 280                 285
```

```
Lys Leu Gln Cys Glu Val Leu Ser Leu Ser Tyr Asn Gln Lys Gly Ile
        290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Thr Ala Pro Ile Arg Asn
                325                 330                 335

Val Lys Glu Met Lys Ile Met Lys Phe Gly Asn Pro Phe Ser Leu Asp
                340                 345                 350

Phe Ile Pro Glu Val Thr Tyr Val Pro Leu Ser Val Met Ile Thr Ala
                355                 360                 365

Phe Lys Lys Asp Lys Val Lys Arg Pro Leu Glu Gly Phe Gly Val Leu
                370                 375                 380

Ile Pro Ser Lys Glu Gln His Asn Gly Leu Lys Thr Leu Gly Thr Leu
385                 390                 395                 400

Phe Ser Ser Met Met Phe Pro Asp Arg Ala Pro Ser Asp Met Cys Leu
                405                 410                 415

Phe Thr Thr Phe Val Gly Gly Ser Arg Asn Arg Lys Leu Ala Asn Ala
                420                 425                 430

Ser Thr Asp Glu Leu Lys Gln Ile Val Ser Ser Asp Leu Gln Gln Leu
                435                 440                 445

Leu Gly Thr Glu Asp Glu Pro Ser Phe Val Asn His Leu Phe Trp Ser
450                 455                 460

Asn Ala Phe Pro Leu Tyr Gly His Asn Tyr Asp Ser Val Leu Arg Ala
465                 470                 475                 480

Ile Asp Lys Met Glu Lys Asp Leu Pro Gly Phe Phe Tyr Ala Gly Asn
                485                 490                 495

His Lys Gly Gly Leu Ser Val Gly Lys Ala Met Ala Ser Gly Cys Lys
                500                 505                 510

Ala Ala Glu Leu Val Ile Ser Tyr Leu Asp Ser His Ile Tyr Val Lys
                515                 520                 525

Met Asp Glu Lys Thr Ala
    530
```

<210> SEQ ID NO 5
<211> LENGTH: 1602
<212> TYPE: DNA
<213> ORGANISM: Amaranthus tuberculatus

<400> SEQUENCE: 5

```
atggtaattc aatccattac ccaccttca ccaaaccttg cattgccatc gccattgtca      60
gtttccacca agaactaccc agtagctgta atgggcaaca tttctgagcg agaagaaccc    120
acttctgcta aagggttgc tgttgttggt gctggagtta gtggacttgc tgctgcatat    180
aagctaaaat cccatggttt gagtgtgaca ttgtttgaag ctgattctag agctggaggc    240
aaacttaaaa ctgttaaaaa agatggtttt atttgggatg aggggggcaaa tactatgaca   300
gaaagtgagg cagaggtctc gagtttgatc gatgatcttg ggcttcgtga aagcaacag    360
ttgccaattt cacaaaataa agatacata gctagacg tcttcctgt gctactacct    420
tcaaatcccg ctgcactact cacgagcaat atcctttcag caaaatcaaa gctgcaaatt    480
atgttggaac catttctctg gagaaaacac aatgctactg aacttctga tgagcatgtt    540
caggaaagcg ttggtgaatt ttttgagcga catttgggga aagagtttgt tgattatgtt    600
attgaccctt tgttgcggg tacatgtgga gatcctcaat cgctttccat gcaccataca    660
```

```
tttccagaag tatggaatat tgaaaaaagg tttggctctg tgtttgctgg actaattcaa    720
tcaacattgt tatctaagaa ggaaaagggt ggagaaaatg cttctattaa gaagcctcgt    780
gtacgtggtt cattttcatt tcaaggtgga atgcagacac ttgttgacac aatgtgcaaa    840
cagcttggtg aagatgaact caaactccag tgtgaggtgc tgtccttgtc atataaccag    900
aagggatcc cctcattagg gaattggtca gtctcttcta tgtcaaataa taccagtgaa     960
gatcaatctt atgatgctgt ggttgtcact gctccaattc gcaatgtcaa agaaatgaag   1020
attatgaaat ttggaaatcc attttcactt gactttattc cagaggtgac gtacgtaccc   1080
ctttccgtta tgattactgc attcaaaaag gataaagtga agagacctct tgagggcttc   1140
ggagttctta tcccctctaa agagcaacat aatggactga agactcttgg tactttattt   1200
tcctccatga tgtttcctga tcgtgctcca tctgacatgt gtctctttac tacatttgtc   1260
ggaggaagca gaaatagaaa acttgcaaac gcttcaacgg atgaattgaa gcaaatagtt   1320
tcttctgacc ttcagcagct gttgggcact gaggacgaac cttcatttgt caatcatctc   1380
ttttggagca acgcattccc attgtatgga cacaattacg attgtgtttt gagagccata   1440
gacaagatgg aaaaggatct tcctggattt ttttatgcag gtaaccataa gggtggactt   1500
tcagtgggaa aagcgatggc ctccggatgc aaggctgcgg aacttgtaat atcctatctg   1560
gactctcata tatacgtgaa gatggatgag aagaccgcgt aa                      1602
```

<210> SEQ ID NO 6  
<211> LENGTH: 533  
<212> TYPE: PRT  
<213> ORGANISM: Amaranthus tuberculatum

<400> SEQUENCE: 6

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205
```

```
Cys Gly Asp Pro Gln Ser Leu Ser Met His His Thr Phe Pro Glu Val
    210                 215                 220
Trp Asn Ile Glu Lys Arg Phe Gly Ser Val Phe Ala Gly Leu Ile Gln
225                 230                 235                 240
Ser Thr Leu Leu Ser Lys Lys Glu Lys Gly Gly Glu Asn Ala Ser Ile
                245                 250                 255
Lys Lys Pro Arg Val Arg Gly Ser Phe Ser Phe Gln Gly Gly Met Gln
            260                 265                 270
Thr Leu Val Asp Thr Met Cys Lys Gln Leu Gly Glu Asp Glu Leu Lys
        275                 280                 285
Leu Gln Cys Glu Val Leu Ser Leu Ser Tyr Asn Gln Lys Gly Ile Pro
    290                 295                 300
Ser Leu Gly Asn Trp Ser Val Ser Ser Met Ser Asn Asn Thr Ser Glu
305                 310                 315                 320
Asp Gln Ser Tyr Asp Ala Val Val Thr Ala Pro Ile Arg Asn Val
                325                 330                 335
Lys Glu Met Lys Ile Met Lys Phe Gly Asn Pro Phe Ser Leu Asp Phe
            340                 345                 350
Ile Pro Glu Val Thr Tyr Val Pro Leu Ser Val Met Ile Thr Ala Phe
        355                 360                 365
Lys Lys Asp Lys Val Lys Arg Pro Leu Glu Gly Phe Gly Val Leu Ile
    370                 375                 380
Pro Ser Lys Glu Gln His Asn Gly Leu Lys Thr Leu Gly Thr Leu Phe
385                 390                 395                 400
Ser Ser Met Met Phe Pro Asp Arg Ala Pro Ser Asp Met Cys Leu Phe
                405                 410                 415
Thr Thr Phe Val Gly Gly Ser Arg Asn Arg Lys Leu Ala Asn Ala Ser
            420                 425                 430
Thr Asp Glu Leu Lys Gln Ile Val Ser Ser Asp Leu Gln Gln Leu Leu
        435                 440                 445
Gly Thr Glu Asp Glu Pro Ser Phe Val Asn His Leu Phe Trp Ser Asn
    450                 455                 460
Ala Phe Pro Leu Tyr Gly His Asn Tyr Asp Cys Val Leu Arg Ala Ile
465                 470                 475                 480
Asp Lys Met Glu Lys Asp Leu Pro Gly Phe Phe Tyr Ala Gly Asn His
                485                 490                 495
Lys Gly Gly Leu Ser Val Gly Lys Ala Met Ala Ser Gly Cys Lys Ala
            500                 505                 510
Ala Glu Leu Val Ile Ser Tyr Leu Asp Ser His Ile Tyr Val Lys Met
        515                 520                 525
Asp Glu Lys Thr Ala
    530

<210> SEQ ID NO 7
<211> LENGTH: 1602
<212> TYPE: DNA
<213> ORGANISM: Amaranthus tuberculatus

<400> SEQUENCE: 7
atggtaattc aatccattac ccacctttca ccaaaccttg cattgccatc gccattgtca      60
gtttccacca agaactaccc agtagctgta atgggcaaca tttctgagcg ggaagaaccc     120
acttctgcta aagggttgc tgttgttggt gctggagtta gtggacttgc tgctgcatat     180
aagctaaaat cccatggttt gagtgtgaca ttgtttgaag ctaattctag agctggaggc    240
```

```
aaacttaaaa ctgttaaaaa agatggtttt atttgggatg aggggggcaaa tactatgaca      300 gaaagtgagg cagaggtctc gagtttgatc gatgatcttg ggcttcgtga aagcaacag       360 ttgccaattt cacaaaataa agatacata gctagagacg tcttcctgt gctactacct       420 tcaaatcccg ctgcactact cacgagcaat atcctttcag caaaatcaaa gctgcaaatt      480
atgttggaac catttctctg gagaaaacac aatgctactg aactttctga tgagcatgtt      540
caggaaagcg ttggtgaatt ttttgagcga cattttggga aagagtttgt tgattatgtt      600
attgaccctt ttgttgcggg tacatgtgga gatcctcaat cgctttccat gtaccataca      660
tttccagaag tatggaatat tgaaaaaagg tttggctctg tgtttgctgg actaattcaa      720
tcaacattgt tatctaagaa ggaaaagggt ggagaaaatg cttctattaa gaagcctcgt      780
gtacgtggtt cattttcatt tcaaggtgga atgcagacac ttgttgacac aatgtgcaaa      840
cagcttggtg aagatgaact caaactccag tgtgaggtgc tgtccttgtc atataaccag      900
aaggggatcc cctcattagg gaattggtca gtctcttcta tgtcaaataa taccagtgaa      960
gatcaatctt atgatgctgt ggttgtcact gctccaattc gcaatgtcaa agaaatgaag     1020
attatgaaat ttggaaatcc attttcactt gactttattc cagaggtgac gtacgtaccc     1080
ctttccgtta tgattactgc attcaaaaag ataaagtga agagacctct tgagggcttc      1140
ggagttctta tccctctaa agagcaacat aatggactga agactcttgg tactttattt     1200
tcctccatga tgtttcctga tcgtgctcca tctgacatgt gtctctttac tacatttgtc     1260
ggaggaagca gaaatagaaa acttgcaaac gcttcaacgg atgaattgaa gcaaatagtt     1320
tcttctgacc ttcagcagct gttgggcact gaggacgaac cttcatttgt caatcatctc     1380
ttttggagca acgcattccc attgtatgga cacaattacg attctgtttt gagagccata     1440
gacaagatgg aaaaggatct tcctggattt ttttatgcag gtaaccataa gggtggactt     1500
tcagtgggaa aagcgatggc ctccggatgc aaggctgcgg aacttgtaat atcctatctg     1560
gactctcata tatacgtgaa gatggatgag aagaccgcgt aa                       1602
```

<210> SEQ ID NO 8
<211> LENGTH: 533
<212> TYPE: PRT
<213> ORGANISM: Amaranthus tuberculatum

<400> SEQUENCE: 8

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asn Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
```

```
            130                 135                 140
Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Asp Pro Gln Ser Leu Ser Met Tyr His Thr Phe Pro Glu Val
        210                 215                 220

Trp Asn Ile Glu Lys Arg Phe Gly Ser Val Phe Ala Gly Leu Ile Gln
225                 230                 235                 240

Ser Thr Leu Leu Ser Lys Lys Glu Lys Gly Gly Glu Asn Ala Ser Ile
                245                 250                 255

Lys Lys Pro Arg Val Arg Gly Ser Phe Ser Phe Gln Gly Gly Met Gln
                260                 265                 270

Thr Leu Val Asp Thr Met Cys Lys Gln Leu Gly Glu Asp Glu Leu Lys
                275                 280                 285

Leu Gln Cys Glu Val Leu Ser Leu Ser Tyr Asn Gln Lys Gly Ile Pro
            290                 295                 300

Ser Leu Gly Asn Trp Ser Val Ser Ser Met Ser Asn Asn Thr Ser Glu
305                 310                 315                 320

Asp Gln Ser Tyr Asp Ala Val Val Val Thr Ala Pro Ile Arg Asn Val
                325                 330                 335

Lys Glu Met Lys Ile Met Lys Phe Gly Asn Pro Phe Ser Leu Asp Phe
                340                 345                 350

Ile Pro Glu Val Thr Tyr Val Pro Leu Ser Val Met Ile Thr Ala Phe
                355                 360                 365

Lys Lys Asp Lys Val Lys Arg Pro Leu Glu Gly Phe Gly Val Leu Ile
                370                 375                 380

Pro Ser Lys Glu Gln His Asn Gly Leu Lys Thr Leu Gly Thr Leu Phe
385                 390                 395                 400

Ser Ser Met Met Phe Pro Asp Arg Ala Pro Ser Asp Met Cys Leu Phe
                405                 410                 415

Thr Thr Phe Val Gly Gly Ser Arg Asn Arg Lys Leu Ala Asn Ala Ser
                420                 425                 430

Thr Asp Glu Leu Lys Gln Ile Val Ser Ser Asp Leu Gln Gln Leu Leu
                435                 440                 445

Gly Thr Glu Asp Glu Pro Ser Phe Val Asn His Leu Phe Trp Ser Asn
450                 455                 460

Ala Phe Pro Leu Tyr Gly His Asn Tyr Asp Ser Val Leu Arg Ala Ile
465                 470                 475                 480

Asp Lys Met Glu Lys Asp Leu Pro Gly Phe Phe Tyr Ala Gly Asn His
                485                 490                 495

Lys Gly Gly Leu Ser Val Gly Lys Ala Met Ala Ser Gly Cys Lys Ala
                500                 505                 510

Ala Glu Leu Val Ile Ser Tyr Leu Asp Ser His Ile Tyr Val Lys Met
            515                 520                 525

Asp Glu Lys Thr Ala
        530

<210> SEQ ID NO 9
```

<211> LENGTH: 1644
<212> TYPE: DNA
<213> ORGANISM: Arabidopsis thaliana

<400> SEQUENCE: 9

| | | | | | |
|---|---|---|---|---|---|
| atgggcctga | ttaaaaacgg | tacccttat | tgtcgttttg | ggataagctg | gaattttgcc | 60 |
| gctgtgtttt | tttctactta | tttccgtcac | tgctttcgac | tggtcagaga | ttttgactct | 120 |
| gaattgttgc | agatagcaat | ggcgtctgga | gcagtagcag | atcatcaaat | tgaagcggtt | 180 |
| tcaggaaaaa | gagtcgcagt | cgtaggtgca | ggtgtaagtg | gacttgcggc | ggcttacaag | 240 |
| ttgaaatcga | ggggtttgaa | tgtgactgtg | tttgaagctg | atggaagagt | aggtgggaag | 300 |
| ttgagaagtg | ttatgcaaaa | tggtttgatt | tgggatgaag | gagcaaacac | catgactgag | 360 |
| gctgagccag | aagttgggag | tttacttgat | gatcttgggc | ttcgtgagaa | caacaattt | 420 |
| ccaatttcac | agaaaaagcg | gtatattgtg | cggaatggtg | tacctgtgat | gctacctacc | 480 |
| aatcccatag | agctggtcac | aagtagtgtg | ctctctaccc | aatctaagtt | caaatcttg | 540 |
| ttggaaccat | ttttatggaa | gaaaaagtcc | tcaaaagtct | cagatgcatc | tgctgaagaa | 600 |
| agtgtaagcg | agttctttca | acgccatttt | ggacaagagg | ttgttgacta | tctcatcgac | 660 |
| ccttttgttg | gtggaacaag | tgctgcggac | cctgattccc | tttcaatgaa | gcattctttc | 720 |
| ccagatctct | ggaatagttt | tggctctatt | atagtcggtg | caatcagaac | aaagtttgct | 780 |
| gctaaaggtg | gtaaaagtag | agacacaaag | agttctcctg | gcacaaaaaa | gggttcgcgt | 840 |
| gggtcattct | cttttaaggg | gggaatgcag | attcttcctg | atacgttgtg | caaaagtctc | 900 |
| tcacatgatg | agatcaattt | agactccaag | gtactctctt | tgtcttacaa | ttctggatca | 960 |
| agacaggaga | actggtcatt | atcttgtgtt | tcgcataatg | aaacgcagag | acaaaacccc | 1020 |
| cattatgatg | ctgctcctct | gtgcaatgtg | aaggagatga | aggttatgaa | aggaggacaa | 1080 |
| cccttcagc | taaactttct | ccccgagatt | aattacatgc | cctctcggt | tttaatcacc | 1140 |
| acattcacaa | aggagaaagt | aaagagacct | cttgaaggct | tgggggtact | cattccatct | 1200 |
| aaggagcaaa | agcatggttt | caaaactcta | ggtacacttt | tttcatcaat | gatgtttcca | 1260 |
| gatcgttccc | ctagtgacgt | tcatctatat | acaacttta | ttggtgggag | taggaaccag | 1320 |
| gaactagcca | agcttccac | tgacgaatta | aaacaagttg | tgacttctga | ccttcagcga | 1380 |
| ctgttggggg | ttgaaggtga | acccgtgtct | gtcaaccatt | actattggag | gaaagcattc | 1440 |
| ccgttgtatg | acagcagcta | tgactcagtc | atggaagcaa | ttgacaagat | ggagaatgat | 1500 |
| ctacctgggt | tcttctatgc | aggtaatcat | cgagggggc | tctctgttgg | gaaatcaata | 1560 |
| gcatcaggtt | gcaaagcagc | tgaccttgtg | atctcatacc | tggagtcttg | ctcaaatgac | 1620 |
| aagaaaccaa | atgacagctt | ataa | | | | 1644 |

<210> SEQ ID NO 10
<211> LENGTH: 547
<212> TYPE: PRT
<213> ORGANISM: Arabidopsis thaliana

<400> SEQUENCE: 10

Met Gly Leu Ile Lys Asn Gly Thr Leu Tyr Cys Arg Phe Gly Ile Ser
1               5                   10                  15

Trp Asn Phe Ala Ala Val Phe Phe Ser Thr Tyr Phe Arg His Cys Phe
                20                  25                  30

Arg Leu Val Arg Asp Phe Asp Ser Glu Leu Leu Gln Ile Ala Met Ala
            35                  40                  45

-continued

Ser Gly Ala Val Ala Asp His Gln Ile Glu Ala Val Ser Gly Lys Arg
 50                  55                  60

Val Ala Val Val Gly Ala Gly Val Ser Gly Leu Ala Ala Ala Tyr Lys
 65                  70                  75                  80

Leu Lys Ser Arg Gly Leu Asn Val Thr Val Phe Glu Ala Asp Gly Arg
                 85                  90                  95

Val Gly Gly Lys Leu Arg Ser Val Met Gln Asn Gly Leu Ile Trp Asp
                100                 105                 110

Glu Gly Ala Asn Thr Met Thr Glu Ala Glu Pro Glu Val Gly Ser Leu
                115                 120                 125

Leu Asp Asp Leu Gly Leu Arg Glu Lys Gln Gln Phe Pro Ile Ser Gln
130                 135                 140

Lys Lys Arg Tyr Ile Val Arg Asn Gly Val Pro Val Met Leu Pro Thr
145                 150                 155                 160

Asn Pro Ile Glu Leu Val Thr Ser Ser Val Leu Ser Thr Gln Ser Lys
                165                 170                 175

Phe Gln Ile Leu Leu Glu Pro Phe Leu Trp Lys Lys Ser Ser Lys
                180                 185                 190

Val Ser Asp Ala Ser Ala Glu Glu Ser Val Ser Glu Phe Phe Gln Arg
                195                 200                 205

His Phe Gly Gln Glu Val Val Asp Tyr Leu Ile Asp Pro Phe Val Gly
                210                 215                 220

Gly Thr Ser Ala Ala Asp Pro Asp Ser Leu Ser Met Lys His Ser Phe
225                 230                 235                 240

Pro Asp Leu Trp Asn Ser Phe Gly Ser Ile Ile Val Gly Ala Ile Arg
                245                 250                 255

Thr Lys Phe Ala Ala Lys Gly Gly Lys Ser Arg Asp Thr Lys Ser Ser
                260                 265                 270

Pro Gly Thr Lys Lys Gly Ser Arg Gly Ser Phe Ser Phe Lys Gly Gly
                275                 280                 285

Met Gln Ile Leu Pro Asp Thr Leu Cys Lys Ser Leu Ser His Asp Glu
                290                 295                 300

Ile Asn Leu Asp Ser Lys Val Leu Ser Leu Ser Tyr Asn Ser Gly Ser
305                 310                 315                 320

Arg Gln Glu Asn Trp Ser Leu Ser Cys Val Ser His Asn Glu Thr Gln
                325                 330                 335

Arg Gln Asn Pro His Tyr Asp Ala Ala Pro Leu Cys Asn Val Lys Glu
                340                 345                 350

Met Lys Val Met Lys Gly Gly Gln Pro Phe Gln Leu Asn Phe Leu Pro
                355                 360                 365

Glu Ile Asn Tyr Met Pro Leu Ser Val Leu Ile Thr Thr Phe Thr Lys
                370                 375                 380

Glu Lys Val Lys Arg Pro Leu Glu Gly Phe Gly Val Leu Ile Pro Ser
385                 390                 395                 400

Lys Glu Gln Lys His Gly Phe Lys Thr Leu Gly Thr Leu Phe Ser Ser
                405                 410                 415

Met Met Phe Pro Asp Arg Ser Pro Ser Asp Val His Leu Tyr Thr Thr
                420                 425                 430

Phe Ile Gly Gly Ser Arg Asn Gln Glu Leu Ala Lys Ala Ser Thr Asp
                435                 440                 445

Glu Leu Lys Gln Val Val Thr Ser Asp Leu Gln Arg Leu Leu Gly Val
450                 455                 460

Glu Gly Glu Pro Val Ser Val Asn His Tyr Tyr Trp Arg Lys Ala Phe

```
       465                 470                 475                 480
Pro Leu Tyr Asp Ser Ser Tyr Asp Ser Val Met Glu Ala Ile Asp Lys
                    485                 490                 495

Met Glu Asn Asp Leu Pro Gly Phe Phe Tyr Ala Gly Asn His Arg Gly
                500                 505                 510

Gly Leu Ser Val Gly Lys Ser Ile Ala Ser Gly Cys Lys Ala Ala Asp
            515                 520                 525

Leu Val Ile Ser Tyr Leu Glu Ser Cys Ser Asn Asp Lys Lys Pro Asn
        530                 535                 540

Asp Ser Leu
545

<210> SEQ ID NO 11
<211> LENGTH: 1647
<212> TYPE: DNA
<213> ORGANISM: Nicotiana tabacum

<400> SEQUENCE: 11
atgacaacaa ctcccatcgc caatcatcct aatattttca ctcaccagtc gtcgtcatcg      60
ccattggcat tcttaaaccg tacgagtttc atccctttct cttcaatctc caagcgcaat     120
agtgtcaatt gcaatggctg agaacacga tgctccgttg ccaaagatta cacagttcct      180
tcctcagcgg tcgacggcgg acccgccgcg gagctggact gtgttatagt tggagcagga     240
attagtggcc tctgcattgc gcaggtgatg tccgctaatt accccaattt gatggtaacc     300
gaggcgagag atcgtgccgg tgcaacata cgactgtgg aaagagacgg ctatttgtgg       360
gaagaaggtc ccaacagttt ccagccgtcc gatcctatgt tgactatggc agtagattgt     420
ggattgaagg atgatttggt gttgggagat cctaatgcgc cccgtttcgt tttgtggaag     480
ggtaaattaa ggcccgtccc ctcaaaactc actgatcttc cctttttttga tttgatgagc    540 attcctggca agttgagagc tggttttggt gccattggcc tccgcccttc acctccaggt     600
catgaggaat cagttgagca gttcgtgcgt cgtaatcttg gtggcgaagt ctttgaacgc     660
ttgatagaac cattttgttc tggtgtttat gctggtgatc cctcaaaact gagtatgaaa     720
gcagcatttg ggaaagtttg gaagttggaa gaaactggtg gtagcattat ggaggaacc     780 tttaaagcaa taaaggagag atccagtaca cctaaagcgc cccgcgatcc gcgtttacct    840
aaaccaaaag gacagacagt tggatcattc aggaagggtc tcagaatgct gccggatgca     900
atcagtgcaa gattgggaag caaattaaaa ctatcatgga agctttctag cattactaag     960
tcagaaaaag gaggatatca cttgacatac gagacaccag aaggagtagt ttctcttcaa    1020
agtcgaagca ttgtcatgac tgtgccatcc tatgtagcaa gcaacatatt acgtcctctt    1080
tcggttgccg cagcagatgc actttcaaat ttctactatc ccccagttgg agcagtcaca    1140
atttcatatc ctcaagaagc tattcgtgat gagcgtctgg ttgatggtga actaaaggga    1200
tttgggcagt tgcatccacg tacacaggga gtggaaacac taggaacgat atatagttca    1260
tcactcttcc ctaaccgtgc cccaaaaggt cgggtgctac tcttgaacta cattggagga    1320
gcaaaaaatc ctgaaatttt gtctaagacg gagagccaac ttgtggaagt agttgatcgt    1380
gacctcagaa aaatgcttat aaaacccaaa gctcaagatc tcttgttgt gggtgtgcga    1440 gtatggccac aagctatccc acagttttg gttggtcatc tggatacgct aagtactgca    1500
aaagctgcta tgaatgataa tgggcttgaa gggctgtttc ttggggtaa ttatgtgtca    1560 ggtgtagcat tggggaggtg tgttgaaggt gcttatgaag ttgcatccga ggtaacagga    1620
```
tttctgtctc ggtatgcata caaatga                                    1647

<210> SEQ ID NO 12
<211> LENGTH: 548
<212> TYPE: PRT
<213> ORGANISM: Nicotiana tabacum

<400> SEQUENCE: 12

Met Thr Thr Thr Pro Ile Ala Asn His Pro Asn Ile Phe Thr His Gln
1               5                   10                  15

Ser Ser Ser Ser Pro Leu Ala Phe Leu Asn Arg Thr Ser Phe Ile Pro
            20                  25                  30

Phe Ser Ser Ile Ser Lys Arg Asn Ser Val Asn Cys Asn Gly Trp Arg
        35                  40                  45

Thr Arg Cys Ser Val Ala Lys Asp Tyr Thr Val Pro Ser Ser Ala Val
    50                  55                  60

Asp Gly Gly Pro Ala Ala Glu Leu Asp Cys Val Ile Val Gly Ala Gly
65                  70                  75                  80

Ile Ser Gly Leu Cys Ile Ala Gln Val Met Ser Ala Asn Tyr Pro Asn
                85                  90                  95

Leu Met Val Thr Glu Ala Arg Asp Arg Ala Gly Gly Asn Ile Thr Thr
            100                 105                 110

Val Glu Arg Asp Gly Tyr Leu Trp Glu Glu Gly Pro Asn Ser Phe Gln
        115                 120                 125

Pro Ser Asp Pro Met Leu Thr Met Ala Val Asp Cys Gly Leu Lys Asp
    130                 135                 140

Asp Leu Val Leu Gly Asp Pro Asn Ala Pro Arg Phe Val Leu Trp Lys
145                 150                 155                 160

Gly Lys Leu Arg Pro Val Pro Ser Lys Leu Thr Asp Leu Pro Phe Phe
                165                 170                 175

Asp Leu Met Ser Ile Pro Gly Lys Leu Arg Ala Gly Phe Gly Ala Ile
            180                 185                 190

Gly Leu Arg Pro Ser Pro Gly His Glu Glu Ser Val Glu Gln Phe
        195                 200                 205

Val Arg Arg Asn Leu Gly Gly Glu Val Phe Glu Arg Leu Ile Glu Pro
    210                 215                 220

Phe Cys Ser Gly Val Tyr Ala Gly Asp Pro Ser Lys Leu Ser Met Lys
225                 230                 235                 240

Ala Ala Phe Gly Lys Val Trp Lys Leu Glu Glu Thr Gly Gly Ser Ile
                245                 250                 255

Ile Gly Gly Thr Phe Lys Ala Ile Lys Glu Arg Ser Ser Thr Pro Lys
            260                 265                 270

Ala Pro Arg Asp Pro Arg Leu Pro Lys Pro Lys Gly Gln Thr Val Gly
        275                 280                 285

Ser Phe Arg Lys Gly Leu Arg Met Leu Pro Asp Ala Ile Ser Ala Arg
    290                 295                 300

Leu Gly Ser Lys Leu Lys Leu Ser Trp Lys Leu Ser Ser Ile Thr Lys
305                 310                 315                 320

Ser Glu Lys Gly Gly Tyr His Leu Thr Tyr Glu Thr Pro Glu Gly Val
                325                 330                 335

Val Ser Leu Gln Ser Arg Ser Ile Val Met Thr Val Pro Ser Tyr Val
            340                 345                 350

Ala Ser Asn Ile Leu Arg Pro Leu Ser Val Ala Ala Asp Ala Leu
        355                 360                 365

```
Ser Asn Phe Tyr Tyr Pro Pro Val Gly Ala Val Thr Ile Ser Tyr Pro
    370                 375                 380

Gln Glu Ala Ile Arg Asp Glu Arg Leu Val Asp Gly Glu Leu Lys Gly
385                 390                 395                 400

Phe Gly Gln Leu His Pro Arg Thr Gln Gly Val Glu Thr Leu Gly Thr
                405                 410                 415

Ile Tyr Ser Ser Ser Leu Phe Pro Asn Arg Ala Pro Lys Gly Arg Val
                420                 425                 430

Leu Leu Leu Asn Tyr Ile Gly Gly Ala Lys Asn Pro Glu Ile Leu Ser
            435                 440                 445

Lys Thr Glu Ser Gln Leu Val Glu Val Val Asp Arg Asp Leu Arg Lys
450                 455                 460

Met Leu Ile Lys Pro Lys Ala Gln Asp Pro Leu Val Val Gly Val Arg
465                 470                 475                 480

Val Trp Pro Gln Ala Ile Pro Gln Phe Leu Val Gly His Leu Asp Thr
                485                 490                 495

Leu Ser Thr Ala Lys Ala Ala Met Asn Asp Asn Gly Leu Glu Gly Leu
                500                 505                 510

Phe Leu Gly Gly Asn Tyr Val Ser Gly Val Ala Leu Gly Arg Cys Val
                515                 520                 525

Glu Gly Ala Tyr Glu Val Ala Ser Glu Val Thr Gly Phe Leu Ser Arg
                530                 535                 540

Tyr Ala Tyr Lys
545

<210> SEQ ID NO 13
<211> LENGTH: 1668
<212> TYPE: DNA
<213> ORGANISM: Cichorium intybus

<400> SEQUENCE: 13
atgacatctc tcacagacgt tgttccctc aactgttgcc gtagctggtc ttcccttccg      60
ccaccggttt ctggtgggtc gttgacgtca agaatccta ggtacctaat cacgtatagt     120
ccggcgcatc gcaaatgcaa taggtggagg ttccgctgct ctatagccaa ggattcccca    180
attactcctc ccatttcaaa tgagttcaac tctcagccat tgttggactg tgtcattgtg    240
ggcgccggca ttagcggcct ttgcattgcg caggccctag cgactaaaca cgcctccgtc    300
tctccggatg tgatcgtcac cgaggcacga gacagagtcg ggggtaatat atcaacggtt    360
gaaagggatg gctatctctg ggaagaaggt cctaacagct tccagccatc tgatgccatg    420
ctcaccatgg tggtggatag tgggttgaag atgatttgg tgttaggtga cccaacagca    480
ccccgctttg tattatgggg aggtgatttg aaaccggttc cttccaaacc ggctgacctc    540
cctttctttg acctcatgag ctttcctgga aaactcagag ccggttttgg tgctcttgga    600
ttccgtcctt cacctccaga tcgcgaagaa tcggttgagg agtttgttag acgtaatctt    660
ggagatgaag ttttcgaacg cttgatagaa ccttttttgct caggtgttta tgctggtgat    720
ccatcaaaac ttagtatgaa agcagcattt gggaaggtct ggaatctgga gcaaaatggt    780
ggtagcattg ttggtggagc cttcaaggct attcaggaca gaaagaatag tcaaaagcct    840
ccacgggacc cgaggttacc gaaaccaaag ggccaaactg ttggatcttt taggaaagga    900
caagcgatgt tgcctaatgc aatctcaacg aggttaggta gcagagtgaa attgtgttgg    960
aagctcacga gtatttcaaa attggagaat agaggttata atttgacata tgaaacacca   1020
caaggatttg aaagtctgca gactaaaact atcgtgatga ctgttccatc ctacgtggcg   1080
```

```
agtgacttgt tgcgtccgct ttcgttgggt gcagcagatg cattgtcaaa attttattat   1140
cctccggttg cagctgtatc aatttcatat ccaaaagacg caattcgtgc tgaccggctg   1200
attgatggtc aactcaaagg ttttgggcaa ttgcatccac gaagtcaagg ggtggaaact   1260
ttaggtacga tctacagttc atctcttttc cctaaccgag cgccacctgg aagggttctg   1320
ctcttgaact acatcggagg ggctacaaat cctgaaattc tatcaaagac ggagggcgaa   1380
attgtggatg cggtggaccg ggacctacgg acgatgctga taaggcgtga tgcggaagat   1440
ccattgacgt tgggggtgcg ggtgtggcct cgagcaatcc cgcagtttct gatcggtcat   1500
tatgacattc tagattctgc aaaagctgct ctgagtagcg gtggattcca aggtatgttt   1560
cttggtggca actatgtgtc tggtgtggct ttaggtaaat gtgtcgaggc tgcttatgat   1620
gttgccgctg aggtaatgaa cttttttgtcg caagggggtgt acaagtga              1668
```

<210> SEQ ID NO 14
<211> LENGTH: 555
<212> TYPE: PRT
<213> ORGANISM: Cichorium

<400> SEQUENCE: 14

```
Met Thr Ser Leu Thr Asp Val Cys Ser Leu Asn Cys Cys Arg Ser Trp
1               5                   10                  15

Ser Ser Leu Pro Pro Val Ser Gly Gly Ser Leu Thr Ser Lys Asn
            20                  25                  30

Pro Arg Tyr Leu Ile Thr Tyr Ser Pro Ala His Arg Lys Cys Asn Arg
        35                  40                  45

Trp Arg Phe Arg Cys Ser Ile Ala Lys Asp Ser Pro Ile Thr Pro Pro
    50                  55                  60

Ile Ser Asn Glu Phe Asn Ser Gln Pro Leu Leu Asp Cys Val Ile Val
65                  70                  75                  80

Gly Ala Gly Ile Ser Gly Leu Cys Ile Ala Gln Ala Leu Ala Thr Lys
                85                  90                  95

His Ala Ser Val Ser Pro Asp Val Ile Val Thr Glu Ala Arg Asp Arg
            100                 105                 110

Val Gly Gly Asn Ile Ser Thr Val Glu Arg Asp Gly Tyr Leu Trp Glu
        115                 120                 125

Glu Gly Pro Asn Ser Phe Gln Pro Ser Asp Ala Met Leu Thr Met Val
    130                 135                 140

Val Asp Ser Gly Leu Lys Asp Leu Val Leu Gly Asp Pro Thr Ala
145                 150                 155                 160

Pro Arg Phe Val Leu Trp Gly Gly Asp Leu Lys Pro Val Pro Ser Lys
                165                 170                 175

Pro Ala Asp Leu Pro Phe Phe Asp Leu Met Ser Phe Pro Gly Lys Leu
            180                 185                 190

Arg Ala Gly Phe Gly Ala Leu Gly Phe Arg Pro Ser Pro Asp Arg
        195                 200                 205

Glu Glu Ser Val Glu Glu Phe Val Arg Arg Asn Leu Gly Asp Glu Val
    210                 215                 220

Phe Glu Arg Leu Ile Glu Pro Phe Cys Ser Gly Val Tyr Ala Gly Asp
225                 230                 235                 240

Pro Ser Lys Leu Ser Met Lys Ala Ala Phe Gly Lys Val Trp Asn Leu
                245                 250                 255

Glu Gln Asn Gly Gly Ser Ile Val Gly Gly Ala Phe Lys Ala Ile Gln
            260                 265                 270
```

```
Asp Arg Lys Asn Ser Gln Lys Pro Pro Arg Asp Pro Arg Leu Pro Lys
        275                 280                 285
Pro Lys Gly Gln Thr Val Gly Ser Phe Arg Lys Gly Gln Ala Met Leu
    290                 295                 300
Pro Asn Ala Ile Ser Thr Arg Leu Gly Ser Arg Val Lys Leu Cys Trp
305                 310                 315                 320
Lys Leu Thr Ser Ile Ser Lys Leu Glu Asn Arg Gly Tyr Asn Leu Thr
                325                 330                 335
Tyr Glu Thr Pro Gln Gly Phe Glu Ser Leu Gln Thr Lys Thr Ile Val
            340                 345                 350
Met Thr Val Pro Ser Tyr Val Ala Ser Asp Leu Leu Arg Pro Leu Ser
                355                 360                 365
Leu Gly Ala Ala Asp Ala Leu Ser Lys Phe Tyr Tyr Pro Pro Val Ala
    370                 375                 380
Ala Val Ser Ile Ser Tyr Pro Lys Asp Ala Ile Arg Ala Asp Arg Leu
385                 390                 395                 400
Ile Asp Gly Gln Leu Lys Gly Phe Gly Gln Leu His Pro Arg Ser Gln
                405                 410                 415
Gly Val Glu Thr Leu Gly Thr Ile Tyr Ser Ser Ser Leu Phe Pro Asn
            420                 425                 430
Arg Ala Pro Pro Gly Arg Val Leu Leu Leu Asn Tyr Ile Gly Gly Ala
    435                 440                 445
Thr Asn Pro Glu Ile Leu Ser Lys Thr Glu Gly Glu Ile Val Asp Ala
    450                 455                 460
Val Asp Arg Asp Leu Arg Thr Met Leu Ile Arg Asp Ala Glu Asp
465                 470                 475                 480
Pro Leu Thr Leu Gly Val Arg Val Trp Pro Arg Ala Ile Pro Gln Phe
                485                 490                 495
Leu Ile Gly His Tyr Asp Ile Leu Asp Ser Ala Lys Ala Ala Leu Ser
                500                 505                 510
Ser Gly Gly Phe Gln Gly Met Phe Leu Gly Gly Asn Tyr Val Ser Gly
    515                 520                 525
Val Ala Leu Gly Lys Cys Val Glu Ala Ala Tyr Asp Val Ala Ala Glu
    530                 535                 540
Val Met Asn Phe Leu Ser Gln Gly Val Tyr Lys
545                 550                 555

<210> SEQ ID NO 15
<211> LENGTH: 1689
<212> TYPE: DNA
<213> ORGANISM: Spinacia oleracea

<400> SEQUENCE: 15
atgagcgcta tggcgttatc gagtacaatg gcccctttcgt tgccgcaatc ttctatgtca    60
ttatcccatt gtaggcacaa ccgtatcacc attttgattc catcttcgtc gcttcgaaga   120
cgaggaggaa gctctatccg ctgctctaca atctcaacct ctaattccgc ggctgcagcc   180
aattaccaga acaaaaacat aggcacaaac ggagttgacg gcggcggagg cggaggaggt   240
gtgttagact gtgtgattgt aggaggtgga atcagtggac tttgcattgc acaggctcta   300
tctactaaat actccaacct ctccacgaat tcattgtca ccgaggctaa ggatcgagtt   360
ggcgggaaca tcactaccat ggaagctgat gggtatttat gggaagaggg tcctaatagc   420
tttcagccat ctgatgcagt gctcaccatg gctgttgaca gtggtttgaa agaggaattg   480
```

-continued

```
gtgctgggag atcccaattc gcctcgcttt tgctgtgga atggcaaatt aaggcctgta    540
ccttccaagc tcactgacct ccctttcttt gatctcatga gcttccctgg aaagattagg    600
gctggtcttg gtgctcttgg cttacgacca tctcctccgg ctcatgagga atccgttgaa    660
caatttgtcc gtcgtaatct tggtgatgag gtctttgaac gcttgatcga accttttgt    720 tcaggtgtgt atgctggtga tccttccaag ttgagtatga aagctgcttt tggcagggtt    780
tgggtcttgg agcaaagggg tggtagtatc attggtggca ccctcaaaac aatccaggaa    840
agaaaggata atcctaagcc acctcgagac ccgcgcctcc ccaaaccaaa gggccagaca    900
gttggatcct tcaggaaagg actgagtatg ttgccaaccg ccatttctga aaggcttggc    960
aacaaagtga agtatcatg gacccttct ggtattgcta agtcgtcgaa cggagagtat    1020
aatctgactt atgaaacacc agatggactg gtttccgtta ggaccaaaag tgttgtgatg   1080
actgtcccgt catatgttgc aagtagcctc cttcgtccac tttcagatgt cgccgcagaa   1140
tctctttcaa aatttcatta tccaccagtt gcagctgtgt cactttccta tcctaaagaa   1200
gcaattagat cagagtgctt gattgacggt gaacttaaag gattcgggca attacattcc   1260
cgcagtcaag gtgtggaaac cttgggaaca atttatagtt catctctttt ccctgggcga   1320
gcaccacctg gtaggacctt gattttgaac tacattggag gtgatactaa ccctggcata   1380
ttagacaaga cgaaagatga actagctgaa gcagttgaca gggatttgag aagaattctc   1440
ataaacccta atgcaaaagc tccccgggtt ttgggtgtga gagtatggcc acaagcaatt   1500
ccccaatttt taattggcca ctttgatctg ctcgatgcag caaaagctgc tttgactgat   1560
ggtggacaca aaggattgtt tcttggtgga aactatgtat caggtgttgc tttgggccga   1620
tgtatagagg gtgcttatga atctgcagcc gaggttgtag attttctgtc acagtactcg   1680
gataaatag                                                           1689
```

<210> SEQ ID NO 16
<211> LENGTH: 562
<212> TYPE: PRT
<213> ORGANISM: Spinacia

<400> SEQUENCE: 16

```
Met Ser Ala Met Ala Leu Ser Ser Thr Met Ala Leu Ser Leu Pro Gln
1               5                   10                  15

Ser Ser Met Ser Leu Ser His Cys Arg His Asn Arg Ile Thr Ile Leu
            20                  25                  30

Ile Pro Ser Ser Leu Arg Arg Gly Gly Ser Ser Ile Arg Cys
        35                  40                  45

Ser Thr Ile Ser Thr Ser Asn Ser Ala Ala Ala Asn Tyr Gln Asn
    50                  55                  60

Lys Asn Ile Gly Thr Asn Gly Val Asp Gly Gly Gly Gly Gly
65                  70                  75                  80

Val Leu Asp Cys Val Ile Val Gly Gly Gly Ile Ser Gly Leu Cys Ile
                85                  90                  95

Ala Gln Ala Leu Ser Thr Lys Tyr Ser Asn Leu Ser Thr Asn Phe Ile
            100                 105                 110

Val Thr Glu Ala Lys Asp Arg Val Gly Gly Asn Ile Thr Thr Met Glu
        115                 120                 125

Ala Asp Gly Tyr Leu Trp Glu Glu Gly Pro Asn Ser Phe Gln Pro Ser
    130                 135                 140

Asp Ala Val Leu Thr Met Ala Val Asp Ser Gly Leu Lys Glu Glu Leu
145                 150                 155                 160
```

```
Val Leu Gly Asp Pro Asn Ser Pro Arg Phe Val Leu Trp Asn Gly Lys
                165                 170                 175

Leu Arg Pro Val Pro Ser Lys Leu Thr Asp Leu Pro Phe Phe Asp Leu
            180                 185                 190

Met Ser Phe Pro Gly Lys Ile Arg Ala Gly Leu Gly Ala Leu Gly Leu
        195                 200                 205

Arg Pro Ser Pro Pro Ala His Glu Glu Ser Val Glu Gln Phe Val Arg
    210                 215                 220

Arg Asn Leu Gly Asp Glu Val Phe Glu Arg Leu Ile Glu Pro Phe Cys
225                 230                 235                 240

Ser Gly Val Tyr Ala Gly Asp Pro Ser Lys Leu Ser Met Lys Ala Ala
                245                 250                 255

Phe Gly Arg Val Trp Val Leu Glu Gln Lys Gly Gly Ser Ile Ile Gly
            260                 265                 270

Gly Thr Leu Lys Thr Ile Gln Glu Arg Lys Asp Asn Pro Lys Pro Pro
        275                 280                 285

Arg Asp Pro Arg Leu Pro Lys Pro Lys Gly Gln Thr Val Gly Ser Phe
    290                 295                 300

Arg Lys Gly Leu Ser Met Leu Pro Thr Ala Ile Ser Glu Arg Leu Gly
305                 310                 315                 320

Asn Lys Val Lys Val Ser Trp Thr Leu Ser Gly Ile Ala Lys Ser Ser
                325                 330                 335

Asn Gly Glu Tyr Asn Leu Thr Tyr Glu Thr Pro Asp Gly Leu Val Ser
            340                 345                 350

Val Arg Thr Lys Ser Val Val Met Thr Val Pro Ser Tyr Val Ala Ser
        355                 360                 365

Ser Leu Leu Arg Pro Leu Ser Asp Val Ala Ala Glu Ser Leu Ser Lys
    370                 375                 380

Phe His Tyr Pro Pro Val Ala Ala Val Ser Leu Ser Tyr Pro Lys Glu
385                 390                 395                 400

Ala Ile Arg Ser Glu Cys Leu Ile Asp Gly Glu Leu Lys Gly Phe Gly
                405                 410                 415

Gln Leu His Ser Arg Ser Gln Gly Val Glu Thr Leu Gly Thr Ile Tyr
            420                 425                 430

Ser Ser Ser Leu Phe Pro Gly Arg Ala Pro Pro Gly Arg Thr Leu Ile
        435                 440                 445

Leu Asn Tyr Ile Gly Gly Asp Thr Asn Pro Gly Ile Leu Asp Lys Thr
    450                 455                 460

Lys Asp Glu Leu Ala Glu Ala Val Asp Arg Asp Leu Arg Arg Ile Leu
465                 470                 475                 480

Ile Asn Pro Asn Ala Lys Ala Pro Arg Val Leu Gly Val Arg Val Trp
                485                 490                 495

Pro Gln Ala Ile Pro Gln Phe Leu Ile Gly His Phe Asp Leu Leu Asp
            500                 505                 510

Ala Ala Lys Ala Ala Leu Thr Asp Gly His Lys Gly Leu Phe Leu
        515                 520                 525

Gly Gly Asn Tyr Val Ser Gly Val Ala Leu Gly Arg Cys Ile Glu Gly
    530                 535                 540

Ala Tyr Glu Ser Ala Ala Glu Val Val Asp Phe Leu Ser Gln Tyr Ser
545                 550                 555                 560

Asp Lys
```

<210> SEQ ID NO 17
<211> LENGTH: 1596
<212> TYPE: DNA
<213> ORGANISM: Spinacia oleracea

<400> SEQUENCE: 17

| | | | | | |
|---|---|---|---|---|---|
| atggtaatac | taccggtttc | ccagctatca | actaatctgg | gtttatcgct | ggtttcaccc | 60 |
| accaagaaca | acccagttat | gggcaacgtt | tctgagcgaa | atcaagtcaa | tcaacccatt | 120 |
| tctgctaaaa | gggttgctgt | tgttggtgct | ggtgttagtg | gacttgctgc | ggcgtataag | 180 |
| ctaaaatcga | atggcttgaa | tgtgacattg | tttgaagctg | atagtagagc | tggtgggaaa | 240 |
| ctcaaaactg | ttgtaaagga | tggtttgatt | tgggatgaag | gggcaaatac | catgacagag | 300 |
| agcgatgagg | aggtcacgag | tttgtttgat | gatctcggga | ttcgtgagaa | gctacagcta | 360 |
| ccaatttcac | aaaacaaaag | atacattgcc | agagatggtc | ttcctgtgct | gttaccttca | 420 |
| aatccagttg | cgctcctgaa | gagcaatatc | cttttcagcaa | aatctaagct | acaaattatg | 480 |
| ttggaacctt | tcttttggaa | aaacacaat | ggtgctaagg | tttctgacga | gaatgcccaa | 540 |
| gaaagtgtgg | ctgagttttt | tgagcggcat | tttgggaaag | agtttgttga | ttatttaatt | 600 |
| gatccttttg | tcgcgggtac | aagtggtgga | gatcctcaat | ctctttctat | gcgtcatgca | 660 |
| tttccagaat | tatggaatat | tgagaacagg | tttggttcag | tgatttctgg | attcattcag | 720 |
| tctaaactgt | catccaagaa | ggaaaagggt | ggagaaaagc | aatcttctaa | taagaagcca | 780 |
| cgtgtacgtg | gttcgttttc | ttttcagggt | ggaatgcaga | cactagttga | cactatatgc | 840 |
| aaagagtttg | gtgaagatga | actcaaactc | cagtctgagg | ttctttcatt | gtcatacagc | 900 |
| cataatggaa | gccttacatc | agagaattgg | tcagtgtctt | ctatgtcaaa | cagcaccatc | 960 |
| caagatcaac | catatgatgc | tgtcgttgtg | accgccccaa | tcaataatgt | caaagaactg | 1020 |
| aagattatga | agtggaaaa | cccatttttct | cttgacttca | ttccagaggt | gagctgtcta | 1080 |
| cccctctctg | ttattattac | tacattcaag | aagaccaatg | tgaagagacc | tcttgagggt | 1140 |
| tttggtgttc | ttgtaccctc | taatgagcaa | cataatgggc | tgaagactct | tggtactttg | 1200 |
| ttttcctcaa | tgatgtttcc | tgatcgtgct | ccctctgatg | tgtatctata | cactaccttt | 1260 |
| gttggaggta | gcagaaatag | agaacttgca | aaagcttcaa | cggatgaact | gaagcaaata | 1320 |
| gtttcttctg | acctccagca | gctgttgggc | accgagggcg | aacctacttt | tgtgaatcat | 1380 |
| ttttactgga | gcaaagcatt | ccctctttat | ggacgcaatt | acgactcagt | tcttagagca | 1440 |
| atagagaaga | tggaaaggga | ccttcctgga | cttttttacg | caggtaacca | taagggtgga | 1500 |
| ctgtctgtgg | gaaagtcaat | agcctctgga | tacaaagctg | ccgagcttgc | gatatcctat | 1560 |
| ctcgagtcta | acaagatgac | cgaggagact | atataa | | | 1596 |

<210> SEQ ID NO 18
<211> LENGTH: 531
<212> TYPE: PRT
<213> ORGANISM: Spinacia

<400> SEQUENCE: 18

Met Val Ile Leu Pro Val Ser Gln Leu Ser Thr Asn Leu Gly Leu Ser
1               5                   10                  15

Leu Val Ser Pro Thr Lys Asn Asn Pro Val Met Gly Asn Val Ser Glu
            20                  25                  30

Arg Asn Gln Val Asn Gln Pro Ile Ser Ala Lys Arg Val Ala Val Val
        35                  40                  45

Gly Ala Gly Val Ser Gly Leu Ala Ala Ala Tyr Lys Leu Lys Ser Asn

```
            50                  55                  60
Gly Leu Asn Val Thr Leu Phe Glu Ala Asp Ser Arg Ala Gly Gly Lys
 65                  70                  75                  80

Leu Lys Thr Val Val Lys Asp Gly Leu Ile Trp Asp Glu Gly Ala Asn
                     85                  90                  95

Thr Met Thr Glu Ser Asp Glu Val Thr Ser Leu Phe Asp Asp Leu
                    100                 105                 110

Gly Ile Arg Glu Lys Leu Gln Leu Pro Ile Ser Gln Asn Lys Arg Tyr
                    115                 120                 125

Ile Ala Arg Asp Gly Leu Pro Val Leu Leu Pro Ser Asn Pro Val Ala
                    130                 135                 140

Leu Leu Lys Ser Asn Ile Leu Ser Ala Lys Ser Lys Leu Gln Ile Met
145                 150                 155                 160

Leu Glu Pro Phe Leu Trp Lys Lys His Asn Gly Ala Lys Val Ser Asp
                    165                 170                 175

Glu Asn Ala Gln Glu Ser Val Ala Glu Phe Phe Glu Arg His Phe Gly
                    180                 185                 190

Lys Glu Phe Val Asp Tyr Leu Ile Asp Pro Phe Val Ala Gly Thr Ser
                    195                 200                 205

Gly Gly Asp Pro Gln Ser Leu Ser Met Arg His Ala Phe Pro Glu Leu
                    210                 215                 220

Trp Asn Ile Glu Asn Arg Phe Gly Ser Val Ile Ser Gly Phe Ile Gln
225                 230                 235                 240

Ser Lys Leu Ser Ser Lys Lys Glu Lys Gly Gly Glu Lys Gln Ser Ser
                    245                 250                 255

Asn Lys Lys Pro Arg Val Arg Gly Ser Phe Ser Phe Gln Gly Gly Met
                    260                 265                 270

Gln Thr Leu Val Asp Thr Ile Cys Lys Glu Phe Gly Asp Glu Leu
                    275                 280                 285

Lys Leu Gln Ser Glu Val Leu Ser Leu Ser Tyr Ser His Asn Gly Ser
                    290                 295                 300

Leu Thr Ser Glu Asn Trp Ser Val Ser Ser Met Ser Asn Ser Thr Ile
305                 310                 315                 320

Gln Asp Gln Pro Tyr Asp Ala Val Val Val Thr Ala Pro Ile Asn Asn
                    325                 330                 335

Val Lys Glu Leu Lys Ile Met Lys Val Glu Asn Pro Phe Ser Leu Asp
                    340                 345                 350

Phe Ile Pro Glu Val Ser Cys Leu Pro Leu Ser Val Ile Ile Thr Thr
                    355                 360                 365

Phe Lys Lys Thr Asn Val Lys Arg Pro Leu Glu Gly Phe Gly Val Leu
                    370                 375                 380

Val Pro Ser Asn Glu Gln His Asn Gly Leu Lys Thr Leu Gly Thr Leu
385                 390                 395                 400

Phe Ser Ser Met Met Phe Pro Asp Arg Ala Pro Ser Asp Val Tyr Leu
                    405                 410                 415

Tyr Thr Thr Phe Val Gly Gly Ser Arg Asn Arg Glu Leu Ala Lys Ala
                    420                 425                 430

Ser Thr Asp Glu Leu Lys Gln Ile Val Ser Ser Asp Leu Gln Gln Leu
                    435                 440                 445

Leu Gly Thr Glu Gly Glu Pro Thr Phe Val Asn His Phe Tyr Trp Ser
                    450                 455                 460

Lys Ala Phe Pro Leu Tyr Gly Arg Asn Tyr Asp Ser Val Leu Arg Ala
465                 470                 475                 480
```

```
Ile Glu Lys Met Glu Arg Asp Leu Pro Gly Leu Phe Tyr Ala Gly Asn
            485                 490                 495

His Lys Gly Gly Leu Ser Val Gly Lys Ser Ile Ala Ser Gly Tyr Lys
        500                 505                 510

Ala Ala Glu Leu Ala Ile Ser Tyr Leu Glu Ser Asn Lys Met Thr Glu
        515                 520                 525

Glu Thr Ile
    530

<210> SEQ ID NO 19
<211> LENGTH: 1674
<212> TYPE: DNA
<213> ORGANISM: Solanum tuberosum

<400> SEQUENCE: 19
atgacaacaa cggccgtcgc caaccatcct agcattttca ctcaccggtc gccgctgccg      60
tcgccgtcgt cctcctcctc atcgccgtca tttttatttt taaaccgtac gaatttcatt     120
ccttactttt ccacctccaa gcgcaatagt gtcaattgca atggctggag aacacgatgt     180
tccgttgcca aggattatac agttcctccc tcggaagtcg acggtaatca gttcccggag     240
ctggattgtg tggtagttgg agcaggaatt agtggactct gcattgctaa ggtgatttcg     300
gctaattatc ccaatttgat ggtgacggag gcgagggatc gtgccggtgg aaacataacg     360
acggtggaaa gagatggata cttatgggaa gaaggtccta acagtttcca gccttcggat     420
cctatgttga caatggctgt agattgtgga ttgaaggatg attggtgtt gggagatcct      480
gatgcgcctc gctttgtctt gtggaaggat aaactaaggc ctgttcccgg caagctcact     540
gatcttccct tctttgattt gatgagtatc cctggcaagc tcagagctgg ttttggtgcc     600
attggccttc gcccttcacc tccaggttat gaggaatcag ttgagcagtt cgtgcgtcgt     660
aatcttggtg cagaagtctt tgaacgtttg attgaaccat tttgttctgg tgtttacgcc     720
ggtgaccct caaaattgat tatgaaagca gcatttggga agtgtggaa gctagaacaa       780
actggtggta gcattattgg gggaaccttt aaagcaatta aggagagatc cagtaaccct     840
aaaccgcctc gtgatccgcg tttaccaaca ccaaaaggac aaactgttgg atcatttagg     900
aagggtctga aatgctgccc ggatgcaatt tgtgaaagac tgggaagcaa agtaaaacta     960
tcatggaagc tttctagcat tacaaagtca gaaaaaggag gatatctctt gacatacgag    1020
acaccagaag gagtagtttc tctgcgaagt cgaagcattg tcatgactgt tccatcctat    1080
gtagcaagca acatattacg ccctctttcg gtcgctgcag cagatgcact ttcaagtttc    1140
tactatcccc cagtagcagc agtgacaatt tcatatcctc aagaggctat tcgtgatgag    1200
cgtctggttg atggtgaact aaagggattt gggcagttgc atccacgttc acagggagtg    1260
gaaacactag gaacaatata tagttcatca ctctttccta accgtgctcc aaatggccgg    1320
gtgctactct tgaactacat tggaggagca acaaatactg aaattgtgtc taagacggag    1380
agccaacttg tggaagcagt tgaccgtgac ctcagaaaaa tgcttataaa acccaaagca    1440
caagatccct tgttacgggt gtgcgagta tggccacaag ctatcccaca gttttggtc     1500
ggacatctgg atacactagg tactgcaaaa actgctctaa gtgataatgg gcttgacggg    1560
ctattccttg ggggtaatta tgtgtctggt gtagcattgg aaggtgtgt tgaaggtgct    1620
tatgaaatag catctgaggt aactggattt ctgtctcagt atgcatacaa atga         1674

<210> SEQ ID NO 20
```

```
<211> LENGTH: 557
<212> TYPE: PRT
<213> ORGANISM: Solanum tuberosum

<400> SEQUENCE: 20

Met Thr Thr Thr Ala Val Ala Asn His Pro Ser Ile Phe Thr His Arg
1               5                   10                  15

Ser Pro Leu Pro Ser Pro Ser Ser Ser Ser Ser Pro Ser Phe Leu
            20                  25                  30

Phe Leu Asn Arg Thr Asn Phe Ile Pro Tyr Phe Ser Thr Ser Lys Arg
        35                  40                  45

Asn Ser Val Asn Cys Asn Gly Trp Arg Thr Arg Cys Ser Val Ala Lys
    50                  55                  60

Asp Tyr Thr Val Pro Pro Ser Glu Val Asp Gly Asn Gln Phe Pro Glu
65                  70                  75                  80

Leu Asp Cys Val Val Val Gly Ala Gly Ile Ser Gly Leu Cys Ile Ala
                85                  90                  95

Lys Val Ile Ser Ala Asn Tyr Pro Asn Leu Met Val Thr Glu Ala Arg
            100                 105                 110

Asp Arg Ala Gly Gly Asn Ile Thr Thr Val Glu Arg Asp Gly Tyr Leu
        115                 120                 125

Trp Glu Glu Gly Pro Asn Ser Phe Gln Pro Ser Asp Pro Met Leu Thr
130                 135                 140

Met Ala Val Asp Cys Gly Leu Lys Asp Asp Leu Val Leu Gly Asp Pro
145                 150                 155                 160

Asp Ala Pro Arg Phe Val Leu Trp Lys Asp Lys Leu Arg Pro Val Pro
                165                 170                 175

Gly Lys Leu Thr Asp Leu Pro Phe Phe Asp Leu Met Ser Ile Pro Gly
            180                 185                 190

Lys Leu Arg Ala Gly Phe Gly Ala Ile Gly Leu Arg Pro Ser Pro Pro
        195                 200                 205

Gly Tyr Glu Glu Ser Val Glu Gln Phe Val Arg Arg Asn Leu Gly Ala
    210                 215                 220

Glu Val Phe Glu Arg Leu Ile Glu Pro Phe Cys Ser Gly Val Tyr Ala
225                 230                 235                 240

Gly Asp Pro Ser Lys Leu Ile Met Lys Ala Ala Phe Gly Lys Val Trp
                245                 250                 255

Lys Leu Glu Gln Thr Gly Gly Ser Ile Ile Gly Gly Thr Phe Lys Ala
            260                 265                 270

Ile Lys Glu Arg Ser Ser Asn Pro Lys Pro Pro Arg Asp Pro Arg Leu
        275                 280                 285

Pro Thr Pro Lys Gly Gln Thr Val Gly Ser Phe Arg Lys Gly Leu Arg
    290                 295                 300

Met Leu Pro Asp Ala Ile Cys Glu Arg Leu Gly Ser Lys Val Lys Leu
305                 310                 315                 320

Ser Trp Lys Leu Ser Ser Ile Thr Lys Ser Glu Lys Gly Gly Tyr Leu
                325                 330                 335

Leu Thr Tyr Glu Thr Pro Glu Gly Val Val Ser Leu Arg Ser Arg Ser
            340                 345                 350

Ile Val Met Thr Val Pro Ser Tyr Val Ala Ser Asn Ile Leu Arg Pro
        355                 360                 365

Leu Ser Val Ala Ala Ala Asp Ala Leu Ser Ser Phe Tyr Tyr Pro Pro
    370                 375                 380

Val Ala Ala Val Thr Ile Ser Tyr Pro Gln Glu Ala Ile Arg Asp Glu
```

```
                385               390               395               400
            Arg Leu Val Asp Gly Glu Leu Lys Gly Phe Gly Gln Leu His Pro Arg
                            405               410               415
            Ser Gln Gly Val Glu Thr Leu Gly Thr Ile Tyr Ser Ser Ser Leu Phe
                            420               425               430
            Pro Asn Arg Ala Pro Asn Gly Arg Val Leu Leu Asn Tyr Ile Gly
                            435               440               445
            Gly Ala Thr Asn Thr Glu Ile Val Ser Lys Thr Glu Ser Gln Leu Val
                450               455               460
            Glu Ala Val Asp Arg Asp Leu Arg Lys Met Leu Ile Lys Pro Lys Ala
            465               470               475               480
            Gln Asp Pro Phe Val Thr Gly Val Arg Val Trp Pro Gln Ala Ile Pro
                            485               490               495
            Gln Phe Leu Val Gly His Leu Asp Thr Leu Gly Thr Ala Lys Thr Ala
                            500               505               510
            Leu Ser Asp Asn Gly Leu Asp Gly Leu Phe Leu Gly Gly Asn Tyr Val
                            515               520               525
            Ser Gly Val Ala Leu Gly Arg Cys Val Glu Gly Ala Tyr Glu Ile Ala
                530               535               540
            Ser Glu Val Thr Gly Phe Leu Ser Gln Tyr Ala Tyr Lys
            545               550               555
```

<210> SEQ ID NO 21
<211> LENGTH: 1608
<212> TYPE: DNA
<213> ORGANISM: Zea mays

<400> SEQUENCE: 21

```
atggtcgccg ccacagccac cgccatggcc accgctgcat cgccgctact caacgggacc      60
cgaatacctg cgcggctccg ccatcgagga ctcagcgtgc gctgcgctgc tgtggcgggc     120
ggcgcggccg aggcaccggc atccaccggc gcgcggctgt ccgcggactg cgtcgtggtg     180
ggcggaggca tcagtggcct ctgcaccgcg caggcgctgg ccacgcggca cggcgtcggg     240
gacgtgcttg tcacggaggc ccgcgcccgc cccggcggca acattaccac cgtcgagcgc     300
cccgaggaag ggtacctctg gaggagggt cccaacagct tccagccctc cgaccccgtt      360
ctcaccatgg ccgtggacag cggactgaag gatgacttgg ttttggggga cccaaacgcg     420
ccgcgtttcg tgctgtggga ggggaagctg aggcccgtgc atccaagcc cgccgaccttc    480
ccgttcttcg atctcatgag catcccaggg aagctcaggg ccggtctagg cgcgcttggc     540
atccgcccgc tcctccagg ccgcgaagag tcagtggagg agttcgtgcg ccgcaacctc      600
ggtgctgagg tctttgagcg cctcattgag cctttctgct caggtgtcta tgctggtgat     660
ccttctaagc tcagcatgaa ggctgcattt gggaaggttt ggcggttgga agaaactgga     720
ggtagtatta ttggtggaac catcaagaca attcaggaga ggagcaagaa tccaaaacca     780
ccgagggatg cccgccttcc gaagccaaaa gggcagacag ttgcatcttt caggaagggt     840
cttgccatgc ttccaaatgc cattacatcc agcttgggta gtaaagtcaa actatcatgg     900
aaactcacga gcattacaaa atcagatgac aagggatatg ttttggagta tgaaacgcca     960
gaagggggttg tttcggtgca ggctaaaagt gttatcatga ctattccatc atatgttgct    1020
agcaacattt tgcgtccact ttcaagcgat gctgcagatg ctctatcaag attctattat    1080
ccaccggttt ctgctgtaac tgtttcgtat ccaaaggaag caattagaaa agaatgctta    1140
attgatgggg aactccaggg cttttggccag ttgcatccac gtagtcaagg agttgagaca    1200
```

```
ttaggaacaa tatacagttc ctcactcttt ccaaatcgtg ctcctgacgg tagggtgtta    1260
cttctaaact acataggagg tgctacaaac acaggaattg tttccaagac tgaaagtgag    1320
ctggtcgaag cagttgaccg tgacctccga aaaatgctta taaattctac agcagtggac    1380
cctttagtcc ttggtgttcg agtttggcca caagccatac ctcagttcct ggtaggacat    1440
cttgatcttc tggaagccgc aaaagctgcc ctggaccgag gtggctacga tgggctgttc    1500
ctaggaggga actatgttgc aggagttgcc ctgggcagat gcgttgaggg cgcgtatgaa    1560
agtgcctcgc aaatatctga cttcttgacc aagtatgcct acaagtga                 1608
```

<210> SEQ ID NO 22
<211> LENGTH: 535
<212> TYPE: PRT
<213> ORGANISM: Zea mays

<400> SEQUENCE: 22

```
Met Val Ala Ala Thr Ala Thr Ala Met Ala Thr Ala Ala Ser Pro Leu
1               5                   10                  15

Leu Asn Gly Thr Arg Ile Pro Ala Arg Leu Arg His Arg Gly Leu Ser
            20                  25                  30

Val Arg Cys Ala Ala Val Ala Gly Ala Ala Glu Ala Pro Ala Ser
        35                  40                  45

Thr Gly Ala Arg Leu Ser Ala Asp Cys Val Val Gly Gly Gly Ile
    50                  55                  60

Ser Gly Leu Cys Thr Ala Gln Ala Leu Ala Thr Arg His Gly Val Gly
65                  70                  75                  80

Asp Val Leu Val Thr Glu Ala Arg Ala Arg Pro Gly Gly Asn Ile Thr
                85                  90                  95

Thr Val Glu Arg Pro Glu Glu Gly Tyr Leu Trp Glu Glu Gly Pro Asn
            100                 105                 110

Ser Phe Gln Pro Ser Asp Pro Val Leu Thr Met Ala Val Asp Ser Gly
        115                 120                 125

Leu Lys Asp Asp Leu Val Phe Gly Asp Pro Asn Ala Pro Arg Phe Val
    130                 135                 140

Leu Trp Glu Gly Lys Leu Arg Pro Val Pro Ser Lys Pro Ala Asp Leu
145                 150                 155                 160

Pro Phe Phe Asp Leu Met Ser Ile Pro Gly Lys Leu Arg Ala Gly Leu
                165                 170                 175

Gly Ala Leu Gly Ile Arg Pro Pro Pro Gly Arg Glu Glu Ser Val
            180                 185                 190

Glu Glu Phe Val Arg Arg Asn Leu Gly Ala Glu Val Phe Glu Arg Leu
        195                 200                 205

Ile Glu Pro Phe Cys Ser Gly Val Tyr Ala Gly Asp Pro Ser Lys Leu
    210                 215                 220

Ser Met Lys Ala Ala Phe Gly Lys Val Trp Arg Leu Glu Glu Thr Gly
225                 230                 235                 240

Gly Ser Ile Ile Gly Gly Thr Ile Lys Thr Ile Gln Glu Arg Ser Lys
                245                 250                 255

Asn Pro Lys Pro Pro Arg Asp Ala Arg Leu Pro Lys Pro Lys Gly Gln
            260                 265                 270

Thr Val Ala Ser Phe Arg Lys Gly Leu Ala Met Leu Pro Asn Ala Ile
        275                 280                 285

Thr Ser Ser Leu Gly Ser Lys Val Lys Leu Ser Trp Lys Leu Thr Ser
    290                 295                 300
```

```
Ile Thr Lys Ser Asp Asp Lys Gly Tyr Val Leu Glu Tyr Glu Thr Pro
305                 310                 315                 320

Glu Gly Val Val Ser Val Gln Ala Lys Ser Val Ile Met Thr Ile Pro
            325                 330                 335

Ser Tyr Val Ala Ser Asn Ile Leu Arg Pro Leu Ser Ser Asp Ala Ala
        340                 345                 350

Asp Ala Leu Ser Arg Phe Tyr Tyr Pro Val Ala Ala Val Thr Val
    355                 360                 365

Ser Tyr Pro Lys Glu Ala Ile Arg Lys Glu Cys Leu Ile Asp Gly Glu
370                 375                 380

Leu Gln Gly Phe Gly Gln Leu His Pro Arg Ser Gln Gly Val Glu Thr
385                 390                 395                 400

Leu Gly Thr Ile Tyr Ser Ser Leu Phe Pro Asn Arg Ala Pro Asp
            405                 410                 415

Gly Arg Val Leu Leu Asn Tyr Ile Gly Gly Ala Thr Asn Thr Gly
            420                 425                 430

Ile Val Ser Lys Thr Glu Ser Glu Leu Val Glu Ala Val Asp Arg Asp
            435                 440                 445

Leu Arg Lys Met Leu Ile Asn Ser Thr Ala Val Asp Pro Leu Val Leu
450                 455                 460

Gly Val Arg Val Trp Pro Gln Ala Ile Pro Gln Phe Leu Val Gly His
465                 470                 475                 480

Leu Asp Leu Leu Glu Ala Ala Lys Ala Ala Leu Asp Arg Gly Gly Tyr
            485                 490                 495

Asp Gly Leu Phe Leu Gly Gly Asn Tyr Val Ala Gly Val Ala Leu Gly
            500                 505                 510

Arg Cys Val Glu Gly Ala Tyr Glu Ser Ala Ser Gln Ile Ser Asp Phe
            515                 520                 525

Leu Thr Lys Tyr Ala Tyr Lys
530                 535

<210> SEQ ID NO 23
<211> LENGTH: 1635
<212> TYPE: DNA
<213> ORGANISM: Zea mays

<400> SEQUENCE: 23
atgctcgctt tgactgcctc agcctcatcc gcttcgtccc atccttatcg ccacgcctcc    60
gcgcacactc gtcgcccccg cctacgtgcg gtcctcgcga tggcgggctc cgacgacccc   120
cgtgcagcgc ccgccagatc ggtcgccgtc gtcggcgccg gggtcagcgg gctcgcggcg   180
gcgtacaggc tcagacagag cggcgtgaac gtaacggtgt cgaagcggc cgacagggcg    240 ggaggaaaga tacggaccaa ttccgagggc gggtttgtct gggatgaagg agctaacacc   300
atgacagaag gtgaatggga ggccagtaga ctgattgatg atcttggtct acaagacaaa   360
cagcagtatc ctaactccca acacaagcgt tacattgtca agatggagc accagcactg    420 attccttcgg atcccatttc gctaatgaaa agcagtgttc tttcgacaaa atcaaagatt   480
gcgttatttt ttgaaccatt tctctacaag aaagctaaca caagaaactc tggaaaagtg   540
tctgaggagc acttgagtga gagtgttggg agcttctgtg aacgccactt tggaagagaa   600
gttgttgact attttgttga tccatttgta gctggaacaa gtgcaggaga tccagagtca   660
ctatctattc gtcatgcatt cccagcattg tggaatttgg aaagaaagta tggttcagtt   720
attgttggtg ccatcttgtc taagctagca gctaaaggtg atccagtaaa gacaagacat   780
```

```
gattcatcag ggaaaagaag aatagacga gtgtcgtttt catttcatgg tggaatgcag    840
tcactaataa atgcacttca caatgaagtt ggagatgata atgtgaagct ggtacagaa    900 gtgttgtcat tggcatgtac atttgatgga gttcctgcac taggcaggtg gtcaatttct   960
gttgattcga aggatagcgg tgacaaggac cttgctagta accaaacctt tgatgctgtt  1020
ataatgacag ctccattgtc aaatgtccgg aggatgaagt tcaccaaagg tggagctccg  1080
gttgttcttg actttcttcc taagatggat tatctaccac tatctctcat ggtgactgct  1140
tttaagaagg atgatgtcaa gaaacctctg gaaggatttg gggtcttaat accttacaag  1200
gaacagcaaa aacatggtct gaaaacccct gggactctct tttcctcaat gatgttccca  1260
gatcgagctc ctgatgacca atatttatat acaacatttg ttgggggtag ccacaataga  1320
gatcttgctg gagctccaac gtctattctg aaacaacttg tgacctctga ccttaaaaaa  1380
ctcttgggcg tagaggggca accaactttt gtcaagcatg tatactgggg aaatgctttt  1440
cctttgtatg gccatgatta tagttctgta ttggaagcta tagaaaagat ggagaaaaac  1500
cttccagggt tcttctacgc aggaaatagc aaggatgggc ttgctgttgg aagtgttata  1560
gcttcaggaa gcaaggctgc tgaccttgca atctcatatc ttgaatctca caccaagcat  1620
aataattcac attga                                                    1635
```

<210> SEQ ID NO 24
<211> LENGTH: 544
<212> TYPE: PRT
<213> ORGANISM: Zea mays

<400> SEQUENCE: 24

Met Leu Ala Leu Thr Ala Ser Ala Ser Ala Ser Ser His Pro Tyr
1               5                   10                  15

Arg His Ala Ser Ala His Thr Arg Arg Pro Arg Leu Arg Ala Val Leu
            20                  25                  30

Ala Met Ala Gly Ser Asp Asp Pro Arg Ala Ala Pro Ala Arg Ser Val
        35                  40                  45

Ala Val Val Gly Ala Gly Val Ser Gly Leu Ala Ala Ala Tyr Arg Leu
    50                  55                  60

Arg Gln Ser Gly Val Asn Val Thr Val Phe Glu Ala Ala Asp Arg Ala
65                  70                  75                  80

Gly Gly Lys Ile Arg Thr Asn Ser Glu Gly Gly Phe Val Trp Asp Glu
                85                  90                  95

Gly Ala Asn Thr Met Thr Glu Gly Glu Trp Glu Ala Ser Arg Leu Ile
            100                 105                 110

Asp Asp Leu Gly Leu Gln Asp Lys Gln Gln Tyr Pro Asn Ser Gln His
        115                 120                 125

Lys Arg Tyr Ile Val Lys Asp Gly Ala Pro Ala Leu Ile Pro Ser Asp
    130                 135                 140

Pro Ile Ser Leu Met Lys Ser Ser Val Leu Ser Thr Lys Ser Lys Ile
145                 150                 155                 160

Ala Leu Phe Phe Glu Pro Phe Leu Tyr Lys Lys Ala Asn Thr Arg Asn
                165                 170                 175

Ser Gly Lys Val Ser Glu Glu His Leu Ser Glu Ser Val Gly Ser Phe
            180                 185                 190

Cys Glu Arg His Phe Gly Arg Glu Val Val Asp Tyr Phe Val Asp Pro
        195                 200                 205

Phe Val Ala Gly Thr Ser Ala Gly Asp Pro Glu Ser Leu Ser Ile Arg

His Ala Phe Pro Ala Leu Trp Asn Leu Glu Arg Lys Tyr Gly Ser Val
225                 230                 235                 240

Ile Val Gly Ala Ile Leu Ser Lys Leu Ala Ala Lys Gly Asp Pro Val
                245                 250                 255

Lys Thr Arg His Asp Ser Ser Gly Lys Arg Arg Asn Arg Arg Val Ser
                260                 265                 270

Phe Ser Phe His Gly Gly Met Gln Ser Leu Ile Asn Ala Leu His Asn
            275                 280                 285

Glu Val Gly Asp Asp Asn Val Lys Leu Gly Thr Glu Val Leu Ser Leu
290                 295                 300

Ala Cys Thr Phe Asp Gly Val Pro Ala Leu Gly Arg Trp Ser Ile Ser
305                 310                 315                 320

Val Asp Ser Lys Asp Ser Gly Asp Lys Asp Leu Ala Ser Asn Gln Thr
                325                 330                 335

Phe Asp Ala Val Ile Met Thr Ala Pro Leu Ser Asn Val Arg Arg Met
                340                 345                 350

Lys Phe Thr Lys Gly Gly Ala Pro Val Val Leu Asp Phe Leu Pro Lys
                355                 360                 365

Met Asp Tyr Leu Pro Leu Ser Leu Met Val Thr Ala Phe Lys Lys Asp
370                 375                 380

Asp Val Lys Lys Pro Leu Glu Gly Phe Gly Val Leu Ile Pro Tyr Lys
385                 390                 395                 400

Glu Gln Gln Lys His Gly Leu Lys Thr Leu Gly Thr Leu Phe Ser Ser
                405                 410                 415

Met Met Phe Pro Asp Arg Ala Pro Asp Asp Gln Tyr Leu Tyr Thr Thr
                420                 425                 430

Phe Val Gly Gly Ser His Asn Arg Asp Leu Ala Gly Ala Pro Thr Ser
                435                 440                 445

Ile Leu Lys Gln Leu Val Thr Ser Asp Leu Lys Lys Leu Leu Gly Val
450                 455                 460

Glu Gly Gln Pro Thr Phe Val Lys His Val Tyr Trp Gly Asn Ala Phe
465                 470                 475                 480

Pro Leu Tyr Gly His Asp Tyr Ser Ser Val Leu Glu Ala Ile Glu Lys
                485                 490                 495

Met Glu Lys Asn Leu Pro Gly Phe Phe Tyr Ala Gly Asn Ser Lys Asp
                500                 505                 510

Gly Leu Ala Val Gly Ser Val Ile Ala Ser Gly Ser Lys Ala Ala Asp
            515                 520                 525

Leu Ala Ile Ser Tyr Leu Glu Ser His Thr Lys His Asn Asn Ser His
530                 535                 540

<210> SEQ ID NO 25
<211> LENGTH: 1692
<212> TYPE: DNA
<213> ORGANISM: Chlamydomonas reinhardtii

<400> SEQUENCE: 25
atgatgttga cccagactcc tgggaccgcc acggcttcta gccggcggtc gcagatccgc     60
tcggctgcgc acgtctccgc caaggtcgcg cctcggccca cgccattctc ggtcgcgagc    120
cccgcgaccg ctgcgagccc cgcgaccgcg gcggcccgcc gcacactcca ccgcactgct    180
gcggcggcca ctggtgctcc cacggcgtcc ggagccggcg tcgccaagac gctcgacaat    240
gtgtatgacg tgatcgtggt cggtggaggt ctctcgggcc tggtgaccgg ccaggccctg    300

-continued

```
gcggctcagc acaaaattca gaacttcctt gttacggagg ctcgcgagcg cgtcggcggc    360
aacattacgt ccatgtcggg cgatggctac gtgtgggagg agggcccgaa cagcttccag    420
cccaacgata gcatgctgca gattgcggtg gactctggct gcgagaagga ccttgtgttc    480
ggtgacccca cggctccccg cttcgtgtgg tgggagggca agctgcgccc cgtgccctcg    540
ggcctggacg ccttcacctt cgacctcatg tccatccccg gcaagatccg cgccgggctg    600
ggcgccatcg gcctcatcaa cggagccatg ccctccttcg aggagagtgt ggagcagttc    660
atccgccgca acctgggcga tgaggtgttc ttccgcctga tcgagcccct ctgctccggc    720
gtgtacgcgg cgacccctc caagctgtcc atgaaggcgg ccttcaacag gatctggatt    780
ctggagaaga acggcggcag cctggtggga ggtgccatca agctgttcca ggaacgccag    840
tccaacccgg ccccgccgcg ggacccgcgc ctgccgccca gcccaagggg ccagacggtg    900
ggctcgttcc gcaagggcct gaagatgctg ccggacgcca ttgagcgcaa catccccgac    960
aagatccgcg tgaactggaa gctggtgtct ctgggccgcg aggcggacgg gcggtacggg    1020
ctggtgtacg acacgcccga gggccgtgtc aaggtgtttg cccgcgccgt ggctctgacc    1080
gcgcccagct acgtggtggc ggacctggtc aaggagcagg cgcccgccgc cgccgaggcc    1140
ctgggctcct tcgactaccc gccggtgggc gccgtgacgc tgtcgtaccc gctgagcgcc    1200
gtgcgggagg agcgcaaggc ctcggacggg tccgtgccgg gcttcggtca gctgcacccg    1260
cgcacgcagg gcatcaccac tctgggcacc atctacagct ccagcctgtt ccccggccgc    1320
gcgcccgagg gccacatgct gctgctcaac tacatcggcg gcaccaccaa cgcgggcatc    1380
gtcaaccaga ccaccgagca gctggtggag caggtggaca aggacctgcg caacatggtc    1440
atcaagcccg acgcgcccaa gcccgtgtgt gtgggcgtgc gcgtgtggcc gcgcgccatc    1500
ccgcagttca acctgggcca cctggagcag ctggacaagg cgcgcaaggc gctggacgcg    1560
gcggggctgc agggcgtgca cctgggggggc aactacgtca gcggtgtggc cctgggcaag    1620
gtggtggagc acggctacga gtccgcagcc aacctggcca gagcgtgtc caaggccgca    1680
gtcaaggcct aa                                                        1692
```

<210> SEQ ID NO 26
<211> LENGTH: 563
<212> TYPE: PRT
<213> ORGANISM: Chlamydomonas

<400> SEQUENCE: 26

Met Met Leu Thr Gln Thr Pro Gly Thr Ala Thr Ala Ser Ser Arg Arg
1               5                   10                  15

Ser Gln Ile Arg Ser Ala Ala His Val Ser Ala Lys Val Ala Pro Arg
                20                  25                  30

Pro Thr Pro Phe Ser Val Ala Ser Pro Ala Thr Ala Ala Ser Pro Ala
            35                  40                  45

Thr Ala Ala Ala Arg Arg Thr Leu His Arg Thr Ala Ala Ala Ala Thr
        50                  55                  60

Gly Ala Pro Thr Ala Ser Gly Ala Gly Val Ala Lys Thr Leu Asp Asn
65                  70                  75                  80

Val Tyr Asp Val Ile Val Val Gly Gly Leu Ser Gly Leu Val Thr
                85                  90                  95

Gly Gln Ala Leu Ala Ala Gln His Lys Ile Gln Asn Phe Leu Val Thr
            100                 105                 110

Glu Ala Arg Glu Arg Val Gly Gly Asn Ile Thr Ser Met Ser Gly Asp

```
                115                 120                 125
Gly Tyr Val Trp Glu Glu Gly Pro Asn Ser Phe Gln Pro Asn Asp Ser
130                 135                 140

Met Leu Gln Ile Ala Val Asp Ser Gly Cys Glu Lys Asp Leu Val Phe
145                 150                 155                 160

Gly Asp Pro Thr Ala Pro Arg Phe Val Trp Glu Gly Lys Leu Arg
                165                 170                 175

Pro Val Pro Ser Gly Leu Asp Ala Phe Thr Phe Asp Leu Met Ser Ile
                180                 185                 190

Pro Gly Lys Ile Arg Ala Gly Leu Gly Ala Ile Gly Leu Ile Asn Gly
                195                 200                 205

Ala Met Pro Ser Phe Glu Glu Ser Val Glu Gln Phe Ile Arg Arg Asn
210                 215                 220

Leu Gly Asp Glu Val Phe Phe Arg Leu Ile Glu Pro Phe Cys Ser Gly
225                 230                 235                 240

Val Tyr Ala Gly Asp Pro Ser Lys Leu Ser Met Lys Ala Ala Phe Asn
                245                 250                 255

Arg Ile Trp Ile Leu Glu Lys Asn Gly Gly Ser Leu Val Gly Gly Ala
                260                 265                 270

Ile Lys Leu Phe Gln Glu Arg Gln Ser Asn Pro Ala Pro Arg Asp
                275                 280                 285

Pro Arg Leu Pro Pro Lys Pro Lys Gly Gln Thr Val Gly Ser Phe Arg
290                 295                 300

Lys Gly Leu Lys Met Leu Pro Asp Ala Ile Glu Arg Asn Ile Pro Asp
305                 310                 315                 320

Lys Ile Arg Val Asn Trp Lys Leu Val Ser Leu Gly Arg Glu Ala Asp
                325                 330                 335

Gly Arg Tyr Gly Leu Val Tyr Asp Thr Pro Glu Gly Arg Val Lys Val
                340                 345                 350

Phe Ala Arg Ala Val Ala Leu Thr Ala Pro Ser Tyr Val Val Ala Asp
                355                 360                 365

Leu Val Lys Glu Gln Ala Pro Ala Ala Glu Ala Leu Gly Ser Phe
370                 375                 380

Asp Tyr Pro Pro Val Gly Ala Val Thr Leu Ser Tyr Pro Leu Ser Ala
385                 390                 395                 400

Val Arg Glu Glu Arg Lys Ala Ser Asp Gly Ser Val Pro Gly Phe Gly
                405                 410                 415

Gln Leu His Pro Arg Thr Gln Gly Ile Thr Thr Leu Gly Thr Ile Tyr
                420                 425                 430

Ser Ser Ser Leu Phe Pro Gly Arg Ala Pro Glu Gly His Met Leu Leu
                435                 440                 445

Leu Asn Tyr Ile Gly Gly Thr Thr Asn Arg Gly Ile Val Asn Gln Thr
                450                 455                 460

Thr Glu Gln Leu Val Glu Gln Val Asp Lys Asp Leu Arg Asn Met Val
465                 470                 475                 480

Ile Lys Pro Asp Ala Pro Lys Pro Arg Val Val Gly Val Arg Val Trp
                485                 490                 495

Pro Arg Ala Ile Pro Gln Phe Asn Leu Gly His Leu Glu Gln Leu Asp
                500                 505                 510

Lys Ala Arg Lys Ala Leu Asp Ala Ala Gly Leu Gln Gly Val His Leu
                515                 520                 525

Gly Gly Asn Tyr Val Ser Gly Val Ala Leu Gly Lys Val Val Glu His
                530                 535                 540
```

Gly Tyr Glu Ser Ala Ala Asn Leu Ala Lys Ser Val Ser Lys Ala Ala
545                 550                 555                 560

Val Lys Ala

<210> SEQ ID NO 27
<211> LENGTH: 1734
<212> TYPE: DNA
<213> ORGANISM: Polytomella sp

<400> SEQUENCE: 27

```
atgtcgagtt ccgcactaag gctattatgc gggcgaacaa gtttctttaa tttatgccaa      60
aaatatcctc cttcctttct gtcacaattg tcgaccttaa atttctcaac ccattcgcct     120
ttcgatagca cttatgatgt cgtcgtcgtt ggtgccggaa tctctgggtt gtctactgcc     180
caagcactta gcattcaaca taagatcgat aatgttctgg ttactgaagc tgatcatcgt     240
gtaggcggta aaattacgac gaaaaggaat aaagatttcc tgtgggagga gggtccaaat     300
agttgcctaa tgaacgacgc tttatatcgc gctgcccgag atgccggcgt ggaatccaaa     360
attctatcgg cggatccaaa attaccacgt tggattctgt ggggtcgtcg tttgcgtgtg     420
gcccccattg gaagctacgc tttaaaatcc gacctttat ctacccaagg cctactccgt      480
gccatccgag gagtcacagg ttttggtgtg tcaccggctc cacctaaggg tcaggaggag     540
agcgtggagg gctttgttcg acggacctta ggagacgaga ttttgagcg actcgttgag      600
cccttttgct ccggggttta tgcggggat cctagcaaat tgtccatgcg tgctgctttc      660
ggaaaacttg tggaattcga agagacgggt gatggtagct acttcgcgg cgtctttcgt      720
tacgtaatga acaaacgacg cgaaagaagg acgggcgggg cgaaagacgg ggacacggtc     780
cctttgaacg agacggccaa ggcacccaaa tcatcctctg gcccaacagt atcgtctttc     840
gagggggga tcgagatcct gcccaaggcc attgcgcaaa agctgggtga tcgagttcgt      900
cttggcctac gactcgtgcg catcgatccc acgcagctcg cggatggtac gacagcgtac     960
cgtctgtcgt accgtcggat gagtcatcaa ggcgatgacg actcgagtcg tacggcaggt    1020
gctgtaccgc gtacggcgga ggggatgtc cggcggggg acgaggacgc cgtggtggag      1080
gtggtggcga agaaggtcgt gctgacgacg ccggcattcg acgccgcgga catcttgtcg    1140
cgttccggct tggtggcggc ggcgaacccg ttgaaggagg tggattaccc gccagtagcg    1200
ttggtcgttc tttcgtacga cgtcgactcg atttccgcca tacaccgcgt gagtcacgtg    1260
gctcatggcc tcagcggctt tggccaactc caccctcgcc cagagggtct ccgtacatta    1320
ggaaccattt acggcagtac attatttccc aaccgttccc ccgtagctcg tacgacgctt    1380
ttaaatttcg ttggtggatc caccgaccgt gcagtgggt ccgcggatcc aatggctttg     1440
gcgatggagg tggatctgga tctgaaaaag agcgggttga tccgagaggg agctgcgaag    1500
ccagaagtcc tcgggtgaa agtatatcca aaggctattc ctcagtttga tattggtcat     1560
ttggatcgag tggaaaaggc caaaatgatg ttaaagaacg aaagggggg tgcagattgg     1620
agtggggtca aattggcggg aaattatgtg tgcggcgtcg cagtgggcag atgcatagaa    1680
tttggattcg aaattgcgga gaacttggcg caggaattgg cgagaaaaaa atag          1734
```

<210> SEQ ID NO 28
<211> LENGTH: 577
<212> TYPE: PRT
<213> ORGANISM: Polytomella

<400> SEQUENCE: 28

```
Met Ser Ser Ser Ala Leu Arg Leu Leu Cys Gly Arg Thr Ser Phe Phe
1               5                   10                  15

Asn Leu Cys Gln Lys Tyr Pro Pro Ser Phe Leu Ser Gln Leu Ser Thr
            20                  25                  30

Leu Asn Phe Ser Thr His Ser Pro Phe Asp Ser Thr Tyr Asp Val Val
        35                  40                  45

Val Val Gly Ala Gly Ile Ser Gly Leu Ser Thr Ala Gln Ala Leu Ser
    50                  55                  60

Ile Gln His Lys Ile Asp Asn Val Leu Val Thr Glu Ala Asp His Arg
65                  70                  75                  80

Val Gly Gly Lys Ile Thr Thr Lys Arg Asn Lys Asp Phe Leu Trp Glu
                85                  90                  95

Glu Gly Pro Asn Ser Cys Leu Met Asn Asp Ala Leu Tyr Arg Ala Ala
                100                 105                 110

Arg Asp Ala Gly Val Glu Ser Lys Ile Leu Ser Ala Asp Pro Lys Leu
            115                 120                 125

Pro Arg Trp Ile Leu Trp Gly Arg Arg Leu Arg Val Ala Pro Ile Gly
        130                 135                 140

Ser Tyr Ala Leu Lys Ser Asp Leu Leu Ser Thr Gln Gly Leu Leu Arg
145                 150                 155                 160

Ala Ile Arg Gly Val Thr Gly Phe Gly Val Ser Pro Ala Pro Pro Lys
                165                 170                 175

Gly Gln Glu Glu Ser Val Glu Gly Phe Val Arg Arg Thr Leu Gly Asp
            180                 185                 190

Glu Ile Phe Glu Arg Leu Val Glu Pro Phe Cys Ser Gly Val Tyr Ala
        195                 200                 205

Gly Asp Pro Ser Lys Leu Ser Met Arg Ala Ala Phe Gly Lys Leu Val
    210                 215                 220

Glu Phe Glu Glu Thr Gly Asp Gly Ser Leu Leu Arg Gly Val Phe Arg
225                 230                 235                 240

Tyr Val Met Asn Lys Arg Arg Glu Arg Arg Thr Gly Gly Ala Lys Asp
                245                 250                 255

Gly Asp Thr Val Pro Leu Asn Glu Thr Ala Lys Ala Pro Lys Ser Ser
            260                 265                 270

Ser Gly Pro Thr Val Ser Ser Phe Glu Gly Gly Ile Glu Ile Leu Pro
        275                 280                 285

Lys Ala Ile Ala Gln Lys Leu Gly Asp Arg Val Arg Leu Gly Leu Arg
    290                 295                 300

Leu Val Arg Ile Asp Pro Thr Gln Leu Ala Asp Gly Thr Thr Ala Tyr
305                 310                 315                 320

Arg Leu Ser Tyr Arg Arg Met Ser His Gln Gly Asp Asp Ser Ser
                325                 330                 335

Arg Thr Ala Gly Ala Val Pro Arg Thr Ala Glu Gly Asp Val Ala Ala
            340                 345                 350

Gly Asp Glu Asp Ala Val Val Glu Val Ala Lys Lys Val Val Leu
        355                 360                 365

Thr Thr Pro Ala Phe Asp Ala Ala Asp Ile Leu Ser Arg Ser Gly Leu
370                 375                 380

Val Ala Ala Ala Asn Pro Leu Lys Glu Val Asp Tyr Pro Pro Val Ala
385                 390                 395                 400

Leu Val Val Leu Ser Tyr Asp Val Asp Ser Ile Ser Ala Ile His Arg
                405                 410                 415
```

Val Ser His Val Ala His Gly Leu Ser Gly Phe Gly Gln Leu His Pro
            420                 425                 430

Arg Pro Glu Gly Leu Arg Thr Leu Gly Thr Ile Tyr Gly Ser Thr Leu
        435                 440                 445

Phe Pro Asn Arg Ser Pro Val Ala Arg Thr Thr Leu Leu Asn Phe Val
    450                 455                 460

Gly Gly Ser Thr Asp Arg Ala Val Gly Ser Asp Pro Met Ala Leu
465                 470                 475                 480

Ala Met Glu Val Asp Leu Asp Leu Lys Lys Ser Gly Leu Ile Arg Glu
            485                 490                 495

Gly Ala Ala Lys Pro Glu Val Leu Gly Val Lys Val Tyr Pro Lys Ala
        500                 505                 510

Ile Pro Gln Phe Asp Ile Gly His Leu Asp Arg Val Glu Lys Ala Lys
    515                 520                 525

Met Met Leu Lys Asn Glu Arg Gly Gly Ala Asp Trp Ser Gly Val Lys
530                 535                 540

Leu Ala Gly Asn Tyr Val Cys Gly Val Ala Val Gly Arg Cys Ile Glu
545                 550                 555                 560

Phe Gly Phe Glu Ile Ala Glu Asn Leu Ala Gln Glu Leu Ala Arg Lys
            565                 570                 575

Lys

<210> SEQ ID NO 29
<211> LENGTH: 1635
<212> TYPE: DNA
<213> ORGANISM: Sorghum bicolor

<400> SEQUENCE: 29

| | | | | | |
|---|---|---|---|---|---|
| atgctcgctc | ggactgccac | ggtctcctcc | acttcgtccc | actccatcc | ttatcgcccc | 60 |
| acctccgctc | gcagtctccg | cctacgtccg | gtcctcgcga | tggcgggctc | cgacgactcc | 120 |
| cgcgcagctc | ccgccaggtc | ggtcgccgtc | gtcggcgccg | gggtcagcgg | gctcgtggcg | 180 |
| gcgtacaggc | tcaggaagag | cggcgtgaat | gtgacggtgt | tcgaggcggc | cgacagggcg | 240 |
| ggaggaaaga | tacggaccaa | ttccgagggc | gggtttctct | gggatgaagg | agcgaacacc | 300 |
| atgacagaag | gtgaattgga | ggccagtaga | ctgatagatg | atctcggtct | acaagacaaa | 360 |
| cagcagtatc | ctaactccca | acacaagcgt | tacattgtca | agatggagc | accagcactg | 420 |
| attccttcgg | atcccatttc | gctgatgaaa | agcagtgttc | tttctacaaa | atcaaagatt | 480 |
| gcgttatttt | ttgaaccatt | tctctacaag | aaagctaaca | caagaaaccc | tggaaaagta | 540 |
| tctgatgagc | atttgagtga | gagtgttggg | agcttctttg | aacgccactt | cggaagagaa | 600 |
| gttgttgact | atcttattga | tccatttgta | gctggaacaa | gtgcaggaga | tccagagtca | 660 |
| ctatctattt | gtcatgcatt | cccagcactg | tggaatttgg | aaagaaaata | tggttcagtt | 720 |
| gttgttggtg | ccatcttgtc | taagctaaca | gctaaaggtg | atccagtaaa | gacaagacgt | 780 |
| gattcatcag | cgaaaagaag | gaatagacgc | gtgtcgtttt | catttcatgg | tggaatgcag | 840 |
| tcactaataa | atgcacttca | caatgaagtt | ggagatgata | atgtgaagct | tggtacagaa | 900 |
| gtgttgtcat | ggcgtgtac | attagatgga | gcccctgcac | caggcgggtg | gtcaatttct | 960 |
| gatgattcga | aggatgctag | tggcaaggac | cttgctaaaa | accaaacctt | tgatgctgtt | 1020 |
| ataatgacag | ctccattgtc | aaatgtccag | aggatgaagt | tcacaaaagg | tggagctcct | 1080 |
| tttgttctag | actttcttcc | taaggtggat | tatctaccac | tatctctcat | ggtgactgct | 1140 |
| tttaagaagg | aagatgtcaa | gaaacctctg | gaaggatttg | gcgtcttaat | accctacaag | 1200 |

```
gaacagcaaa aacatggtct aaaaacccctt gggactctct tctcctcaat gatgttccca    1260
gatcgagctc ctgacgacca atatttatat acaacatttg ttgggggtag ccacaataga    1320
gatcttgctg gagctccaac gtctattctg aaacaacttg tgacctctga ccttaaaaaa    1380
ctcttaggcg tacaggggca accaactttt gtcaagcata tatactgggg aaatgctttt    1440
cctttgtatg gtcatgatta caattctgta ttggaagcta tagaaaagat ggagaaaaat    1500
cttccagggt tcttctacgc aggaaataac aaggatgggc ttgctgttgg gagtgttata    1560
gcttcaggaa gcaaggctgc tgaccttgca atctcgtatc ttgaatctca caccaagcat    1620
aataatttac attga                                                    1635
```

<210> SEQ ID NO 30
<211> LENGTH: 544
<212> TYPE: PRT
<213> ORGANISM: Sorghum

<400> SEQUENCE: 30

```
Met Leu Ala Arg Thr Ala Thr Val Ser Ser Thr Ser Ser His Ser His
1               5                   10                  15

Pro Tyr Arg Pro Thr Ser Ala Arg Ser Leu Arg Leu Arg Pro Val Leu
            20                  25                  30

Ala Met Ala Gly Ser Asp Asp Ser Arg Ala Ala Pro Ala Arg Ser Val
        35                  40                  45

Ala Val Val Gly Ala Gly Val Ser Gly Leu Val Ala Ala Tyr Arg Leu
    50                  55                  60

Arg Lys Ser Gly Val Asn Val Thr Val Phe Glu Ala Ala Asp Arg Ala
65                  70                  75                  80

Gly Gly Lys Ile Arg Thr Asn Ser Glu Gly Gly Phe Leu Trp Asp Glu
                85                  90                  95

Gly Ala Asn Thr Met Thr Glu Gly Glu Leu Glu Ala Ser Arg Leu Ile
            100                 105                 110

Asp Asp Leu Gly Leu Gln Asp Lys Gln Gln Tyr Pro Asn Ser Gln His
        115                 120                 125

Lys Arg Tyr Ile Val Lys Asp Gly Ala Pro Ala Leu Ile Pro Ser Asp
    130                 135                 140

Pro Ile Ser Leu Met Lys Ser Ser Val Leu Ser Thr Lys Ser Lys Ile
145                 150                 155                 160

Ala Leu Phe Phe Glu Pro Phe Leu Tyr Lys Lys Ala Asn Thr Arg Asn
                165                 170                 175

Pro Gly Lys Val Ser Asp Glu His Leu Ser Glu Ser Val Gly Ser Phe
            180                 185                 190

Phe Glu Arg His Phe Gly Arg Glu Val Val Asp Tyr Leu Ile Asp Pro
        195                 200                 205

Phe Val Ala Gly Thr Ser Ala Gly Asp Pro Glu Ser Leu Ser Ile Cys
    210                 215                 220

His Ala Phe Pro Ala Leu Trp Asn Leu Glu Arg Lys Tyr Gly Ser Val
225                 230                 235                 240

Val Val Gly Ala Ile Leu Ser Lys Leu Thr Ala Lys Gly Asp Pro Val
                245                 250                 255

Lys Thr Arg Arg Asp Ser Ser Ala Lys Arg Arg Asn Arg Arg Val Ser
            260                 265                 270

Phe Ser Phe His Gly Gly Met Gln Ser Leu Ile Asn Ala Leu His Asn
        275                 280                 285
```

```
Glu Val Gly Asp Asp Asn Val Lys Leu Gly Thr Glu Val Leu Ser Leu
    290                 295                 300
Ala Cys Thr Leu Asp Gly Ala Pro Ala Pro Gly Gly Trp Ser Ile Ser
305                 310                 315                 320
Asp Asp Ser Lys Asp Ala Ser Gly Lys Asp Leu Ala Lys Asn Gln Thr
                325                 330                 335
Phe Asp Ala Val Ile Met Thr Ala Pro Leu Ser Asn Val Gln Arg Met
            340                 345                 350
Lys Phe Thr Lys Gly Gly Ala Pro Phe Val Leu Asp Phe Leu Pro Lys
        355                 360                 365
Val Asp Tyr Leu Pro Leu Ser Leu Met Val Thr Ala Phe Lys Lys Glu
370                 375                 380
Asp Val Lys Lys Pro Leu Glu Gly Phe Gly Val Leu Ile Pro Tyr Lys
385                 390                 395                 400
Glu Gln Gln Lys His Gly Leu Lys Thr Leu Gly Thr Leu Phe Ser Ser
                405                 410                 415
Met Met Phe Pro Asp Arg Ala Pro Asp Asp Gln Tyr Leu Tyr Thr Thr
            420                 425                 430
Phe Val Gly Gly Ser His Asn Arg Asp Leu Ala Gly Ala Pro Thr Ser
        435                 440                 445
Ile Leu Lys Gln Leu Val Thr Ser Asp Leu Lys Lys Leu Leu Gly Val
450                 455                 460
Gln Gly Gln Pro Thr Phe Val Lys His Ile Tyr Trp Gly Asn Ala Phe
465                 470                 475                 480
Pro Leu Tyr Gly His Asp Tyr Asn Ser Val Leu Glu Ala Ile Glu Lys
                485                 490                 495
Met Glu Lys Asn Leu Pro Gly Phe Phe Tyr Ala Gly Asn Asn Lys Asp
            500                 505                 510
Gly Leu Ala Val Gly Ser Val Ile Ala Ser Gly Ser Lys Ala Ala Asp
        515                 520                 525
Leu Ala Ile Ser Tyr Leu Glu Ser His Thr Lys His Asn Asn Leu His
530                 535                 540

<210> SEQ ID NO 31
<211> LENGTH: 1611
<212> TYPE: DNA
<213> ORGANISM: Oryza sativa

<400> SEQUENCE: 31
atggccgccg ccgccgcagc catggccacc gccacctccg ccacggcagc gccgccgctc      60
cgcattcgcg acgccgcgag gaggacccgc cgacgcggcc acgttcgctg cgccgtcgcc     120
agcggcgcgg ccgaggcgcc cgcggcgccc ggggcgcggg tgtcggcgga ctgcgtcgtg     180
gtgggcggcg gcatcagcgg gctctgcacc gcgcaggcgc tggccacaaa gcacggcgtc     240
ggcgacgtgc tcgtcacgga ggcccgcgcc cgccccggcg caacatcac caccgccgag      300 cgcgccggcg agggctacct ctgggaggag gggcccaaca gcttccagcc ttccgacccc     360
gtcctcacca tggccgtgga cagcgggctc aaggacgatc tcgtgttcgg gaccccaac     420 gcgccgcggt tcgtgctgtg ggaggggaag ctaaggccgg tgccgtccaa gcccggcgac     480
ctgccgttct tcgacctcat gagcatcccc ggcaagctca gggccggcct ggcgcgctc      540 ggcgttcgag cgccacctcc agggcgtgag gagtcggtgg aggacttcgt gcggcgcaac     600 ctcggcgcg aggtctttga gcgctcatt gagcctttct gctcaggtgt gtatgctggt      660
gatccttcaa agctcagtat gaaggctgca tttgggaagg tgtggaggct ggaggatact     720
```

```
ggaggtagca ttattggtgg aaccatcaaa acaatccagg agaggggga aaaccccaaa      780 ccgccgaggg atccccgcct tccaacgcca aagggggaca cagttgcatc tttcaggaag      840
ggtctgacta tgctcccgga tgctattaca tctaggttgg gtagcaaagt caaactttca      900
tggaagttga caagcattac aaagtcgac aacaaaggat atgcattagt gtatgaaaca       960
ccagaagggg tggtctcggt gcaagctaaa actgttgtca tgaccatccc atcatatgtt     1020
gctagtgata tcttgcggcc actttcaagt gatgcagcag atgctctgtc aatattctat     1080
tatccaccag ttgctgctgt aactgtttca tatccaaaag aagcaattag aaaagaatgc     1140
ttaattgacg gagagctcca gggtttcggc cagctgcatc cgcgtagtca gggagttgag     1200
actttaggaa caatatatag ctcatcactc tttccaaatc gtgctccagc tggaagggtg     1260
ttacttctga actacatagg aggttctaca aatacaggga ttgttccaa gactgaaagt      1320 gagctggtag aagcagttga ccgtgacctc aggaagatgc tgataaatcc taaagcagtg     1380 gacccttttgg tccttggcgt ccgggtatgg ccacaagcca taccacagtt cctcattggc    1440
catcttgatc atcttgaggc tgcaaaatct gccctgggca aggtggtta tgatggattg      1500 ttcctcggag ggaactatgt tgcaggagtt gccctgggcc gatgcgttga aggtgcatat     1560
gagagtgcct cacaaatatc tgactacttg accaagtacg cctacaagtg a              1611
```

<210> SEQ ID NO 32
<211> LENGTH: 536
<212> TYPE: PRT
<213> ORGANISM: Oryza sativa

<400> SEQUENCE: 32

```
Met Ala Ala Ala Ala Ala Met Ala Thr Ala Thr Ser Ala Thr Ala
1               5                   10                  15

Ala Pro Pro Leu Arg Ile Arg Asp Ala Ala Arg Arg Thr Arg Arg
                20                  25                  30

Gly His Val Arg Cys Ala Val Ala Ser Gly Ala Ala Glu Ala Pro Ala
            35                  40                  45

Ala Pro Gly Ala Arg Val Ser Ala Asp Cys Val Val Gly Gly Gly
        50                  55                  60

Ile Ser Gly Leu Cys Thr Ala Gln Ala Leu Ala Thr Lys His Gly Val
65                  70                  75                  80

Gly Asp Val Leu Val Thr Glu Ala Arg Ala Arg Pro Gly Gly Asn Ile
                85                  90                  95

Thr Thr Ala Glu Arg Ala Gly Glu Gly Tyr Leu Trp Glu Glu Gly Pro
            100                 105                 110

Asn Ser Phe Gln Pro Ser Asp Pro Val Leu Thr Met Ala Val Asp Ser
        115                 120                 125

Gly Leu Lys Asp Asp Leu Val Phe Gly Asp Pro Asn Ala Pro Arg Phe
    130                 135                 140

Val Leu Trp Glu Gly Lys Leu Arg Pro Val Pro Ser Lys Pro Gly Asp
145                 150                 155                 160

Leu Pro Phe Phe Asp Leu Met Ser Ile Pro Gly Lys Leu Arg Ala Gly
                165                 170                 175

Leu Gly Ala Leu Gly Val Arg Ala Pro Pro Gly Arg Glu Glu Ser
            180                 185                 190

Val Glu Asp Phe Val Arg Arg Asn Leu Gly Ala Glu Val Phe Glu Arg
        195                 200                 205

Leu Ile Glu Pro Phe Cys Ser Gly Val Tyr Ala Gly Asp Pro Ser Lys
```

```
                     210                215                 220
Leu Ser Met Lys Ala Ala Phe Gly Lys Val Trp Arg Leu Glu Asp Thr
225                 230                 235                 240

Gly Gly Ser Ile Ile Gly Gly Thr Ile Lys Thr Ile Gln Glu Arg Gly
                245                 250                 255

Lys Asn Pro Lys Pro Pro Arg Asp Pro Arg Leu Pro Thr Pro Lys Gly
            260                 265                 270

Gln Thr Val Ala Ser Phe Arg Lys Gly Leu Thr Met Leu Pro Asp Ala
        275                 280                 285

Ile Thr Ser Arg Leu Gly Ser Lys Val Lys Leu Ser Trp Lys Leu Thr
    290                 295                 300

Ser Ile Thr Lys Ser Asp Asn Lys Gly Tyr Ala Leu Val Tyr Glu Thr
305                 310                 315                 320

Pro Glu Gly Val Val Ser Val Gln Ala Lys Thr Val Val Met Thr Ile
                325                 330                 335

Pro Ser Tyr Val Ala Ser Asp Ile Leu Arg Pro Leu Ser Ser Asp Ala
                340                 345                 350

Ala Asp Ala Leu Ser Ile Phe Tyr Tyr Pro Pro Val Ala Ala Val Thr
            355                 360                 365

Val Ser Tyr Pro Lys Glu Ala Ile Arg Lys Glu Cys Leu Ile Asp Gly
        370                 375                 380

Glu Leu Gln Gly Phe Gly Gln Leu His Pro Arg Ser Gln Gly Val Glu
385                 390                 395                 400

Thr Leu Gly Thr Ile Tyr Ser Ser Leu Phe Pro Asn Arg Ala Pro
                405                 410                 415

Ala Gly Arg Val Leu Leu Leu Asn Tyr Ile Gly Gly Ser Thr Asn Thr
                420                 425                 430

Gly Ile Val Ser Lys Thr Glu Ser Glu Leu Val Glu Ala Val Asp Arg
            435                 440                 445

Asp Leu Arg Lys Met Leu Ile Asn Pro Lys Ala Val Asp Pro Leu Val
        450                 455                 460

Leu Gly Val Arg Val Trp Pro Gln Ala Ile Pro Gln Phe Leu Ile Gly
465                 470                 475                 480

His Leu Asp His Leu Glu Ala Ala Lys Ser Ala Leu Gly Lys Gly Gly
                485                 490                 495

Tyr Asp Gly Leu Phe Leu Gly Asn Tyr Val Ala Gly Val Ala Leu
                500                 505                 510

Gly Arg Cys Val Glu Gly Ala Tyr Glu Ser Ala Ser Gln Ile Ser Asp
            515                 520                 525

Tyr Leu Thr Lys Tyr Ala Tyr Lys
530                 535

<210> SEQ ID NO 33
<211> LENGTH: 1518
<212> TYPE: DNA
<213> ORGANISM: Amaranthus tuberculatus

<400> SEQUENCE: 33
atgggcaaca tttctgagcg ggatgaaccc acttctgcta aagggttgc tgttgttggt      60 gctggagtta gtggacttgc tgctgcatat aagctaaaat cccatggttt gaatgtgaca     120
ttgtttgaag ctgattctag agctggaggc aaacttaaaa ctgttaaaaa agatggtttt     180
atttgggatg agggggcaaa tactatgaca gaaagtgagg cagaagtctc gagtttgatc     240
gatgatcttg gcttcgtga gaagcaacag ttgccaattt cacaaaataa agatacata      300
```

```
gctagagatg gtcttcctgt gctactacct tcaaatcccg ctgcactgct cacgagcaat    360
atcctttcag caaaatcaaa gctgcaaatt atgttggaac cattttctg gagaaaacac     420
aatgctactg agctttctga tgagcatgtt caggaaagcg ttggtgaatt ttttgagcga    480
cattttggga aagagtttgt tgattatgtt attgaccctt tgttgcggg tacatgtggt     540
ggagatcctc aatcgctttc tatgcaccat acatttccag aagtatggaa tattgaaaaa    600
aggtttggct ctgtgtttgc tggactaatt caatcaacat tgttatctaa gaaggaaaag    660
ggtggaggag gaaatgcttc tatcaagaag cctcgtgtac gtggttcatt tcattccat    720
ggtggaatgc agacacttgt tgacacaata tgcaaacagc ttggtgaaga tgaactcaaa    780
ctccagtgtg aggtgctgtc cttgtcatac aaccagaagg ggatcccttc attagggaat    840
tggtcagtct cttctatgtc aaataatacc agtgaagatc aatcttatga tgctgtggtt    900
gtcactgctc caattcgcaa tgtcaaagaa atgaagatta tgaaattcgg aaatccattt    960
tcacttgact ttattccaga ggtgagttac gtacccctct ctgttatgat tactgcattc   1020
aagaaggata agtgaagag accactcgag ggctttggag ttcttatccc ctctaaagag    1080
caacataatg gactgaagac tcttggtact ttattttcct ccatgatgtt tcccgatcgt   1140
gctccatctg acatgtgtct ctttactaca tttgtcggag gaagcagaaa tagaaaactt   1200
gcaaacgctt caacggatga attgaagcaa atagtttctt ctgaccttca gcagctgttg   1260
ggcactgagg acgaaccttc attttgtcaat catctcttt ggagcaacgc attccgttg    1320
tatggacaca attacgattc tgttttgaga gccatagaca agatggaaaa ggatcttcct   1380
ggattttttt atgcaggtaa ccataagggt ggactttcag tgggaaaagc gatggcctcc   1440
ggatgcaagg ctgcggaact tgtaatatcc tatctggact ctcatatata tgtgaagatg   1500
gatgagaaga ccgcgtaa                                                 1518
```

<210> SEQ ID NO 34
<211> LENGTH: 505
<212> TYPE: PRT
<213> ORGANISM: Amaranthus

<400> SEQUENCE: 34

Met Gly Asn Ile Ser Glu Arg Asp Glu Pro Thr Ser Ala Lys Arg Val
1               5                   10                  15

Ala Val Val Gly Ala Val Ser Gly Leu Ala Ala Tyr Lys Leu
            20                  25                  30

Lys Ser His Gly Leu Asn Val Thr Leu Phe Glu Ala Asp Ser Arg Ala
        35                  40                  45

Gly Gly Lys Leu Lys Thr Val Lys Lys Asp Gly Phe Ile Trp Asp Glu
    50                  55                  60

Gly Ala Asn Thr Met Thr Glu Ser Glu Ala Glu Val Ser Ser Leu Ile
65                  70                  75                  80

Asp Asp Leu Gly Leu Arg Glu Lys Gln Gln Leu Pro Ile Ser Gln Asn
                85                  90                  95

Lys Arg Tyr Ile Ala Arg Asp Gly Leu Pro Val Leu Leu Pro Ser Asn
            100                 105                 110

Pro Ala Ala Leu Leu Thr Ser Asn Ile Leu Ser Ala Lys Ser Lys Leu
        115                 120                 125

Gln Ile Met Leu Glu Pro Phe Phe Trp Arg Lys His Asn Ala Thr Glu
    130                 135                 140

Leu Ser Asp Glu His Val Gln Glu Ser Val Gly Glu Phe Phe Glu Arg

```
             145                 150                 155                 160
His Phe Gly Lys Glu Phe Val Asp Tyr Val Ile Asp Pro Phe Val Ala
                 165                 170                 175
Gly Thr Cys Gly Gly Asp Pro Gln Ser Leu Ser Met His His Thr Phe
             180                 185                 190
Pro Glu Val Trp Asn Ile Glu Lys Arg Phe Gly Ser Phe Ala Gly
         195                 200                 205
Leu Ile Gln Ser Thr Leu Leu Ser Lys Lys Lys Gly Gly Gly Gly
    210                 215                 220
Asn Ala Ser Ile Lys Lys Pro Arg Val Arg Gly Ser Phe Ser Phe His
225                 230                 235                 240
Gly Gly Met Gln Thr Leu Val Asp Thr Ile Cys Lys Gln Leu Gly Glu
                 245                 250                 255
Asp Glu Leu Lys Leu Gln Cys Glu Val Leu Ser Leu Ser Tyr Asn Gln
                 260                 265                 270
Lys Gly Ile Pro Ser Leu Gly Asn Trp Ser Val Ser Ser Met Ser Asn
        275                 280                 285
Asn Thr Ser Glu Asp Gln Ser Tyr Asp Ala Val Val Thr Ala Pro
    290                 295                 300
Ile Arg Asn Val Lys Glu Met Lys Ile Met Lys Phe Gly Asn Pro Phe
305                 310                 315                 320
Ser Leu Asp Phe Ile Pro Glu Val Ser Tyr Val Pro Leu Ser Val Met
                 325                 330                 335
Ile Thr Ala Phe Lys Lys Asp Lys Val Lys Arg Pro Leu Glu Gly Phe
                 340                 345                 350
Gly Val Leu Ile Pro Ser Lys Glu Gln His Asn Gly Leu Lys Thr Leu
             355                 360                 365
Gly Thr Leu Phe Ser Ser Met Met Phe Pro Asp Arg Ala Pro Ser Asp
    370                 375                 380
Met Cys Leu Phe Thr Thr Phe Val Gly Gly Ser Arg Asn Arg Lys Leu
385                 390                 395                 400
Ala Asn Ala Ser Thr Asp Glu Leu Lys Gln Ile Val Ser Ser Asp Leu
                 405                 410                 415
Gln Gln Leu Leu Gly Thr Glu Asp Glu Pro Ser Phe Val Asn His Leu
             420                 425                 430
Phe Trp Ser Asn Ala Phe Pro Leu Tyr Gly His Asn Tyr Asp Ser Val
    435                 440                 445
Leu Arg Ala Ile Asp Lys Met Glu Lys Asp Leu Pro Gly Phe Phe Tyr
450                 455                 460
Ala Gly Asn His Lys Gly Gly Leu Ser Val Gly Lys Ala Met Ala Ser
465                 470                 475                 480
Gly Cys Lys Ala Ala Glu Leu Val Ile Ser Tyr Leu Asp Ser His Ile
                 485                 490                 495
Tyr Val Lys Met Asp Glu Lys Thr Ala
             500                 505

<210> SEQ ID NO 35
<211> LENGTH: 1521
<212> TYPE: DNA
<213> ORGANISM: Arabidopsis thaliana

<400> SEQUENCE: 35
atggagttat ctcttctccg tccgacgact caatcgcttc ttccgtcgtt ttcgaagccc      60
aatctccgat taaatgttta taagcctctt agactccgtt gttcagtggc cggtggacca     120
```

```
accgtcggat cttcaaaaat cgaaggcgga ggaggcacca ccatcacgac ggattgtgtg    180
attgtcggcg gaggtattag tggtctttgc atcgctcagg cgcttgctac taagcatcct    240
gatgctgctc cgaatttaat tgtgaccgag gctaaggatc gtgttggagg caacattatc    300
actcgtgaag agaatggttt tctctgggaa gaaggtccca atagttttca accgtctgat    360
cctatgctca ctatggtggt agatagtggt ttgaaggatg atttggtgtt gggagatcct    420
actgcgccaa ggtttgtgtt gtggaatggg aaattgaggc cggttccatc gaagctaaca    480
gacttaccgt tctttgattt gatgagtatt ggtgggaaga ttagagctgg ttttggtgca    540
cttggcattc gaccgtcacc tccaggtcgt gaagaatctg tggaggagtt tgtacggcgt    600
aacctcggtg atgaggtttt tgagcgcctg attgaaccgt tttgttcagg tgtttatgct    660
ggtgatcctt caaaactgag catgaaagca gcgtttggga aggtttggaa actagagcaa    720
aatggtggaa gcataatagg tggtactttt aaggcaattc aggagaggaa aaacgctccc    780
aaggcagaac gagacccgcg cctgccaaaa ccacagggcc aaacagttgg ttctttcagg    840
aagggacttc gaatgttgcc agaagcaata tctgcaagat taggtagcaa agttaagttg    900
tcttggaagc tctcaggtat cactaagctg gagagcggag gatacaactt aacatatgag    960
actccagatg gtttagtttc cgtgcagagc aaaagtgttg taatgacggt gccatctcat   1020
gttgcaagtg gtctcttgcg ccctctttct gaatctgctg caaatgcact ctcaaaacta   1080 tattcccac cagttgcagc agtatctatc tcgtacccga agaagcaat ccgaacagaa     1140 tgtttgatag atggtgaact aaagggtttt gggcaattgc atccacgcac gcaaggagtt   1200
gaaacattag gaactatcta cagctcctca ctctttccaa atcgcgcacc gcccggaaga   1260
attttgctgt tgaactacat tggcgggtct acaaacaccg gaattctgtc caagtctgaa   1320
ggtgagttag tggaagcatt tctagttggt cactttgata tccttgacac ggctaaatca   1380
tctctaacgt cttcgggcta cgaagggcta ttttggggtg caattacgt cgctggtgta   1440 gccttaggcc ggtgtgtaga aggcgcatat gaaaccgcga ttgaggtcaa caacttcatg   1500
tcacggtacg cttacaagta a                                             1521
```

<210> SEQ ID NO 36
<211> LENGTH: 506
<212> TYPE: PRT
<213> ORGANISM: Arabidopsis

<400> SEQUENCE: 36

Met Glu Leu Ser Leu Leu Arg Pro Thr Thr Gln Ser Leu Leu Pro Ser
1               5                   10                  15

Phe Ser Lys Pro Asn Leu Arg Leu Asn Val Tyr Lys Pro Leu Arg Leu
                20                  25                  30

Arg Cys Ser Val Ala Gly Gly Pro Thr Val Gly Ser Ser Lys Ile Glu
            35                  40                  45

Gly Gly Gly Gly Thr Thr Ile Thr Thr Asp Cys Val Ile Val Gly Gly
        50                  55                  60

Gly Ile Ser Gly Leu Cys Ile Ala Gln Ala Leu Ala Thr Lys His Pro
65                  70                  75                  80

Asp Ala Ala Pro Asn Leu Ile Val Thr Glu Ala Lys Asp Arg Val Gly
                85                  90                  95

Gly Asn Ile Ile Thr Arg Glu Glu Asn Gly Phe Leu Trp Glu Glu Gly
                100                 105                 110

Pro Asn Ser Phe Gln Pro Ser Asp Pro Met Leu Thr Met Val Val Asp

```
                    115                 120                 125
Ser Gly Leu Lys Asp Asp Leu Val Leu Gly Asp Pro Thr Ala Pro Arg
    130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                    165                 170                 175

Gly Phe Gly Ala Leu Gly Ile Arg Pro Ser Pro Gly Arg Glu Glu
                180                 185                 190

Ser Val Glu Glu Phe Val Arg Arg Asn Leu Gly Asp Glu Val Phe Glu
            195                 200                 205

Arg Leu Ile Glu Pro Phe Cys Ser Gly Val Tyr Ala Gly Asp Pro Ser
        210                 215                 220

Lys Leu Ser Met Lys Ala Ala Phe Gly Lys Val Trp Lys Leu Glu Gln
225                 230                 235                 240

Asn Gly Gly Ser Ile Ile Gly Gly Thr Phe Lys Ala Ile Gln Glu Arg
                    245                 250                 255

Lys Asn Ala Pro Lys Ala Glu Arg Asp Pro Arg Leu Pro Lys Pro Gln
                260                 265                 270

Gly Gln Thr Val Gly Ser Phe Arg Lys Gly Leu Arg Met Leu Pro Glu
            275                 280                 285

Ala Ile Ser Ala Arg Leu Gly Ser Lys Val Lys Leu Ser Trp Lys Leu
        290                 295                 300

Ser Gly Ile Thr Lys Leu Glu Ser Gly Gly Tyr Asn Leu Thr Tyr Glu
305                 310                 315                 320

Thr Pro Asp Gly Leu Val Ser Val Gln Ser Lys Ser Val Val Met Thr
                    325                 330                 335

Val Pro Ser His Val Ala Ser Gly Leu Leu Arg Pro Leu Ser Glu Ser
                340                 345                 350

Ala Ala Asn Ala Leu Ser Lys Leu Tyr Tyr Pro Pro Val Ala Ala Val
            355                 360                 365

Ser Ile Ser Tyr Pro Lys Glu Ala Ile Arg Thr Glu Cys Leu Ile Asp
        370                 375                 380

Gly Glu Leu Lys Gly Phe Gly Gln Leu His Pro Arg Thr Gln Gly Val
385                 390                 395                 400

Glu Thr Leu Gly Thr Ile Tyr Ser Ser Ser Leu Phe Pro Asn Arg Ala
                    405                 410                 415

Pro Pro Gly Arg Ile Leu Leu Leu Asn Tyr Ile Gly Gly Ser Thr Asn
                420                 425                 430

Thr Gly Ile Leu Ser Lys Ser Glu Gly Glu Leu Val Glu Ala Phe Leu
            435                 440                 445

Val Gly His Phe Asp Ile Leu Asp Thr Ala Lys Ser Ser Leu Thr Ser
        450                 455                 460

Ser Gly Tyr Glu Gly Leu Phe Leu Gly Gly Asn Tyr Val Ala Gly Val
465                 470                 475                 480

Ala Leu Gly Arg Cys Val Glu Gly Ala Tyr Glu Thr Ala Ile Glu Val
                    485                 490                 495

Asn Asn Phe Met Ser Arg Tyr Ala Tyr Lys
                500                 505

<210> SEQ ID NO 37
<211> LENGTH: 1515
<212> TYPE: DNA
<213> ORGANISM: Nicotiana tabacum
```

<400> SEQUENCE: 37

```
atggctcctt ctgccggaga agataaacac agttctgcga agagagtcgc agtcattggt    60
gcaggcgtca gtgggcttgc tgcagcatac aagttgaaaa tccatggctt gaatgtgaca   120
gtatttgaag cagaagggaa agctggaggg aagttacgta gcgtgagcca agatggcctg   180
atatgggatg aaggggcaaa tactatgact gaaagtgaag gtgatgttac atttttgatt   240
gattctcttg gactccgaga aaagcaacaa tttccacttt cacaaaacaa gcgctacatt   300
gccagaaatg gtactcctgt actgttacct tcaaatccaa ttgatctgat caaaagcaat   360
tttctttcca ctggatcaaa gcttcagatg cttctggaac caatattatg gaagaataaa   420
aagctctccc aggtgtctga ctcacatgaa agtgtcagtg gattcttcca gcgtcatttt   480
ggaaaggagg ttgttgacta tctaattgac ccttttgttg ctggaacgtg tggtggtgat   540
cctgactcgc tttcaatgca ccattcattt ccagagttgt ggaatttaga gaaaaggttt   600
ggctcagtca tacttggagc tattcgatct aagttatccc ctaaaaatga aaagaagcaa   660
gggccaccca aaacttcagc aaataagaag cgccagcggg gatcttttc cttttttggc    720
ggaatgcaaa cacttactga tgcaaatatgc aaagatctca gagaagatga acttagacta   780
aactctagag ttctggaatt atcttgtagc tgtactgagg actctgcgat agatagctgg   840
tcaattattt ctgcctctcc acacaaaagg caatcagaag aagaatcatt tgatgctgta   900
attatgacgg ccccactctg tgatgttaag agtatgaaga ttgctaagag aggaaatcca   960
tttctactca actttattcc tgaggttgat tatgtaccgc tatctgttgt tataaccaca  1020
tttaagaggg aaaacgtaaa gtatcccctt gagggttttg gggttcttgt accttccaag  1080
gagcaacaac atggtctcaa gacactaggc accctcttct cttctatgat gtttccagat  1140
cgggcaccaa acaatgttta tctctatact acttttgttg gtggaagccg aaatagaaa    1200
cttgcaaaag cctcaaggac tgagctgaaa gagatagtaa cttctgacct taagcagctg  1260
ttgggtgctg agggagagcc aacatatgtg aatcatctat actggagtaa agcatttcca  1320
ttgtacgggc ataactatga ttcagtccta gatgcaattg acaaaatgga gaaaaatctt  1380
cctggattat tctatgcagg taaccacagg gggggattgt cagttggcaa agcattatct  1440
tctggatgca atgcagctga tcttgttata tcatatcttg aatccgtctc aactgactcc  1500
aaaagacatt gctga                                                    1515
```

<210> SEQ ID NO 38
<211> LENGTH: 504
<212> TYPE: PRT
<213> ORGANISM: Nicotiana

<400> SEQUENCE: 38

```
Met Ala Pro Ser Ala Gly Glu Asp Lys His Ser Ser Ala Lys Arg Val
1               5                   10                  15

Ala Val Ile Gly Ala Gly Val Ser Gly Leu Ala Ala Ala Tyr Lys Leu
            20                  25                  30

Lys Ile His Gly Leu Asn Val Thr Val Phe Glu Ala Glu Gly Lys Ala
        35                  40                  45

Gly Gly Lys Leu Arg Ser Val Ser Gln Asp Gly Leu Ile Trp Asp Glu
    50                  55                  60

Gly Ala Asn Thr Met Thr Glu Ser Glu Gly Asp Val Thr Phe Leu Ile
65                  70                  75                  80

Asp Ser Leu Gly Leu Arg Glu Lys Gln Gln Phe Pro Leu Ser Gln Asn
```

```
            85                  90                  95
Lys Arg Tyr Ile Ala Arg Asn Gly Thr Pro Val Leu Leu Pro Ser Asn
            100                 105                 110

Pro Ile Asp Leu Ile Lys Ser Asn Phe Leu Ser Thr Gly Ser Lys Leu
            115                 120                 125

Gln Met Leu Leu Glu Pro Ile Leu Trp Lys Asn Lys Lys Leu Ser Gln
130                 135                 140

Val Ser Asp Ser His Glu Ser Val Ser Gly Phe Phe Gln Arg His Phe
145                 150                 155                 160

Gly Lys Glu Val Val Asp Tyr Leu Ile Asp Pro Phe Val Ala Gly Thr
                165                 170                 175

Cys Gly Gly Asp Pro Asp Ser Leu Ser Met His His Ser Phe Pro Glu
                180                 185                 190

Leu Trp Asn Leu Glu Lys Arg Phe Gly Ser Val Ile Leu Gly Ala Ile
            195                 200                 205

Arg Ser Lys Leu Ser Pro Lys Asn Glu Lys Lys Gln Gly Pro Pro Lys
            210                 215                 220

Thr Ser Ala Asn Lys Lys Arg Gln Arg Gly Ser Phe Ser Phe Leu Gly
225                 230                 235                 240

Gly Met Gln Thr Leu Thr Asp Ala Ile Cys Lys Asp Leu Arg Glu Asp
                245                 250                 255

Glu Leu Arg Leu Asn Ser Arg Val Leu Glu Leu Ser Cys Ser Cys Thr
                260                 265                 270

Glu Asp Ser Ala Ile Asp Ser Trp Ser Ile Ile Ser Ala Ser Pro His
            275                 280                 285

Lys Arg Gln Ser Glu Glu Ser Phe Asp Ala Val Ile Met Thr Ala
            290                 295                 300

Pro Leu Cys Asp Val Lys Ser Met Lys Ile Ala Lys Arg Gly Asn Pro
305                 310                 315                 320

Phe Leu Leu Asn Phe Ile Pro Glu Val Asp Tyr Val Pro Leu Ser Val
                325                 330                 335

Val Ile Thr Thr Phe Lys Arg Glu Asn Val Lys Tyr Pro Leu Glu Gly
                340                 345                 350

Phe Gly Val Leu Val Pro Ser Lys Glu Gln Gln His Gly Leu Lys Thr
            355                 360                 365

Leu Gly Thr Leu Phe Ser Ser Met Met Phe Pro Asp Arg Ala Pro Asn
            370                 375                 380

Asn Val Tyr Leu Tyr Thr Thr Phe Val Gly Gly Ser Arg Asn Arg Glu
385                 390                 395                 400

Leu Ala Lys Ala Ser Arg Thr Glu Leu Lys Glu Ile Val Thr Ser Asp
                405                 410                 415

Leu Lys Gln Leu Leu Gly Ala Glu Gly Glu Pro Thr Tyr Val Asn His
            420                 425                 430

Leu Tyr Trp Ser Lys Ala Phe Pro Leu Tyr Gly His Asn Tyr Asp Ser
            435                 440                 445

Val Leu Asp Ala Ile Asp Lys Met Glu Lys Asn Leu Pro Gly Leu Phe
450                 455                 460

Tyr Ala Gly Asn His Arg Gly Gly Leu Ser Val Gly Lys Ala Leu Ser
465                 470                 475                 480

Ser Gly Cys Asn Ala Ala Asp Leu Val Ile Ser Tyr Leu Glu Ser Val
                485                 490                 495

Ser Thr Asp Ser Lys Arg His Cys
            500
```

<210> SEQ ID NO 39
<211> LENGTH: 1509
<212> TYPE: DNA
<213> ORGANISM: Glycine max

<400> SEQUENCE: 39

| | | | | | |
|---|---|---|---|---|---|
| atggcttcct | ctgcaacaga | cgataaccca | agatctgtaa | aaagagtagc | tgttgttggt | 60 |
| gctggggtaa | gtgggcttgc | tgcggcttac | aaattgaaat | cacatggtct | ggatgtcact | 120 |
| gtatttgaag | ctgagggaag | agctggaggg | aggttgagaa | gtgtttctca | ggatggtcta | 180 |
| atttgggatg | agggagctaa | tacaatgact | gaaagtgaaa | ttgaggttaa | aggttttgatt | 240 |
| gatgctcttg | gacttcaaga | aaagcagcag | tttccaatat | cacagcataa | gcgctatatt | 300 |
| gtgaaaaatg | gggcaccact | tctggtaccc | acaaatcctg | ctgcactact | gaagagtaaa | 360 |
| ctgctttctg | cacaatcaaa | gatccatctc | attttgaac | catttatgtg | aaaagaagt | 420 |
| gaccccctcta | atgtgtgtga | tgaaaattct | gtggaaagtg | taggcaggtt | ctttgaacgt | 480 |
| catttttggaa | agaggttgt | ggactatctg | attgatcctt | tgttggggg | cactagtgca | 540 |
| gcagatcctg | aatctctctc | tatgcgccat | tctttcccag | agctatggaa | tttggagaaa | 600 |
| aggtttggct | ccattatagc | cggggcattg | caatctaagt | tattcgccaa | aagggaaaaa | 660 |
| actggagaaa | ataggactgc | actaagaaaa | aacaaacaca | agcgtggttc | gtttttctttc | 720 |
| cagggtggga | tgcagacact | gacagataca | ttgtgcaaag | agcttggcaa | agacgacctt | 780 |
| aaattaaatg | aaaaggtttt | gacattagct | tatggtcatg | atggaagttc | ctcttcacaa | 840 |
| aactggtcta | ttactagtgc | ttctaaccaa | agtacacaag | atgttgatgc | agtaatcatg | 900 |
| acggctcctc | tatataatgt | caaggacatc | aagatcacaa | aaggggaac | tcccttttcca | 960 |
| cttaattttc | ttcccgaggt | aagctacgtg | ccaatctcag | tcatgattac | taccttcaaa | 1020 |
| aaggagaatg | taaagagacc | tttggaggga | tttggagttc | ttgttccttc | taaagagcaa | 1080 |
| aaaaatggtt | taaaaaccct | tggtacactt | ttttcctcta | tgatgttccc | agatcgtgca | 1140 |
| cctagtgatt | tatatctcta | taccaccttc | attggcggaa | ctcaaaacag | ggaacttgct | 1200 |
| caagcttcaa | ctgacgagct | taggaaaatt | gttacttctg | acctgagaaa | gttgttggga | 1260 |
| gcagaggggg | aaccaacatt | tgttaaccat | ttctattgga | gtaaaggctt | cctttgtat | 1320 |
| ggacgtaact | atgggtcagt | tcttcaagca | attgataaga | tagaaaaaga | tcttcccgga | 1380 |
| ttttctttg | caggtaacta | caaaggtgga | ctctcagttg | gcaaagcaat | agcctcaggc | 1440 |
| tgcaaagcag | ctgatcttgt | gatatcctac | ctcaactctg | cttcagacaa | cacagtgcct | 1500 |
| gataaatga | | | | | | 1509 |

<210> SEQ ID NO 40
<211> LENGTH: 502
<212> TYPE: PRT
<213> ORGANISM: Glycine

<400> SEQUENCE: 40

Met Ala Ser Ser Ala Thr Asp Asp Asn Pro Arg Ser Val Lys Arg Val
1               5                   10                  15

Ala Val Val Gly Ala Gly Val Ser Gly Leu Ala Ala Ala Tyr Lys Leu
            20                  25                  30

Lys Ser His Gly Leu Asp Val Thr Val Phe Glu Ala Glu Gly Arg Ala
        35                  40                  45

Gly Gly Arg Leu Arg Ser Val Ser Gln Asp Gly Leu Ile Trp Asp Glu

```
                50               55                60
Gly Ala Asn Thr Met Thr Glu Ser Glu Ile Glu Val Lys Gly Leu Ile
 65                      70                      75              80

Asp Ala Leu Gly Leu Gln Glu Lys Gln Gln Phe Pro Ile Ser Gln His
                85                      90                  95

Lys Arg Tyr Ile Val Lys Asn Gly Ala Pro Leu Leu Val Pro Thr Asn
                    100                     105             110

Pro Ala Ala Leu Leu Lys Ser Lys Leu Leu Ser Ala Gln Ser Lys Ile
                115                     120                 125

His Leu Ile Phe Glu Pro Phe Met Trp Lys Arg Ser Asp Pro Ser Asn
    130                     135                 140

Val Cys Asp Glu Asn Ser Val Glu Ser Val Gly Arg Phe Phe Glu Arg
145                     150                     155             160

His Phe Gly Lys Glu Val Val Asp Tyr Leu Ile Asp Pro Phe Val Gly
                    165                     170             175

Gly Thr Ser Ala Ala Asp Pro Glu Ser Leu Ser Met Arg His Ser Phe
                180                     185                 190

Pro Glu Leu Trp Asn Leu Glu Lys Arg Phe Gly Ser Ile Ile Ala Gly
                195                     200             205

Ala Leu Gln Ser Lys Leu Phe Ala Lys Arg Glu Lys Thr Gly Glu Asn
210                     215                     220

Arg Thr Ala Leu Arg Lys Asn Lys His Lys Arg Gly Ser Phe Ser Phe
225                     230                     235             240

Gln Gly Gly Met Gln Thr Leu Thr Asp Thr Leu Cys Lys Glu Leu Gly
                    245                     250             255

Lys Asp Asp Leu Lys Leu Asn Glu Lys Val Leu Thr Leu Ala Tyr Gly
                260                     265             270

His Asp Gly Ser Ser Ser Ser Gln Asn Trp Ser Ile Thr Ser Ala Ser
                275                     280             285

Asn Gln Ser Thr Gln Asp Val Asp Ala Val Ile Met Thr Ala Pro Leu
    290                     295                 300

Tyr Asn Val Lys Asp Ile Lys Ile Thr Lys Arg Gly Thr Pro Phe Pro
305                     310                     315             320

Leu Asn Phe Leu Pro Glu Val Ser Tyr Val Pro Ile Ser Val Met Ile
                    325                     330             335

Thr Thr Phe Lys Lys Glu Asn Val Lys Arg Pro Leu Glu Gly Phe Gly
                340                     345             350

Val Leu Val Pro Ser Lys Glu Gln Lys Asn Gly Leu Lys Thr Leu Gly
                355                     360             365

Thr Leu Phe Ser Ser Met Met Phe Pro Asp Arg Ala Pro Ser Asp Leu
    370                     375                 380

Tyr Leu Tyr Thr Thr Phe Ile Gly Gly Thr Gln Asn Arg Glu Leu Ala
385                     390                     395             400

Gln Ala Ser Thr Asp Glu Leu Arg Lys Ile Val Thr Ser Asp Leu Arg
                405                     410             415

Lys Leu Leu Gly Ala Glu Gly Glu Pro Thr Phe Val Asn His Phe Tyr
                420                     425             430

Trp Ser Lys Gly Phe Pro Leu Tyr Gly Arg Asn Tyr Gly Ser Val Leu
    435                     440                 445

Gln Ala Ile Asp Lys Ile Glu Lys Asp Leu Pro Gly Phe Phe Phe Ala
    450                     455                 460

Gly Asn Tyr Lys Gly Gly Leu Ser Val Gly Lys Ala Ile Ala Ser Gly
465                     470                     475             480
```

Cys Lys Ala Ala Asp Leu Val Ile Ser Tyr Leu Asn Ser Ala Ser Asp
            485                 490                 495

Asn Thr Val Pro Asp Lys
            500

<210> SEQ ID NO 41
<211> LENGTH: 1205
<212> TYPE: DNA
<213> ORGANISM: Cucumis sativus

<400> SEQUENCE: 41

| | | | | | |
|---|---|---|---|---|---|
| agcttccaac | cttccgatcc | tattctcacc | atggtggtgg | atagtggctt | aaaagatgat | 60 |
| ttagttctgg | gagacccaga | tgcacctcga | tttgtattgt | ggaatggaaa | gctcagacca | 120 |
| gtgcctgcga | aacctaatga | tctacctttc | tttgacctga | tgagcattgg | tggaaaaatc | 180 |
| agagcaggct | ttggtgccct | gggcattcgc | cctcctcctc | aggtcgaga | ggaatcagtt | 240 |
| gaagaatttg | tccgtcggaa | ccttggcaat | gaagttttg | aacgtttgat | agagccattt | 300 |
| tgttctggtg | tatacgctgg | tgacccttca | aagctaagca | tgaaagcagc | ttttggtaag | 360 |
| gtttggaggc | tagagcaaaa | tggtggtagt | attattggtg | ggactttcaa | agcacttcaa | 420 |
| gaaaggaata | aaactaccaa | accaccaaga | gatccgcgtc | taccaaagcc | taagggccaa | 480 |
| actgttggat | cttttcggaa | aggacttacc | atgttgccaa | atgctatttc | tacttgtttg | 540 |
| gggagtaaag | taaagtatc | ttggaagcta | tctagtatca | gtaaagtgga | tgacggaggt | 600 |
| tatagtttga | catacgaaac | accagaagga | ctagtctcca | tactaagcag | aagtgtcatc | 660 |
| atgacggttc | cttcttatat | tgctggcact | ctgttgcgtc | caatctcggg | gaaagctgca | 720 |
| gatgcacttt | caaaatttta | ttatccacca | gttgcatcag | tgaccatatc | atatccaaaa | 780 |
| ggagcaatta | ggaaagaatg | cttgattgat | ggtgaactaa | aggggtttgg | tcaattgcac | 840 |
| cctcgtagcc | aggggggtgac | tactttggga | actatataca | gctcatcact | ttttcctaat | 900 |
| cgagcgccag | atggaagggt | attgctcttg | aactacattg | gagggggctac | taatactgga | 960 |
| attctttctc | agacagagag | cgagctcata | gaagtagttg | atcgggattt | aagaaaaatc | 1020 |
| ctcataaacc | caaacgcaga | ggatcctcta | ccattgagcg | tgagggtgtg | gccacaagcc | 1080 |
| attccacagt | tcttgattgg | ccatctcgat | gttctagaca | ccgccaaggc | cggactgaga | 1140 |
| gaggctggaa | tggagggggct | attttttaggt | ggaaactatg | tatgcggtgt | ggccttgggg | 1200 |
| agatg | | | | | | 1205 |

<210> SEQ ID NO 42
<211> LENGTH: 401
<212> TYPE: PRT
<213> ORGANISM: Cucumis

<400> SEQUENCE: 42

Ser Phe Gln Pro Ser Asp Pro Ile Leu Thr Met Val Val Asp Ser Gly
1               5                   10                  15

Leu Lys Asp Asp Leu Val Leu Gly Asp Pro Asp Ala Pro Arg Phe Val
            20                  25                  30

Leu Trp Asn Gly Lys Leu Arg Pro Val Pro Ala Lys Pro Asn Asp Leu
        35                  40                  45

Pro Phe Phe Asp Leu Met Ser Ile Gly Gly Lys Ile Arg Ala Gly Phe
    50                  55                  60

Gly Ala Leu Gly Ile Arg Pro Pro Pro Gly Arg Glu Glu Ser Val
65                  70                  75                  80

Glu Glu Phe Val Arg Arg Asn Leu Gly Asn Glu Val Phe Glu Arg Leu
                85                  90                  95

Ile Glu Pro Phe Cys Ser Gly Val Tyr Ala Gly Asp Pro Ser Lys Leu
            100                 105                 110

Ser Met Lys Ala Ala Phe Gly Lys Val Trp Arg Leu Glu Gln Asn Gly
        115                 120                 125

Gly Ser Ile Ile Gly Gly Thr Phe Lys Ala Leu Gln Glu Arg Asn Lys
    130                 135                 140

Thr Thr Lys Pro Pro Arg Asp Pro Arg Leu Pro Lys Pro Lys Gly Gln
145                 150                 155                 160

Thr Val Gly Ser Phe Arg Lys Gly Leu Thr Met Leu Pro Asn Ala Ile
                165                 170                 175

Ser Thr Cys Leu Gly Ser Lys Val Lys Val Ser Trp Lys Leu Ser Ser
            180                 185                 190

Ile Ser Lys Val Asp Asp Gly Gly Tyr Ser Leu Thr Tyr Glu Thr Pro
        195                 200                 205

Glu Gly Leu Val Ser Ile Leu Ser Arg Ser Val Ile Met Thr Val Pro
    210                 215                 220

Ser Tyr Ile Ala Gly Thr Leu Leu Arg Pro Ile Ser Gly Lys Ala Ala
225                 230                 235                 240

Asp Ala Leu Ser Lys Phe Tyr Tyr Pro Pro Val Ala Ser Val Thr Ile
                245                 250                 255

Ser Tyr Pro Lys Gly Ala Ile Arg Lys Glu Cys Leu Ile Asp Gly Glu
            260                 265                 270

Leu Lys Gly Phe Gly Gln Leu His Pro Arg Ser Gln Gly Val Thr Thr
        275                 280                 285

Leu Gly Thr Ile Tyr Ser Ser Ser Leu Phe Pro Asn Arg Ala Pro Asp
    290                 295                 300

Gly Arg Val Leu Leu Leu Asn Tyr Ile Gly Gly Ala Thr Asn Thr Gly
305                 310                 315                 320

Ile Leu Ser Gln Thr Glu Ser Glu Leu Ile Glu Val Val Asp Arg Asp
                325                 330                 335

Leu Arg Lys Ile Leu Ile Asn Pro Asn Ala Glu Asp Pro Leu Pro Leu
            340                 345                 350

Ser Val Arg Val Trp Pro Gln Ala Ile Pro Gln Phe Leu Ile Gly His
        355                 360                 365

Leu Asp Val Leu Asp Thr Ala Lys Ala Gly Leu Arg Glu Ala Gly Met
    370                 375                 380

Glu Gly Leu Phe Leu Gly Gly Asn Tyr Val Cys Gly Val Ala Leu Gly
385                 390                 395                 400

Arg

<210> SEQ ID NO 43
<211> LENGTH: 1521
<212> TYPE: DNA
<213> ORGANISM: Oryza sativa

<400> SEQUENCE: 43
atggccgcct ccgacgaccc ccgcggcggg aggtccgtcg ccgtcgtcgg cgccggcgtc      60
agtgggctcg cggcggcgta caggctgagg aagcgcggcg tgcaggtgac ggtgttcgag     120
gcggccgaca gggcgggtgg gaagatacgg accaactccg agggcgggtt catctgggac     180
gaaggggcca acaccatgac agagagtgaa ttggaggcaa gcaggcttat tgacgatctt     240

```
ggcctacaag gcaaacagca gtatcctaac tcacaacaca agcgttacat tgtcaaagat    300
ggagcaccaa cactgattcc ctcagatccc attgcgctca tgaaaagcac tgttctttct    360
acaaaatcaa agctcaagct atttctggaa ccatttctct atgagaaatc tagcagaagg    420
acctcgggaa aagtgtctga tgaacattta agtgagagtg tgattttcct gtgtatatgt    480
agagataatc aggttgttga ttatcttatt gatccatttg tggctggaac aagcggagga    540
gatcctgagt cattatcaat tcgtcatgca tttccagcat tatggaattt ggagaataag    600
tatggctctg tcattgctgg tgccatcttg tccaaactat ccactaaggg tgattcagtg    660
aagacaggag gtgcttcgcc agggaaagga aggaataaac gtgtgtcatt ttcatttcat    720
ggtggaatgc agtcactaat agatgcactt cacaatgaag ttggagatgg taacgtgaag    780
cttggtacag aagtgttgtc attggcatgt tgctgtgatg gagtctcttc ttctggtggt    840
tggtcaattt ctgttgattc aaaagatgct aaagggaaag atctcagaaa gaaccaatct    900
ttcgatgctg ttataatgac tgctccattg tctaatgtcc agaggatgaa gtttacaaaa    960
ggtggagttc cctttgtgct agactttctt cctaaggtcg attatctacc actatctctc   1020
atggtaacag cttttaagaa ggaagatgtc aaaaaaccat tggaaggatt tggtgccttg   1080
atacccctata aggaacagca aaagcatggt ctcaaaaccc ttgggaccct cttctcctcg   1140
atgatgtttc cagatcgagc tcctaatgat caatatctat atacatcttt cattgggggg   1200
agccataata gagacctcgc tggggctcca acggctattc tgaaacaact tgtgacctct   1260
gacctaagaa agctcttggg tgttgaggga caacctactt ttgtgaagca tgtacattgg   1320
agaaatgctt ttcctttata tggccagaat tatgatctgg tactggaagc tatagcaaaa   1380
atggagaaca atcttccagg gttctttac gcaggaaata acaaggatgg gttggctgtt   1440
ggaaatgtta tagcttcagg aagcaaggct gctgaccttg tgatctctta tcttgaatct   1500
tgcacagatc aggacaatta g                                             1521
```

<210> SEQ ID NO 44
<211> LENGTH: 506
<212> TYPE: PRT
<213> ORGANISM: Oryza sativa

<400> SEQUENCE: 44

```
Met Ala Ala Ser Asp Asp Pro Arg Gly Gly Arg Ser Val Ala Val Val
1               5                   10                  15

Gly Ala Gly Val Ser Gly Leu Ala Ala Ala Tyr Arg Leu Arg Lys Arg
            20                  25                  30

Gly Val Gln Val Thr Val Phe Glu Ala Ala Asp Arg Ala Gly Gly Lys
        35                  40                  45

Ile Arg Thr Asn Ser Glu Gly Gly Phe Ile Trp Asp Glu Gly Ala Asn
    50                  55                  60

Thr Met Thr Glu Ser Glu Leu Glu Ala Ser Arg Leu Ile Asp Asp Leu
65                  70                  75                  80

Gly Leu Gln Gly Lys Gln Tyr Pro Asn Ser Gln His Lys Arg Tyr
                85                  90                  95

Ile Val Lys Asp Gly Ala Pro Thr Leu Ile Pro Ser Asp Pro Ile Ala
            100                 105                 110

Leu Met Lys Ser Thr Val Leu Ser Thr Lys Ser Lys Leu Lys Leu Phe
        115                 120                 125

Leu Glu Pro Phe Leu Tyr Glu Lys Ser Ser Arg Arg Thr Ser Gly Lys
    130                 135                 140
```

```
Val Ser Asp Glu His Leu Ser Glu Ser Val Ile Phe Leu Cys Ile Cys
145                 150                 155                 160

Arg Asp Asn Gln Val Val Asp Tyr Leu Ile Asp Pro Phe Val Ala Gly
            165                 170                 175

Thr Ser Gly Gly Asp Pro Glu Ser Leu Ser Ile Arg His Ala Phe Pro
        180                 185                 190

Ala Leu Trp Asn Leu Glu Asn Lys Tyr Gly Ser Val Ile Ala Gly Ala
    195                 200                 205

Ile Leu Ser Lys Leu Ser Thr Lys Gly Asp Ser Val Lys Thr Gly Gly
210                 215                 220

Ala Ser Pro Gly Lys Gly Arg Asn Lys Arg Val Ser Phe Ser Phe His
225                 230                 235                 240

Gly Gly Met Gln Ser Leu Ile Asp Ala Leu His Asn Glu Val Gly Asp
            245                 250                 255

Gly Asn Val Lys Leu Gly Thr Glu Val Leu Ser Leu Ala Cys Cys Cys
            260                 265                 270

Asp Gly Val Ser Ser Gly Gly Trp Ser Ile Ser Val Asp Ser Lys
        275                 280                 285

Asp Ala Lys Gly Lys Asp Leu Arg Lys Asn Gln Ser Phe Asp Ala Val
290                 295                 300

Ile Met Thr Ala Pro Leu Ser Asn Val Gln Arg Met Lys Phe Thr Lys
305                 310                 315                 320

Gly Gly Val Pro Phe Val Leu Asp Phe Leu Pro Lys Val Asp Tyr Leu
            325                 330                 335

Pro Leu Ser Leu Met Val Thr Ala Phe Lys Lys Glu Asp Val Lys Lys
        340                 345                 350

Pro Leu Glu Gly Phe Gly Ala Leu Ile Pro Tyr Lys Glu Gln Gln Lys
        355                 360                 365

His Gly Leu Lys Thr Leu Gly Thr Leu Phe Ser Ser Met Met Phe Pro
    370                 375                 380

Asp Arg Ala Pro Asn Asp Gln Tyr Leu Tyr Thr Ser Phe Ile Gly Gly
385                 390                 395                 400

Ser His Asn Arg Asp Leu Ala Gly Ala Pro Thr Ala Ile Leu Lys Gln
            405                 410                 415

Leu Val Thr Ser Asp Leu Arg Lys Leu Leu Gly Val Glu Gly Gln Pro
        420                 425                 430

Thr Phe Val Lys His Val His Trp Arg Asn Ala Phe Pro Leu Tyr Gly
        435                 440                 445

Gln Asn Tyr Asp Leu Val Leu Glu Ala Ile Ala Lys Met Glu Asn Asn
    450                 455                 460

Leu Pro Gly Phe Phe Tyr Ala Gly Asn Asn Lys Asp Gly Leu Ala Val
465                 470                 475                 480

Gly Asn Val Ile Ala Ser Gly Ser Lys Ala Ala Asp Leu Val Ile Ser
            485                 490                 495

Tyr Leu Glu Ser Cys Thr Asp Gln Asp Asn
        500                 505

<210> SEQ ID NO 45
<211> LENGTH: 1725
<212> TYPE: DNA
<213> ORGANISM: Oryza sativa

<400> SEQUENCE: 45
atgctctctc ctgccaccac cttctcctcc tcctcctcct cctcgtcgcc gtcgcgcgcc    60
```

-continued

| | |
|---|---|
| cacgctcgcg ctcccacccg cttcgcggtc gcagcatccg cgcgcgccgc acggttccgc | 120 |
| cccgcgcgcg ccatggccgc ctccgacgac cccgcggcg ggaggtccgt cgccgtcgtc | 180 |
| ggcgccggcg tcagtgggct cgcggcggcg tacaggctga ggaagcgcgg cgtgcaggtg | 240 |
| acggtgttcg aggcggccga cagggcgggt gggaagatac ggaccaactc cgagggcggg | 300 |
| ttcatctggg acgaaggggc caacaccatg acagagagtg aattggaggc aagcaggctt | 360 |
| attgacgatc ttggcctaca aggcaaacag cagtatccta actcacaaca caagcgttac | 420 |
| attgtcaaag atggagcacc aacactgatt ccctcagatc ccattgcgct catgaaaagc | 480 |
| actgttcttt ctacaaaatc aaagctcaag ctatttctgg aaccatttct ctatgagaaa | 540 |
| tctagcagaa ggacctcggg aaaagtgtct gatgaacatt taagtgagag tgttgcaagt | 600 |
| ttctttgaac gccactttgg aaaagaggtt gttgattatc ttattgatcc atttgtggct | 660 |
| ggaacaagcg gaggagatcc tgagtcatta tcaattcgtc atgcatttcc agcattatgg | 720 |
| aatttggaga taagtatgg ctctgtcatt gctggtgcca tcttgtccaa actatccact | 780 |
| aagggtgatt cagtgaagac aggaggtgct tcgccaggga aggaaggaa taaacgtgtg | 840 |
| tcattttcat ttcatggtgg aatgcagtca ctaatagatg cacttcacaa tgaagttgga | 900 |
| gatggtaacg tgaagcttgg tacagaagtg ttgtcattgg catgttgctg tgatggagtc | 960 |
| tcttcttctg gtggttggtc aatttctgtt gattcaaaag atgctaaagg gaaagatctc | 1020 |
| agaaagaacc aatctttcga tgctgttata atgactgctc cattgtctaa tgtccagagg | 1080 |
| atgaagttta caaaggtgg agttcccttt gtgctagact ttcttcctaa ggtcgattat | 1140 |
| ctaccactat ctctcatggt aacagctttt aagaaggaag atgtcaaaaa accattggaa | 1200 |
| ggatttggtg ccttgatacc ctataaggaa cagcaaaagc atggtctcaa aacccttggt | 1260 |
| caccctgcta gctgtattga actcaatata caaatcaacc ttgctacatt gctctacttt | 1320 |
| ttctcaggga ccctcttctc ctcgatgatg tttccagatc gagctcctaa tgatcaatat | 1380 |
| ctatatacat ctttcattgg ggggagccat aatagagacc tcgctggggc tccaacggct | 1440 |
| attctgaaac aacttgtgac ctctgaccta agaaagctct tgggtgttga gggacaacct | 1500 |
| acttttgtga agcatgtaca ttggagaaat gcttttcctt tatatggcca gaattatgat | 1560 |
| ctggtactgg aagctatagc aaaaatggag aacaatcttc cagggttctt ttacgcagga | 1620 |
| aataacaagg atgggttggc tgttggaaat gttatagctt caggaagcaa ggctgctgac | 1680 |
| cttgtgatct cttatcttga atcttgcaca gatcaggaca attag | 1725 |

<210> SEQ ID NO 46
<211> LENGTH: 574
<212> TYPE: PRT
<213> ORGANISM: Oryza sativa

<400> SEQUENCE: 46

```
Met Leu Ser Pro Ala Thr Thr Phe Ser Ser Ser Ser Ser Ser Ser
1               5                   10                  15

Pro Ser Arg Ala His Ala Arg Ala Pro Thr Arg Phe Ala Val Ala Ala
            20                  25                  30

Ser Ala Arg Ala Ala Arg Phe Arg Pro Ala Arg Ala Met Ala Ala Ser
        35                  40                  45

Asp Asp Pro Arg Gly Gly Arg Ser Val Ala Val Val Gly Ala Gly Val
    50                  55                  60

Ser Gly Leu Ala Ala Ala Tyr Arg Leu Arg Lys Arg Gly Val Gln Val
65                  70                  75                  80
```

```
Thr Val Phe Glu Ala Ala Asp Arg Ala Gly Lys Ile Arg Thr Asn
             85                  90                  95

Ser Glu Gly Gly Phe Ile Trp Asp Gly Ala Asn Thr Met Thr Glu
            100                 105                 110

Ser Glu Leu Glu Ala Ser Arg Leu Ile Asp Asp Leu Gly Leu Gln Gly
            115                 120                 125

Lys Gln Gln Tyr Pro Asn Ser Gln His Lys Arg Tyr Ile Val Lys Asp
            130                 135                 140

Gly Ala Pro Thr Leu Ile Pro Ser Asp Pro Ile Ala Leu Met Lys Ser
145                 150                 155                 160

Thr Val Leu Ser Thr Lys Ser Lys Leu Lys Leu Phe Leu Glu Pro Phe
            165                 170                 175

Leu Tyr Glu Lys Ser Ser Arg Arg Thr Ser Gly Lys Val Ser Asp Glu
            180                 185                 190

His Leu Ser Glu Ser Val Ala Ser Phe Phe Glu Arg His Phe Gly Lys
            195                 200                 205

Glu Val Val Asp Tyr Leu Ile Asp Pro Phe Val Ala Gly Thr Ser Gly
            210                 215                 220

Gly Asp Pro Glu Ser Leu Ser Ile Arg His Ala Phe Pro Ala Leu Trp
225                 230                 235                 240

Asn Leu Glu Asn Lys Tyr Gly Ser Val Ile Ala Gly Ala Ile Leu Ser
            245                 250                 255

Lys Leu Ser Thr Lys Gly Asp Ser Val Lys Thr Gly Gly Ala Ser Pro
            260                 265                 270

Gly Lys Gly Arg Asn Lys Arg Val Ser Phe Ser Phe His Gly Gly Met
            275                 280                 285

Gln Ser Leu Ile Asp Ala Leu His Asn Glu Val Gly Asp Gly Asn Val
            290                 295                 300

Lys Leu Gly Thr Glu Val Leu Ser Leu Ala Cys Cys Cys Asp Gly Val
305                 310                 315                 320

Ser Ser Ser Gly Gly Trp Ser Ile Ser Val Asp Ser Lys Asp Ala Lys
            325                 330                 335

Gly Lys Asp Leu Arg Lys Asn Gln Ser Phe Asp Ala Val Ile Met Thr
            340                 345                 350

Ala Pro Leu Ser Asn Val Gln Arg Met Lys Phe Thr Lys Gly Gly Val
            355                 360                 365

Pro Phe Val Leu Asp Phe Leu Pro Lys Val Asp Tyr Leu Pro Leu Ser
            370                 375                 380

Leu Met Val Thr Ala Phe Lys Lys Glu Asp Val Lys Lys Pro Leu Glu
385                 390                 395                 400

Gly Phe Gly Ala Leu Ile Pro Tyr Lys Glu Gln Gln Lys His Gly Leu
            405                 410                 415

Lys Thr Leu Gly His Pro Ala Ser Cys Ile Glu Leu Asn Ile Gln Ile
            420                 425                 430

Asn Leu Ala Thr Leu Leu Tyr Phe Phe Ser Gly Thr Leu Phe Ser Ser
            435                 440                 445

Met Met Phe Pro Asp Arg Ala Pro Asn Asp Gln Tyr Leu Tyr Thr Ser
            450                 455                 460

Phe Ile Gly Gly Ser His Asn Arg Asp Leu Ala Gly Ala Pro Thr Ala
465                 470                 475                 480

Ile Leu Lys Gln Leu Val Thr Ser Asp Leu Arg Lys Leu Leu Gly Val
            485                 490                 495

Glu Gly Gln Pro Thr Phe Val Lys His Val His Trp Arg Asn Ala Phe
```

|   |   |   | 500 |   |   | 505 |   |   | 510 |   |   |
|---|---|---|---|---|---|---|---|---|---|---|---|
| Pro | Leu | Tyr | Gly | Gln | Asn | Tyr | Asp | Leu | Val | Leu | Glu | Ala | Ile | Ala | Lys |

Pro Leu Tyr Gly Gln Asn Tyr Asp Leu Val Leu Glu Ala Ile Ala Lys
             515             520             525

Met Glu Asn Asn Leu Pro Gly Phe Phe Tyr Ala Gly Asn Asn Lys Asp
 530             535             540

Gly Leu Ala Val Gly Asn Val Ile Ala Ser Gly Ser Lys Ala Ala Asp
545             550             555             560

Leu Val Ile Ser Tyr Leu Glu Ser Cys Thr Asp Gln Asp Asn
             565             570

<210> SEQ ID NO 47
<211> LENGTH: 1725
<212> TYPE: DNA
<213> ORGANISM: Amaranthus tuberculatus

<400> SEQUENCE: 47

```
atgctctctc ctgccaccac cttctcctcc tcctcctcct cctcgtcgcc gtcgcgcgcc      60
cacgctcgcg ctcccacccg cttcgcggtc gcagcatccg cgcgcgccgc acggttccgc     120
cccgcgcgcg ccatggccgc ctccgacgac ccccgcggcg ggaggtccgt cgccgtcgtc     180
ggcgccggcg tcagtgggct cgcggcggcg tacaggctga ggaagcgcgg cgtgcaggtg     240
acggtgttcg aggcggccga cagggcgggt gggaagatac ggaccaactc cgagggcggg     300
ttcatctggg acgaaggggc caacaccatg acagagagtg aattggaggc aagcaggctt     360
attgacgatc ttggcctaca aggcaaacag cagtatccta actcacaaca caagcgttac     420
attgtcaaag atggagcacc aacactgatt ccctcagatc ccattgcgct catgaaaagc     480
actgttcttt ctacaaaatc aaagctcaag ctatttctgg aaccatttct ctatgagaaa     540
tctagcagaa ggacctcggg aaaagtgtct gatgaacatt taagtgagag tgttgcaagt     600
ttcttgaac gccactttgg aaaagaggtt gttgattatc ttattgatcc atttgtggct     660
ggaacaagcg gaggagatcc tgagtcatta tcaattcgtc atgcatttcc agcattatgg     720
aatttggaga ataagtatgg ctctgtcatt gctggtgcca tcttgtccaa actatccact     780
aagggtgatt cagtgaagac aggaggtgct tcgccaggga aggaaggaa taaacgtgtg     840
tcatttcat tcatggtgg aatgcagtca ctaatagatg cacttcacaa tgaagttgga     900
gatggtaacg tgaagcttgg tacagaagtg ttgtcattgg catgttgctg tgatggagtc     960
tcttcttctg gtggttggtc aatttctgtt gattcaaaag atgctaaagg aaagatctc    1020
agaaagaacc aatcttttcga tgctgttata atgactgctc cattgtctaa gtccagagg    1080
atgaagttta caaaggtgg agttcccttt gtgctagact ttcttcctaa ggtcgattat    1140
ctaccactat ctctcatggt aacagctttt aagaaggaag atgtcaaaaa accattggaa    1200
ggatttggtg ccttgatacc ctataaggaa cagcaaaagc atggtctcaa aacccttggt    1260
caccctgcta gctgtattga actcaatata caaatcaacc ttgctacatt gctctacttt    1320
ttctcaggga ccctcttctc ctcgatgatg tttccagatc gagctcctaa tgatcaatat    1380
ctatatacat cttttcattgg ggggagccat aatagagacc tcgctggggc tccaacggct    1440
attctgaaac aacttgtgac ctctgaccta agaaagctct gggtgttga gggacaacct    1500
actttgtga agcatgtaca ttggagaaat gcttttcctt tatatggcca gaattatgat    1560
ctggtactgg aagctatagc aaaaatggag aacaatcttc cagggttctt ttacgcagga    1620
aataacaagg atgggttggc tgttggaaat gttatagctt caggaagcaa ggctgctgac    1680
cttgtgatct cttatcttga atcttgcaca gatcaggaca attag                    1725
```

<210> SEQ ID NO 48
<211> LENGTH: 550
<212> TYPE: PRT
<213> ORGANISM: Amaranthus tuberculatus

<400> SEQUENCE: 48

```
Met Ser Ala Met Ala Leu Ser Ser Ile Leu Gln Cys Pro Pro His
1               5                   10                  15

Ser Asp Ile Ser Phe Arg Phe Ala His Thr Arg Thr Gln Pro Pro
            20                  25                  30

Ile Phe Phe Gly Arg Pro Arg Lys Leu Ser Tyr Ile His Cys Ser Thr
            35                  40                  45

Ser Ser Ser Ser Thr Ala Asn Tyr Gln Asn Thr Ile Thr Ser Gln Gly
50                      55                      60

Glu Gly Asp Lys Val Leu Asp Cys Val Ile Val Gly Ala Gly Ile Ser
65                  70                  75                  80

Gly Leu Cys Ile Ala Gln Ala Leu Ser Thr Lys His Ile Gln Ser Asn
                85                  90                  95

Leu Asn Phe Ile Val Thr Glu Ala Lys His Arg Val Gly Gly Asn Ile
                100                 105                 110

Thr Thr Met Glu Ser Asp Gly Tyr Ile Trp Glu Glu Gly Pro Asn Ser
            115                 120                 125

Phe Gln Pro Ser Asp Pro Val Leu Thr Met Ala Val Asp Ser Gly Leu
        130                 135                 140

Lys Asp Asp Leu Val Leu Gly Asp Pro Asn Ala Pro Arg Phe Val Leu
145                 150                 155                 160

Trp Asn Gly Lys Leu Arg Pro Val Pro Ser Lys Pro Thr Asp Leu Pro
                165                 170                 175

Phe Phe Asp Leu Met Ser Phe Pro Gly Lys Ile Arg Ala Gly Leu Gly
            180                 185                 190

Ala Leu Gly Leu Arg Pro Pro Pro Ser Tyr Glu Glu Ser Val Glu
                195                 200                 205

Glu Phe Val Arg Arg Asn Leu Gly Asp Glu Val Phe Glu Arg Leu Ile
    210                 215                 220

Glu Pro Phe Cys Ser Gly Val Tyr Ala Gly Asp Pro Ala Lys Leu Ser
225                 230                 235                 240

Met Lys Ala Ala Phe Gly Lys Val Trp Thr Leu Glu Gln Lys Gly Gly
                245                 250                 255

Ser Ile Ile Ala Gly Thr Leu Lys Thr Ile Gln Glu Arg Lys Asn Asn
            260                 265                 270

Pro Pro Pro Pro Arg Asp Pro Arg Leu Pro Lys Pro Lys Gly Gln Thr
        275                 280                 285

Val Gly Ser Phe Arg Lys Gly Leu Ile Met Leu Pro Thr Ala Ile Ala
    290                 295                 300

Ala Arg Leu Gly Ser Lys Val Lys Leu Ser Trp Thr Leu Ser Asn Ile
305                 310                 315                 320

Asp Lys Ser Leu Asn Gly Glu Tyr Asn Leu Thr Tyr Gln Thr Pro Asp
                325                 330                 335

Gly Pro Val Ser Val Arg Thr Lys Ala Val Val Met Thr Val Pro Ser
            340                 345                 350

Tyr Ile Ala Ser Ser Leu Leu Arg Pro Leu Ser Asp Val Ala Ala Asp
        355                 360                 365

Ser Leu Ser Lys Phe Tyr Tyr Pro Pro Val Ala Ala Val Ser Leu Ser
```

370                 375                 380
Tyr Pro Lys Glu Ala Ile Arg Pro Glu Cys Leu Ile Asp Gly Glu Leu
385                 390                 395                 400

Lys Gly Phe Gly Gln Leu His Pro Arg Ser Gln Gly Val Glu Thr Leu
            405                 410                 415

Gly Thr Ile Tyr Ser Ser Leu Phe Pro Gly Arg Ala Pro Pro Gly
            420                 425                 430

Arg Thr Leu Ile Leu Ser Tyr Ile Gly Gly Ala Thr Asn Leu Gly Ile
            435                 440                 445

Leu Gln Lys Ser Glu Asp Glu Leu Ala Glu Thr Val Asp Lys Asp Leu
            450                 455                 460

Arg Lys Ile Leu Ile Asn Pro Asn Ala Lys Gly Ser Arg Val Leu Gly
465                 470                 475                 480

Val Arg Val Trp Pro Lys Ala Ile Pro Gln Phe Leu Val Gly His Phe
                485                 490                 495

Asp Val Leu Asp Ala Ala Lys Ala Gly Leu Ala Asn Ala Gly Gln Lys
            500                 505                 510

Gly Leu Phe Leu Gly Gly Asn Tyr Val Ser Gly Val Ala Leu Gly Arg
            515                 520                 525

Cys Ile Glu Gly Ala Tyr Asp Ser Ala Ser Glu Val Val Asp Phe Leu
            530                 535                 540

Ser Gln Tyr Lys Asp Lys
545                 550

<210> SEQ ID NO 49
<211> LENGTH: 47
<212> TYPE: PRT
<213> ORGANISM: Zea mays

<400> SEQUENCE: 49

Met Leu Ala Leu Thr Ala Ser Ala Ser Ser Ser His Pro Tyr
1               5                   10                  15

Arg His Ala Ser Ala His Thr Arg Arg Pro Arg Leu Arg Ala Val Leu
                20                  25                  30

Ala Met Ala Gly Ser Asp Asp Pro Arg Ala Ala Pro Ala Arg Ser
            35                  40                  45

<210> SEQ ID NO 50
<211> LENGTH: 47
<212> TYPE: PRT
<213> ORGANISM: Sorghum

<400> SEQUENCE: 50

Met Leu Ala Arg Thr Ala Thr Val Ser Ser Thr Ser Ser His Ser His
1               5                   10                  15

Pro Tyr Arg Pro Thr Ser Ala Arg Ser Leu Arg Leu Arg Pro Val Leu
                20                  25                  30

Ala Met Ala Gly Ser Asp Asp Ser Arg Ala Ala Pro Ala Arg Ser
            35                  40                  45

<210> SEQ ID NO 51
<211> LENGTH: 57
<212> TYPE: PRT
<213> ORGANISM: Zea mays

<400> SEQUENCE: 51

Met Val Ala Ala Thr Ala Thr Ala Thr Ala Met Ala Thr Ala Ala Ser
1               5                   10                  15

-continued

Pro Leu Leu Asn Gly Thr Arg Ile Pro Ala Arg Leu Arg His Arg Gly
            20                  25                  30

Leu Ser Val Arg Cys Ala Ala Val Ala Gly Gly Ala Ala Glu Ala Pro
        35                  40                  45

Ala Ser Thr Gly Ala Arg Leu Ser Ala
    50                  55

<210> SEQ ID NO 52
<211> LENGTH: 56
<212> TYPE: PRT
<213> ORGANISM: Sorghum bicolor

<400> SEQUENCE: 52

Met Val Ala Ala Ala Met Ala Thr Ala Ala Ser Ala Ala Ala Pro
1               5                   10                  15

Leu Leu Asn Gly Thr Arg Arg Pro Ala Arg Leu Arg Arg Gly Leu
            20                  25                  30

Arg Val Arg Cys Ala Ala Val Ala Gly Gly Ala Ala Glu Ala Pro Ala
        35                  40                  45

Ser Thr Gly Ala Arg Leu Ser Ala
    50                  55

<210> SEQ ID NO 53
<211> LENGTH: 51
<212> TYPE: PRT
<213> ORGANISM: Silene pratensis

<400> SEQUENCE: 53

Met Ala Ser Thr Leu Ser Thr Leu Ser Val Ser Ala Ser Leu Leu Pro
1               5                   10                  15

Lys Gln Gln Pro Met Val Ala Ser Ser Leu Pro Thr Asn Met Gly Gln
            20                  25                  30

Ala Leu Phe Gly Leu Lys Ala Gly Ser Arg Gly Arg Val Thr Ala Met
        35                  40                  45

Ala Thr Tyr
    50

<210> SEQ ID NO 54
<211> LENGTH: 153
<212> TYPE: DNA
<213> ORGANISM: Silene pratensis

<400> SEQUENCE: 54
atggcttcta cactctctac cctctcggtg agcgcatcgt tgttgccaaa gcaacaaccg      60
atggtcgcct catcgctacc aactaatatg ggccaagcct tgtttggact gaaagccggt     120
tctcgtggca gagtgactgc aatggccaca tac                                  153

<210> SEQ ID NO 55
<211> LENGTH: 153
<212> TYPE: DNA
<213> ORGANISM: Silene pratensis

<400> SEQUENCE: 55
atggctagca ccttgagcac tcttagcgtt agcgctagcc ttttgcctaa gcagcaacct      60
atggtggcta gctcactccc tactaatatg ggtcaggctc tcttcggact taaggctgga     120 tctagggta gagttactgc tatggctacc tac                                   153

<210> SEQ ID NO 56
<211> LENGTH: 537
<212> TYPE: PRT
<213> ORGANISM: Zea mays

<400> SEQUENCE: 56

```
Met Val Ala Ala Thr Ala Thr Ala Thr Met Ala Thr Ala Ala Ser
1               5                   10                  15

Pro Leu Leu Asn Gly Thr Arg Ile Pro Ala Arg Leu Arg His Arg Gly
            20                  25                  30

Leu Ser Val Arg Cys Ala Ala Val Ala Gly Ala Ala Glu Ala Pro
        35                  40                  45

Ala Ser Thr Gly Ala Arg Leu Ser Ala Asp Cys Val Val Gly Gly
    50                  55                  60

Gly Ile Ser Gly Leu Cys Thr Ala Gln Ala Leu Ala Thr Arg His Gly
65                  70                  75                  80

Val Gly Asp Val Leu Val Thr Glu Ala Arg Ala Arg Pro Gly Gly Asn
                85                  90                  95

Ile Thr Thr Val Glu Arg Pro Glu Glu Gly Tyr Leu Trp Glu Glu Gly
            100                 105                 110

Pro Asn Ser Phe Gln Pro Ser Asp Pro Val Leu Thr Met Ala Val Asp
        115                 120                 125

Ser Gly Leu Lys Asp Asp Leu Val Phe Gly Asp Pro Asn Ala Pro Arg
    130                 135                 140

Phe Val Leu Trp Glu Gly Lys Leu Arg Pro Val Pro Ser Lys Pro Ala
145                 150                 155                 160

Asp Leu Pro Phe Phe Asp Leu Met Ser Ile Pro Gly Lys Leu Arg Ala
                165                 170                 175

Gly Leu Gly Ala Leu Gly Ile Arg Pro Pro Pro Gly Arg Glu Glu
            180                 185                 190

Ser Val Glu Glu Phe Val Arg Arg Asn Leu Gly Ala Glu Val Phe Glu
    195                 200                 205

Arg Leu Ile Glu Pro Phe Cys Ser Gly Val Tyr Ala Gly Asp Pro Ser
210                 215                 220

Lys Leu Ser Met Lys Ala Ala Phe Gly Lys Val Trp Arg Leu Glu Glu
225                 230                 235                 240

Thr Gly Gly Ser Ile Ile Gly Gly Thr Ile Lys Thr Ile Gln Glu Arg
                245                 250                 255

Ser Lys Asn Pro Lys Pro Pro Arg Asp Ala Arg Leu Pro Lys Pro Lys
            260                 265                 270

Gly Gln Thr Val Ala Ser Phe Arg Lys Gly Leu Ala Met Leu Pro Asn
        275                 280                 285

Ala Ile Thr Ser Ser Leu Gly Ser Lys Val Lys Leu Ser Trp Lys Leu
    290                 295                 300

Thr Ser Ile Thr Lys Ser Asp Asp Lys Gly Tyr Val Leu Glu Tyr Glu
305                 310                 315                 320

Thr Pro Glu Gly Val Val Ser Val Gln Ala Lys Ser Val Ile Met Thr
                325                 330                 335

Ile Pro Ser Tyr Val Ala Ser Asn Ile Leu Arg Pro Leu Ser Ser Asp
            340                 345                 350

Ala Ala Asp Ala Leu Ser Arg Phe Tyr Tyr Pro Pro Val Ala Ala Val
        355                 360                 365

Thr Val Ser Tyr Pro Lys Glu Ala Ile Arg Lys Glu Cys Leu Ile Asp
    370                 375                 380
```

-continued

```
Gly Glu Leu Gln Gly Phe Gly Gln Leu His Pro Arg Ser Gln Gly Val
385                 390                 395                 400

Glu Thr Leu Gly Thr Ile Tyr Ser Ser Ser Leu Phe Pro Asn Arg Ala
                405                 410                 415

Pro Asp Gly Arg Val Leu Leu Leu Asn Tyr Ile Gly Gly Ala Thr Asn
            420                 425                 430

Thr Gly Ile Val Ser Lys Thr Glu Ser Glu Leu Val Trp Ala Val Asp
        435                 440                 445

Arg Asp Leu Arg Lys Met Leu Ile Asn Ser Thr Ala Val Asp Pro Leu
    450                 455                 460

Val Leu Gly Val Arg Val Trp Pro Gln Ala Ile Pro Gln Phe Leu Val
465                 470                 475                 480

Gly His Leu Asp Leu Leu Glu Ala Ala Lys Ala Ala Leu Asp Arg Gly
                485                 490                 495

Gly Tyr Asp Gly Leu Phe Leu Gly Gly Asn Tyr Val Ala Gly Val Ala
            500                 505                 510

Leu Gly Arg Cys Val Glu Gly Ala Tyr Glu Ser Ala Ser Gln Ile Ser
        515                 520                 525

Asp Phe Leu Thr Lys Tyr Ala Tyr Lys
530                 535
```